United States Patent
Kilburn et al.

(10) Patent No.: US 10,238,654 B2
(45) Date of Patent: *Mar. 26, 2019

(54) BENZAMIDES-CONTAINING COMPOUNDS AND THEIR USE IN THE TREATMENT OF EPILEPSY

(71) Applicant: MINDIMMUNE THERAPEUTICS, INC., Kingston, RI (US)

(72) Inventors: John Paul Kilburn, Haslev (DK); Lars Kyhn Rasmussen, Vanløse (DK); Mikkel Jessing, København ç (DK); Eman Mohamed Eldemenky, Wayne, NJ (US); Bin Chen, East Windsor, NJ (US); Yu Jiang, East Windsor, NJ (US); Allen T. Hopper, Katonah, NY (US)

(73) Assignee: MINDIMMUNE THERAPEUTICS, INC., Kingston, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/479,972

(22) Filed: Apr. 5, 2017

(65) Prior Publication Data

US 2017/0202836 A1  Jul. 20, 2017

Related U.S. Application Data

(63) Continuation of application No. 14/744,103, filed on Jun. 19, 2015, now Pat. No. 9,649,308, which is a continuation of application No. 14/050,431, filed on Oct. 10, 2013, now Pat. No. 9,102,591.

(60) Provisional application No. 61/713,113, filed on Oct. 12, 2012.

(51) Int. Cl.
| | |
|---|---|
| *A61K 31/505* | (2006.01) |
| *C07C 233/66* | (2006.01) |
| *C07C 233/75* | (2006.01) |
| *C07C 233/78* | (2006.01) |
| *C07D 211/26* | (2006.01) |
| *C07D 213/40* | (2006.01) |
| *C07D 233/64* | (2006.01) |
| *C07D 237/08* | (2006.01) |
| *C07D 239/26* | (2006.01) |
| *C07D 241/12* | (2006.01) |
| *C07D 309/04* | (2006.01) |
| *C07D 401/06* | (2006.01) |
| *C07D 403/06* | (2006.01) |
| *C07D 405/04* | (2006.01) |
| *C07D 405/06* | (2006.01) |
| *C07D 231/12* | (2006.01) |
| *C07D 403/04* | (2006.01) |
| *C07D 213/61* | (2006.01) |
| *C07C 233/73* | (2006.01) |

(52) U.S. Cl.
CPC .......... *A61K 31/505* (2013.01); *C07C 233/66* (2013.01); *C07C 233/73* (2013.01); *C07C 233/75* (2013.01); *C07C 233/78* (2013.01); *C07D 211/26* (2013.01); *C07D 213/40* (2013.01); *C07D 213/61* (2013.01); *C07D 231/12* (2013.01); *C07D 233/64* (2013.01); *C07D 237/08* (2013.01); *C07D 239/26* (2013.01); *C07D 241/12* (2013.01); *C07D 309/04* (2013.01); *C07D 401/06* (2013.01); *C07D 403/04* (2013.01); *C07D 403/06* (2013.01); *C07D 405/04* (2013.01); *C07D 405/06* (2013.01); *C07C 2601/08* (2017.05)

(58) Field of Classification Search
CPC .. A61K 31/505; C07D 211/26; C07D 213/40; C07D 213/61; C07D 231/12; C07D 233/64; C07D 237/08; C07D 239/26; C07D 241/12; C07D 309/04; C07D 401/06; C07D 403/04; C07D 403/06; C07D 405/04; C07D 405/06
See application file for complete search history.

(56) References Cited

U.S. PATENT DOCUMENTS

| | | |
|---|---|---|
| 6,194,458 B1 | 2/2001 | Baker et al. |
| 6,303,637 B1 | 10/2001 | Bao et al. |
| 6,974,812 B2 | 12/2005 | Dombroski et al. |
| 7,560,567 B2 | 7/2009 | Coqueron et al. |

(Continued)

FOREIGN PATENT DOCUMENTS

| | | |
|---|---|---|
| GB | 1026408 | 4/1966 |
| TW | 200300083 | 5/2003 |

(Continued)

OTHER PUBLICATIONS

Types of Epilepsy reference (Nov. 2017).*

(Continued)

*Primary Examiner* — Valerie Rodriguez-Garcia
(74) *Attorney, Agent, or Firm* — Ziegler IP Law Group, LLC

(57) ABSTRACT

The present invention is directed to benzamide-containing compounds of formula I

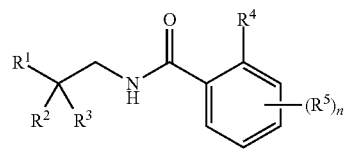

or pharmaceutically acceptable salts thereof which inhibit the $P2X_7$ receptor, and their use in the treatment of epilepsy.

18 Claims, No Drawings

(56) References Cited

U.S. PATENT DOCUMENTS

| | | | |
|---|---|---|---|
| 7,825,135 B2 | 11/2010 | Blackaby et al. | |
| 9,102,591 B2 * | 8/2015 | Kilburn | C07C 233/66 |
| 9,108,938 B2 * | 8/2015 | Kilburn | C07D 211/38 |
| 9,415,055 B2 | 8/2016 | Kilburn | |
| 9,593,105 B2 * | 3/2017 | Kilburn | C07D 211/38 |
| 2009/0163545 A1 | 6/2009 | Goldfarb | |
| 2011/0136831 A1 | 6/2011 | Oda et al. | |
| 2014/0107340 A1 | 4/2014 | Kilburn | |
| 2015/0283134 A1 | 10/2015 | Kilburn | |

FOREIGN PATENT DOCUMENTS

| | | |
|---|---|---|
| WO | WO 2003/042191 | 5/2003 |
| WO | WO 2003/088908 | 10/2003 |
| WO | WO 2005/013914 | 2/2005 |
| WO | WO 2007/045572 | 4/2007 |
| WO | WO 2007/072782 | 6/2007 |
| WO | WO 2010/040803 | 4/2010 |
| WO | WO 2012/007868 | 1/2012 |
| WO | WO 2012/118139 | 7/2012 |

OTHER PUBLICATIONS

Types of Seizures (Nov. 2017).*

Engel et al. (Int J Physiol Pathophysiol Pharmacol. 2012;4(4):174-87. Epub Dec. 26, 2012).*

Bronstein-Sitton, N. (2004) "Regulating the Immune Response: the Unexpected Role of Ion Channels:" Modulators 18:1-5.

CAS Registry No. 1091018-63-1 (Dec. 28, 2008).
CAS Registry No. 1091125-77-7 (Dec. 28, 2008).
CAS Registry No. 1091126-81-6 (Dec. 28, 2008).
CAS Registry No. 1091153-62-6 (Dec. 28, 2008).
CAS Registry No. 1091154-42-5 (Dec. 28, 2008).
CAS Registry No. 1091474-02-0 (Dec. 29, 2008).

Chan, J., et al. (2007) "Rh(II)-Catalyzed Intermolecular Oxidative Sulfamidation of Aldehydes: A Mild Efficient Synthesis of N-Sulfonylcarboxamides," J. Am. Chem. Soc. 129(46):14106-14107.

Kunitomo, J., et al. (1982) "Structure of Menispoiphine: a New Type of Isoquinoline Alkaloid," Chemical and Pharmaceutical Bulletin 30(7):2659-2660.

Massah, A.R., et al. (2008) "Synthesis, in vitro Antibacterial and Carbonic Anhydrase II Inhibitory Activities of N-acylsulfonamides Using Silica Sulfuric Acid as an Efficient Catalyst Under Both Solvent-Free and Heterogeneous Conditions," Bioorg. & Med. Chem. 16(10):5465-5472.

McClure, K.J., et al. (2011) "Discovery of a Novel Series of Selective HCN1 Blockers," Bioorg. Med. Chem. Lett. 21(18):5197-5201.

Roberts, B., et al. (2010) "Novel Aryl and Heteroaryl Acyl Sulfamide Synthesis via Microwave-Assisted Palladium-Catalyzed Carbonylation," Org. Lett. 12(6):1264-1267.

Tsatsas, G. (1952) "New Spasmolytic Derivatives of 1-phenylisoquinoline," Annales Pharmaceutiques Francaises 10:76-291.

* cited by examiner

BENZAMIDES-CONTAINING COMPOUNDS AND THEIR USE IN THE TREATMENT OF EPILEPSY

CROSS-REFERENCE TO RELATED APPLICATIONS

The present application is a continuation of U.S. application Ser. No. 14/744,103, filed Jun. 19, 2015, pending, which is a continuation of U.S. application Ser. No. 14/050,431, filed Oct. 10, 2013, patented (U.S. Pat. No. 9,102,591; Aug. 11, 2015), which application claims benefit of U.S. Provisional Application No. 61/713,113, filed Oct. 12, 2012. Each of these applications is hereby incorporated by reference in its entirety.

FIELD OF THE INVENTION

The present invention is directed to novel compounds which inhibit the P2X$_7$ receptor. Separate aspects of the invention are directed to pharmaceutical compositions comprising said compounds and uses of the compounds to treat pain, inflammation, neurological disorders, or neuropsychiatric disorders.

BACKGROUND ART

The purinergic 2X$_7$ (P2X$_7$) receptor is a ligand-gated ion channel which is activated by extracellular ATP and is present on a variety of cell types, including microglia in the central nervous system and other cells involved in inflammation and immune system function. The P2X$_7$ receptor has been shown to have a role in cytolysis in the immune system (Surprenant, et al. Science, 272, 735-41, 1996), and is involved in activation of lymphocytes and monocyte/macrophages leading to the increased release of pro-inflammatory cytokines (e.g., TNFα and IL1β) from these cells (Ferrari, et al. Neuropharmacol, 36, 1295-301, 1997).

Studies have shown that inhibiting P2X$_7$ receptor activation in situations of inflammation (e. g., rheumatoid arthritis and other autoimmune diseases, osteoarthritis, asthma, chronic obstructive pulmonary disease and inflammatory bowel disease) or interstitial fibrosis results in a therapeutic effect (DiVirgilio, et al. Drug Dev Res, 45, 207-13, 1998). These and other studies indicate that P2X$_7$ receptor antagonists may find use in the treatment and prophylaxis of pain, including acute, chronic and neuropathic pain (Chessel, et al, Pain, 114, 386-96, 2005).

Inhibiting P2X$_7$ activation may also diminish or reduce cell death caused by prolongation of activated P2X$_7$ receptors, indicating a potential therapeutic intervention for said antagonists in nervous system injury or degeneration (Sperlagh, et al., Progress in Neurobiology, 7, 327-346, 2006). Vianna, et al. (Epilepsia, 43, 27-229, 2002) also revealed a potential role for P2X$_7$ receptors in the pathogenesis of epilepsy. Interestingly, because of the P2X$_7$ receptor's role in microglia activation and proliferation in the central nervous system (CNS), a self-propagating cycle of neuroinflammation and neurodegeneration results from P2X$_7$ receptor activation in areas of the brain (Monif, et al., J Neurosci, 29, 3781-91, 2009).

Thus, P2X$_7$ receptor antagonists, particularly small molecules with sufficient brain-penetrable properties, are desirable as useful agents for therapeutic intervention in the central nervous system for treating pain, inflammation, neurological and neurodegenerative disorders, neuropsychiatric disorders, or other disorders for which the reduction or otherwise stabilization of pro-inflammatory cytokines is beneficial. The present invention fulfills this need, and provides further related advantages.

SUMMARY OF THE INVENTION

An objective of the present invention is to provide compounds that inhibit P2X$_7$ receptors. Accordingly, the present invention relates to compounds of Formula I.

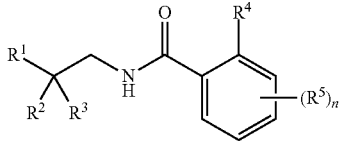

Formula I wherein $R^1$ is phenyl, pyridyl, pyrazinyl, pyridazinyl, pyrimidyl or 5 membered heteroaryl, each of which is optionally substituted with one or more $C_{1-6}$ alkyl, halogen, hydroxy, $C_{1-6}$ hydroxyalkyl, $C_{1-4}$ fluoroalkyl, $C_{1-3}$ cycloalkyl, $C_{1-4}$ alkoxy, $C_{1-4}$ fluoroalkoxy, cyano or $SO_2R^8$;

wherein $R^2$ is $C_{3-6}$ cycloalkyl, $C_{3-6}$ cyclohetalkyl, $C_{1-4}$ fluoroalkyl, $C_{1-4}$ fluoroalkoxy, $C_{1-4}$ alkoxy, $C_{1-6}$ alkenyl, $C_{1-6}$ alkynyl, 6 membered heteroaryl, phenyl or $C_{1-4}$ alkyl optionally substituted with one or more $R^9$;

wherein $R^3$ is hydrogen, fluorine, $C_{1-4}$ alkyl or $C_{1-4}$ fluoroalkyl; or wherein $R^2$ and $R^3$ combine with the carbon to which they are attached to form cyclohexyl, tetrahydropyranyl, piperazinyl, pipe ridinyl, morpholinyl, pyrrolidinyl, azetidinyl, homomorpholinyl, homopiperidinyl or homopiperazinyl each of which is optionally substituted with one or more $C_{1-6}$ alkyl, $C_{1-6}$ alkenyl, $C_{3-6}$-cycloalkyl, $C_{1-6}$ alkoxy, oxo, —NR$^6$R$^7$ or fluorine;

wherein $R^4$ is halogen, $C_{1-4}$fluoroalkyl, cyano, cyclopropyl, $C_{1-4}$alkyloxy, $C_{1-4}$fluoroalkyloxy, —SO$_2$R$^8$, —NR$^6$R$^7$ or $C_{1-6}$alkyl;

wherein $R^5$ is halogen, $C_{1-6}$ alkyl, $C_{1-4}$ fluoroalkyl, cyano, —SO$_2$R$^8$, —NR$^6$R$^7$, $C_{1-6}$ alkoxy, $C_{1-4}$fluoroalkoxy or $C_{3-6}$-cycloalkyl;

wherein $R^6$ and $R^7$ independently of each other are hydrogen or $C_{1-6}$ alkyl;

wherein $R^8$ is $C_{1-6}$ alkyl, $C_{3-6}$ cycloalkyl or $C_{1-4}$fluoroalkyl;

wherein $R^9$ is $C_{1-6}$alkyl, $C_{3-6}$cycloalkyl, $C_{1-4}$fluoroalkyl or 3 to 7 membered heterocyclyl which is optionally substituted with one or more $C_{1-6}$ alkyl, halogen, hydroxy, $C_{1-4}$fluoroalkyl, $C_{3-6}$cycloalkyl, $C_{1-4}$ alkoxy, $C_{1-4}$ fluoroalkoxy or cyano;

wherein $R^{10}$ and $R^{11}$ independently of each other are hydrogen or $C_{1-6}$ alkyl; or wherein $R^{10}$ and $R^{11}$ combine with the nitrogen to which they are attached to form piperazinyl, piperidinyl, morpholinyl, pyrrolidinyl, azetidinyl, homomorpholinyl, homopiperidinyl or homopiperazinyl each of which is optionally substituted with one or more $C_{1-6}$ alkyl, $C_{1-6}$ alkoxy, oxo or fluorine; and wherein n is 0-3; or a pharmaceutically acceptable salt thereof.

The invention also provides a pharmaceutical composition comprising a compound of the invention or a pharmaceutically acceptable salt thereof and optionally a pharmaceutically acceptable carrier, excipient or diluent.

The compounds of Formula I may contain one or more stereogenic or asymmetric centers, such as one or more asymmetric carbon atoms. The compounds of Formula I may thus be present as mixtures of stereoisomers or preferably as pure stereoisomers. Mixtures of stereoisomers can be separated in a manner known to a person skilled in the art.

The present invention further provides methods for treating pain or inflammation in a subject, comprising administering to a subject suffering from pain or inflammation a therapeutically effective amount of a compound of Formula I.

The present invention further provides methods for treating an affective disorder in a subject comprising administering to a subject suffering from an affective disorder a therapeutically effective amount of at least one compound of Formula I.

The present invention further provides methods for treating a neurological disorder or neurodegenerative disorder in a subject comprising administering to a subject suffering from a neurological disorder or neurodegenerative disorder a therapeutically effective amount of at least one compound of Formula I.

The present invention further provides methods for treating depression, major depressive disorder, treatment resistant depression, anxiety, obsessive-compulsive disorder, post-traumatic stress disorder (PTSD), neuropathic pain, osteoarthritis, rheumatoid arthritis, psoriatic arthritis, inflammatory bowel disease, multiple sclerosis, epilepsy, Parkinson's Disease, Huntington's Disease and Alzheimer's disease, which involves administering a compound of Formula I.

The present invention also provides the use a compound of Formula I for the manufacture of a medicament for the treatment of affective disorders.

The present invention also provides a compound of Formula I for use in treating an affective disorder in a subject.

These and other aspects of the invention will become apparent upon reference to the following detailed description.

DETAILED DESCRIPTION OF THE INVENTION

As previously indicated, the present invention is based on the discovery of the compounds of Formula I, which are inhibitors of the $P2X_7$ receptor, and as such, are useful for the treatment of related disorders. Additionally, certain aspects of the invention are explained in greater detail below but this description is not intended to be a detailed catalog of all the different ways in which the invention may be implemented, or all the features that may be added to the instant invention. Hence, the following specification is intended to illustrate some embodiments of the invention, and not to exhaustively specify all permutations, combinations and variations thereof.

In one embodiment, $R^1$ is optionally substituted phenyl.
In one embodiment, $R^1$ is optionally substituted pyridyl.
In another embodiment, $R^1$ is optionally substituted pyrazinyl.
In one embodiment, $R^1$ is optionally substituted pyrimidyl.
In one embodiment, $R^1$ is optionally substituted 5 membered heteroaryl.
In one embodiment, $R^2$ and $R^3$ combine with the nitrogen to which they are attached to form optionally substituted piperazinyl.
In yet embodiment, $R^2$ and $R^3$ combine with the nitrogen to which they are attached to form optionally substituted piperidinyl.
In one embodiment, $R^2$ and $R^3$ combine with the nitrogen to which they are attached to form optionally substituted morpholinyl.
In one embodiment, $R^2$ and $R^3$ combine with the nitrogen to which they are attached to form optionally substituted pyrrolidinyl.
In one embodiment, $R^2$ and $R^3$ combine with the nitrogen to which they are attached to form optionally substituted pyrrolo.
In one embodiment, $R^2$ and $R^3$ combine with the nitrogen to which they are attached to form optionally substituted imidazo.
In one embodiment, $R^2$ and $R^3$ combine with the nitrogen to which they are attached to form optionally substituted homomorpholinyl
In one embodiment, $R^2$ and $R^3$ combine with the nitrogen to which they are attached to form optionally substituted homopiperidinyl
In one embodiment, $R^2$ and $R^3$ combine with the nitrogen to which they are attached to form optionally substituted homopiperazinyl
In one embodiment, $R^2$ and $R^3$ combine with the nitrogen to which they are attached to form optionally substituted azetidinyl.
In one embodiment, $R^4$ is chlorine, methyl or trifluoromethyl.
In one embodiment, n is 0.
In one embodiment, n is 1.
In one embodiment, n is 2.

As used herein, the term "$C_1$-$C_6$ alkyl" refers to a straight chained or branched saturated hydrocarbon having from one to six carbon atoms inclusive. Examples of such substituents include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "straight chained or branched $C_1$-$C_3$ alkyl" refers to a saturated hydrocarbon having from one to three carbon atoms inclusive. Examples of such substituents include, but are not limited to, methyl, ethyl and n-propyl.

Likewise, the term "$C_1$-$C_6$ alkoxy" refers to a straight chained or branched saturated alkoxy group having from one to six carbon atoms inclusive with the open valency on the oxygen. Examples of such substituents include, but are not limited to, methoxy, ethoxy, n-butoxy, t-butoxy and n-hexyloxy.

As used herein, the term "$C_1$-$C_4$ fluoroalkyl" refers to a straight chained or branched saturated hydrocarbon having from one to four carbon atoms inclusive substituted with one or more fluorine atoms. Examples of such substituents include, but are not limited to, trifluoromethyl, pentafluoroethyl, 1-fluoroethyl, monofluoromethyl, difluoromethyl and 1,2-difluoroethyl.

Likewise, the term "$C_{1-6}$ hydroxyalkyl" refers to a straight chained or branched saturated hydrocarbon group substituted with one hydroxyl group. Examples of such substituents include, but are not limited to, hydroxymethyl, 1-hydroxy-1-methyl-ethyl and 1-hydroxyethyl.

Likewise, the term "$C_{1-6}$ alkenyl" refers to a straight chained or branched hydrocarbon containing 1-6 carbon atoms and having one or more double bonds. Examples of such substituents include, but are not limited to, allyl, butenyl and 2-hexenyl.

Likewise, the term "$C_{1-6}$ alkynyl" refers to a straight chained or branched hydrocarbon containing 1-6 carbon atoms and having one or more triple bonds. Examples of such substituents include, but are not limited to, ethynyl, propargyl and 3-hexynyl.

Likewise, the term "$C_1$-$C_4$ fluoroalkoxy" refers to a straight chained or branched saturated alkoxy group having from one to four carbon atoms inclusive with the open valency on the oxygen and in which one or more carbon atoms are substituted with one or more fluorine atoms. Examples of such substituents include, but are not limited to, monofluoromethoxy, 1,1-difluoroethoxy and 1-monofluoro-n-butoxy.

Likewise the term "$C_{3-6}$ cycloalkyl" refers to saturated monocyclic hydrocarbon groups. Examples of such systems include, but are not limited to, cyclopropyl, cyclobutyl or cyclohexyl Likewise the term "5 membered heteroaryl" refers to a fully unsaturated aromatic monocyclic ring system having 1-4 heteroatoms. Examples of such systems include, but are not limited to, thienyl, furyl, imidazolyl and prrolyl.

Likewise the term "6 membered heteroaryl" refers to a fully unsaturated aromatic monocyclic ring system having 1-3 heteroatoms. Examples of such systems include, but are not limited to, pyridinyl, pyrimidinyl, pyrazinyl and pyridazinyl.

Likewise the term "3 to 7 membered heterocycle" refers to fully saturated monocyclic ring system having 1-3 heteroatoms. Examples of such systems include, but are not limited to, tetrahydropyranyl, piperazinyl, piperidinyl, morpholinyl, pyrrolidinyl, azetidinyl, homomorpholinyl, homopiperidinyl and homopiperazinyl The term "halogen" refers to fluorine, chlorine, bromine and iodine.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "effective amount" is the amount of the combination sufficient to cause the intended biological effect.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., J. Pharm. Sci., 1977, 66, 2.

Furthermore, the compounds of this invention may exist in unsolvated as well as in solvated forms with pharmaceutically acceptable solvents such as water, ethanol and the like.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Pharmaceutical Compositions

The present invention further provides a pharmaceutical composition comprising a therapeutically effective amount of a compound of Formula I and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by an oral route. Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

The term "inhibit" or "inhibiting" as used herein means to reduce, diminish, block or even eliminate, such as in e.g. "inhibiting P2X$_7$ receptor activity". "Inhibiting P2X$_7$ receptor activity" or "inhibiting P2X$_7$ activity" as used herein means, e.g. reducing or even eliminating the ability of a P2X$_7$ receptor to exhibit a cellular response, such as inhibiting the response to stimuli or agonist ligands, or inhibiting the production or accumulation of IL1β.

The present invention also provides a method of treating a disease or disorder, the method comprising administering a therapeutically effective amount of at least one compound of the present invention or a pharmaceutically acceptable salt thereof to a mammal suffering from (or at risk for) the disease or disorder, or otherwise in need of the treatment. The present invention also provides a method of treating pain or inflammation, the method comprising administering a therapeutically effective amount of at least one compound of the present invention or a pharmaceutically acceptable salt thereof to a mammal in need thereof. In an embodiment, the pain that may be treated using the compounds described herein, including acute, chronic or inflammatory pain, is caused by neuropathic pain, post-operative pain, morphine tolerance, fibromyalgia, neuralgias, headache, osteoarthritis, rheumatoid arthritis, psoriatic arthritis, irritable bowel syndrome or inflammatory bowel disease.

In other embodiments, the disease or disorder that may be treated using the compounds described herein is a neurological disorder or neurodegenerative disorder, such as epilepsy, multiple sclerosis, Parkinson's disease, Huntington's disease or Alzheimer's disease. As used herein, the term "neurological disorder" means a disorder of the nervous system, and includes, but is not limited to, the disorders as described hereinabove. Based on the well-known meaning of disorders of the nervous system, neurological disorders result from structural, biochemical, electrical, or cellular (neuronal or microglial) signaling abnormalities that may occur in the brain or spinal cord of the afflicted mammal. As used herein, the term "neurodegenerative disorder" means a disorder characterized by symmetrical and progressive loss of structure or function of neurons, such as death of neurons or reduced growth of neurons. Such loss of neurons may affect motor, sensory, or cognitive neuronal systems. As such, treating a neurological or neurodegenerative disorder using the compounds described herein may result in the amelioration or relief of symptoms of the neurological or neurodegenerative disorder, such symptoms as paralysis, muscle weakness, poor coordination, uncontrolled movements, seizures, confusion, altered levels of consciousness, memory loss, emotional instability, loss of sensation, pain, and similar symptoms.

In an embodiment, the disease or disorder is a neuropsychiatric disorder, such as an affective disorder. As used herein, "affective disorder" means a mental disorder characterized by a consistent, pervasive alteration of mood, and affecting thoughts, emotions and behaviors. Affective disorders include mood disorders as described in DSM-IV-TR® (American Psychiatric Association, 2000, *Diagnostic and Statistical Manual of Mental Disorders* (4th ed., text rev.) doi:10.1176/appi.books.9780890423349; which is incorporated by reference herein). As such, treating an affective disorder using the compounds described herein may result in the amelioration, stabilization or otherwise diminishment or relief of symptoms of the affective disorder, such symptoms as mood instability, manic episodes, feelings of guilt or worthlessness, sleep disturbances, agitation, or the like. Examples of affective disorders include, but are not limited to, depressive disorders, anxiety disorders, bipolar disorders, dysthymia and schizoaffective disorders. Anxiety disorders include, but are not limited to, generalized anxiety disorder, panic disorder, obsessive-compulsive disorder, phobias, and post-traumatic stress disorder (PTSD). Depressive disorders include, but are not limited to, major depressive disorder (MDD), catatonic depression, melancholic depression, atypical depression, psychotic depression, postpartum depression, treatment-resistant depression, bipolar depression, including bipolar I and bipolar II, and mild, moderate or severe depression. Personality disorders include, but are not limited to, paranoia, antisocial and borderline personality disorders.

In an embodiment of the invention, the affective disorder treated using the compounds described herein is depression, major depressive disorder (MDD), treatment-resistant depression, bipolar disorder, generalized anxiety disorder, panic disorder, obsessive-compulsive disorder, or post-traumatic stress disorder (PTSD), or a combination thereof.

The present invention provides a method of treating an affective disorder in a subject, comprising administering to a subject in need of such treatment a therapeutically effective amount of at least one compound of Formula I.

The present invention provides a method of inhibiting P2X$_7$ activity in a subject, comprising administering to a subject in need thereof a therapeutically effective amount of at least one compound of Formula I.

The present invention also provides a method of inhibiting production or accumulation of IL1β, comprising administering to a subject in need of such treatment a therapeutically effective amount of at least one compound of Formula I.

In an embodiment, the present invention provides the use of a compound of Formula I for the manufacture of a medicament for the treatment of affective disorders. The present invention also provides the use of a compound of Formula I for the manufacture of a medicament for the inhibition of P2X$_7$ activity. The present invention further provides the use of a compound of Formula I for the manufacture of a medicament for the inhibition of production or accumulation of IL1β.

In an embodiment, the present invention provides at least one compound of Formula I for use in treating an affective disorder in a subject. In an embodiment, the present invention provides at least one compound of Formula I for use in inhibiting P2X$_7$ activity in a subject. In an embodiment, the present invention provides at least one compound of Formula I for use in inhibiting production or accumulation of IL1β in a subject.

The invention also provides a compound of Formula I for use in therapy of a subject, for example, in the treatment of affective disorders.

Experimental Section

The compounds of the present invention of the general formula I, wherein $R^1$, $R^2$, $R^3$, $R^4$, $R^5$, $R^6$, $R^7$, $R^8$, $R^9$, $R^{10}$, $R^{11}$ and n are as defined above can be prepared by the methods outlined in the following reaction scheme 1 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

The schemes may involve the use of selective protecting groups during the synthesis of the compounds of the invention. One skilled in the art would be able to select the appropriate protecting group for a particular reaction. It may be necessary to incorporate protection and de-protection strategies for substituents such as amino, amido, carboxylic acid and hydroxyl groups in the synthetic methods described below to synthesize the compounds of Formula I. Methods for protection and de-protection of such groups are well known in the art, and may be found in T. Green, et al., Protective Groups in Organic Synthesis, 1991, $2^{nd}$ Edition, John Wiley & Sons, New York.

General Methods

Analytical LC-MS Data were Obtained Using One of the Methods Identified Below.

Method A: Performed using electrospray ionization (ESI) operating in positive mode via a Waters ZQ (Waters Corp.) mass spectrometer (all from Waters Corp., Milford, Mass., USA), an Agilent 1100 LC pump (Agilent Technologies, Inc., Santa Clara, Calif.), and Agilent 1100 autosampler, with a 200 μl/min split to the ESI source with inline Agilent 1100 diode array detector (DAD) and variable wavelength detector (VWD) at 254 nm, and an 800 uL/min split to a Waters evaporative light scattering detector (ELSD). Separation was performed on a Inertsil ODS-3 3 μm 50×4.6 mm column using a mobile phase of A) Water 1% Acetonitrile and 0.2% Ammonium formate; and B) acetonitrile, which was delivered in a gradient fashion over 1.70 minutes going from 20% B to 85% B. Then stepped to 100% B at 1.85 minutes and maintained at 100% B until 1.99 minutes.

Method B: Performed using electrospray ionization (ESI) operating in positive mode via a Waters ZQ (Waters Corp.) mass spectrometer (all from Waters Corp., Milford, Mass., USA), an Agilent 1100 LC pump (Agilent Technologies, Inc., Santa Clara, Calif.), and Agilent 1100 autosampler, with a 200 μl/min split to the ESI source with inline Agilent 1100 diode array detector (DAD) and variable wavelength detector (VWD) at 254 nm, and an 800 uL/min split to a Waters evaporative light scattering detector (ELSD). Separation was performed on a Inertsil C8 3 μm 50×4.6 mm column using a mobile phase of A) Water 1% Acetonitrile and 0.2% Ammonium formate; and B) acetonitrile, which was delivered in a gradient fashion over 1.70 minutes going from 30% B to 90% B. Then stepped to 100% B at 1.85 minutes and maintained at 100% B until 1.99 minutes.

Method C: A PE Sciex API 150EX instrument equipped with atmospheric pressure photo ionisation and a Shimadzu LC-8A/SLC-10A LC system was used. Column: 3.0×30 mm Waters Symmetry C18 column with 2.2 μm particle size; Column temperature: 50° C.; Solvent system: A=water/trifluoroacetic acid (99.965:0.035) and B=acetonitrile/trifluoroacetic acid (99.965:0.035); Method: Linear gradient elution with A:B=90:10 to 20:80 in 1.5 minutes and with a flow rate of 1.2 mL/minutes.

Method D: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/minutes.

Method E: A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/minutes.

Method F: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/minutes.

Method G: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/minutes.

Preparative LC-MS-purification was performed on a PE Sciex API 150EX instrument with atmospheric pressure chemical ionization. Column: 50×20 mm YMC ODS-A with 5 μm particle size; Solvent system: A=water/trifluoroacetic acid (99.965:0.035) and B=acetonitrile/water/trifluoroacetic acid (94.965:5:0.035); Method: Linear gradient elution with A:B=80:20 to 0:100 in 7 minutes and with a flow rate of 22.7 mL/minute. Fraction collection was performed by split-flow MS detection.

Preparative SFC was performed on a Thar 80 instrument. Exemplified conditions can be, but not limited to: Column AD 250×30 mm with 20 μm particle size; Column temperature: 38° C., Mobile phase: Supercritical $CO_2$/EtOH (0.2% $NH_3H_2O$)=45/55.

$^1$H NMR spectra were recorded at 300, 400, 500 or 600 MHz on Bruker Avance instruments. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Benzoic acids of formula II are commercially available or available by methods described in the literature (see for example Shaikh, Tanveer Mahammad Ali, *J. Org. Chem* (2006), 71, 5043-5046 and Mongin, Florence; Tetrahedron Lett. (1996), 37, 6551-6554).

Abbreviations are in accordance with to the ACS Style Guide: "The ACS Style guide—A manual for authors and editors" Janet S. Dodd, Ed. 1997, ISBN: 0841234620

PREPARATION OF INTERMEDIATES

1-Bromomethyl-1-trifluoromethyl-cyclopropane

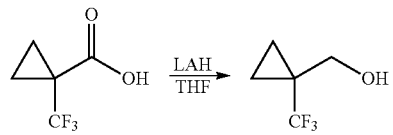

Step 1: To a solution of compound 1-trifluoromethyl-cyclopropanecarboxylic acid (2 g, 13 mmol) in dry THF (80 mL) was added LAH (592 mg, 16 mmol) in portions at 0° C. and the resulting mixture was heated at 40° C. overnight. H₂O (592 mg, 16 mmol) was added to quench the reaction at 0° C. and followed by 2N NaOH (0.6 mL). After filtration, the filtrate was distilled to remove the most solvent to give crude (1-trifluoromethyl-cyclopropyl)-methanol (1.2 g crude), which was used in the next step without further purification.

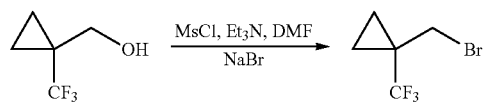 [SMILES: OCC1(C(F)(F)F)CC1 ; "NaBr" ; FC(F)(F)C1(CBr)CC1]

To a solution of (1-trifluoromethyl-cyclopropyl)-methanol (1.2 g, 8.57 mmol) and Et₃N (1.04 g, 10.28 mmol) in dry DMF (10 mL) at −10° C. was added methanesulfonyl chloride (981 mg, 8.57 mmol) over 20 minutes, while retaining the inner temperature at 0° C. After the addition was complete, the resulting solution was stirred at 0° C. for 30 minutes, the resulting mixture was filtered and washed with DMF (3 mL). To the combined filtrates was added sodium bromide (3.7 g, 36 mmol) and the resulting mixture was stirred at room temperature overnight. The mixture was cooled in ice, followed by addition of pentane (20 mL) and water (15 mL) while retaining the mixture at 0° C., prior to liquid separation. The organic phase was dried over Na₂SO₄ and filtered. The filtrate was distilled to remove the most of pentane to give 1-bromomethyl-1-trifluoromethyl-cyclopropane (0.9 g crude), which was used without further purification.

1-Bromomethyl-1-difluoromethyl-cyclopropane

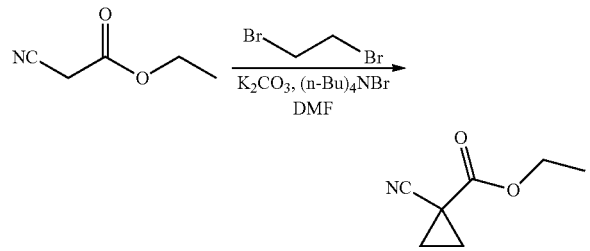

Step 1: A suspension of cyano-acetic acid ethyl ester (11.3 g, 0.1 mol), 1,2-Dibromo-ethane, Na₄(n-Bu)₄Br and K₂CO₃ in DMF (100 mL) was heated to 80° C. overnight. The mixture was poured into water (600 mL) and extracted with EtOAc (3×50 mL). The combined organic layer was washed with brine, dried over Na₂SO₄, concentrated under reduced pressure to give the crude product, which was purified by column chromatography on silica gel (petroleum ether: EtOAc=10:1~5:1) to give 1-cyano-cyclopropanecarboxylic acid ethyl ester (10 g, yield: 72%). ¹H NMR (CDCl₃ 400 MHz): δ4.21 (q, J=7.2 Hz, 2H), 1.65-1.61 (m, 2H), 1.58-1.55 (m, 2H), 1.28 (t, J=7.2 Hz, 3H).

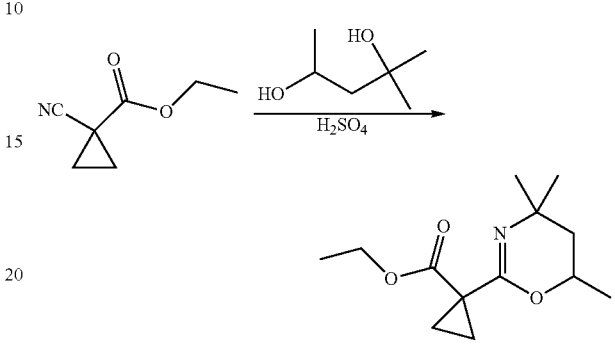

Step 2: To concentrated sulfuric acid (102 mL) was added 1-cyano-cyclopropanecarboxylic acid ethyl ester (60 g, 0.43 mol) dropwise followed by 2-methylpentan-2,4-diol (52 g, 0.44 mmol) dropwise at 0° C. The mixture was stirred for an additional 1 h at 0° C. then poured onto ice-water. The aqueous phase was washed with AcOEt (3×200 mL) and then basified to pH 12 with 10 M NaOH. The resulting mixture was extracted with EtOAc (3×500 mL). The combined organic layer was washed with brine, dried over Na₂SO₄ and concentrated. The residue was purified by column chromatography on silica gel to give 1-(4,4,6-trimethyl-5,6-dihydro-4H-[1,3]oxazin-2-yl)-cyclopropanecarboxylic acid ethyl ester (65 g, yield: 63.2%). ¹H NMR (CDCl₃ 400 MHz): δ 4.21-4.06 (in, 311), 1.73-1.69 (m, 1H), 1.40-1.10 (m, 17H).

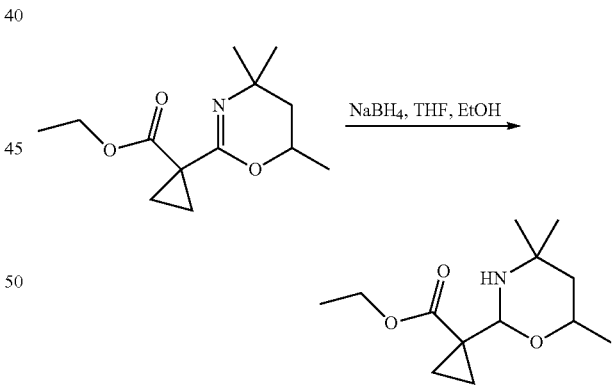

Step 3: NaBH₄ (3.18 g, 13.3 mmol) was dissolved in H₂O (10 mL) and a drop of 10 M NaOH was added. To a solution of 1-(4,4,6-trimethyl-5,6-dihydro-4H-[1,3]oxazin-2-yl)-cyclopropanecarboxylic acid ethyl ester (10 g, 0.04 mol) in THF (33 mL) and ethanol (33 mL) was added the above alkaline solution of NaBH₄ dropwise at −40° C. followed by 12M HCl (about 0.1 mL, the pH of the reaction mixture was adjusted to 6~8). The resulting mixture was stirred at −40° C. for 1.5 hour. The reaction mixture was poured into water (100 mL) and basified with 10M NaOH to pH=10. The mixture was extracted with EtOAc (3×100 mL). The combined organic extracts were washed with brine, dried over Na$_2$SO$_4$ and concentrated to give crude 1-(4,4,6-trimethyl-[1,3]oxazinan-2-yl)-cyclopropanecarboxylic acid ethyl ester (9.0 g), which was used in the next step without purification.

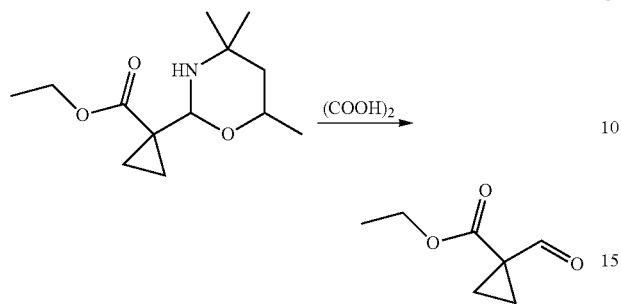

Step 4: Oxalic acid (11.2 g, 0.124 mol) was dissolved in water (40 mL) and 1-(4,4,6-trimethyl-[1,3]oxazinan-2-yl)-cyclopropanecarboxylic acid ethyl ester (15 g, 0.062 mol) was added. Steam distillation of this mixture was carried out until 500 mL of distillate had been collected. The distillate was saturated with NaCl and extracted with EtOAc (2×100 mL). The organic extracts were dried over Na$_2$SO$_4$ and concentrated under reduced pressure to give 1-formyl-cyclopropanecarboxylic acid ethyl ester (4.5 g, 51%). $^1$H NMR (CDCl$_3$ 400 MHz): δ10.39 (s, 1H), 4.26 (q, J=7.2 Hz, 2H), 1.67-1.64 (m, 2H), 1.61-1.58 (m, 2H), 1.31 (t, J=7.2 Hz, 3H).

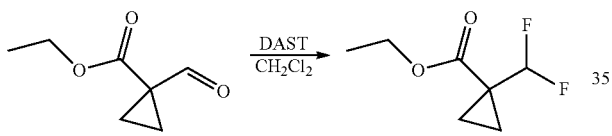

Step 5: To a solution of 1-formyl-cyclopropanecarboxylic acid ethyl ester (4.0 g, 28.1 mmol) in DCM (40 mL) was added DAST (18.6 mL, 0.14 mol) at 0° C. dropwise and the resulting mixture was stirred at room temperature overnight. NaHCO$_3$ solution (10 mL) was added to quench the reaction and extracted with DCM (100×3 mL). The organic extracts were dried over Na$_2$SO$_4$ and concentrated under reduced pressure to give 1-difluoromethyl-cyclopropanecarboxylic acid ethyl ester (3 g, 65%). $^1$H NMR (CDCl$_3$ 400 MHz): δ6.42 J=57.2 Hz, 1H), 4.18 (q, J=7.2 Hz, 2H), 1.28-1.21 (m, 7H).

1-Bromomethyl-1-difluoromethyl-cyclopropane was prepared as described above for the synthesis of 1-Bromomethyl-1-trifluoromethyl-cyclopropane starting from 1-difluoromethyl-cyclopropanecarboxylic acid ethyl ester 3-Acetyl-3-chlorodihydrofuran-2(3H)-one

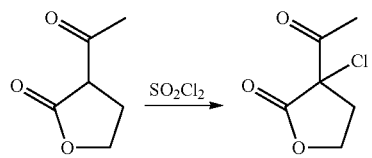

SO$_2$Cl$_2$ (68 g, 0.504 mol) was added to 3-acetyldihydrofuran-2(3H)-one (64 g, 0.499 mol) dropwise at room temperature under stirring for a period of 1~1.5 h. Then the mixture was stirred at room temperature for 2 h. The resulting mixture was diluted with water, stirred for 30 minutes, the organic layer was separated and dried over MgSO$_4$, filtered and distilled with oil pump at 80° C. to give 3-acetyl-3-chlorodihydrofuran-2(3H)-one as colorless oil (54 g, 66.8% yield). $^1$H NMR (CDCl$_3$ 400 MHz): δ 4.45-4.36 (m, 2H), 3.19-3.15 (m, 1H), 2.54 (s, 3H), 2.53-2.44 (m, 1H).

3-Acetyl-3-fluorodihydrofuran-2(3H)-one

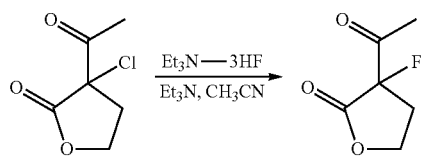

Et$_3$N-3HF (112.2 g, 0.66 mol) and Et$_3$N (66.7 g, 0.66 mol) was added to solution of 3-acetyl-3-chlorodihydrofuran-2 (3H)-one (54 g, 0.33 mol) in CH$_3$CN (165 mL). The mixture was heated to 80° C. for 3 h under stirring. Subsequently, approximately 140 mL of CH$_3$CN are distilled off, and the residue was poured into water. The mixture was extracted with DCM, washed with aq.NaHCO$_3$, dried over MgSO$_4$, concentrated to give the crude product, which was purified by distillation with oil pump at 70° C. to give 3-acetyl-3-fluorodihydrofuran-2(3H)-one as colorless oil (28.8 g, yield: 60%). $^1$H NMR (CDCl$_3$ 400 MHz): δ 4.48-4.40 (m, 2H), 2.83-2.57 (m, 1H), 2.55-2.41 (m, 4H).

1-(1-Fluorocyclopropyl)ethanone

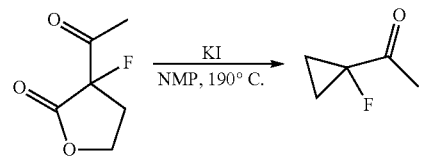

3-acetyl-3-fluorodihydrofuran-2(3H)-one (26 g, 0.178 mol) was added to the solution of KI (12 g, 0.07 mol) in NMP (50 ml) dropwise at 190° C. under a pressure of 0.5 bar. By distilling off continuously, 8 g of crude product was obtained and the crude product was purified by distillation again at 100° C. under a pressure of 0.5 bar to give 1-(1-fluorocyclopropyl)ethanone as light yellow oil (3.3 g, yield: 18%). $^1$H NMR (CDCl$_3$ 400 MHz): δ2.40 (s, 3H), 1.38-1.33 (m, 4H).

1-Fluorocyclopropanecarboxylic acid

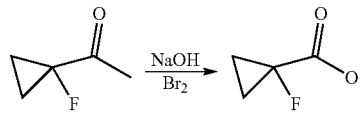

Bromine (14.8 g, 93 mmol) was added slowly to NaOH (12.36 g, 300 mmol) in water (50 mL) below 10° C.

Afterwards, 1-(1-fluorocyclopropyl)ethanone (3.3 g, 30 mmol) was added slowly below 0° C. and the reaction mixture was then stirred for one hour at room temperature. $Na_2S_2O_5$ was added until a colorless solution was formed. 50 mL of AcOEt was added. The aqueous phase was separated and acidified to pH 2 with aq. HCl (2M) and extracted with AcOEt (3×50 mL). This organic phase was dried over $Na_2SO_4$ and concentrated to give 1-fluorocyclopropanecarboxylic acid as a white solid (2.2 g, 66% yield). $^1$H NMR (CDCl$_3$ 400 MHz): δ 1.49-1.45 (m, 4H).

1-Bromomethyl-1-fluoromethyl-cyclopropane was prepared as described above for the synthesis of 1-Bromomethyl-1-trifluoromethyl-cyclopropane starting from 1-fluorocyclopropanecarboxylic acid.

(6-Trifluoromethyl-pyridin-3-yl)-acetonitrile

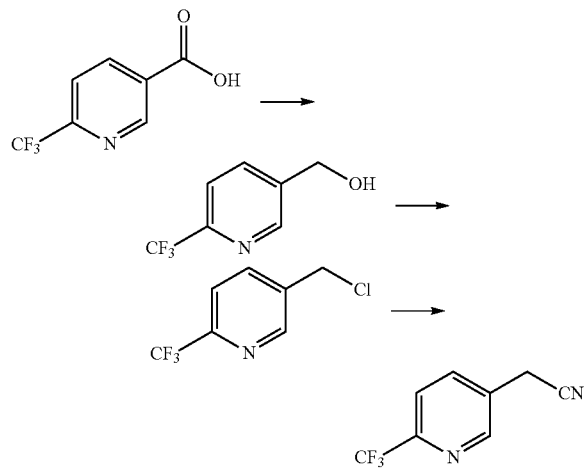

Step 1: (6-Trifluoromethyl-pyridin-3-yl)-methanol

BH$_3$.THF (1 M solution in THF, 393 mL, 393 mmol) was added to a solution of 6-trifluoromethyl-nicotinic acid (25.0 g, 131 mmol) in dry THF (300 mL) at 0° C. under nitrogen with vigorous stirring. The mixture was gradually warmed to room temperature and stirred for 16 hours. The mixture was concentrated under reduced pressure and the residue was then dissolved in DCM and cooled to 0° C. Methanol was carefully added until gas evolution ceased and the solution was concentrated again under reduced pressure. The residue was purified by silica gel chromatography (5% methanol in DCM). The fractions containing product were collected and concentrated under reduced pressure. The residue was dissolved in DCM, washed with saturated aqueous sodium bicarbonate, brine, dried over sodium sulfate, filtered and concentrated under reduced pressure to afford (6-trifluoromethylpyridin-3-yl)-methanol as a yellow oil (19.7 g, 85%). 1H NMR (400 MHz, CDCl$_3$) δ ppm 8.63 (s, 1H), 7.91 (d, J=8.0 Hz, 1H), 7.67 (d, J=8.0 Hz 1H), 4.80 (s, 2H), 3.84 (br. s., 1H). 19F NMR (400 MHz, CDCl$_3$):168 cm-1. MS m/z 178.12

Step 2: 5-Chloromethyl-2-trifluoromethylpyridine

Thionyl chloride (40.3 mL, 554 mmol) was slowly added to a solution of (6-trifluoromethylpyridin-3-yl)-methanol (19.6 g, 111 mmol) in DCM (195 mL) at room temperature under nitrogen. The reaction mixture was stirred at reflux for 16 hours then concentrated under reduced pressure. The residue was dissolved in AcOEt (200 mL), washed with saturated aqueous sodium bicarbonate, brine, dried over sodium sulfate, filtered and concentrated under reduced pressure to give crude 5-chloromethyl-2-trifluoromethylpyridine as a brown oil which was used in the following step without further purification (19.5 g, 90%). $^1$H NMR (400 MHz, CDCl$_3$) δ ppm 8.74 (s, 1H), 7.94 (d, J=8.4 Hz, 1H), 7.72 (d, J=8.4 Hz 1H), 4.66 (s, 2H). 19F NMR (400 MHz, CDCl$_3$):168 cm-1. MS m/z 196.15; 198.09

Step 3: (6-Trifluoromethylpyridin-3-yl)-acetonitrile

5-Chloromethyl-2-trifluoromethylpyridine (19.5 g, 99.7 mmol) in ethanol (160 mL) was added to a solution of potassium cyanide (9.74 g, 150 mmol) in water (80 mL) at 90° C. over 30 minutes. The mixture was stirred at 90° C. for 3 hours. Most of the ethanol was removed under reduced pressure and the aqueous layer was extracted with AcOEt (3×100 mL). The combined organic extracts were washed with water, brine, dried over sodium sulfate, filtered and concentrated under reduced pressure. The residue was purified by silica gel chromatography (30% AcOEt in hexanes) to afford (6-trifluoromethylpyridin-3-yl)-acetonitrile as a brown oil (9.79 g, 75%). $^1$H NMR (400 MHz, CDCl$_3$) δ ppm 8.63 (s, 1H), 7.90 (d, J=8.0 Hz, 1H), 7.70 (d, J=8.0 Hz 1H), 3.88 (s, 2H). 19F NMR (400 MHz, CDCl$_3$):168 cm-1. MS m/z 187.14

(2-Methyl-pyrimidin-5-yl)-methanol

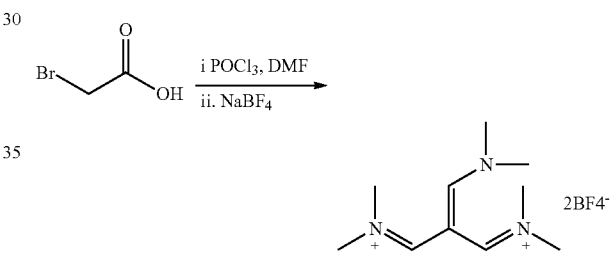

Step 1: A three-neck 2-L round bottomed flask with an immersion thermometer and an addition funnel was charged with DMF (400 mL) and cooled to 0° C. POCl$_3$ (178 g, 1.16 mol) was carefully added to the reaction via an addition funnel maintaining an internal temperature of 5-10° C. After 2 h, the yellow solution was treated with bromoacetic acid (50 g, 0.36 mol) and heated to 90° C. overnight. The mixture was cooled and a short-path distillation head was attached. DMF was distilled from the red-orange oil at 120° C. under high vacuum. The tarry residue was cooled to room temperature and treated with ice (about 10 g). Aqueous NaBF$_4$ (80 g in 160 mL H$_2$O) was added at 0° C. As the solid residue slowly dissolved, a vigorous exotherm occurred. The yellow-orange precipitate that formed at 0° C. was collected by filtration and re-dissolved in hot CH$_3$CN (2 L). After hot-filtration, excess NaBF$_4$ was removed and the filtrate was cooled to −30° C. The crystalline precipitate was collected and dried in vacuum to give the intermediate salt (60 g, yield: 47%).

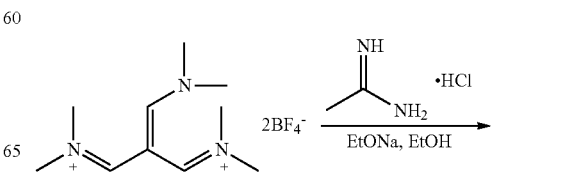

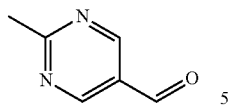

Step 2: To 500 mL of EtOH was added sodium (12 g, 0.50 mol) in portions at room temperature and the resulting mixture was stirred until the sodium was dissolved completely. To a suspension of the previously prepared salt (60 g, 0.17 mol) and acetamidine hydrochloride (17.4 g, 0.19 mol) in EtOH (2.5 L) was added the above solution at room temperature and the resulting mixture was heated to reflux for 5 h. After filtration, the solvent was removed under reduced pressure to give the remains, which was suspended in H$_2$O (200 mL) and extracted with DCM (3 mL×100). The organic layer was washed with brine, dried over Na$_2$SO$_4$ and concentrated. The crude product was purified by column chromatography on silica gel (petroleum ether:EtOAc=5:1 to 2:1) to afford 2-methyl-pyrimidine-5-carbaldehyde (10 g, yield: 50%). $^1$H NMR (CDCl$_3$ 400 MHz): δ10.10 (s, 1H), 9.07 (s, 2H), 2.84 (s, 3H).

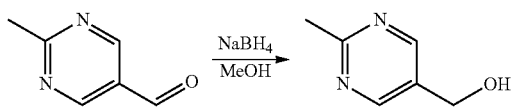

A solution of 2-methyl-pyrimidine-5-carbaldehyde (5 g, 41 mmol) in MeOH (100 mL) was added NaBH$_4$ (2.3 g, 61.5 mmol) at 0° C. in portions and the resulting mixture was stirred at room temperature for 1 h. The solvent was removed under reduced pressure to give the remains, which was suspended in H$_2$O (20 mL) and extracted with EtOAc (5×50 ml). The organic layer was dried over Na$_2$SO$_4$ and concentrated to afford the title compound (2 g, yield: 39%). $^1$H NMR (CDCl$_3$ 400 MHz): δ 8.64 (s, 2H), 4.72 (s, 2H), 2.73 (s, 3H).

(2-Methyl-pyrimidin-5-yl)-acetonitrile was prepared as described above for the synthesis of (6-trifluoromethyl-pyridin-3-yl)-acetonitrile starting from (2-methyl-pyrimidin-5-yl)-methanol (5-Chloro-pyridin-3-yl)-acetonitrile

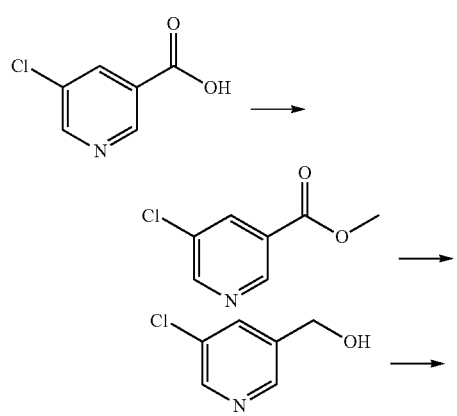

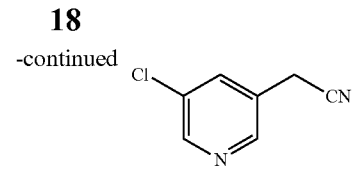

Step 1: 5-Chloro-nicotinic acid methyl ester

To a solution of 5-chloro-nicotinic acid (20.0 g, 127 mmol, purchased from Matrix Scientific, Columbia, S.C., USA) in methanol (200 mL) at 0° C. was added thionyl chloride (18.6 mL, 255 mmol). The reaction mixture was refluxed for 4 hours. After cooling to room temperature the mixture was diluted with saturated aqueous sodium bicarbonate, extracted with AcOEt (3×300 mL), dried over sodium sulfate, filtered and concentrated under reduced pressure to afford crude 5-chloro-nicotinic acid methyl ester (17.2 g, 79%). $^1$H NMR (400 MHz, CDCl$_3$) δ ppm 9.10 (d, J=1.4 Hz, 1H), 8.75 (d, J=2.3 Hz, 1H), 8.29 (d, J=2.0 Hz, 1H), 3.98 (s, 3H). MS m/z 171.8

Step 2: (5-Chloro-pyridin-3-yl)-methanol

To a solution of 5-chloro-nicotinic acid methyl ester (17.2 g, 101 mmol) in methanol (230 mL) and DCM (230 mL) at 0° C. was added sodium borohydride (16.4 g, 434 mmol). The reaction mixture was stirred at room temperature for 18 hours. After completion, the reaction mixture was concentrated under reduced pressure, diluted with water (300 mL) and extracted with AcOEt (3×300 mL). The combined organic layer was dried over sodium sulfate, filtered, and concentrated under reduced pressure. The residue was then purified by silica gel chromatography to afford (5-chloro-pyridin-3-yl)-methanol (7.8 g, 54%). $^1$H NMR (400 MHz, DMSO-d6) δ ppm 8.45-8.52 (m, 2H), 7.83 (s, 1H), 5.45 (t, J=5.8 Hz, 1H), 4.55 (t, J=5.7 Hz, 2H). MS m/z 144.1

Step 3 and 4: (5-Chloro-pyridin-3-yl)-acetonitrile

Conversion of the hydroxyl group to the chloride using thionyl chloride, followed by the displacement of the chloride by potassium cyanide was performed using the same procedures described for (6-trifluoromethyl-pyridin-3-yl)-acetonitrile. $^1$H NMR (400 MHz, CDCl3) δ ppm 8.55 (d, J=2.0 Hz, 1H), 8.50 (d, J=1.1 Hz, 1H), 7.73 (s, 1H), 4.58 (s, 2H). MS m/z 153.0

The following intermediates were prepared in a similar way (5-Fluoro-pyridin-3-yl)-acetonitrile, from 5-fluoro-nicotinic acid;

(2,6-Dimethyl-pyridin-3-yl)-acetonitrile, from (2,6-dimethylpyridin-3-yl)-methanol;

(2-Methyl-pyrimidin-5-yl)-acetonitrile, from (2-methyl-pyrimidin-5-yl)-methanol;

3-Cyclopropyl-2-(2-trifluoromethyl-pyrimidin-5-yl)-propionitrile

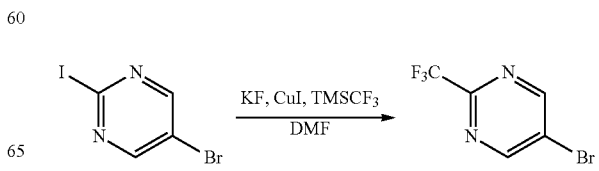

Step 1: A mixture of 5-bromo-2-iodo-pyrimidine (30 g, 0.11 mol), TMSCF₃ (30 g, 0.21 mol), KF (9.2 g, 0.16 mol) and CuI (30 g, 0.16 mol) in DMF (300 mL) was stirred at room temperature overnight. The reaction mixture was quenched by NH₃.H₂O (600 mL) and extracted with EtOAc (500 mL×3). The organic layer was washed with brine, dried over Na₂SO₄ and concentrated. The residue was purified by column chromatography on silica gel (Petroleum ether) to give 5-bromo-2-trifluoromethyl-pyrimidine (4 g, yield: 16.7%). ¹H NMR (CDCl₃ 400 Hz): δ8.90 (s, 2H).

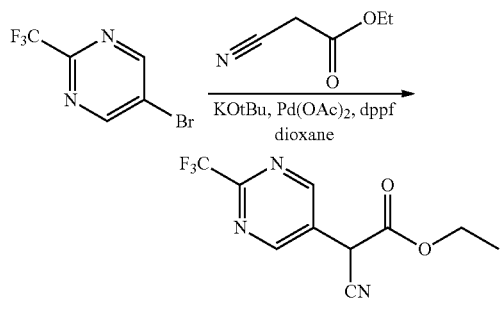

Step 2: A mixture of 5-bromo-2-trifluoromethyl-pyrimidine (1.0 g, 4.41 mmol) and cyano-acetic acid ethyl ester (1.0 g, 4.41 mmol) was added into a suspension of t-BuOK (17.64 mL, 17.64 mmol, 1M in THF) in 1,4-dioxane (10 mL) under Ar atmosphere. To the resulting mixture was added a solution of Pd(OAc)₂ (10 mg, 44.1 μmop and dppf (48.9 mg, 88.2 μmol) in 1,4-dioxane (1 mL). The resulting mixture was heated to 70° C. for 1 h. The reaction mixture was adjusted pH to 7~8 with 1N AcOH and extracted with EtOAc (3×20 ml). The organic layer was dried over Na₂SO₄ and concentrated. The residue was purified by column chromatography on silica gel (EtOAc: petroleum ether=1:10) to give cyano-(2-trifluoromethyl-pyrimidin-5-yl)-acetic acid ethyl ester (140 mg, yield: 12.3%). ¹H NMR (CDCl₃ 400 Hz): 69.03 (s, 2H), 4.88 (s, 1H), 4.34 (q, J=7.2 Hz, 2H), 1.35 (t, J=7.2 Hz, 3H).

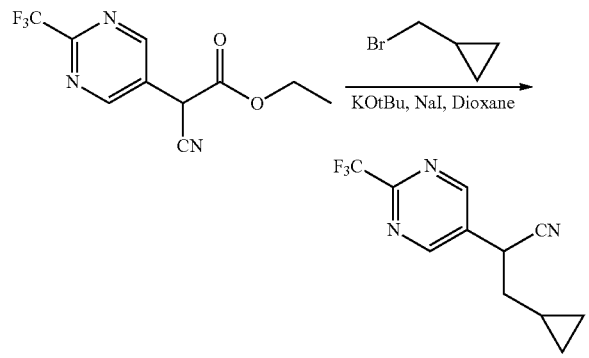

Step 3: A mixture of cyano-(2-trifluoromethyl-pyrimidin-5-yl)-acetic acid ethyl ester (240 mg, 0.93 mmol), bromomethyl cyclopropane (375 mg, 2.78 mmol) and NaI (139 mg, 0.93 mmol) in dry dioxane (2 mL) was degassed and ButOK in THF (1.11 mL, 1.11 mmol) was added at room temperature. The resulting mixture was heated to 100-110° C. for 24 h. Saturated NH₄Cl solution was added to quench the reaction at 0° C. and extracted with EtOAc (5 mL×3). The organic layer was washed with brine, dried over Na₂SO₄ and concentrated. The crude product was purified by column chromatography on silica gel (petroleum ether/EtOAc=20:1~5:1) to give the title compound (100 mg, yield: 44.6%). ¹H NMR (CDCl₃ 400 MHz): δ8.94 (s, 2H), 4.09-4.01 (m, 1H), 2.05-1.95 (m, 1H), 1.93-1.80 (m, 1H), 0.91-0.79 (m, 1H), 0.69-0.60 (m, 2H), 0.25-0.14 (m, 2H).

The following intermediates were prepared in a similar way:
3-(1-fluorocyclopropyl)-2-(2-(trifluoromethyl)pyrimidin-5-yl)propanenitrile;
3-(1-(trifluoromethyl)cyclopropyl)-2-(2-(trifluoromethyl)pyrimidin-5-yl)propanenitrile;

4-(4-Trifluoromethyl-phenyl)-tetrahydro-pyran-4-carbonitrile

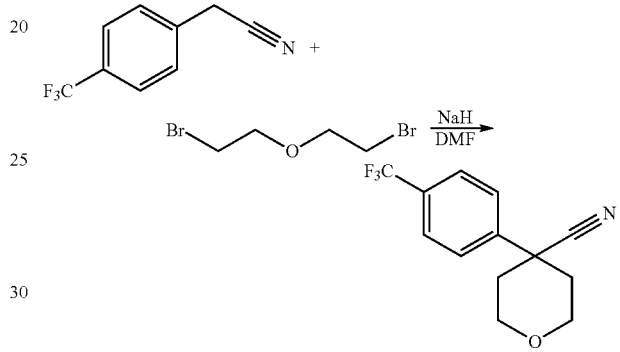

A solution of 4-trifluoromethylbenzyl cyanide (0.92 g, 5.0 mmol) and bis(2-bromoethyl)ether (2.3 mL, 18 mmol) in DMF (10 mL) at room temperature was treated portion wise with sodium hydride (60% in mineral oil, 0.6 g, 15 mmol) over a period of 10 mins followed by stirring at the same temperature for 1 h. The mixture was then stirred at 70° C. for 16 h. Then cooled to room temperature and the reaction mixture was quenched with slow addition of methanol. Water (100 mL) was added and the mixture was extracted with EtOAc (3×50 mL). The combined organic extracts were washed with water and brine and dried over sodium sulfate, filtered and concentrated. The concentrate was purified by column chromatography using a gradient of 5% EtOAc in hexanes to 30% EtOAc in hexanes to give the title compound (1.11 g, yield: 87%). ¹H NMR (CDCl₃ 300 MHz): δ ppm 7.75 (d, 2H), 7.65 (d, 2H), 4.20-4.09 (m, 2H), 4.00-3.85 (m, 2H), 2.27-2.05 (m, 4H).

The following intermediates were prepared in a similar way:
4-(4-Chloro-phenyl)-tetrahydro-pyran-4-carbonitrile;
4-(6-Methylpyridin-3-yl)-tetrahydropyran-4-carbonitrile;
4-(6-Trifluoromethylpyridin-3-yl)-tetrahydropyran-4-carbonitrile;
4-(2-methylpyrimidin-5-yl)tetrahydro-2H-pyran-4-carbonitrile;
4-(2-(trifluoromethyl)pyrimidin-5-yl)tetrahydro-2H-pyran-4-carbonitrile;
3-(2-methylpyrimidin-5-yl)tetrahydrofuran-3-carbonitrile;
1-(pyridin-3-yl)cyclopentanecarbonitrile;
1-(4-methoxyphenyl)cyclopentanecarbonitrile;
1-methyl-4-phenylpiperidine-4-carbonitrile;
4-(4-chlorophenyl)-1-methylpiperidine-4-carbonitrile;
2-(4-chlorophenyl)-4-(dimethylamino)butanenitrile;

4-(4-(trifluoromethyl)phenyl)tetrahydro-2H-pyran-4-carbonitrile;

4-Methyl-2-(6-methylpyridin-3-yl)-pentanenitrile

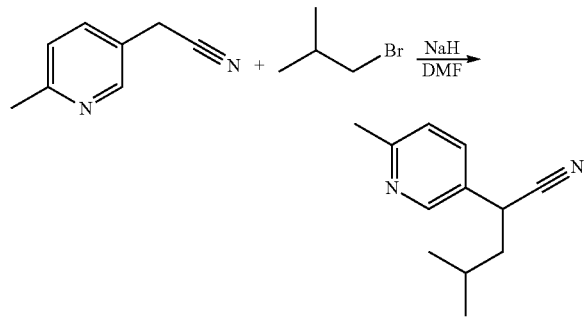

To a cooled (0° C.) slurry of NaH (60% dispersion in oil, 2.74 g, 68.5 mmol) in THF (120 mL) was added a solution of (6-methylpyridin-3-yl)-acetonitrile (8.23 g, 62.3 mmol) in THF (60 mL). The mixture was stirred at room temperature for 3 h and then warmed to 40° C. for 1 h. The resulting reddish brown slurry was cooled to −20° C. and a solution of 1-bromo-2-methylpropane (8.53 g, 62.3 mmol) in THF (30 mL) was added dropwise and then stirred for 18 h at room temperature. The reaction was quenched with water and extracted with AcOEt. The organic extracts were combined and washed with brine, dried over $Na_2SO_4$, filtered and concentrated under reduced pressure. The residue was purified by column chromatography on silica gel (15% EtOAc in hexane) to give 7.52 g (64% yield) of 4-methyl-2-(6-methylpyridin-3-yl)-pentanenitrile as an oil. $^1$H NMR (400 MHz, CDCl3) δ ppm 1.00 (dd, J=6.64, 4.30 Hz, 6H), 1.53-1.70 (m, 1H), 1.71-1.99 (m, 2H), 2.57 (s, 3H), 3.81 (dd, J=9.57, 6.45 Hz, 1H), 7.19 (d, J=7.82 Hz, 1H), 7.59 (dd, J=7.82, 2.34 Hz, 1H), 8.43 (d, J=2.34 Hz, 1H).

The following intermediates were prepared in a similar way:
1-(4-Methoxyphenyl)-1-cyclopentanecarbonitrile;
4-(4-Chloro-phenyl)-1-methyl-piperidine-4-carbonitrile;
2-(4-Chloro-phenyl)-4-dimethylamino-butyronitrile;
3-cyclopropyl-2-(pyridin-5-yl)propanenitrile;
Cyclopropyl-(6-trifluoromethyl-pyridin-3-yl)-acetonitrile;
3-Cyclopropyl-2-(6-trifluoromethyl-pyridin-3-yl)-propionitrile;
2-(5-Chloro-pyridin-3-yl)-3-cyclopropyl-propionitrile;
2-(6-Chloropyridin-3-yl)-3-cyclopropylpropanenitrile;
3-cyclopropyl-2-(6-fluoropyridin-5-yl)propanenitrile;
3-Cyclopropyl-2-(2,6-dimethyl-pyridin-3-yl)-propionitrile;
2-(2-Methyl-pyrimidin-5-yl)-3-(1-trifluoromethyl-cyclopropyl)-propionitrile;
3-(1-Trifluoromethyl-cyclopropyl)-2-(6-trifluoromethyl-pyridin-3-yl)-propionitrile;
3-(1-Difluoromethyl-cyclopropyl)-2-(6-trifluoromethyl-pyridin-3-yl)-propionitrile;
2-(6-Cyclopropyl-pyridin-3-yl)-3-(1-trifluoromethyl-cyclopropyl)-propionitrile;
2-(6-Cyclopropyl-pyridin-3-yl)-3-(1-difluoromethyl-cyclopropyl)-propionitrile;
3-Cyclopropyl-2-(2-methyl-pyrimidin-5-yl)-propionitrile;
2-(2-methylpyrimidin-5-yl)-3-(1-(trifluoromethyl)cyclopropyl)propanenitrile;
3-(1-fluorocyclopropyl)-2-(6-(trifluoromethyl)pyridin-3-yl)propanenitrile;
3-Cyclopropyl-2-(5-methyl-pyrazin-2-yl)-propionitrile;

5-Cyano-5-(6-fluoro-pyridin-3-yl)-2-hydroxy-cyclohex-1-enecarboxylic acid methyl ester

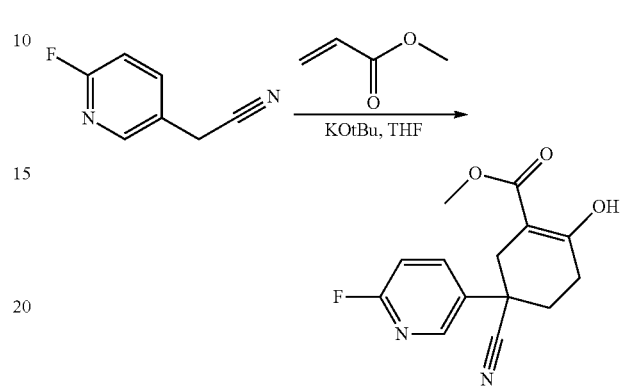

To a solution of (6-fluoro-pyridin-3-yl)-acetonitrile (15 g, 0.11 mol) and methyl acrylate (19 g, 0.22 mol) in dry THF (150 mL) cooled to −70° C. in dry ice-EtOH bath was added t-BuOK-THF solution (1M, 330 mL, 0.33 mol) in portions. The reaction mixture was stirred at −70° C. for 4 h. After completion (LCMS) 1N HCl (aq) was added slowly at −70° C. (the temperature of reaction mixture don't rise above −50° C.) to adjust the pH to 5-6. The THF layer was separated and the aqueous phase was extracted with EtOAc (2×150 mL). The combined organic layers were washed with brine, dried over anhydrous sodium sulphate, filtered and concentrated under reduced pressure to provide the crude title compound (32 g), which was used directly for the next step.

The following intermediates were prepared in a similar way:
5-Cyano-5-(6-trifluoromethyl-pyridin-3-yl)-2-hydroxy-cyclohex-1-enecarboxylic acid methyl ester;
5-Cyano-5-(6-methoxy-pyridin-3-yl)-2-hydroxy-cyclohex-1-enecarboxylic acid methyl ester;
5-Cyano-2-hydroxy-5-(2-(trifluoromethyl)pyrimidin-5-yl) cyclohex-1-enecarboxylic acid methyl ester;
Methyl 5-cyano-2-hydroxy-5-(2-methylpyrimidin-5-yl)cyclohex-1-enecarboxylate;
Methyl 5-cyano-2-hydroxy-5-(pyrimidin-5-yl)cyclohex-1-enecarboxylate;

1-(6-Fluoro-pyridin-3-yl)-4-oxo-cyclohexanecarbonitrile

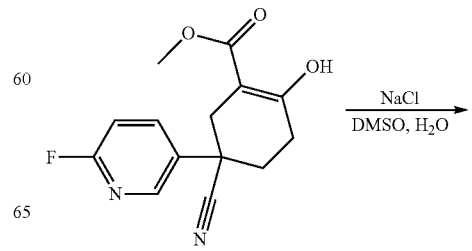

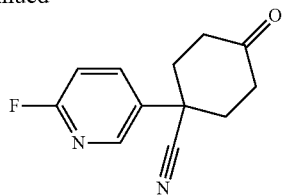

To a solution of 5-Cyano-5-(6-fluoro-pyridin-3-yl)-2-hydroxy-cyclohex-1-enecarboxylic acid methyl ester (32 g crude, 0.11 mmol) in DMSO (110 mL) was added NaCl (7.78 g, 0.133 mol) and water (6.5 mL). The reaction mixture was heated at 160° C. for 3 h. It was cooled to room temperature and poured into water (300 mL). The aqueous layer was extracted with EtOAc (3×200 mL). The combined organic layer was washed with brine (300 mL), dried over sodium sulphate, filtered and concentrated under reduced pressure. The residue was purified by flash column chromatography on silica gel (eluting with a gradient elution of between 10-25% EtOAc in petroleum ether) to give the title compound (12 g, 50% over two steps). $^1$H NMR (CDCl$_3$ 400 MHz): δ ppm 8.34 (d, J=2.4 Hz, 1H), 7.95-7.82 (m, 1H), 7.00-6.92 (m, 1H), 2.95-2.87 (m, 2H), 2.60-2.2. (m, 2H), 2.50-2.40 (m, 2H), 2.28-2.20 (m, 2H).

The following intermediates were prepared in a similar way:

1-(6-Trifluoromethyl-pyridin-3-yl)-4-oxo-cyclohexanecarbonitrile;
1-(6-Methoxy-pyridin-3-yl)-4-oxo-cyclohexanecarbonitrile;
4-Oxo-1-(2-(trifluoromethyl)pyrimidin-5-yl)cyclohexanecarbonitrile;
4-Oxo-1-(2-methylpyrimidin-5-yl)cyclohexanecarbonitrile;
4-Oxo-1-(pyrimidin-5-yl)cyclohexanecarbonitrile;

4,4-Difluoro-1-(6-fluoro-pyridin-3-yl)-cyclohexanecarbonitrile

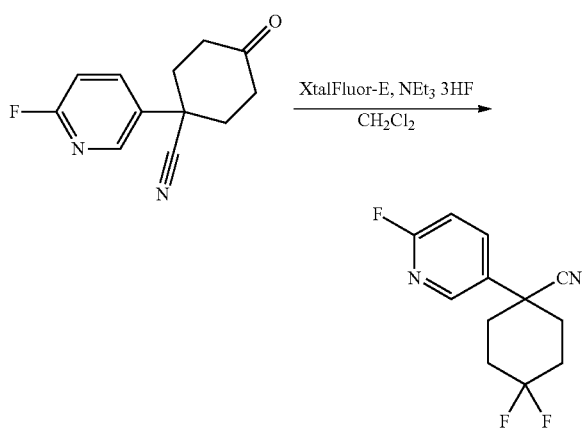

To a stirred suspension of diethylamino difluorosulfiinium tetrafluoroborate salt (23.8 g, 0.104 mol) in dry DCM (100 mL) at room temperature was added 1-(6-fluoro-pyridin-3-yl)-4-oxo-cyclohexanecarbonitrile (12 g, 0.052 mol) followed by triethylamine trihydrofluoride (25.12 g, 0.156 mol) under a nitrogen atmosphere. The reaction mixture was stirred overnight at room temperature. The resulting mixture was then quenched with saturated aq. NaHCO$_3$ solution (300 mL), stirred for 10 minutes, and the resulting mixture was extracted with DCM (3×100 mL). The combined organic layer was washed with brine, dried over sodium sulphate, filtered and concentrated under reduced pressure to give the crude product, which was purified by column chromatography on silica gel (eluting with a gradient elution of between 2-10% EtOAc in petroleum ether) to afford the title compound (8 g, yield: 64%). $^1$H NMR (CDCl$_3$ 400 MHz): δ ppm 8.40-8.35 (m, 1H), 7.95-7.84 (m, 1H), 7.05-6.96 (m, 1H), 2.40-2.10 (m, 8H).

The following intermediates were prepared in a similar way:

4,4-Difluoro-1-(6-trifluoromethyl-pyridin-3-yl)-cyclohexanecarbonitrile;
4,4-Difluoro-1-(6-methoxy-pyridin-3-yl)-cyclohexanecarbonitrile;
4,4-Difluoro-1-(2-methyl-pyrimidin-5-yl)-cyclohexanecarbonitrile;
4,4-Difluoro-1-(2-(trifluoromethyl)pyrimidin-5-yl)cyclohexanecarbonitrile;
4,4-Difluoro-1-(pyrimidin-5-yl)-cyclohexanecarbonitrile;
4,4-difluoro-1-(5-fluoropyridin-3-yl)cyclohexanecarbonitrile;

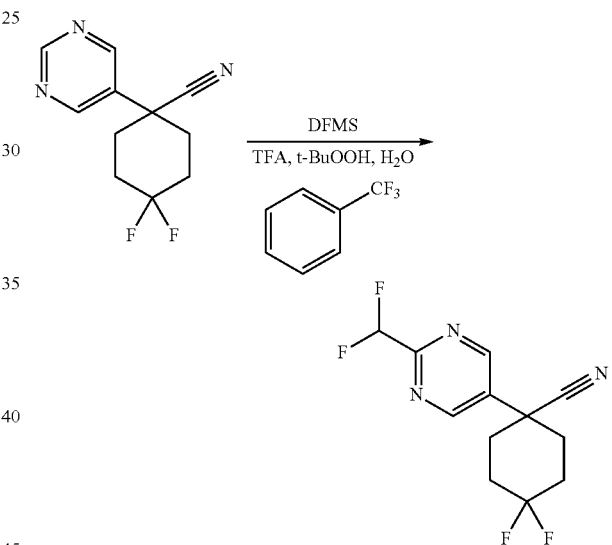

To a solution of compound 4,4-difluoro-1-(pyrimidin-5-yl)-cyclohexanecarbonitrile (1.5 g, 6.72 mmol) and DFMS (6.0 g, 0.02 mol) in trifluoromethylbenzene (53 mL) and H$_2$O (21 mL) at room temperature was added TFA (766 mg, 6.72 mmol) followed by slow addition of t-BuOOH (5.2 g, 70% solution in H$_2$O) with vigorous stirring. The reaction mixture was stirred at room temperature overnight. TLC indicates about 50% starting material remained, a second addition of DFMS (6.0 g, 0.02 mol) and t-BuOOH (5.2 g, 70% solution in H$_2$O) were added to the reaction mixture. Upon consumption of starting material, the reaction mixture was portioned between DCM (20 mL) and saturated NaHCO$_3$ solution (20 mL), the organic layer was separated and the aqueous layer was extracted with DCM (3×20 ml). The organic layer was washed with brine, dried over Na$_2$SO$_4$ and concentrated. The crude product was purified by flash chromatography (Petroleum ether:EtOAc=3:1) to give 1-(2-(difluoromethyl)pyrimidin-5-yl)-4,4-difluorocyclohexanecarbonitrile (800 mg, Yield: 44.4%). $^1$H NMR (CDCl$_3$ 400 MHz): δ 9.03 (s, 2H), 6.71 (t, J=54.4 Hz, 1H), 2.40-2.27 (m, 6H).

1-(6-Bromo-pyridin-3-yl)-4,4-difluoro-cyclohexanecarbonitrile

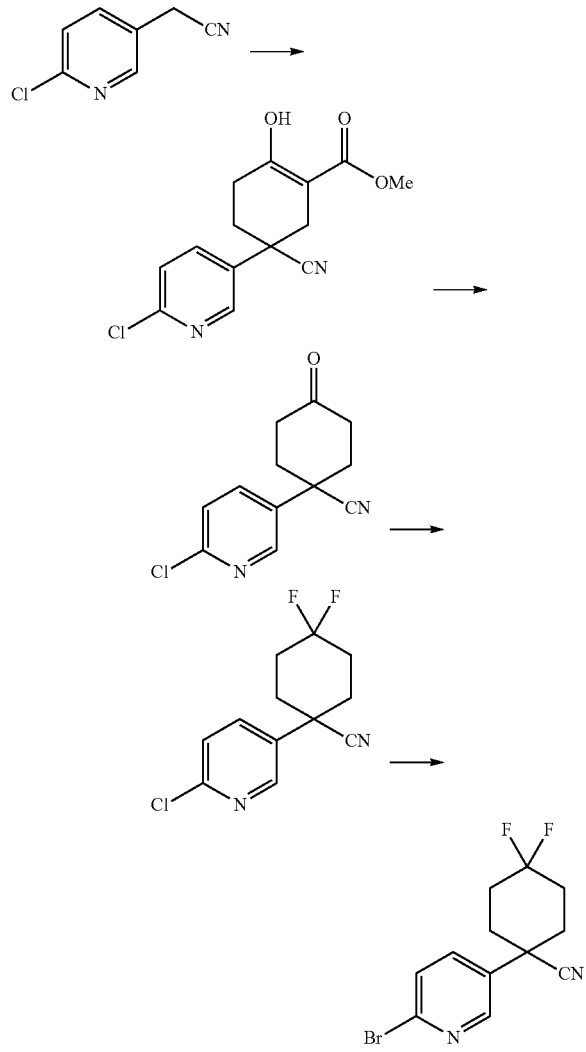

Step 1: 5-(6-Chloro-pyridin-3-yl)-5-cyano-2-hydroxy-cyclohex-1-enecarboxylic acid methyl ester To a solution of 2-(6-chloro-3-pyridinyl)acetonitrile (4.3 g, 28 mmol, purchased from Matrix Scientific, Columbia, S.C., USA) and methyl acrylate (4.8 g, 56 mmol) in dry THF (150 mL) cooled to 65° C. was added solid potassium tert-butoxide (7.9 g, 70 mmol) under nitrogen atmosphere. The reaction mixture was stirred at 65° C. for 45 minutes. The reaction mixture was then acidified with 3 N HCl and extracted with DCM (3×150 mL). The combined organic layer was dried over sodium sulfate, filtered and concentrated under reduced pressure to give crude 5-(6-chloro-pyridin-3-yl)-5-cyano-2-hydroxy-cyclohex-1-enecarboxylic acid methyl ester which was used in the next step without purification (6.0 g, 75%).

Step 2: 1-(6-Chloro-pyridin-3-yl)-4-oxo-cyclohexanecarbonitrile

To a solution of 5-(6-chloro-pyridin-3-yl)-5-cyano-2-hydroxy-cyclohex-1-enecarboxylic acid methyl ester (4.2 g, 14 mmol) in DMSO (15 mL) was added sodium chloride (0.90 g, 16 mmol) and water (0.77 mL). The reaction mixture was heated at 160° C. for 6 hours. The reaction mixture was then cooled to room temperature and poured into water (50 mL). The aqueous layer was extracted with diethyl ether (3×250 mL). The combined organic layer was dried over sodium sulfate, filtered and concentrated under reduced pressure. The residue obtained was purified by column chromatography on silica gel to afford 1-(6-chloro-pyridin-3-yl)-4-oxo-cyclohexanecarbonitrile (1.7 g, 52%). $^1$H NMR (400 MHz, CDCl$_3$) δ ppm 8.59 (s, 1H), 7.83 (dd, J=8.4, 2.2 Hz, 1H), 7.44 (d, J=8.5 Hz, 1H), 2.89-2.98 (m, 2H), 2.60-2.66 (m, 2H), 2.48-2.54 (m, 2H), 2.25-2.33 (m, 2H).

Step 3: 1-(6-Chloro-pyridin-3-yl)-4,4-difluoro-cyclohexanecarbonitrile

To a stirred suspension of (diethylamino)difluorosulfonium tetrafluoroborate (16.5 g, 72.1 mmol) in DCM (150 mL) at room temperature under nitrogen atmosphere was added 1-(6-chloro-pyridin-3-yl)-4-oxo-cyclohexanecarbonitrile (4.2 g, 18 mmol) followed by triethylamine trihydrofluoride (8.68 g, 53.8 mmol). The reaction mixture was stirred for 6 hours at room temperature. The resulting mixture was then quenched by adding a saturated aqueous solution of sodium bicarbonate, stirred for 10 minutes, and the resulting mixture was extracted with DCM (3×25 mL). The combined organic layer was dried over sodium sulfate, filtered and concentrated under reduced pressure. The crude residue was purified by column chromatography on silica gel (1:10 to 1:5 AcOEt/hexanes) to afford 1-(6-chloro-pyridin-3-yl)-4,4-difluoro-cyclohexanecarbonitrile (2.5 g, 54%). LC-MS (m/z) 257.0 (MH+). $^1$H NMR (400 MHz, CDCl$_3$) δ ppm 8.56 (d, J=2.2 Hz, 1H), 7.79 (dd, J=8.4, 2.6 Hz, 1H), 7.42 (d, J=8.4 Hz, 1H), 2.09-2.41 (in, 8H).

Step 4: 1-(6-Bromo-pyridin-3-yl)-4,4-difluoro-cyclohexanecarbonitrile

To a stirred solution of 1-(6-chloro-pyridin-3-yl)-4,4-difluoro-cyclohexanecarbonitrile (1.3 g, 5.1 mmol) in butyronitrile (100 mL) at room temperature under nitrogen atmosphere was added bromotrimethylsilane (1.55 g, 10.2 mmol). The reaction mixture was heated at 120° C. for 24 hours. The reaction mixture was then cooled to room temperature and poured into water (25 mL) and 10% aqueous NaOH solution (25 mL). The aqueous layer was extracted with diethyl ether (3×250 mL). The combined organic layer was dried over sodium sulfate, filtered and concentrated under reduced pressure. The crude residue was then purified by column chromatography on silica gel to afford 1-(6-bromo-pyridin-3-yl)-4,4-difluoro-cyclohexanecarbonitrile as a white solid (1.0 g, 65%). LC-MS (m/z) 301.0 (MH+). $^1$H NMR (400 MHz, CDCl$_3$) δ ppm 8.55 (d, J=2.7 Hz, 1H), 7.69 (dd, J=8.4, 2.8 Hz, 1H), 7.57 (d, J=8.4 Hz, 1H), 2.09-2.41 (in, 8H).

1-(6-Cyclopropyl-pyridin-3-yl)-4,4-difluoro-cyclohexanecarbonitrile

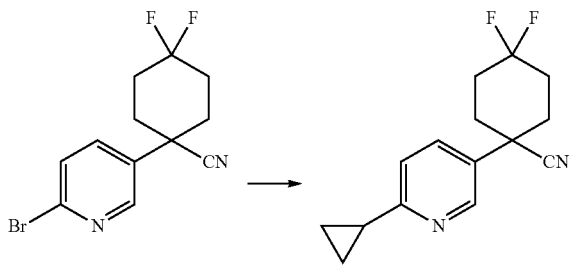 [SMILES: N#CC1(c2ccc(Br)nc2)CCC(F)(F)CC1 ; N#CC1(c2ccc(C3CC3)nc2)CCC(F)(F)CC1]

A suspension of cyclopropylboronic acid (0.94 g, 11 mmol), 1-(6-bromo-pyridin-3-yl)-4,4-difluoro-cyclohexanecarbonitrile (1.10 g, 3.67 mmol) and potassium phosphate tribasic (2.30 g, 10.8 mmol) in a mixture of toluene (16 mL) and water (4 mL) at room temperature was purged with nitrogen gas for 1 hour. Then palladium acetate (31 mg, 0.14 mmol) and tricyclohexylphosphine (51 mg, 0.18 mmol) were added and the mixture was heated at 110° C. for 18 hours. After cooling to room temperature a saturated aqueous solution of ammonium chloride was added, followed by water. The organic layer was separated and the aqueous layer was extracted again three times with AcOEt. The combined organic layers were washed with brine, dried over sodium sulfate, filtered and concentrated under reduced pressure. The crude product was then purified by silica gel chromatography to afford 1-(6-cyclopropyl-pyridin-3-yl)-4,4-difluoro-cyclohexanecarbonitrile (400 mg, 27%). LC-MS (m/z) 263.0 (MH+). $^1$H NMR (400 MHz, CDCl$_3$) δ ppm 8.59 (d, J=2.5 Hz, 1H), 7.64 (dd, J=8.3, 2.5 Hz, 1H), 7.19 (d, J=8.3 Hz, 1H), 2.00-2.39 (m, 9H), 0.99-1.06 (m, 4H).

1-(6-Ethoxy-pyridin-3-yl)-4,4-difluoro-cyclohexanecarbonitrile

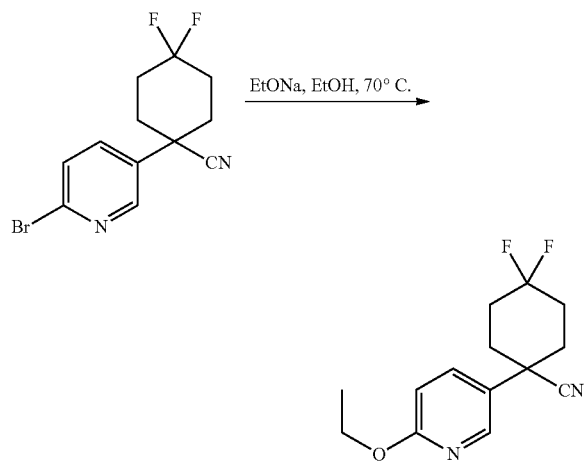

Sodium metal (229 mg, 9.96 mmol) was added to ethanol (5 mL) at room temperature. To this solution was added 1-(6-bromo-pyridin-3-yl)-4,4-difluoro-cyclohexanecarbonitrile (300 mg, 1.00 mmol) and the reaction was heated at 70° C. for 6 hours. After cooling to room temperature the volatiles were removed under reduced pressure. The residue was diluted with water and extracted with AcOEt (2×50 mL). The combined organic layer was dried over sodium sulfate, filtered and concentrated under reduced pressure. The residue was purified by silica gel chromatography to afford 1-(6-ethoxy-pyridin-3-yl)-4,4-difluoro-cyclohexanecarbonitrile (130 mg, 49%). LC-MS (m/z) 241.4 (MH+). $^1$H NMR (400 MHz, CDCl$_3$) δ ppm 8.30 (d, J=2.7 Hz, 1H), 7.66 (dd, J=8.8, 2.7 Hz, 1H), 6.78 (d, J=8.8, Hz, 1H), 4.38 (q, J=7.1, Hz, 2H), 2.07-2.42 (m, 8H), 1.41 (t, J=7.1, Hz, 3H).

1-(6-Methoxy-pyridin-3-yl)-4,4-difluoro-cyclohexanecarbonitrile was prepared analogously to 1-(6-Ethoxy-pyridin-3-yl)-4,4-difluoro-cyclohexanecarbonitrile

1-[5-(1-Aminomethyl-4,4-difluoro-cyclohexyl)-pyridin-2-yl]-ethanol

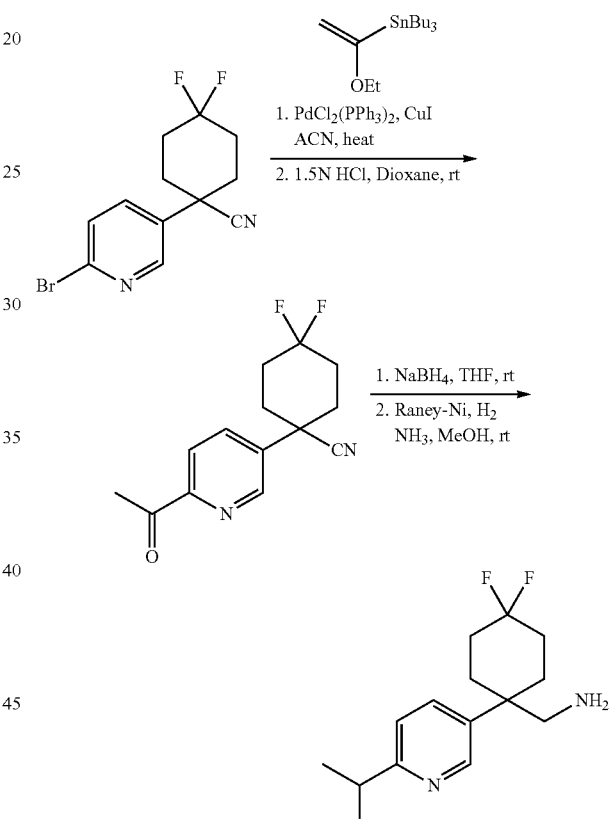

Step 1: 1-(6-Acetyl-pyridin-3-yl)-4,4-difluoro-cyclohexanecarbonitrile

To a microwave vial was added 1-(6-bromo-pyridin-3-yl)-4,4-difluoro-cyclohexanecarbonitrile (276 mg, 0.918 mmol), tributyl(1-ethoxyvinyl)tin (663 mg, 1.84 mmol), copper iodide (26.2 mg, 0.138 mmol), PdCl$_2$(PPh$_3$)$_2$ (32.2 mg, 0.0459 mmol) and acetonitrile (7.3 mL). The vial was purged under nitrogen, capped then heated in an oil bath at 80° C. for 16 hours. After cooling to room temperature the crude reaction mixture was filtered through celite with acetonitrile and the volatiles were then removed under reduced pressure. The residue obtained was dissolved in 1,4-dioxane (20 mL), treated with 1.5 N aqueous HCl (20 mL) and stirred vigorously at room temperature for 1.5 hours. The mixture was then made basic by adding solid potassium carbonate and transferred to a 250-mL separatory funnel with water (50 mL). The aqueous layer was extracted with AcOEt (3×50 mL). The combined organic layers were washed with brine, dried over sodium sulfate, filtered and concentrated under reduced pressure. The residue obtained was treated with a saturated solution of potassium fluoride in methanol (6 mL), stifled for a few minutes, diluted with DCM, adsorbed onto silica gel and purified by silica gel chromatography to afford 1-(6-acetyl-pyridin-3-yl)-4,4-difluoro-cyclohexanecarbonitrile as a white solid (178 mg, 73%). LC-MS (m/z) 265.0 (MH$^+$); $t_R$=1.21. $^1$H NMR (300 MHz, CDCl$_3$) δ ppm 8.86 (d, 1=2.0 Hz, 1H), 8.09 (dd, J=8.3, 0.5 Hz, 1H), 7.95 (dd, J=8.3, 2.5 Hz, 1H), 2.73 (s, 3H), 2.46-2.14 (m, 8H).

Step 2 and 3: 1-[5-(1-Aminomethyl-4,4-difluoro-cyclohexyl)-pyridin-2-yl]-ethanol To a solution of 1-(6-acetyl-pyridin-3-yl)-4,4-difluoro-cyclohexanecarbonitrile (80 mg, 0.30 mmol) in THF (4.0 mL) at room temperature was added sodium borohydride (23 mg, 0.60 mmol) and the reaction was stirred at room temperature for 2.5 hours. The reaction was quenched with methanol and the volatiles were then removed under reduced pressure. The residue was taken up in AcOEt (about 10 mL) and washed with saturated aqueous sodium bicarbonate (about 10 mL). The layers were separated and the aqueous layer was extracted again with AcOEt (2×5 mL). The combined organic layers were washed with brine, dried over sodium sulfate, filtered and concentrated under reduced pressure. The residue was then dissolved in a 7 N ammonia solution in methanol (6.7 mL) and treated with the tip of a spatula of Raney-nickel. The flask was purged three times then left to stir under one atmosphere of hydrogen for 15 hours. The catalyst was removed by filtration through celite and washed with methanol. The solvent was then removed under reduced pressure to afford 1-[5-(1-aminomethyl-4,4-difluoro-cyclohexyl)-pyridin-2-yl]ethanol as a white solid (64 mg, 78%). LC-MS (m/z) 271.1 (WO; $t_R$=0.55.

2-[5-(1-Aminomethyl-4,4-difluoro-cyclohexyl)-pyridin-2-yl]-propan-2-ol

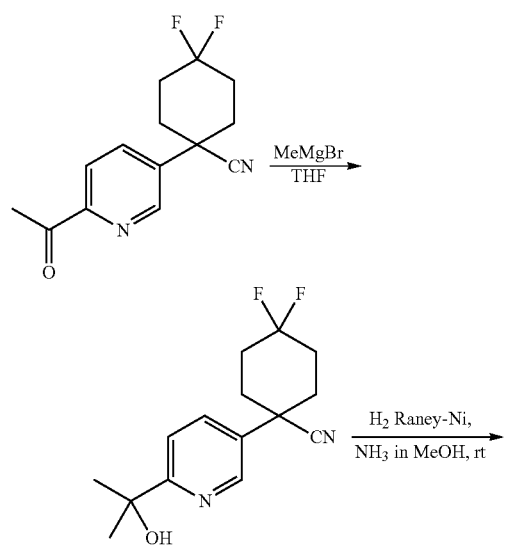

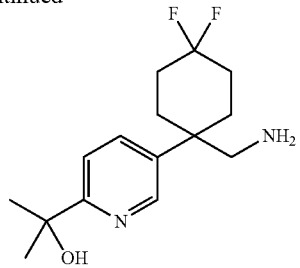

Step 1: 4,4-Difluoro-1-[6-(1-hydroxy-1-methyl-ethyl)-pyridin-3-yl]-cyclohexanecarbonitrile A solution of 1-(6-acetyl-pyridin-3-yl)-4,4-difluoro-cyclohexanecarbonitrile (17 mg, 0.064 mmol) in THF (1.2 mL) was cooled at 50° C. and treated with a 3.0 M solution of methylmagnesium bromide in ether (110 µL, 0.32 mmol). After stirring at 50° C. for 3 hours, the reaction was quenched by adding saturated aqueous ammonium chloride (5 mL) and stirred at room temperature for a few minutes. AcOEt (5 mL) was added and the biphasic mixture was stirred vigorously for a few seconds. The layers were separated and the aqueous layer was extracted again with AcOEt (5 mL). The combined organic layers were dried over sodium sulfate, filtered and concentrated under reduced pressure. The residue was then purified by preparative TLC, eluting with 60% AcOEt in hexanes to afford 4,4-difluoro-1-[6-(1-hydroxy-1-methyl-ethyl)-pyridin-3-yl]-cyclohexanecarbonitrile as a colorless oil (8.7 mg, 48%). LC-MS (m/z) 280.0 (MH$^+$); $t_R$=1.11.

Step 2: 2-[5-(1-Aminomethyl-4,4-difluoro-cyclohexyl)-pyridin-2-yl]-propan-2-ol

Reduction of the cyano group was performed following the same procedure used in the preparation of 1-[5-(1-aminomethyl-4,4-difluoro-cyclohexyl)-pyridin-2-yl]-ethanol. The solvent was removed under reduced pressure to afford 2-[5-(1-aminomethyl-4,4-difluoro-cyclohexyl)-pyridin-2-yl]-propan-2-ol as a colorless oil (8.8 mg, 100%). LC-MS (m/z) 285.1 (MIT); $t_R$=0.61.

3-cyclopropyl-2-(6-(1-ethoxyvinyl)pyridin-3-yl)propanenitrile

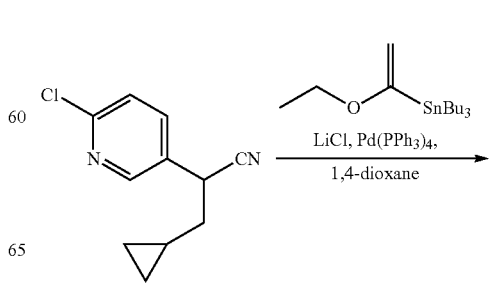

-continued

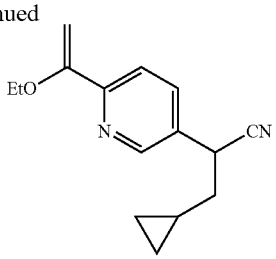

A solution of 2-(6-chloropyridin-3-yl)-3-cyclopropylpropanenitrile (1.0 g, 4.86 mmol), tributyl(1-ethoxyvinyl)stannane (3.4 g, 9.72 mmol), LiCl (0.612 g, 14.58 mmol) and Pd(PPh$_3$)$_4$ (0.282 mg, 0.243 mmol) in 1,4-dioxane (20 mL) was degassed and heated to 120° C. under N$_2$ overnight. The reaction mixture was diluted with water and extracted with EtOAc (3×30 mL). The combined organic layers were dried over Na$_2$SO$_4$ and concentrated to give 3-cyclopropyl-2-(6-(1-ethoxyvinyl)pyridin-3-yl)propanenitrile (2 g), which was used for the next step without further purification.

2-(6-acetylpyridin-3-yl)-3-cyclopropylpropanenitrile

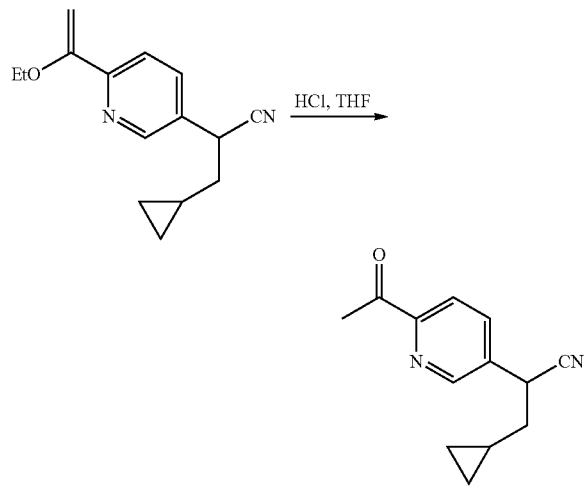

A solution of 3-cyclopropyl-2-(6-(1-ethoxyvinyl)pyridin-3-yl)propanenitrile (2 g, crude) in THF (10 mL) was added 4N HCl (10 mL) and stirred at room temperature for 2 h. The reaction mixture was adjusted pH to 6~7 by 4M aq.NaOH and extracted with EtOAc (3×20 mL). The combined organic layers were dried over Na$_2$SO$_4$ and concentrated. The crude product was purified by column chromatography on silica gel (EtOAc: Petroleum ether=1:10) to give 2-(6-acetylpyridin-3-yl)-3-cyclopropylpropanenitrile (600 mg, yield: 60%) $^1$H NMR (CDCl$_3$ varian 400): δ 8.58-8.51 (m, 1H), 7.95 (d, J=8.0 Hz, 1H), 7.75 (dd, J=8.0 Hz, 2.4 Hz, 1H), 3.92-3.85 (m, 1H), 2.61 (s, 3H), 1.88-1.79 (m, 1H), 1.71-1.65 (m, 1H), 0.75-0.67 (m, 1H), 0.49-0.45 (M, 2H), 0.10-0.03 (in, 2H).

3-cyclopropyl-2-(6-(2-hydroxypropan-2-yl)pyridin-3-yl)propanenitrile

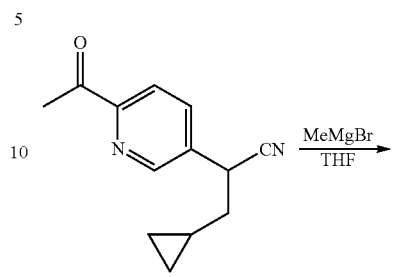

A solution of 2-(6-acetylpyridin-3-yl)-3-cyclopropylpropanenitrile (520 mg, 2.43 mmol) in THF (6 mL) was added MeMgBr (0.89 mL, 2.67 mmol, 3M in Et$_2$O) at 0° C. under N$_2$ and stirred at room temperature for 2 h. The solution was quenched with water and extracted with EtOAc (3×20 mL). The organic layer was dried over Na$_2$SO$_4$ and concentrated. The crude product was purified by column chromatography on silica gel (EtOAc: Petroleum ether=1:10) to give 3-cyclopropyl-2-(6-(2-hydroxypropan-2-yl)pyridin-3-yl)propanenitrile (200 mg, yield: 35.6%). $^1$H NMR (CDCl$_3$ varian 400): δ 8.41 (d, J=2.4 Hz, 1H), 7.67 (dd, J=8.0 Hz, 2.4 Hz, 1H), 7.36 (dd, J=8.4 Hz, 0.8 Hz, 1H), 4.62 (s, 1H), 3.90-3.82 (m, 1H), 1.90-1.83 (m, 1H), 1.75-1.68 (m, 1H), 1.48 (s, 6H), 0.81-0.73 (m, 1H), 0.55-0.50 (m, 2H), 0.15-0.09 (in, 2H).

[4-(4-Trifluoromethyl-phenyl)-tetrahydro-pyran-4-yl]-methylamine

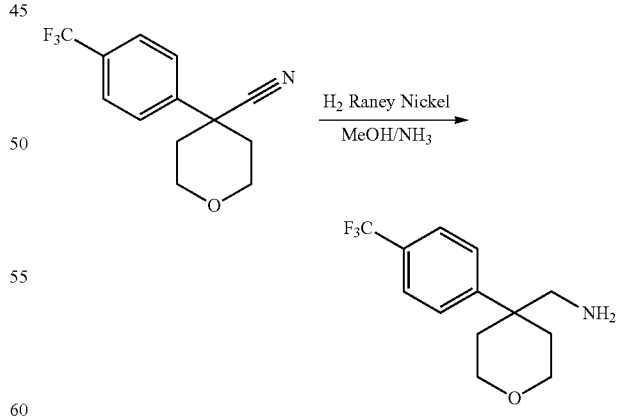

To a solution of 4-(4-trifluoromethyl-phenyl)-tetrahydropyran-4-carbonitrile (1.11 g, 4.35 mmol) in methanol (54 mL) and 7N ammonia in methanol (6 mL) was added Raney-Nickel (300 mg). The mixture was purged 3 times with hydrogen gas then left to stir under 1 atmosphere of hydrogen at room temperature overnight. The crude reaction mixture was filtered through celite, washed with methanol and the filtrate concentrated under reduced pressure to yield the title compound (1.07 g, yield: 95%) as a white solid. ¹H NMR (CDCl₃ 300 MHz): δ ppm 7.67 (d, 2H), 7.45 (d, 2H), 3.90-3.79 (m, 2H), 3.61-3.50 (m, 2H), 2.90 (s, 2H), 2.24-2.12 (m, 2H), 2.00-1.88 (m, 2H), 0.87 (bs, 2H).

The following intermediates were prepared in a similar way:

[4-(4-chloro-phenyl)-tetrahydro-pyran-4-yl]-methylamine;
(1-(pyridin-3-yl)cyclopentyl)methanamine;
(4-(4-(frifluoromethyl)phenyl)tetrahydro-2H-pyran-4-yl) methanamine;
4-Methyl-2-(6-methylpyridin-3-yl)-pentylamine (hydrogenation at 50 psi overnight);
C-[4-(6-Methylpyridin-3-yl)-tetrahydropyran-4-yl]methylamine;
3-Cyclopropyl-2-(2,6-dimethyl-pyridin-3-yl)-propylamine;
C-[4,4-Difluoro-1-(6-fluoro-pyridin-3-yl)-cyclohexyl]-methylamine;
3-Cyclopropyl-2-(6-fluoro-pyridin-3-yl)-propylamine;
C-[1-(6-Methoxy-pyridin-3-yl)-4,4-difluoro-cyclohexyl]-methylamine;
C-[1-(6-Ethoxy-pyridin-3-yl)-4,4-difluoro-cyclohexyl]-methylamine;
C-[1-(6-Cyclopropyl-pyridin-3-yl)-4,4-difluoro-cyclohexyl]-methylamine;
2-(6-Cyclopropyl-pyridin-3-yl)-3-(1-difluoromethyl-cyclopropyl)-propylamine (hydrogenation at 30 psi overnight);
2-(6-Cyclopropyl-pyridin-3-yl)-3-(1-trifluoromethyl-cyclopropyl)-propylamine (hydrogenation at 50 psi for 12 h);
3-Cyclopropyl-2-(6-trifluoromethyl-pyridin-3-yl)-propylamine;
C-[4-(6-trifluoromethylpyridin-3-yl)-tetrahydropyran-4-yl]-methylamine (hydrogenation at 45 psi for 3 h);
C-[4,4-Difluoro-1-(6-trifluoromethyl-pyridin-3-yl)-cyclohexyl]-methylamine (hydrogenation at 50 psi overnight);
3-(1-Difluoromethyl-cyclopropyl)-2-(6-trifluoromethyl-pyridin-3-yl)-propylamine (hydrogenation at 50 psi overnight);
3-(1-Trifluoromethyl-cyclopropyl)-2-(6-trifluoromethyl-pyridin-3-yl)-propylamine (hydrogenation at 50 psi overnight);
C-[4,4-Difluoro-1-(2-methyl-pyrimidin-5-yl)-cyclohexyl]-methylamine (hydrogenation at 30 psi for 2 h);
3-Cyclopropyl-2-(2-methyl-pyrimidin-5-yl)-propylamine (hydrogenation at 30 psi for 30 min);
2-(2-Methyl-pyrimidin-5-yl)-3-(1-trifluoromethyl-cyclopropyl)-propylamine (hydrogenation at 50 psi for 30 min);
3-Cyclopropyl-2-(2-trifluoromethyl-pyrimidin-5-yl)-propylamine (hydrogenation at 50 psi for 30 min);
2-(2-(Trifluoromethyl)pyrimidin-5-yl)-3-(1-trifluoromethyl-cyclopropyl)-propylamine;
2-(2-(Trifluoromethyl)pyrimidin-5-yl)-3-(1-difluoromethyl-cyclopropyl)-propylamine;
[4,4-Difluoro-1-(2-(trifluoromethyl)pyrimidin-5-yl)cyclohexyl]methanamine; 3-Cyclopropyl-2-(5-methyl-pyrazin-2-yl)-propylamine;

[1-(4-Methoxyphenyl)-cyclopentyl]-methylamine

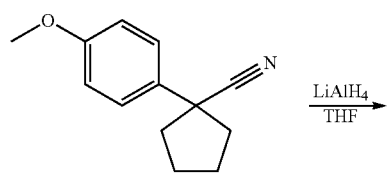

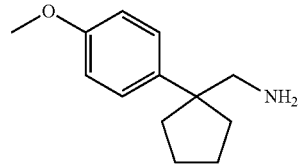

To a stirred solution of 1-(4-Methoxyphenyl)-1-cyclopentanecarbonitrile (4.02 g, 20 mmol) in THF (50 mL) cooled to 0° C. was added lithium aluminium hydride (1.52 g, 40 mmol) and the reaction was allowed to warm to room temperature and stirred for 16 h. To the reaction mixture was added cautiously water (2.0 mL) then 2N NaOH (aq) (2 mL). The mixture was filtered and concentrated in vacuo to yield the title compound which was used without further purification (1.07 g, yield: 95%). ¹H NMR (CDCl₃ 300 MHz): δ ppm 7.12 (d, 2H), 6.80 (d, 2H), 3.71 (s, 2H), 2.62 (s, 3H), 1.88-1.58 (m, 8H).

The following intermediates were prepared in a similar way:

[4-(4-Chloro-phenyl)-1-methyl-piperidine-4-yl]-methyl amine;
(1-methyl-4-phenylpiperidin-4-yl)methanamine;
3-(4-Chloro-phenyl)-N1,N1-dimethyl-butane-1, 4-diamine;

2-Cyclopropyl-2-(6-trifluoromethyl-pyridin-3-yl)-ethylamine

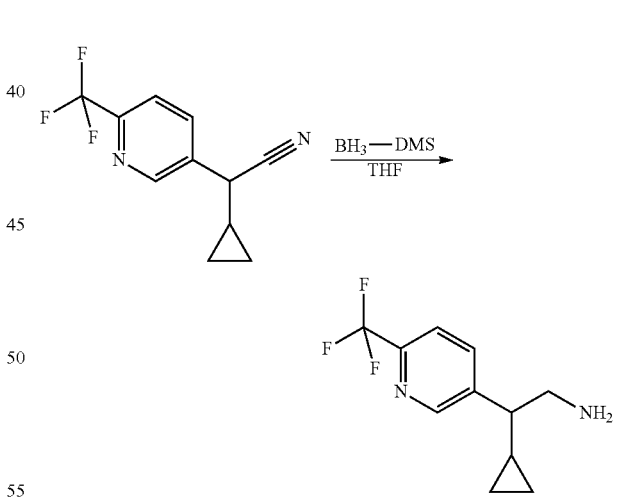

A solution of Cyclopropyl-(6-trifluoromethyl-pyridin-3-yl)-acetonitrile (93 mg, 0.41 mmol) in THF (2.8 mL) in a 5 mL microwave vial was treated with borane-methyl sulfide complex (0.51 mL, 5.4 mmol). The reaction vessel was capped and the mixture was heated in the microwave reactor for 20 mins at 100° C. The reaction mixture was concentrated in vacuo to yield the crude title compound which was used without further purification (95 mg, purity: 73%, yield: 73%). LCMS (MH+): m/z=231.1, $t_R$ (minutes, Method D)=0.40

The following intermediates were prepared in a similar way:

2-(5-Chloro-pyridin-3-yl)-3-cyclopropyl-propylamine;

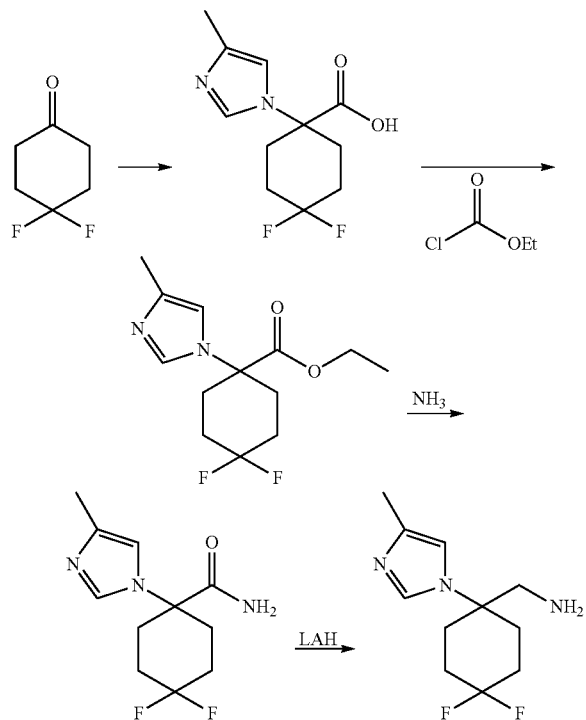

4,4-difluoro-1-(4-methyl-1H-imidazol-1-yl)cyclohexanecarboxylic acid:

4-methylimidazole (1.67 g, 20.3 mmol) was dissolved in THF (200 mL, 2000 mmol). Powdered sodium hydroxide (4.19 g, 104.8 mmol) was added together with 4,4-difluorocyclohexanone (2.90 g, 22 mmol). Chloroform (7.9 mL, 99 mmol) was added dropwise and the reaction was stirred overnight at room temperature.

The reaction was acidified with 2M HCl and filtered. The solid was treated with MeOH, to dissolve the product and leave back NaCl. The reaction was filtered again and the residue was concentrated to give the title compound as the hydrochloride salt (3.498 g, 58%).

ethyl 4,4-difluoro-1-(4-methyl-1H-imidazol-1-yl)cyclohexanecarboxylate 4,4-Difluoro-1-(4-methyl-imidazol-1-yl)-cyclohexanecarboxylic acid; hydrochloride (662 mg, 1.18 mmol) was dissolved in THF (20 mL, 200 mmol) and cooled in ice. N,N-Diisopropylethylamine (0.850 mL, 4.88 mmol) was added dropwise over 5 minutes at 5-10° C. The mixture was stirred for 15 minutes. Ethyl chloroformate (0.150 mL, 1.57 mmol) was added dropwise over 5 minutes at 5-7° C. The mixture was stirred 50 minutes at 5° C. Then warmed to room temperature. After 1 hour the reaction was concentrated down and the residue was purified by flash column chromatography on silica gel (eluding w a gradient elution from heptane to AcOEt) to give the title compound (199 mg, 59%) $^1$H NMR (CDCl$_3$ 500 MHz): δ ppm 7.59 (s, 1H), 6.76 (s, 1H), 4.20 (m, 2H), 2.61 (m, 2H), 2.43 (m, 2H), 2.24 (s, 311), 2.03 (m, 4H), 1.22 (in, 3H).

4,4-difluoro-1-(4-methyl-1H-imidazol-1-yl)cyclohexanecarboxamide 4,4-Difluoro-1-(4-methyl-imidazol-1-yl)-cyclohexanecarboxylic acid ethyl ester (199 mg, 0.731 mmol was dissolved in 7 M ammonia in methanol (5 mL) and stirred for 72 hours. The sample was concentrated and the residue was purified by flash column chromatography on silica gel (eluding w a gradient elution from heptane to AcOEt to 5% Et$_3$N/10% MeOH/85% AcOEt) to give the title compound (84 mg, 45%) $^1$H NMR (CDCl$_3$ 500 MHz): δ ppm 7.64 (s, 1H), 6.82 (s, 1H), 5.17 (m, 211), 2.68 (m, 211), 2.41 (in, 211), 2.30 (s, 311), 2.23 (m, 211), 1.85 (m, 211).

(4, 4-difluoro-1-(4-methyl-1H-imidazol-1-yl)cyclohexyl)methanamine

Into a round bottom flask was added 4,4-Difluoro-1-(4-methyl-imidazol-1-yl)-cyclohexanecarboxylic acid amide (99 mg, 0.39 mmol) and THF (10 mL, 100 mmol) at room temperature, to the reaction mixture was added lithium tetrahydroaluminate (365 mg, 9.62 mmol). The reaction was refluxed for 6 hours, before being quenched with water (0.4 ml), 2M NaOH (0.4 ml) and water (0.8 ml). The reaction mixture was filtered and conc. The residue was purified by flash column chromatography on silica gel (eluding w a mixture of 5% Et$_3$N/10% MeOH/85% AcOEt) to give the title compound (44 mg, 47%). $^1$H NMR (CDCl$_3$ 500 MHz): δ ppm 7.55 (s, 1H), 6.71 (s, 1H), 2.70 (s, 2H), 2.4-1.7 (m, 8H), 2.21 (s, 3H).

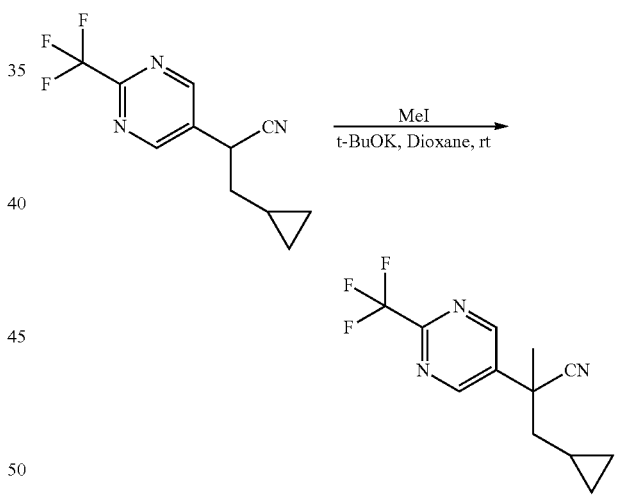

3-cyclopropyl-2-methyl-2-(2-(trifluoromethyl)pyrimidin-5-yl)propanenitrile

To a solution of 3-cyclopropyl-2-(2-(trifluoromethyl)pyrimidin-5-yl)propanenitrile (310 mg, 1.29 mmol) and MeI (0.27 g, 1.9 mmol) in dioxane (10 ml) was added t-BuOK (1.39 mL, 1.39 mmol, 1M in THF) dropwise at room temperature under N$_2$. The mixture was stirred for 1 h, then quenched by sat.aq. NH$_4$Cl (10 mL), and extracted with EtOAc(3×10 ml). The organic layer was concentrated under reduced pressure to give crude product, which was purified by column chromatography on silica gel (EtOAc/Petroleum ether=1:4) to give compound the title compound (120 mg, yield: 36%). $^1$H NMR (CDCl$_3$ varian 400): δ 9.02 (s, 2H), 1.92 (d, J=6.8 Hz, 2H), 1.87 (s, 3H), 0.80-0.67 (m, 1H), 0.65-0.56 (m, 1H), 0.55-0.45 (m, 1H), 0.30-0.20 (m, 1H), 0.05-0.04 (m, 1H).

3-Cyclopropyl-2-(2-(difluoromethyl)pyrimidin-5-yl)-2-methylpropan-1-amine

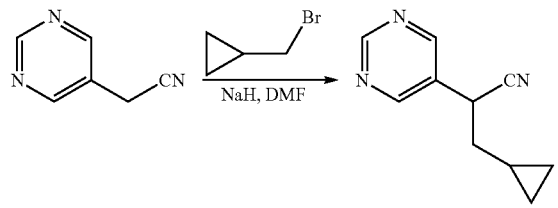

A solution of 2-(pyrimidin-5-yl)acetonitrile (1.8 g, 15.1 mmol) in DMF (20 mL) was degassed and (bromomethyl) cyclopropane was added (2.04 g, 15.1 mmol). The reaction mixture was cooled to −10° C., NaH was added (720 mg, 18.1 mmol, 60% in mineral oil) in portions under N₂ and stirred at the same temperature for 45 mins. The reaction mixture was quenched with sat. NH₄Cl and extracted with EtOAc (30 ml×3). The organic layer was washed with brine, dried over Na₂SO₄ and concentrated. The crude product was purification by column chromatography on silica gel (petroleum ether:EtOAc=3:1) to give 3-cyclopropyl-2-(pyrimidin-5-yl)propanenitrile (2.25 g, yield: 85%). ¹H NMR (CDCl₃ 400 MHz): δ 9.22 (s, 1H), δ 8.78 (s, 2H), 3.80 (t, J=8 Hz, 2H), 1.98-1.92 (m, 1H), 1.83-1.79 (m, 1H), 0.87-0.83 (m, 1H), 0.61-0.59 (m, 2H), 0.21-0.13 (m, 2H).

The following intermediate was prepared in a similar way:
2-(Pyrimidin-5-yl)-3-(1-(trifluoromethyl)cyclopropyl)propanenitrile;
2-(5-chloropyridin-3-yl)-3-cyclopropylpropanenitrile;
3-cyclopropyl-2-(pyrimidin-5-yl)propanenitrile;
3-(1-fluorocyclopropyl)-2-(pyrimidin-5-yl)propanenitrile;

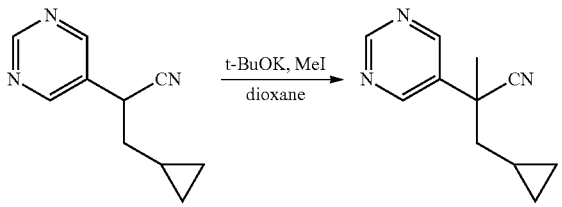

To a solution of 3-cyclopropyl-2-(pyrimidin-5-yl)propanenitrile (1.5 g, 8.67 mmol) and MeI (1.45 g, 13.0 mmol) in 1,4-dioxane (20 ml) was added t-BuOK (9.57 ml, 9.57 mmol) dropwise at room temperature under N₂. The mixture was stirred for 1 h at room temperature then quenched by sat.aq NH₄Cl (20 ml) and extracted with EtOAc (3×30 ml). The organic layer was dried over Na₂SO₄ and concentrated under reduced pressure to give 3-cyclopropyl-2-methyl-2-(pyrimidin-5-yl)propanenitrile (1.5 g), which was used directly for next step.

The following intermediate was prepared in a similar way:
3-cyclopropyl-2-methyl-2-(2-(trifluoromethyl)pyrimidin-5-yl)propanenitrile;

3-cyclopropyl-2-(2-(difluoromethyl)pyrimidin-5-yl)-2-methylpropanenitrile

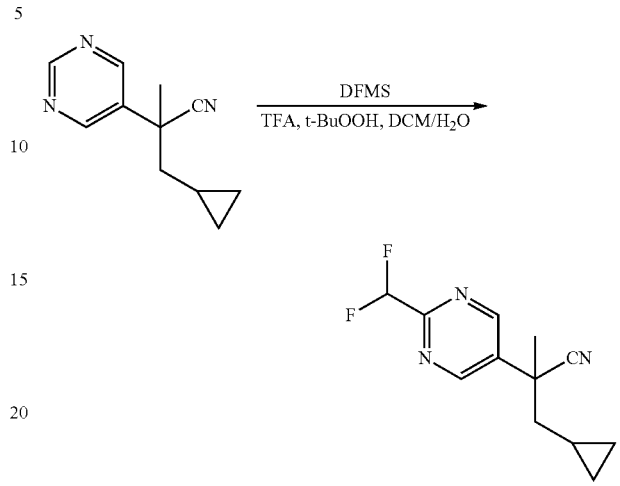

To a solution of 3-cyclopropyl-2-methyl-2-(pyrimidin-5-yl)propanenitrile (2.5 g, 13.4 mmol) and DMFS (7.8 g, 26.7 mmol) in DCM (40 ml) and H₂O (12 ml) at room temperature was added TFA (1.5 g, 13.4 mmol) followed by slow addition of t-BuOOH (8.6 g, 67 mmol) with vigorous stirring. The reaction mixture was stirred at room temperature overnight. To the reaction mixture was added additional DMFS (7.8 g, 26.7 mmol) and t-BuOOH (8.6 g, 67 mmol). The reaction mixture was stirred at room temperature overnight. The reaction mixture was added aq. NaHCO₃ and extracted with EtOAc (3×50 ml). The organic layer was dried over Na₂SO₄ and concentrated. The crude product was purification by column chromatography on silica gel (petroleum ether:EtOAc=4:1) to give 3-cyclopropyl-2-(2-(difluoromethyl)pyrimidin-5-yl)-2-methylpropanenitrile (1.1 g, yield: 35%). ¹H NMR (CDCl₃ 400 MHz): δ 8.97 (s, 2H), 6.82-6.55 (m, 1H), 1.92-1.90 (m, 2H), 1.85 (s, 3H), 0.71-0.65 (m, 1H), 0.60-0.57 (m, 1H), 0.51-0.47 (m, 1H), 0.26-0.20 (m, 1H), 0.03-0.00 (m, 1H).

The following intermediate was prepared in a similar way:
2-(2-(Difluoromethyl)pyrimidin-5-yl)-3-(1-(trifluoromethyl)cyclopropyl)propanenitrile;
2-(2-(Difluoromethyl)pyrimidin-5-yl)-3-(1-(fluoro)cyclopropyl)propanenitrile;
3-cyclopropyl-2-methyl-2-(2-(difluoromethyl)pyrimidin-5-yl)propanenitrile;
3-cyclopropyl-2-(2-(difluoromethyl)pyridin-5-yl)propanenitrile;
3-cyclopropyl-2-(2-(difluoromethyl)pyrimidin-5-yl)propanenitrile;
3-(1-fluorocyclopropyl)-2-(2-(difluoromethyl)pyrimidin-5-yl)propanenitrile;
3-(1-(trifluoromethyl)cyclopropyl)-2-(2-(difluoromethyl)pyrimidin-5-yl)propanenitrile;

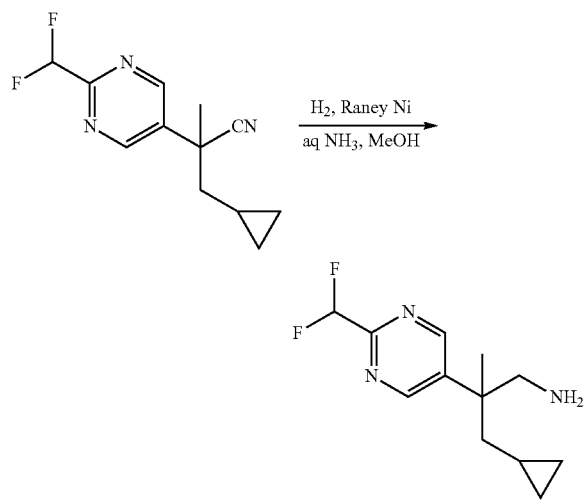

A mixture of 3-cyclopropyl-2-(2-(difluoromethyl)pyrimidin-5-yl)-2-methylpropanenitrile (1 g, 4.2 mmol) and NH$_3$.H$_2$O (3 mL) in MeOH (20 mL) was hydrogenated with Raney Ni (1.5 g) under 50 Psi for 3 h. The reaction mixture was filtered and concentrated to give 3-cyclopropyl-2-(2-(difluoromethyl)pyrimidin-5-yl)-2-methylpropan-1-amine (1 g), which was used directly for next step.

The following intermediates were prepared in a similar way:

2-(2-(Difluoromethyl)pyrimidin-5-yl)-3-(1-fluorocyclopropyl)propan-1-amine;

2-(2-(Difluoromethyl)pyrimidin-5-yl)-3-(1-(trifluoromethyl)cyclopropyl)propan-1-amine;

(4, 4-difluoro-1-(5-fluoropyridin-3-yl)cyclohexyl)methanamine;

3-(1-fluorocyclopropyl)-2-(2-(trifluoromethyl)pyridin-5-yl)propan-1-amine;

3-(1-fluorocyclopropyl)-2-(2-(trifluoromethyl)pyrimidin-5-yl)propan-1-amine;

3-cyclopropyl-2-(2-(difluoromethyl)pyrimidin-5-yl)propan-1-amine;

3-(1-fluorocyclopropyl)-2-(2-(difluoromethyl)pyrimidin-5-yl)propan-1-amine;

2-(2-(difluoromethyl)pyrimidin-5-yl)-3-(1-(trifluoromethyl)cyclopropyl)propan-1-amine;

3-cyclopropyl-2-methyl-2-(2-(difluoromethyl)pyrimidin-5-yl)propan-1-amine;

3-cyclopropyl-2-methyl-2-(2-(trifluoromethyl)pyrimidin-5-yl)propan-1-amine;

3-(1-fluorocyclopropyl)-2-(2-methylpyrimidin-5-yl)propan-1-amine;

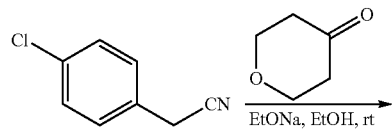

2-(4-Chlorophenyl)-2-(dihydro-2H-pyran-4(3H)-ylidene)acetonitrile

Sodium (152 mg, 6.6 mmol) was added into EtOH (10 ml) and stirred at room temperature for 20 minutes. 2-(4-Chlorophenyl)acetonitrile (500 mg, 3.3 mmol) was added to the solution, after all the sodium had dissolved, and the reaction was stirred at room temperature for 0.5 h. To the resulting mixture was added dihydro-2H-pyran-4(3H)-one (330 mg, 3.3 mmol) and stifled at room temperature for 1.5 h. The solvent was removed. To the residue was added water and extracted with EtOAc (3×20 mL). The combined organic solution were dried over Na$_2$SO$_4$ and concentrated to give crude product, which was purified by flash column chromatography (petroleum ether:EtOAc=10:1) to give compound 2-(4-chlorophenyl)-2-(dihydro-2H-pyran-4(3H)-ylidene)acetonitrile (300 mg) which was used for the next step without further purification.

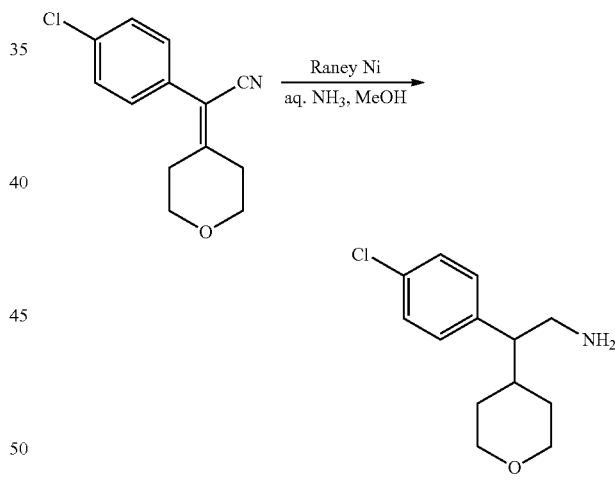

2-(4-chlorophenyl)-2-(tetrahydro-2H-pyran-4-yl)ethanamine

A mixture of 2-(4-chlorophenyl)-2-(dihydro-2H-pyran-4(3H)-ylidene)acetonitrile (200 mg, 0.85 mmol) and NH$_3$.H$_2$O (2 mL) in MeOH (30 mL) was hydrogenated with Raney Ni (500 mg) under H$_2$ (50 Psi) overnight. The reaction mixture was filtered and concentrated to give 2-(4-chlorophenyl)-2-(tetrahydro-2H-pyran-4-yl)ethanamine (190 mg, 93%). $^1$H NMR (CDCl$_3$ 400 MHz): δ 7.39-7.29 (m, 2H), 7.19-7.09 (m, 2H), 4.03-3.95 (m, 1H), 3.89-3.80 (m, 1H), 3.51-3.45 (m, 2H), 3.40-3.32 (m, 1H), 3.30-3.20 (m, 1H), 2.61-2.49 (m, 2H), 1.82-1.69 (m, 2H), 1.49-1.31 (m, 1H), 1.29-1.10 (in, 2H).

The following intermediates were prepared in a similar way:

2-(2-Methylpyrimidin-5-yl)-2-(tetrahydro-2H-pyran-4-yl)ethanamine;

2-(Tetrahydro-2H-pyran-4-yl)-2-(2-(trifluoromethyl)pyrimidin-5-yl)ethanamine;

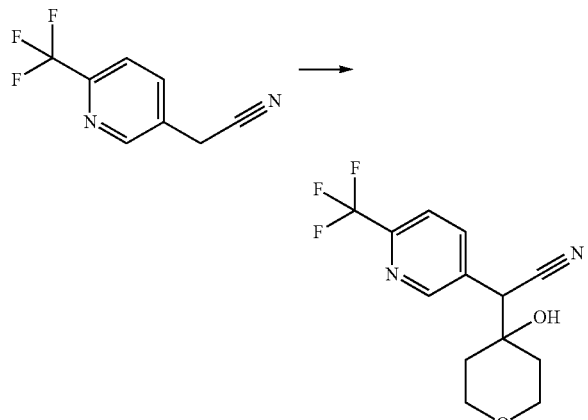

2-(4-Hydroxytetrahydro-2H-pyran-4-yl)-2-(6-(trifluoromethyl)pyridin-3-yl)acetonitrile 2-(6-(Trifluoromethyl)pyridin-3-yl)acetonitrile (260 mg, 1.4 mmol) was dissolved in THF (3 mL, 30 mmol) under Ar and cooled at −78° C. A solution of 0.6 M sodium bis (trimethylsilyl)amide in toluene (3.49 mL) was added dropwise. After stirring a t−78° C. for 4 hours the reaction was allowed to reach −50° C. for 30 minutes. Then tetrahydro-4H-pyran-4-one (0.189 mL, 2.10 mmol) was added dropwise at −60° C. and the reaction was kept at this temperature for 45 minutes. To the reaction was added sat. aq. NH₄Cl (10 mL) and it was extracted AcOEt (3×20 mL). The combined organic phases were washed with brine, dried over MgSO₄ and concentrated in vacuo. The crude product was purified by flash chromatography to yield 2-(4-Hydroxytetrahydro-2H-pyran-4-yl)-2-(6-(trifluoromethyl)pyridin-3-yl)acetonitrile (189 mg, 0.660 mmol, 47%).

$^1$H NMR (600 MHz, DMSO) δ 8.72 (d, J=1.9 Hz, 1H), 8.08 (dd, J=8.1, 2.0 Hz, 1H), 8.00 (d, J=8.0 Hz, 1H), 4.56 (s, 1H), 3.78-3.68 (m, 1H), 3.67-3.61 (m, 1H), 3.59-3.52 (m, 1H), 3.44 (td, J=11.7, 2.3 Hz, 1H), 1.81-1.72 (m, 1H), 1.73-1.60 (m, 2H), 1.04 (dd, J=13.4, 2.3 Hz, 1H).

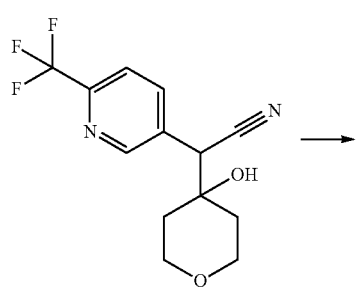

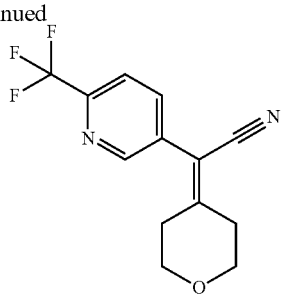

2-(Dihydro-2H-pyran-4(3H)-ylidene)-2-(6-(trifluoromethyl)pyridin-3-yl)acetonitrile (4-Hydroxy-tetrahydro-pyran-4-yl)-(6-trifluoromethyl-pyridin-3-yl)-acetonitrile (1.15 g, 4.02 mmol) was dissolved in thionyl chloride (50 mL, 600 mmol). One drop of DMF was added and the mixture was heated at reflux for 1 hour and then cooled to room temperature and concentrated in vacuo. The resulting crude product was purified by flash chromatography to yield 2-(dihydro-2H-pyran-4(3H)-ylidene)-2-(6-(trifluoromethyl)pyridin-3-yl)acetonitrile (1.04 g, 3.9 mmol, 95%).

$^1$H NMR (600 MHz, CDCl₃) δ 8.68 (d, J=2.1 Hz, 1H), 7.89 (ddd, J=8.1, 2.2, 0.5 Hz, 1H), 7.80 (dd, J=8.1, 0.7 Hz, 1H), 3.93 (t, J=5.5 Hz, 2H), 3.74 (t, J=5.5 Hz, 2H), 2.94-2.86 (m, 2H), 2.52 (t, J=5.5 Hz, 2H).

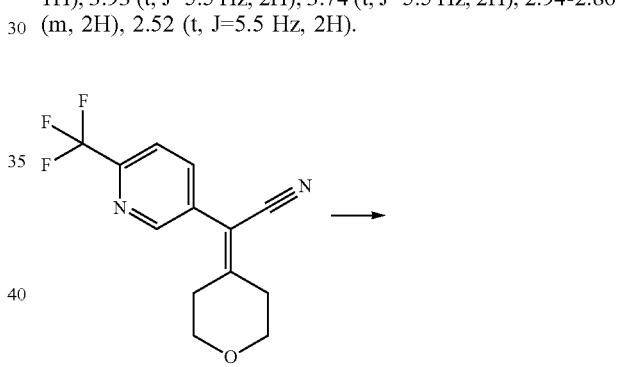

2-(Tetrahydro-2H-pyran-4-yl)-2-(6-(trifluoromethyl)pyridin-3-yl)ethanamine 2-(Dihydro-2H-pyran-4(3H)-ylidene)-2-(6-(trifluoromethyl)pyridin-3-yl)acetonitrile (1.04 g, 3.88 mmol) was dissolved in methanol (50 mL) and 7 M NH₃ in methanol (20 mL) was added. The solution was flushed with Ar. Raney nickel (0.033 g, 0.39 mmol) was added and mixture hydrogenated on a Parr Apparatus at room temperature for 4 hours. Then filtered through a plug of celite and concentrated in vacuo. The crude product was used for the next step without further purification.

LC-MS (m/z) 275.2 (MH+), $t_R$ (minutes, Method E)=0.33.

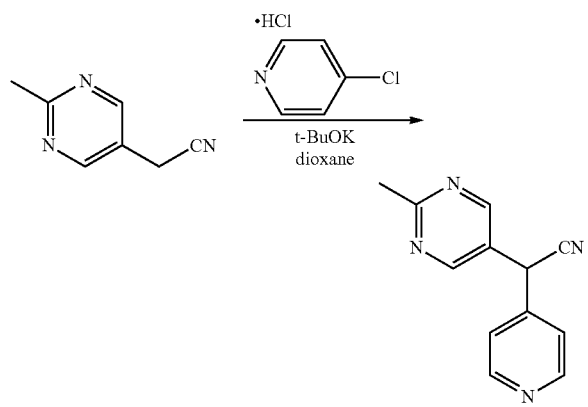

2-(2-methylpyrimidin-5-yl)-2-(pyridin-4-yl)acetonitrile

A solution of 2-(2-methylpyrimidin-5-yl)acetonitrile (1.0 g, 7.51 mmol) and 4-chloropyridine hydrochloride (1.13 g, 7.51) in dioxane (20 mL) in a dried flask was degassed and filled with nitrogen. t-BuOK (18.8 mL, 1M in THF) was added. The mixture was stirred at 100° C. for 4 h and cooled to room temperature, quenched by cooled sat. aq. NH$_4$Cl (20 mL). The resulting mixture was extracted with EtOAc (3×10 mL). The combined organic layers were washed with brine (3×10 mL), dried over Na$_2$SO$_4$, concentrated under reduced pressure to give the crude product, which was purified by column chromatography on silica gel (MEOH:EtOAc=1:10) to give 2-(2-methylpyrimidin-5-yl)-2-(pyridin-4-yl)acetonitrile (700 mg, crude).

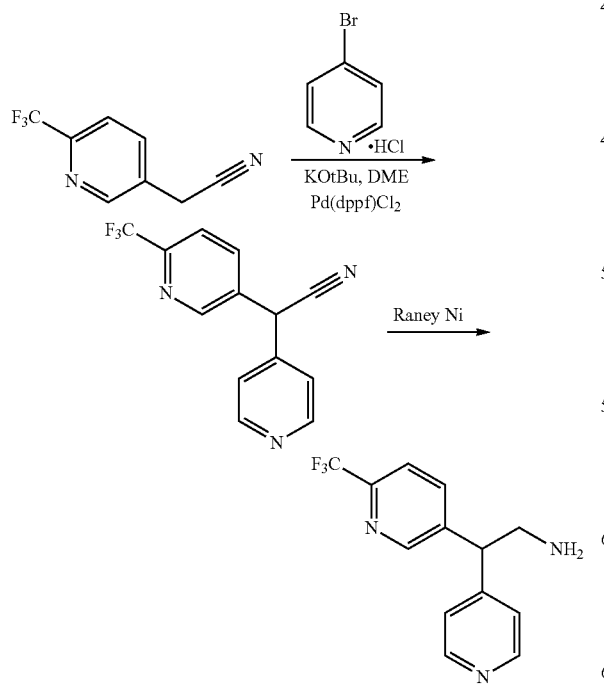

2-(pyridin-4-yl)-2-(6-(trifluoromethyl)pyridin-3-yl)acetonitrile

A dried flask was charged with 2-(6-(trifluoromethyl)pyridin-3-yl)acetonitrile (1.0 g, 5.38 mmol) in DME (20 ml). The mixture was degassed and filled with N$_2$, then t-BuOK (30 ml, 30 mmol, 1M in THF), 4-bromopyridine hydrochloride (2.1 g, 10.7 mmol) and Pd(dppf)Cl$_2$ (39.6 mg, 0.538 mmol) was added. The mixture was stirred at 60° C. for 3 h. After cooling to room temperature, sat.aq NH$_4$Cl (15 ml) was added and the solution was extracted with EtOAc (3×30 ml). The combined organic layers were washed with brine and dried over Na$_2$SO$_4$, concentrated in vacuo. The residue was purified by column chromatography on silica gel (EtOAc: Petroleum ether=4:1) to give 2-(pyridin-4-yl)-2-(6-(trifluoromethyl)pyridin-3-yl)acetonitrile (360 mg, yield: 25.7%). $^1$H NMR (CDCl$_3$ 400 MH$_Z$): δ 8.75 (d, J=1.6 H$_Z$, 1H), 8.71 (d, J=6.0 H$_Z$, 2H), 7.90 (dd, J=8.0 H$_Z$, 2.0 H$_Z$, 1H), 7.77 (d, J=8.4 H$_Z$, 1H), 7.31 (d, J=6.0 H$_Z$, 2H), 5.26 (s, 1H).

2-(pyridin-4-yl)-2-(6-(trifluoromethyl)pyridin-3-yl)ethanamine

A mixture of 2-(pyridin-4-yl)-2-(6-(trifluoromethyl)pyridin-3-yl)acetonitrile (360 mg, 1.36 mmol) and NH$_3$.H$_2$O (2 mL) in MeOH (30 mL) was hydrogenated with Raney Ni (700 mg) under H$_2$ (50 Psi) for 5 h. The reaction mixture was filtered and concentrated to give 2-(pyridin-4-yl)-2-(6-(trifluoromethyl)pyridin-3-yl)ethanamine (300 mg), which was used in the next step without further purification.

The following intermediates were prepared in a similar way:

2-(Pyridin-4-yl)-2-(2-(trifluoromethyl)pyrimidin-5-yl)ethanamine;

2-Phenyl-2-(6-(trifluoromethyl)pyridin-3-yl)ethanamine;

2-(2-methylpyrimidin-5-yl)-2-(pyridin-4-yl)ethanamine;

2-(4-fluorophenyl)-2-(6-(trifluoromethyl)pyridin-3-yl)ethanamine;

2-(4-fluorophenyl)-2-(6-(trifluoromethyl)pyrimidin-3-yl)ethanamine;

2-phenyl-2-(6-(trifluoromethyl)pyridin-3-yl)ethanamine;

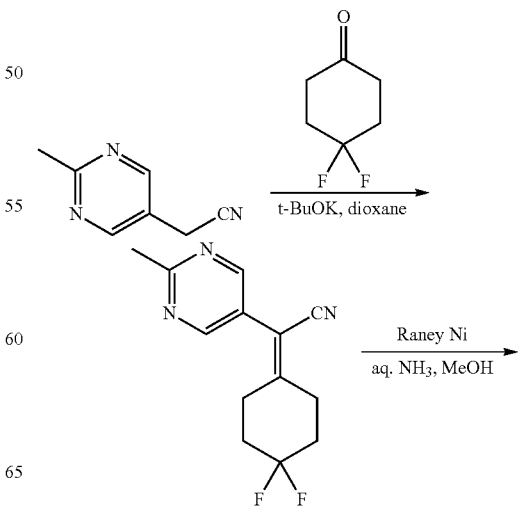

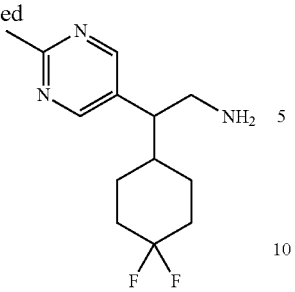

2-(4,4-difluorocyclohexylidene)-2-(2-methylpyrimidin-5-yl)acetonitrile

To a solution of 2-(2-methylpyrimidin-5-yl)acetonitrile (1 g, 7.52 mmol) and 4,4-difluorocyclohexanone (1.1 g, 8.27 mmol) in 1,4-dioxane (40 mL) was added t-BuOK (0.8 g, 8.27 mmol) in two portions. After the addition was completed, the reaction was heated to 60° C. and stirred overnight. The reaction solution was cooled to 0° C., quenched by saturated NH$_4$Cl aq. solution and extracted with EtOAC (50 m×3). The combined organic layer was washed with brine, dried over Na$_2$SO$_4$ and concentrated to get the crude product, which was purified by column chromatography on silica gel (Petroleum ether:EtOAc=4:12:1) to afford 2-(4,4-difluorocyclohexylidene)-2-(2-methylpyrimidin-5-yl)acetonitrile (440 mg, yield: 23.5%). $^1$H NMR (CDCl3 varian 400 MHz): δ 8.61 (s, 2H), 2.97 (t, J=8.0 Hz, 2H), 2.80 (s, 3H), 2.55 (t, J=8.0 Hz, 2H), 2.27-2.17 (m, 2H), 2.09-1.98 (in, 2H).

2-(4,4-difluorocyclohexyl)-2-(2-methylpyrimidin-5-yl)ethanamine

A mixture of 2-(4,4-difluorocyclohexylidene)-2-(2-methylpyrimidin-5-yl)acetonitrile (290 mg, 0.57 mmol), Raney-Ni (1.5 g), NH$_3$.H$_2$O (2 mL) in MeOH (30 mL) was degassed and purged with nitrogen and H$_2$ each 3 times. The mixture was stirred at room temperature under H$_2$ (50 psi) for 4 h. The resulting mixture was filtered through the celite. The filtrate was concentrated under reduced pressure to give 2-(4,4-difluorocyclohexyl)-2-(2-methylpyrimidin-5-yl)ethanamine (280 mg, crude), which was used in the next step without further purification.

The following intermediates were prepared in a similar way:

2-(4,4-difluorocyclohexyl)-2-(2-(trifluoromethyl)pyrimidin-5-yl)ethanamine;

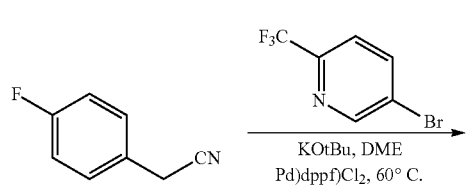

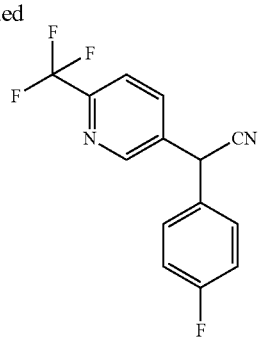

2-(4-fluorophenyl)-2-(6-(trifluoromethyl)pyridin-3-yl)acetonitrile

A solution of 2-(4-fluorophenyl)acetonitrile (2 g, 14.8 mmol) in DME (50 mL) was degassed. KOtBu (6.63 g, 59.2 mmol) was added in portions. After addition was completed, the mixture was stirred for 5 min at room temperature and a brown suspension was formed. Then 5-bromo-2-(trifluoromethyl)pyridine (6.69 g, 29.6 mmol) was added followed by Pf(dppf)Cl2 (1.35 g, 1.48 mmol). The resulting mixture was heated to 60° C. for 4 h. The reaction mixture was cooled to room temperature and quenched by aq. NH4Cl to pH=5-6. The mixture was extracted with EtOAc(50 mL×3). The combined organic layer was washed with brine, dried over Na2SO4 and concentrated. The residue was purified by flash combi (Petroleum ether/EtOAc=15:1) to give 2-(4-fluorophenyl)-2-(6-(trifluoromethyl)pyridin-3-yl)acetonitrile (18 g, 70% purity +350 mg, pure, yield: 51.8%). $^1$H NMR (CDCl3 400 MHz) δ 8.98 (s, 1H), 7.89 (dd, J=8.4, 2.4 Hz, 1H), 7.73 (d, J=8.4 Hz, 1H), 7.40-7.30 (m, 2H), 7.20-7.10 (m, 2H), 5.26 (s, 1H).

The following intermediates were prepared in a similar way:

2-(4-fluorophenyl)-2-(2-(trifluoromethyl)pyrimidin-5-yl)acetonitrile;

2-phenyl-2-(6-(trifluoromethyl)pyridin-3-yl)acetonitrile;

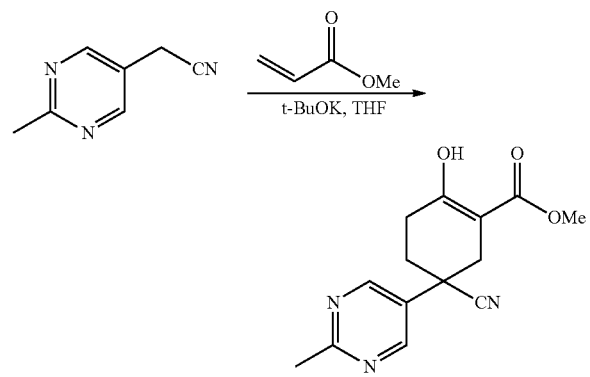

methyl 5-cyano-2-hydroxy-5-(2-methylpyrimidin-5-yl)cyclohex-1-enecarboxylate A solution of 2-(2-methylpyrimidin-5-yl)acetonitrile (4 g, 0.03 amol) and methyl acrylate (5.69 g, 0.066 mol) in THF (60 mL) was added t-BuOK (93 mL, 0.093 mol, 1M in THF) and stirred at room temperature for 4 h. The reaction mixture was quenched by sat. NH₄Cl and extracted with EtOAc (3×150 mL). The organic layer was dried over Na₂SO₄ and concentracted to give methyl 5-cyano-2-hydroxy-5-(2-methylpyrimidin-5-yl)cyclohex-1-enecarboxylate (5.5 g), which was used for the next step directly.

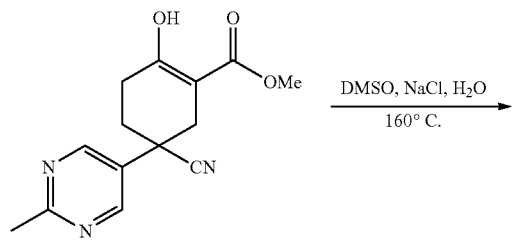

1-(2-methylpyrimidin-5-yl)-4-oxocyclohexanecarbonitrile

A solution of methyl 5-cyano-2-hydroxy-5-(2-methylpyrimidin-5-yl)cyclohex-1-enecarboxylate (6.2 g, 0.023 mol), NaCl (1.46 g, 0.025 mol) and H₂O (1.24 mL, 0.069 mol) in DMSO (50 mL) was heated to 160° C. for 3 h. After cooling to room temperature, the reaction was added water and extracted with EtOAc (6×100 mL). The organic layer was washed with brine, dried over Na₂SO₄ and concentracted. The crude product was purified by flash chromatography (EtOAc: Petroluem ether=1:3~3:2) to give 1-(2-methylpyrimidin-5-yl)-4-oxocyclohexanecarbonitrile (2 g, yield: 41%). ¹H NMR (CDCl₃ 400 MHz): δ 8.80 (s, 2H), 3.00-2.90 (m, 2H), 2.77 (s, 3H), 2.70-2.60 (m, 2H), 2.60-2.50 (m, 2H), 2.40-2.25 (m, 1H).

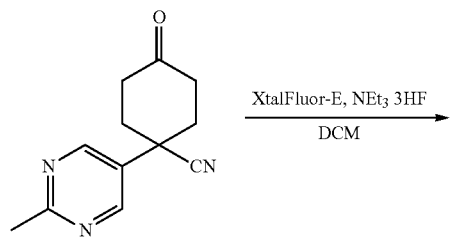

4,4-difluoro-1-(2-methylpyrimidin-5-yl)cyclohexanecarbonitrile

A solution of 1-(2-methylpyrimidin-5-yl)-4-oxocyclohexanecarbonitrile (2.0 g, 9.3 mmol), XtalFlour-E (4.69 g, 20.47 mmol) and Et₃N.3HF (4.79 g, 29.76 mmol) in DCM (40 mL) was stirred at room temperature overnight. The reaction mixture was quenched by sat. NaHCO₃ and extracted with DCM (3×50 mL). The organic layer was dried over Na₂SO₄ and concentrated. The crude product was purified by flash column chromatography to give 4,4-difluoro-1-(2-methylpyrimidin-5-yl)cyclohexanecarbonitrile (1.2 g, yield: 54%), which was not pure and used directly for next step.

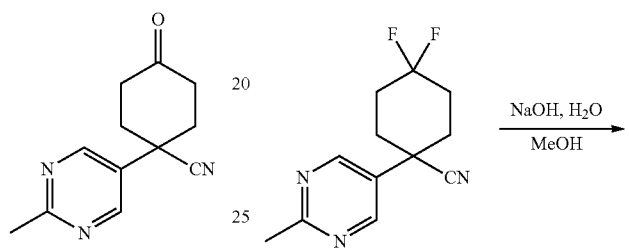

4,4-difluoro-1-(2-methylpyrimidin-5-yl)cyclohexanecarboxylic acid

To a mixture of 4,4-difluoro-1-(2-methylpyrimidin-5-yl)cyclohexanecarbonitrile (1.2 g, 5.1 mmol) in MeOH/H₂O (20 mL, 1:1) was added NaOH (612 mg, 15.3 mmol) and heated to 100° C. overnight. The MeOH was removed in vacua. The aqueous layer was extracted with EtOAc (3×30 mL) and the organic layers was discarded. The aqueous layer was adjusted pH to 3~4 with 3N HCl and extracted with EtOAc (3×30 mL). The organic layer was dried over Na₂SO₄ and concentracted to give 4,4-difluoro-1-(2-methylpyrimidin-5-yl)cyclohexanecarboxylic acid (1.2 g, yield: 92%). ¹H NMR (CDCl₃ 400 MHz): δ 8.81 (s, 2H), 2.80-2.60 (m, 5H), 2.20-2.00 (in, 6H).

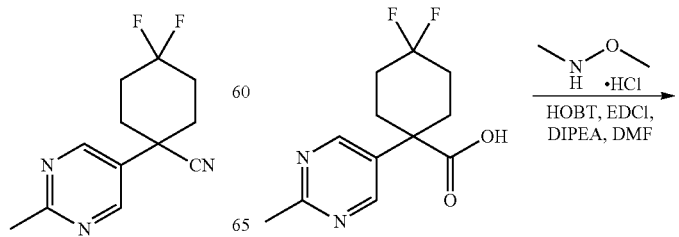

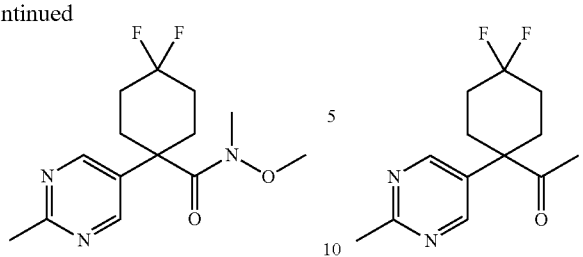

4,4-difluoro-N-methoxy-N-methyl-1-(2-methylpyrimidin-5-yl)cyclohexanecarboxamide A solution of 4,4-difluoro-1-(2-methylpyrimidin-5-yl)cyclohexanecarboxylic acid (1.2 g, 4.68 mmol), N,O-dimethylhydroxylamine hydrochloride (456 mg, 4.68 mmol), HOBt (759.33 mg, 5.62 mmol), EDCI.HCl (1.08 g, 5.62 mmol) and DIPEA (3.23 mL, 18.73 mmol) in DMF (20 mL) was stirred at room temperature. The reaction mixture was added water and extracted with EtOAc (3×50 mL). The organic layer was washed with brine, dried over $Na_2SO_4$ and concentrated to give 4,4-difluoro-N-methoxy-N-methyl-1-(2-methylpyrimidin-5-yl)cyclohexanecarboxamide (380 mg), which was used for the next step directly. About 0.9 g of 4,4-difluoro-1-(2-methylpyrimidin-5-yl)cyclohexanecarboxylic acid was recycled.

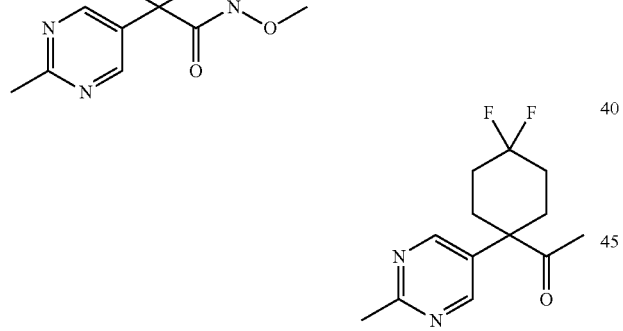

1-(4,4-difluoro-1-(2-methylpyrimidin-5-yl)cyclohexyl)ethanone

A solution of 4,4-difluoro-N-methoxy-N-methyl-1-(2-methylpyrimidin-5-yl)cyclohexanecarboxamide (700 mg, 2.34 mmol) in THF (20 mL) was added MeMgBr (11.7 mL, 35.12 mmol, 3M in $Et_2O$) at 0° C. and stirred at room temperature for 4 h. The reaction mixture was quenched by saturated $NH_4Cl$ at 0° C. and extracted with EtOAc (2×50 mL). The organic layer was washed with brine, dried over $Na_2SO_4$ and concentrated to give crude product, which was purified by flash chromatography (EtOAc: petroluem ether=1:3~3:2) to give 1-(4,4-difluoro-1-(2-methylpyrimidin-5-yl)cyclohexyl)ethanone (350 mg, yield: 59%). $^1$H NMR ($CDCl_3$ 400 MHz): δ 8.58 (s, 2H), 2.73 (s, 3H), 2.55-2.45 (m, 2H), 2.20-1.85 (in, 9H).

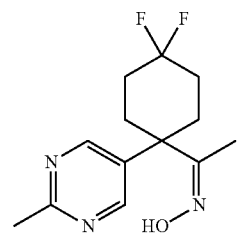

(Z)-1-(4,4-difluoro-1-(2-methylpyrimidin-5-yl)cyclohexyl)ethanone oxime

A mixture of 1-(4,4-difluoro-1-(2-methylpyrimidin-5-yl)cyclohexyl)ethanone (350 mg, 1.38 mmol), $NH_2OH.HCl$ (143.7 mg, 2.07 mmol) and NaOH (165.6 mg, 4.14 mmol) in $EtOH/H_2O$ (16 mL, 1:1) was heated to 80° C. overnight. The EtOH was removed. The residue was extracted with EtOAc (2×20 mL). The organic layer was dried over $Na_2SO_4$ and concentrated to give (Z)-1-(4,4-difluoro-1-(2-methylpyrimidin-5-yl)cyclohexyl)ethanone oxime (320 mg), which was used for the next step directly.

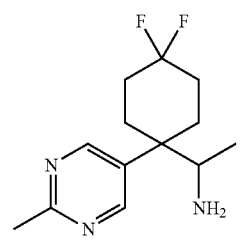

1-(4,4-difluoro-1-(2-methylpyrimidin-5-yl)cyclohexyl)ethanamine

A mixture of (Z)-1-(4,4-difluoro-1-(2-methylpyrimidin-5-yl)cyclohexyl)ethanone oxime (320 mg, 1.19 mmol) and aq.$NH_3$ (2 mL) was hydrogenated with Raney Ni (300 mg) under $H_2$ (50 Psi) for 3 h. The reaction mixture was filtered and concentrated. The residue was dissolved in EtOAc (15 mL), dried over $Na_2SO_4$ and concentrated to give 1-(4,4-difluoro-1-(2-methylpyrimidin-5-yl)cyclohexyl)ethanamine (300 mg), which was used for the next step directly.

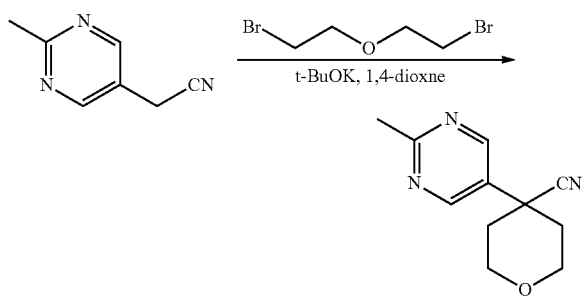

4-(2-methylpyrimidin-5-yl)tetrahydro-2H-pyran-4-carbonitrile

A solution of 2-(2-methylpyrimidin-5-yl)acetonitrile (4 g, 0.03 amol) and 1-bromo-2-(2-bromoethoxy)ethane (7.66 g, 0.033 mol) in 1,4-dioxane (60 mL) was added t-BuOK (66 mL, 0.066 mol, 1M in THF) and heated to 80° C. for 4 h. The reaction mixture was cooled to room temperature, quenched by sat.NH$_4$Cl. The 1,4-dioxane was removed under reduced pressure. The residue aqueous layer was extracted with EtOAc (3×150 mL). The organic layer was dried over Na$_2$SO$_4$ and concentracted to give 4-(2-methylpyrimidin-5-yl)tetrahydro-2H-pyran-4-carbonitrile (5.5 g, yield: 90.5%). $^1$H NMR (CDCl$_3$ 400 MHz): δ 8.75 (s, 2H), 4.15-4.05 (m, 2H), 3.95-3.85 (m, 2H), 2.75 (s, 3H), 2.15-2.00 (m, 4H).

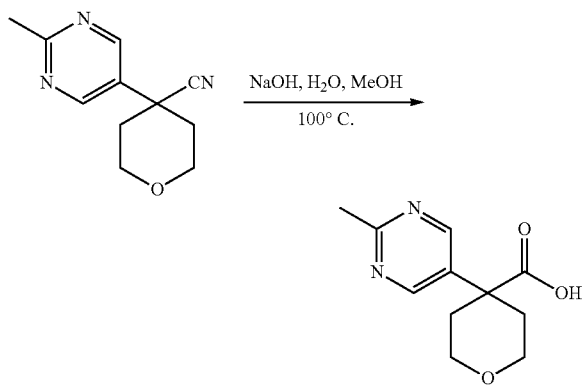

4-(2-methylpyrimidin-5-yl)tetrahydro-2H-pyran-4-carboxylic acid

A mixture of 4-(2-methylpyrimidin-5-yl)tetrahydro-2H-pyran-4-carbonitrile (5.5 g, 0.027 mol) in MeOH/H$_2$O (60 mL, 1:1) was added NaOH (3.25 g, 0.081 mol) and heated to 100° C. overnight. The MeOH was removed in vacuo. The aqueous layer was extracted with EtOAc (2×30 mL) and the organic layers was discarded. The aqueous layer was adjusted pH to 2~3 with 3N HCl and extracted with EtOAc (6×50 mL). The organic layer was dried over Na$_2$SO$_4$ and concentracted to give 4-(2-methylpyrimidin-5-yl)tetrahydro-2H-pyran-4-carboxylic acid (4.0 g, yield: 67%). $^1$H NMR (DMSO-d$_6$ 400 MHz): δ13.04 (br, 1H), 8.71 (s, 2H), 3.80-3.70 (m, 2H), 3.60-3.40 (m, 2H), 2.61 (s, 3H), 2.40-2.30 (m, 2H), 2.00-1.85 (m, 2H).

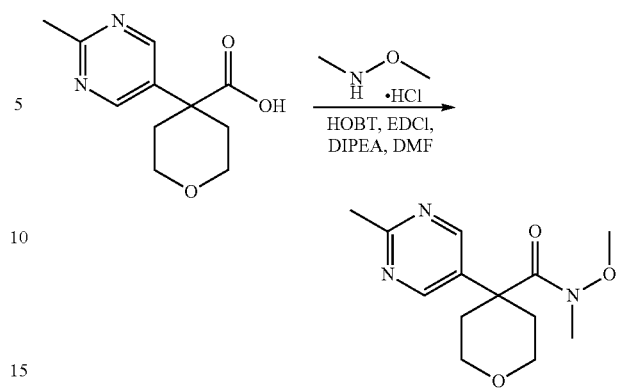

N-methoxy-N-methyl-4-(2-methylpyrimidin-5-yl)tetrahydro-2H-pyran-4-carboxamide A solution of 4-(2-methylpyrimidin-5-yl)tetrahydro-2H-pyran-4-carboxylic acid (4.0 g, 18.02 mmol), N,O-dimethylhydroxylamine hydrochloride (2.1 g, 21.6 mmol), HOBt (2.92 g, 21.6 mmol), EDCI.HCl (4.15 g, 21.62 mmol) and DIPEA (15.6 mL, 90.1 mmol) in DMF (50 mL) was stirred at room temperature overnight. To the reaction mixture was added water and extracted with EtOAc (3×200 mL). The organic layer was washed with brine, dried over Na$_2$SO$_4$ and concentrated to give crude product, which was purified by flash column chromatography (EtOAc:petroleum ether=1:1) to give N-methoxy-N-methyl-4-(2-methylpyrimidin-5-yl)tetrahydro-2H-pyran-4-carboxamide (3.0 g, yield: 63%). $^1$H NMR (CDCl$_3$ 400 MHz): δ 8.55 (s, 2H), 3.90-3.75 (m, 4H), 3.14 (s, 3H), 2.95 (s, 3H), 2.72 (s, 3H), 2.55-2.45 (m, 2H), 2.06-1.95 (m, 2H).

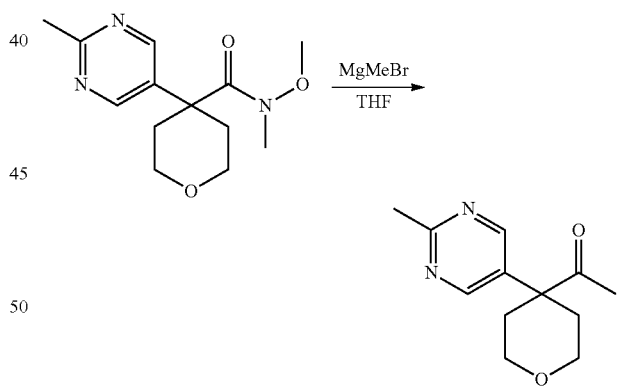

1-(4-(2-methylpyrimidin-5-yl)tetrahydro-2H-pyran-4-yl)ethanone

To a solution of N-methoxy-N-methyl-4-(2-methylpyrimidin-5-yl)tetrahydro-2H-pyran-4-carboxamide (1.0 g, 3.0 mmol, 80% purity in LC-MS) in THF (10 mL) was added MeMgBr (7.05 mL, 21.1 mmol, 3M in Et$_2$O) at 0° C. and stirred at room temperature for 3 h. The reaction mixture was quenched by saturated NH$_4$Cl at 0° C. and extracted with EtOAc (3×50 mL). The organic layer was washed with brine, dried over Na$_2$SO$_4$ and concentrated to give crude product, which was purified by flash column chromatography (EtOAc:petroleum ether=1:1) to give 1-(4-(2-methyl-pyrimidin-5-yl)tetrahydro-2H-pyran-4-yl)ethanone (0.3 g, yield: 69.3%). $^1$H NMR (CDCl$_3$ 400 MHz): δ 8.58 (s, 2H), 3.90-3.80 (m, 2H), 3.65-3.55 (m, 2H), 2.75 (s, 3H), 2.50-2.40 (m, 2H), 2.15-2.05 (m, 2H), 2.02 (s, 3H).

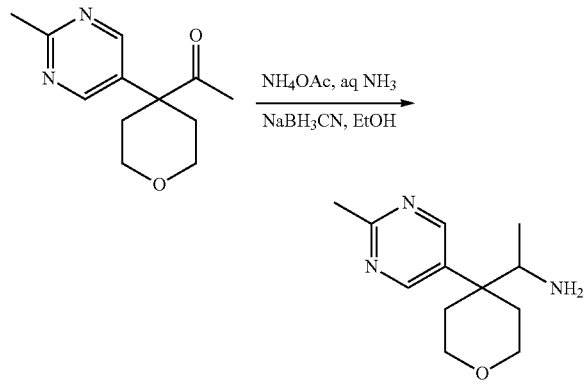

1-(4-(2-methylpyrimidin-5-yl)tetrahydro-2H-pyran-4-yl)ethanamine

A mixture of 1-(4-(2-methylpyrimidin-5-yl)tetrahydro-2H-pyran-4-yl)ethanone (300 mg, 1.35 mmol), saturated NH$_4$OAc in EtOH (15 mL) and aq.NH$_3$ (5 mL) was added NaCNBH$_3$ (255 mg, 4.05 mmol) and heated to reflux overnight. The EtOH was removed. The residue was extracted with EtOAc (5×10 mL) and the organic layer was discarded. The precipitation of solid was collected by filtration from the aqueous layer after 16 hours to give 1-(4-(2-methylpyrimidin-5-yl)tetrahydro-2H-pyran-4-yl)ethanamine (100 mg, yield: 33.3%). $^1$H NMR (DMSO-d$_6$ 400 MHz): δ 8.67 (s, 2H), 3.80-3.65 (m, 2H), 3.20-3.05 (m, 2H), 2.63 (s, 3H), 2.45-2.35 (m, 1H), 2.35-2.25 (m, 2H), 1.81-1.70 (m, 2H), 0.87 (d, J=6.4 Hz, 3H).

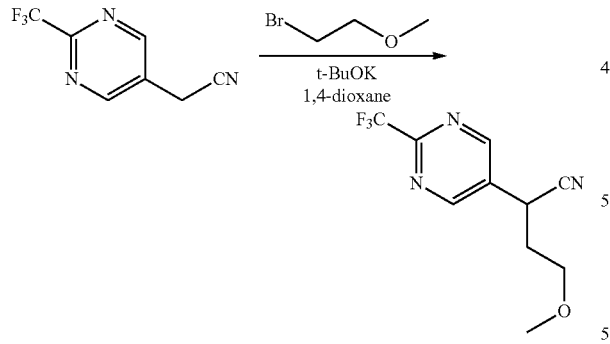

4-methoxy-2-(2-(trifluoromethyl)pyrimidin-5-yl)butanenitrile

A solution of 2-(2-(trifluoromethyl)pyrimidin-5-yl)acetonitrile (500 mg, 2.67 mmol) and 1-bromo-2-methoxyethane (419 mg, 2.81 mmol) in 1,4-dioxane (5 mL) was degassed and added t-BuOK (2.81 mL, 2.81 mmol, 1M in THF) at 0° C. The resulting mixture was stirred at room temperature overnight. The reaction mixture was quenched by sat.NH$_4$Cl and extracted with EtOAc (3×10 mL). The organic layer was dried over Na$_2$SO$_4$ and concentrated. The crude product was purified by flash column chromatography (EtOAc: petroleum ether=1:10) to give 4-methoxy-2-(2-(trifluoromethyl)pyrimidin-5-yl)butanenitrile (100 mg, yield: 15%, 85% purity in LCMS, [M+H]=246).

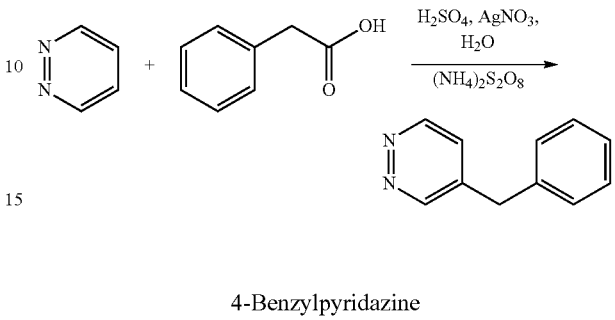

4-Benzylpyridazine

A solution of pyridazine (2.2 g, 27.5 mmol) and 2-phenylacetic acid (18.7 g, 137.5 mmol), AgNO$_3$ (1.4 g, 8.25 mmol) in 2N H$_2$SO$_4$ (27.7 ml) was heated to 60-70° C. under stirring, then, a solution of (NH$_4$)$_2$S$_2$O$_8$ (18.6 g, 82.5 mmol) in 80 ml of water was added within 20 minutes, After heating to 70-90° C. for 1.5 hour, the reaction solution was cooled to room temperature and extracted with DCM (2×100 ml), the combined organic layers were washed with 2N H$_2$SO$_4$ (3×70 ml), then, the combined aqueous layer was made alkaline with 50% NaOH and extracted with DCM (3×80 ml), dried over Na$_2$SO$_4$ and concentrated to get the crude product, which was purified by column chromatography on silica gel (petroleum Ether:EtOAc=2:1) to afford 4-benzylpyridazine (1.0 g, yield: 22%). $^1$H NMR (CDCl$_3$ 400 MHz): δ 9.09 (s, 1H), 9.06 (d, J=5.2 Hz, 1H), 7.40-7.28 (m, 3H), 7.25-7.20 (m, 1H), 7.18 (d, J=7.2 Hz, 2H), 4.0 (s, 2H).

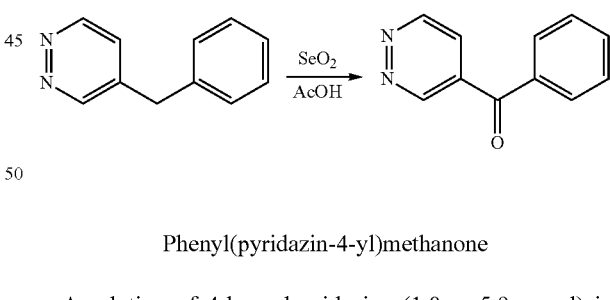

Phenyl(pyridazin-4-yl)methanone

A solution of 4-benzylpyridazine (1.0 g, 5.9 mmol) in AcOH (28 mL) was added dropwise to a stirring suspension of SeO$_2$ (3.2 g, 29.5 mmol) in AcOH (28 mL), the resulting mixture was heated to 100° C. for 1 h. TLC showed the starting material had disappeared, then the reaction solution was filtrated, the filtration was concentrated under reduced pressure, and Sat.aq Na$_2$CO$_3$ was added to adjust PH=9-10, then, extracted with DCM (50 mL×3), washed by brine, dried over Na$_2$SO$_4$ and concentrated to get the phenyl (pyridazin-4-yl)methanone (1.0 g, yield: 91%). $^1$H NMR (CDCl$_3$ 400 MHz): δ 9.50-9.45 (m, 2H), 7.83 (d, J=7.6 Hz, 2H), 7.78-7.74 (dd, J=5.2, 2.4 Hz, 1H), 7.74-7.68 (m, 1H), 7.57 (t, J=7.2 Hz, 2H).

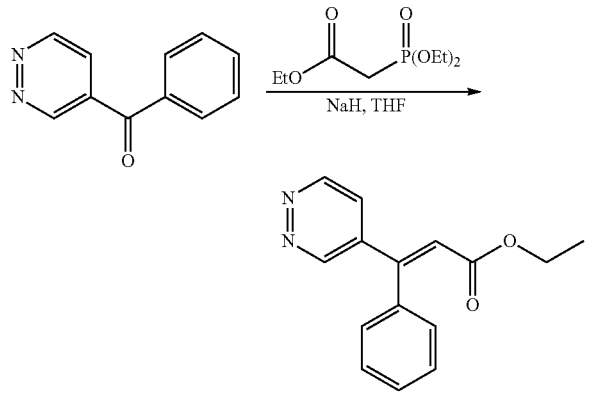

(E)-Ethyl 3-phenyl-3-(pyridazin-4-yl)acrylate

To a solution of ethyl 2-(diethoxyphosphoryl)acetate (1.46 g, 7.93 mmol) in THF (40 mL) was added NaH (476 mg, 11.9 mmol) in portions at 0° C., the resulting mixture was stirred at 0° C. for 20 minutes, then, the phenyl (pyridazin-4-yl)methanone was added in portions, the resulting mixture was stirred at 0° C. for 4 hour. The LC-MS showed the MS signal of desired product was detected, then, the reaction solution was added sat. aq. NH$_4$Cl at 0° C., then, extracted with AcOEt (3×50 ml), the combined organic layers were washed with brine, dried over Na$_2$SO$_4$ and concentrated to get the crude product, which was purified by column chromatography on silica gel (petroleum Ether: EtOAc=2:1) to afford (E)-ethyl 3-phenyl-3-(pyridazin-4-yl) acrylate (1.68 g, yield: 83.2%). $^1$H NMR (CDCl$_3$ 400 MHz): δ 9.25 (d, J=5.2 Hz, 1H), 9.06 (s, 1H), 7.47-7.32 (m, 4H), 7.30-7.20 (m, 2H), 6.55 (s, 1H), 4.95 (q, J=7.2 Hz, 2H), 1.16 (t, J=7.2 Hz, 3H).

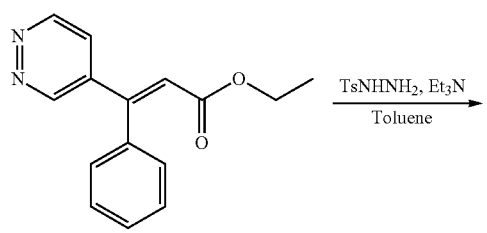

Ethyl 3-phenyl-3-(pyridazin-4-yl)propanoate

To a solution of (E)-ethyl 3-phenyl-3-(pyridazin-4-yl) acrylate (1.8 g, 7.09 mmol) in PhMe (40 mL), TsNHNH$_2$ (2.64 g, 14.2 mmol) and Et$_3$N (2.15 g, 21.3 mmol) was added, the resulting mixture was heated to 100° C. overnight. The reaction was detected by TLC, TLC showed the appearance of desired product, then, the solvent was removed under reduced pressure, H$_2$O was added and extracted with AcOEt (3×50 ml), the combined organic layers were washed by brine, dried over Na$_2$SO$_4$ and concentrated to get the crude product, which was purified by column chromatography on silica gel (Petroleum Ether: EtOAc=3:2) to afford ethyl 3-phenyl-3-(pyridazin-4-yl)propanoate (1.20 g, yield: 66%). $^1$H NMR (CDCl$_3$ 400 MHz): δ 9.12 (d, J=2.0 Hz, 1H), 9.09 (d, J=6.8 Hz, 1H), 7.40-7.24 (m, 4H), 7.20 (d, J=7.2 Hz, 2H), 4.56 (t, J=8.0 Hz, 1H), 4.08 (q, J=7.2 Hz, 2H), 3.09 (d, J=8.0 Hz, 2H), 1.15 (t, J=7.2 Hz, 3H).

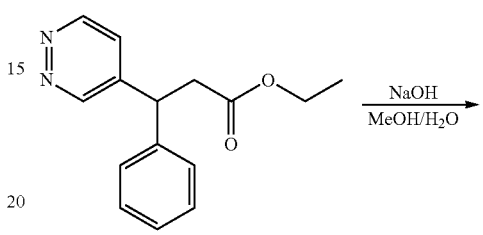

3-Phenyl-3-(pyridazin-4-yl)propanoic acid

Toa solution of ethyl 3-phenyl-3-(pyridazin-4-yl)propanoate (1.0 g, 3.9 mmol) in MeOH (20 mL) was added 2N NaOH (6 mL, 11.7 mmol), the resulting mixture was stirred at room temperature overnight. MeOH was removed under reduced pressure and pH adjusted to 4-5 by aq. HCl (2N), extracted with AcOEt (6×100 ml), the combined organic layer was washed with brine, dried over Na$_2$SO$_4$ and concentrated to get the 3-phenyl-3-(pyridazin-4-yl)propanoic acid (750 mg, yield: 84%). $^1$H NMR (CDCl$_3$ 400 MHz): δ 9.27 (d, J=1.2 Hz, 1H), 9.09 (dd, J=4.0, 1.2 Hz, 1H), 7.67 (dd, J=5.6, 2.4 Hz, 1H), 7.41-7.36 (m, 2H), 7.34-7.27 (m, 2H), 7.24-7.18 (m, 1H), 4.48 (t, J=8.0 Hz, 1H), 3.27-3.15 (m, 1H), 3.10-3.00 (m, 1H).

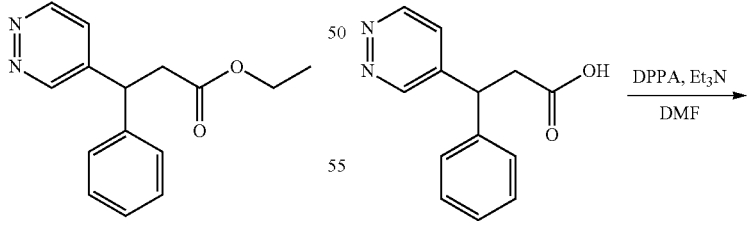

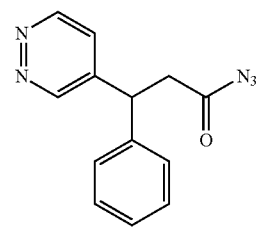

3-Phenyl-3-(pyridazin-4-yl)propanoyl azide

To a solution of 3-phenyl-3-(pyridazin-4-yl)propanoic acid (570 mg, 2.5 mmol) in DMF (30 mL) was added Et₃N (505 mg, 5.0 mmol), followed by the DPPA (722 mg, 2.6 mmol) in portions at 0° C., the resulting mixture was stirred at room temperature for 1.5 hour. The reaction was diluted with water, extracted with AcOEt (3×40 ml), the combined organic layer was washed by brine, dried over Na₂SO₄ and concentrated to get the 3-phenyl-3-(pyridazin-4-yl)propanoyl azide (crude 650 mg), which was used for next step directly.

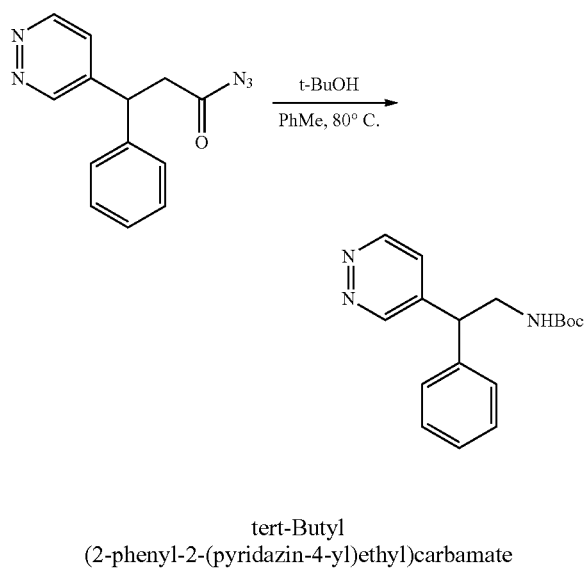

tert-Butyl (2-phenyl-2-(pyridazin-4-yl)ethyl)carbamate

A solution of 3-phenyl-3-(pyridazin-4-yl)propanoyl azide (650 mg, 2.57 mmol) in t-BuOH (3 ml) and PhMe (10 ml) was stirred at 80° C. overnight. The reaction was detected by LC-MS, LC-MS indicate the desired product was formed, then, the solvent was removed under reduced pressure to get the crude product, which was purified by column chromatography on silica gel (petroleum Ether:EtOAc=3:2-1:2) to afford tert-butyl (2-phenyl-2-(pyridazin-4-yl)ethyl)carbamate (200 mg, yield: 26%). ¹H NMR (CDCl₃, 400 MHz): δ 9.12-9.07 (m, 2H), 7.42-7.28 (m, 4H), 7.23-7.18 (m, 2H), 4.62 (m, 1H), 4.30-4.20 (t, J=7.6 Hz, 1H), 3.95-3.83 (m, 1H), 3.75-3.65 (m, 1H), 1.40 (s, 9H).

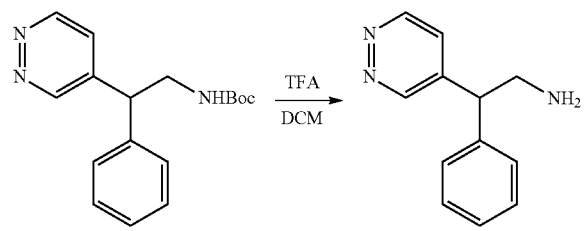 [SMILES: CC(C)(C)OC(=O)NCC(c1ccccc1)c1ccnnc1 ; NCC(c1ccccc1)c1ccnnc1]

2-Phenyl-2-(pyridazin-4-yl)ethanamine

A solution of tert-butyl (2-phenyl-2-(pyridazin-4-yl)ethyl)carbamate (120 mg, 0.40 mmol) in DCM (2 ml) and TFA (2 ml) was stirred at room temperature for 4 hours. The solvent was removed under reduced pressure and the residue was diluted with sat.aq Na₂CO₃ to adjust pH=9-10, then, extracted with AcOEt (3×30 ml), the combined organic layer was washed with brine, dried over Na₂SO₄ and concentrated to get the 2-phenyl-2-(pyridazin-4-yl)ethanamine (crude 80 mg), which was used for next step directly.

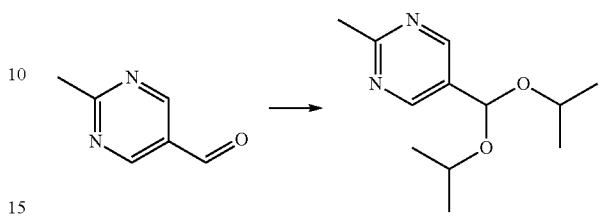

5-(Diisopropoxymethyl)-2-methylpyrimidine

To a mixture of 2-methylpyrimidine-5-carbaldehyde (1.0 g, 8.2 mmol) and triisopropoxymethane (2.3 g, 12 mmol) in isopropanol (15 ml) was added methanesulfonic acid (0.079 g, 0.053 ml, 0.819 mmol). The reaction was stirred at room temperature for 23 hours. Potassium carbonate (1.132 g, 8.19 mmol) was added and the mixture was filtered and the solution was concentrated in vacuo. The crude mixture was purified by flash chromatography to yield 5-(diisopropoxymethyl)-2-methylpyrimidine (536 mg, 29%)

¹H NMR (500 MHz, CDCl₃) δ 8.71 (s, 2H), 5.60 (s, 1H), 3.93 (dt, J=12.3, 6.1 Hz, 2H), 2.74 (s, 3H), 1.21 (dd, J=14.8, 6.1 Hz, 12H).

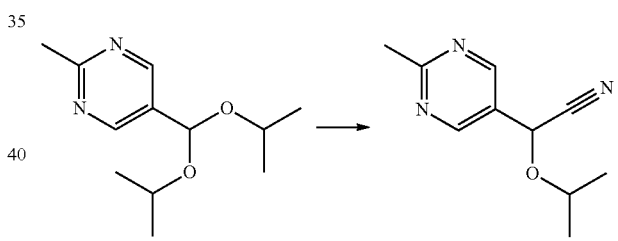

2-Isopropoxy-2-(2-methylpyrimidin-5-yl)acetonitrile

A solution of 5-diisopropoxymethyl-2-methyl-pyrimidine (335 mg, 1.49 mmol) in DCM (5 mL, 80 mmol) was cooled at 0° C. Zinc diiodide (47.7 mg, 0.149 mmol) TMSCN (219 uL, 1.64 mmol) were added and cooling removed. After stirring for 24 hours TLC indicated that starting materiale was present. TMSCN (60 uL, 0.45 mmol) and zinc diiodide (48 mg, 0.15 mmol) were added and the reaction was stirred for a further 3.5 hours. The reaction was poured into water (20 mL) and extracted with DCM (3×20 mL). The combined organic phases were washed with brine, dried over MgSO₄ and concentrated in vacuo. The crude product was purified by flash chromatography 2-Isopropoxy-2-(2-methylpyrimidin-5-yl)acetonitrile (217 mg, 76%).

¹H NMR (500 MHz, CDCl₃) δ 8.75 (s, 2H), 5.29 (s, 1H), 4.21-3.95 (m, 1H), 2.78 (s, 3H), 1.32 (dd, J=21.7, 6.1 Hz, 6H).

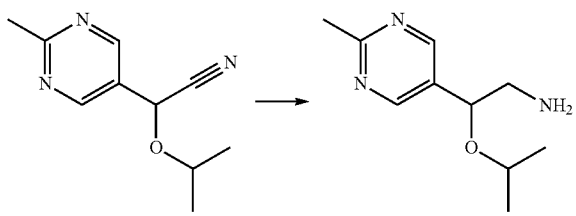

2-Isopropoxy-2-(2-methylpyrimidin-5-yl)ethanamine

2-Isopropoxy-2-(2-methylpyrimidin-5-yl)acetonitrile (169 mg, 0.884 mmol) was dissolved in methanol (10 ml) and 7M NH$_3$ in methanol (4 ml). Argon was bubbled through the solution for 5 minutes. To the reaction was added Raney nickel (100 mg, 1.704 mmol) and it was fitted with a H$_2$-filled balloon. After stirring at room temperature for 20 hours LCMS shows only around 30% conversion and raney nickel (100 mg, 1.70 mmol) was added. The reaction was stirred for another 72 hours, then filtered through a plug of celite and concentrated in vacuo. The crude product used for next reaction without further purification.

LC-MS (m/z) 196.2 (MH+), $t_R$ (minutes, Method D)=0.29.

The following intermediates were prepared in a similar way:
4-methoxy-2-(2-(trifluoromethyl)pyrimidin-5-yl)butan-1-amine;

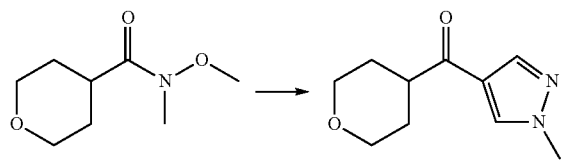

(1-Methyl-1H-pyrazol-4-yl)(tetrahydro-2H-pyran-4-yl)methanone

A solution of 4-iodo-1-methyl-1H-pyrazole (0.80 g, 3.9 mmol) in THF (7.04 g, 8.00 ml, 98 mmol) was cooled at 0° C. A solution of isopropylmagnesium chloride lithium chloride complex in THF (5.42 ml, 4.23 mmol, 0.78 molar) was added dropwise and the reaction was stifled for 1½ hour. A solution of N-methoxy-N-methyltetrahydro-2H-pyran-4-carboxamide (0.733 g, 4.23 mmol) in THF (2 mL) was added dropwise. Cooling was removed after 15 min and reaction was then stirred for 2 hours. To the mixture was added 2 M HCl (20 mL) and it was extracted with AcOEt (3×25 mL). The combined organic phases were washed with brine, dried over MgSO$_4$ and concentrated in vacuo. The crude product was purified by flash chromatography to yield (1-methyl-1H-pyrazol-4-yl)(tetrahydro-2H-pyran-4-yl)methanone (220 mg, 1.13 mmol, 29.4% yield).

$^1$H NMR (600 MHz, CDCl$_3$) δ 7.87 (s, 1H), 7.87 (s, 1H), 4.03 (ddd, J=11.4, 4.1, 2.4 Hz, 211), 3.92 (s, 3H), 3.49 (td, J=11.7, 2.3 Hz, 2H), 3.06 (tt, J=11.3, 3.8 Hz, 1H), 1.86 (dtd, J=13.8, 11.7, 4.4 Hz, 2H), 1.72 (ddd, J=13.4, 3.7, 2.0 Hz, 2H).

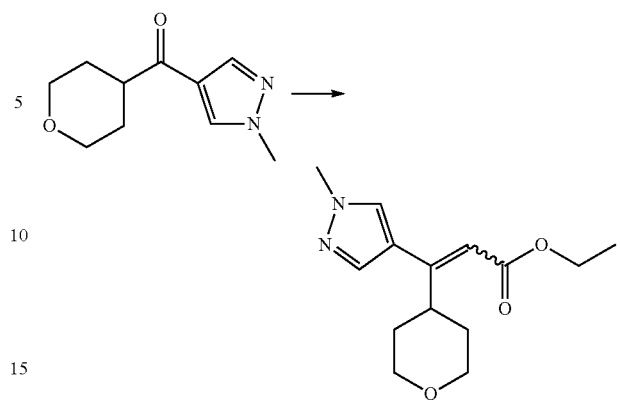

Ethyl 3-(1-methyl-1H-pyrazol-4-yl)-3-(tetrahydro-2H-pyran-4-yl)acrylate

Sodium hydride (60% suspension in mineral oil) (96 mg, 2.41 mmol, 60%) was suspended in THF (2 ml) under argon. Triethyl phosphonoacetate (492 mg, 0.435 ml, 2.19 mmol) was added dropwise to the mixture over a period of 30 min and the reaction was then stirred for 60 minutes. (1-Methyl-1H-pyrazol-4-yl)(tetrahydro-2H-pyran-4-yl)methanone (213 mg, 1.097 mmol) in THF (2.0 mL) was added dropwise. The reaction was stirred for 3 hours at room temperature. Heated for 22 hours at reflux and cooled to room temperature. The reaction was poured into H$_2$O (25 mL) and extracted with AcOEt (3×25 mL), the combined organic phases were washed with brine, dried over MgSO$_4$ and concentrated in vacuo. The crude product was used for the next step without further purification.

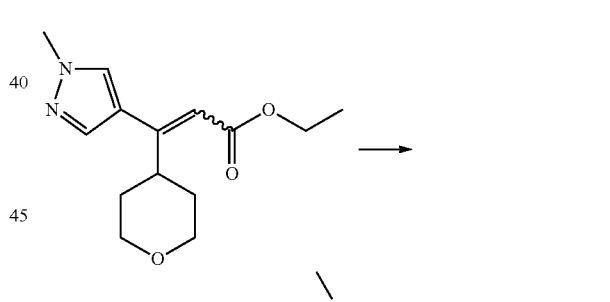

Ethyl 3-(1-methyl-1H-pyrazol-4-yl)-3-(tetrahydro-2H-pyran-4-yl)propanoate

Ethyl 3-(1-methyl-1H-pyrazol-4-yl)-3-(tetrahydro-2H-pyran-4-yl)acrylate (205 mg, 0.78 mmol) was dissolved in methanol (10 ml) and argon was bubbled through the solution for 5 minutes. To the solution was added 10% Pd/C (41 mg) and the flask was fitted with a balloon containing hydrogen. The reaction was stirred at room temperature for 16 hours. The catalyst was removed by filtration through a plug of celite. And solution was concentrated in vacuo. The crude product was used directly in the next reaction.

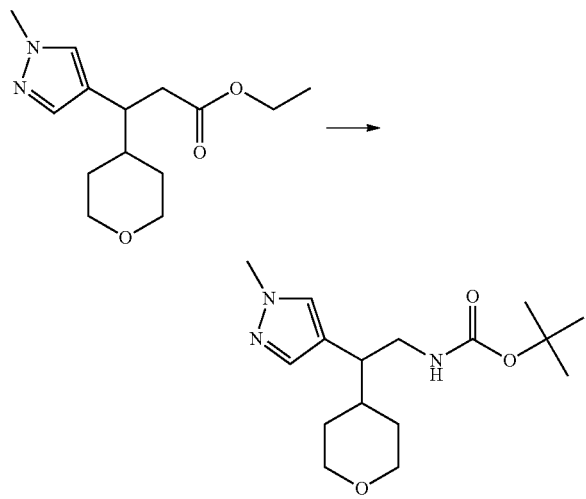

tert-Butyl (2-(1-methyl-1H-pyrazol-4-yl)-2-(tetrahydro-2H-pyran-4-yl)ethyl)carbamate Crude ethyl-3-(1-methyl-1H-pyrazol-4-yl)-3-(tetrahydro-2H-pyran-4-yl)propanoate (207 mg, 0.777 mmol) dissolved in THF (5 ml). Trimethylsilanol, sodium salt solution in TEM (0.855 ml, 0.855 mmol, 1 molar) was added at room temperature. The mixture stirred for 3 days and concentrated in vacuo. LCMS showed only partial conversion. Trimethylsilanol, sodium salt solution in THF (10 ml, 10.00 mmol, 1 molar) was added and mixture stirred overnight at room temperature. A 2 M HCl in solution in THF (20 mL) was added to the reaction and it was stirred for 30 minutes. The mixture was now filtered through a plug of celite and concentrated in vacuo. The crude carboxylic acid salt was suspended in tert-butanol (5 ml). Triethyl amine (0.189 g, 0.260 ml, 1.865 mmol) and diphenylphosphoryl azide (0.280 g, 0.219 ml, 1.017 mmol) were added and the mixture was heated at 80° C. overnight. The reaction was cooled to room temperature and poured into H$_2$O (15 mL) and extracted with AcOEt (3×15 mL). The combined organic phases were washed with brine, dried over MgSO4 and concentrated in vacuo. The crude product was purified by flash chromatography.

LC-MS (m/z) 310.2 (MH+), t$_R$ (minutes, Method D)=0.62.

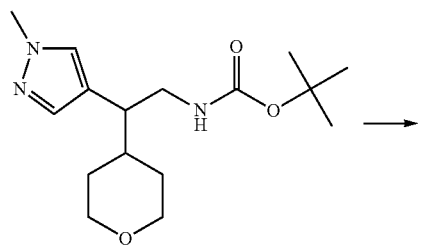

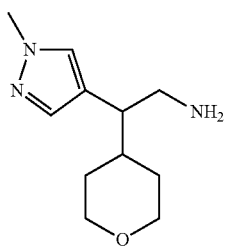

2-(1-Methyl-1H-pyrazol-4-yl)-2-(tetrahydro-2H-pyran-4-yl)ethanamine tert-Butyl (2-(1-methyl-1H-pyrazol-4-yl)-2-(tetrahydro-2H-pyran-4-yl)ethyl)carbamate (49 mg, 0.132 mmol) was dissolved in DCM (5 ml) and cooled at 0° C. TFA (740 mg, 0.5 ml, 6.49 mmol) was added and mixture stirred for 30 min after which cooling was removed and the mixture was stirred for a further 30 minutes.

Concentrated in vacuo to yield the crude amine as the trifluoroacetic acid salt.

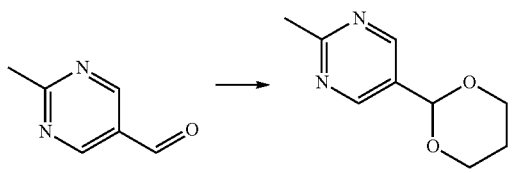

5-(1,3-Dioxan-2-yl)-2-methylpyrimidine

To a solution of 2-methylpyrimidine-5-carbaldehyde (0.808 g, 6.62 mmol) and propane-1,3-diol (1.01 g, 0.868 ml, 13.2 mmol) in toluene (7.6 ml) and THF (1.9 ml) was added p-toluenesulfonic acid (11 mg, 0.066 mmol). The reaction was heated at 65° C. for 4.5 hours. The reaction mixture was then poured into H$_2$O (50 mL) and extracted with AcOEt (3×50 mL). The combined organic phases were washed with brine, dried over MgSO$_4$ and concentrated in vacuo to yield 5-(1,3-dioxan-2-yl)-2-methylpyrimidine (620 mg, 3.44 mmol, 52%) used for next step without further purification.

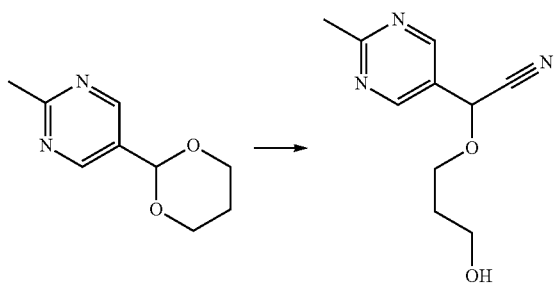

2-(3-Hydroxypropoxy)-2-(2-methylpyrimidin-5-yl)acetonitrile

To an ice-cold solution of 5-(1,3-dioxan-2-yl)-2-methylpyrimidine (140 mg, 0.78 mmol) in DCM (5.0 ml) was added zinc iodide (124 mg, 0.39 mmol). Trimethylsilyl cyanide (116 mg, 0.155 ml, 1.17 mmol) was added dropwise over a period of 10 minutes. Cooling was removed and the reaction was stirred for 40 hours at room temperature. The mixture was poured into H₂O (20 mL) and extracted with DCM (3×20 mL), the combined org. phases were washed with brine, dried over MgSO₄ and concetrated in vacuo. The crude product was used for next step without further purification.

¹H NMR (600 MHz, CDCl₃) δ 8.78 (s, 2H), 5.32 (s, 1H), 4.00 (dt, J=8.9, 6.0 Hz, 1H), 3.82 (dt, J=8.9, 6.1 Hz, 1H), 3.78 (t, J=6.0 Hz, 2H), 2.79 (s, 3H), 1.95 (p, J=6.0 Hz, 2H).

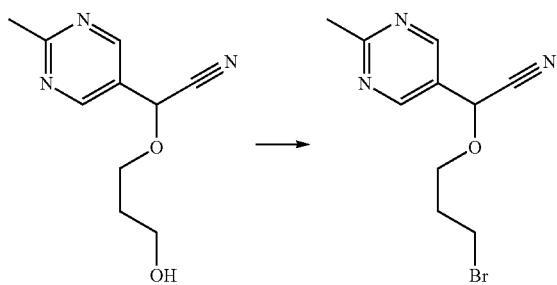

2-(3-Bromopropoxy)-2-(2-methylpyrimidin-5-yl) acetonitrile

A solution of 2-(3-hydroxypropoxy)-2-(2-methylpyrimidin-5-yl)acetonitrile (54 mg, 0.26 mmol) and CBr₄ (259 mg, 0.782 mmol) in DCM (3 ml) was cooled at 0° C. Triphenylphosphine (205 mg, 0.782 mmol) in DCM (1 ml) was added dropwise over a period of 5 minutes. The reaction was stirred for 2 hours and then allowed to warm to room temperature. To the mixture was added Et₂O (5 mL) and the cloudy solution was filtered through a plug of celite. The resulting solution was concentrated in vacuo and purified by flash chromatography to yield 2-(3-Bromopropoxy)-2-(2-methylpyrimidin-5-yl)acetonitrile.

¹H NMR (500 MHz, CDCl₃) δ 8.75 (s, 2H), 5.27 (s, 1H), 3.97 (m, 1H), 3.79 (m, 1H), 3.47 (t, J=6.3 Hz, 2H), 2.77 (s, 3H), 2.24-2.12 (m, 2H).

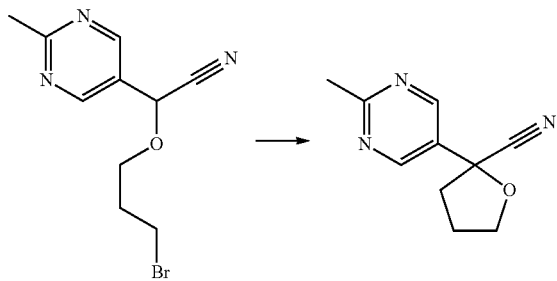

2-(2-Methylpyrimidin-5-yl)tetrahydrofuran-2-carbonitrile

A solution of 2-(3-bromopropoxy)-2-(2-methylpyrimidin-5-yl)acetonitrile (24 mg, 0.089 mmol) in THF (3 mL) was cooled at −78° C. Lithium bis(trimethylsilyl)amide in THF (141 μl, 0.141 mmol, 1 molar) was added slowly and the mixture was stirred for 1 hour at −78° C. To the reaction mixture was added sat. aq. NH₄Cl (10 mL) and the mixture was allowed to warm to room temperature. The reaction mixture was diluted with H₂O (10 mL) and extracted with AcOEt (3×15 mL). The combined org. phases were washed with brine, dried over MgSO₄ and concentrated in vacuo. The crude product was used directly for next step without further purification.

LC-MS (m/z) 190.1 (MIFF), t_R (minutes, Method D)=0.38.

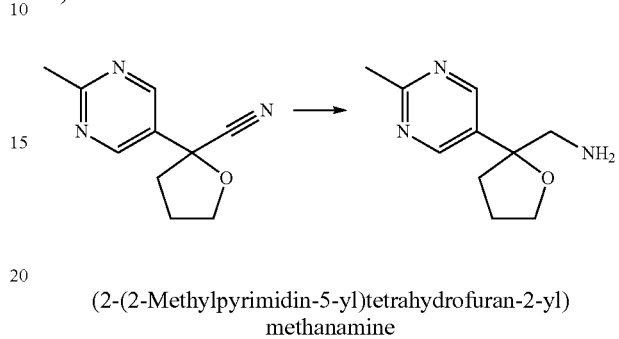

(2-(2-Methylpyrimidin-5-yl)tetrahydrofuran-2-yl) methanamine 2-(2-Methylpyrimidin-5-yl)tetrahydrofuran-2-carbonitrile (18 mg, 0.095 mmol) was dissolved in MeOH (5 ml) and 7M NH₃ in MeOH (1 ml). Argon was bubbled through the solution. Raney Nickel (6 mg, 0.1 mmol) was added and the flask was fitted with a H₂-balloon and stirred at room temperature for 1½ hour. Reaction was filtered through a plug of celite and concentrated in vacuo. Used for next step without further purification. LC-MS (m/z) 194.0 (MH+), t_R (minutes, Method D)=0.17.

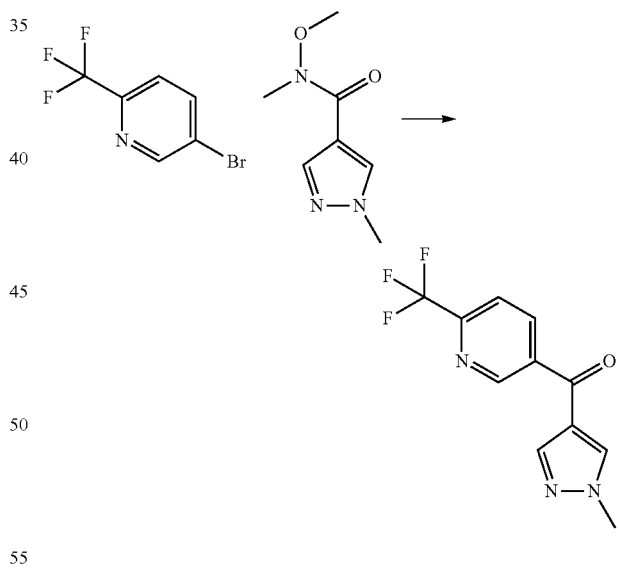

(1-methyl-1H-pyrazol-4-yl)(6-(trifluoromethyl)pyridin-3-yl)methanone

A solution of 5-bromo-2-(trifluoromethyl)pyridine (3.80 g, 16.82 mmol) in THF (24 ml) was cooled at −18° C. A solution of isopropylmagnesium chloride lithium chloride complex in THF (17.97 ml, 14.02 mmol, 0.78 molar) was added dropwise over a period of 30 minutes. The reaction was then cooled at −78° C. kept there for P/2 hour. The reaction was allowed to reach −3° C. before being cooled to −10° C. A solution of N-methoxy-N,1-dimethyl-1H-pyrazole-4-carboxamide (2.372 g, 14.02 mmol) in THF (8 ml) was added dropwise over a period of 5 minutes. The reaction was allowed to warm to room temperature and stirred over night. Cooled to 0° C. and a 2 M HCl solution (150 mL) was added slowly. The crude mixture was extracted with AcOEt (3×150 mL), the combined org. phases were washed with brine, dried over MgSO$_4$ and concentrated in vacuo. The crude product was purified by column chromatography to yield (1-methyl-1H-pyrazol-4-yl)(6-(trifluoromethyl)pyridin-3-yl)methanone 1.22 g (34%) as a light yellow solid.

$^1$H NMR (600 MHz, DMSO) δ 9.12 (d, J=2.0 Hz, 1H), 8.53 (s, 1H), 8.45 (ddd, J=8.0, 2.1, 0.4 Hz, 1H), 8.10 (dd, J=8.1, 0.7 Hz, 1H), 8.06 (d, J=0.7 Hz, 1H), 3.93 (s, 3H). LC-MS (m/z) 256.0 (MH+), t$_R$ (minutes, Method D)=0.54.

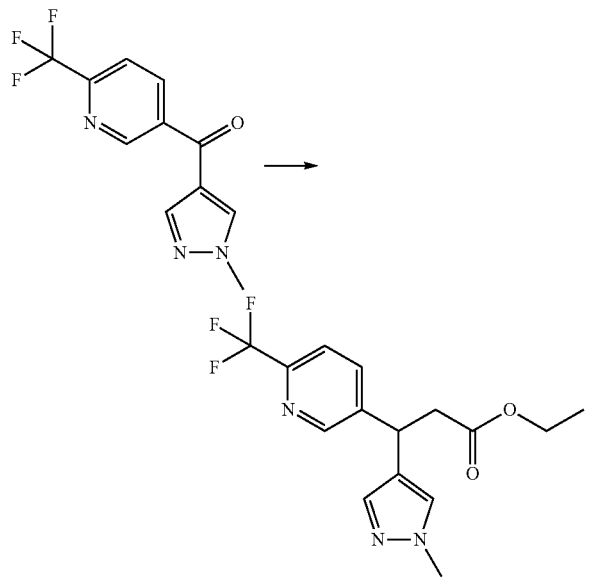

Ethyl 3-(1-methyl-1H-pyrazol-4-yl)-3-(6-(trifluoromethyl)pyri din-3-yl)propanoate Triethyl phosphonoacetate (2.1 g, 1.9 ml, 9.4 mmol) was added dropwise to a suspension of sodium hydride suspension (0.41 g, 10.3 mmol, 60%) in THF (10 ml). The mixture was stirred for 1½ hour and then a solution of (1-methyl-1H-pyrazol-4-yl)(6-(trifluoromethyl)pyridin-3-yl)methanone (1.2 g, 4.7 mmol) in THF (10 ml) was added dropwise. The reaction was stirred for 2 hours at room temperature and then heated at 65° C. overnight. The mixture was cooled to room temperature and poured into H$_2$O (25 mL), extracted with EA (3×25 mL). The combined org. phases washed were washed with brine, dried over MgSO$_4$ and concentrated in vacuo.

To the crude product was added MeOH (20 ml) and 10% Pd/C (0.500 g) and the mixture was flushed with argon for 5 min and then fitted with a balloon containing H$_2$. After stirring at room temperature overnight complete conversion was observed by TLC. The reaction was filtered through celite, concentrated in vacuo and purified by flash chromatography to yield 1.15 g (75%) ethyl 3-(1-methyl-1H-pyrazol-4-yl)-3-(6-(trifluoromethyl)pyridin-3-yl)propanoate.

$^1$H NMR (600 MIL, DMSO) δ 8.75 (d, J=2.0 Hz, 1H), 8.01 (dd, J=8.1, 2.1 Hz, 1H), 7.84 (d, J=8.1 Hz, 1H), 7.57 (s, 1H), 7.37 (d, J=0.5 Hz, 1H), 4.50 (t, J=8.0 Hz, 1H), 3.97 (qd, J=7.1, 0.9 Hz, 2H), 3.75 (s, 3H), 3.11 (d, J=8.0 Hz, 2H), 1.05 (t, J=7.1 Hz, 3H).

LC-MS (m/z) 328.0 (MI-1+), t$_R$ (minutes, Method E)=0.60.

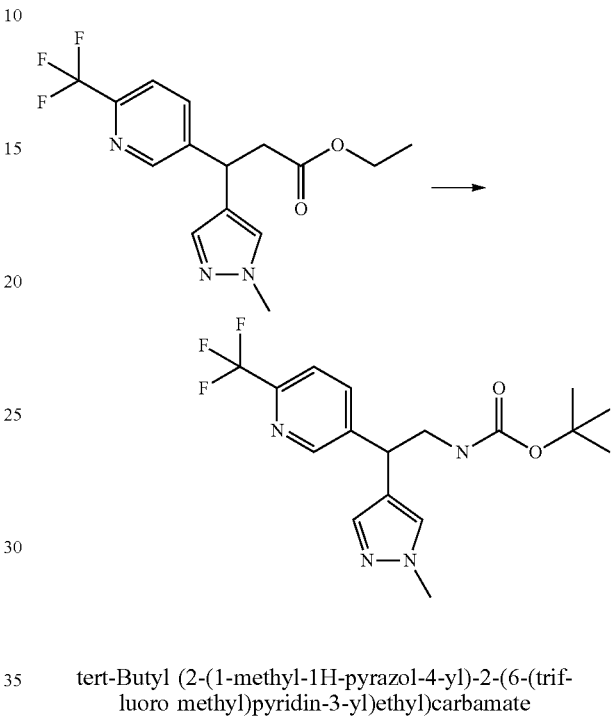

tert-Butyl (2-(1-methyl-1H-pyrazol-4-yl)-2-(6-(trifluoro methyl)pyridin-3-yl)ethyl)carbamate Ethyl 3-(1-methyl-1H-pyrazol-4-yl)-3-(6-(trifluoromethyl)pyridin-3-yl)propanoate (1.15 g, 3.51 mmol) was mixed with trimethylsilanol, sodium salt solution in THF (30 ml, 30.0 mmol, 1 molar) and stirred for 24 hours at room temperature. Trimethylsilanol, sodium salt solution in THF (30 ml, 30.0 mmol, 1 molar) added and mixture stirred overnight at room temperature, LCMS shows incomplete comversion and reaction heated at reflux for 3 hours. The mixture was cooled on an ice bath and HCl in Et2O (48.0 g, 40 ml, 80 mmol, 2 molar) was added and after 10 min the mixture was concentrated in vacuo. The crude reaction mixture was then suspended dry THF (150 mL) and the solid filtered off. The liquid phase was concentrated in vacuo and used for next step without purification. 3-(1-methyl-1H-pyrazol-4-yl)-3-(6-(trifluoromethyl)pyri din-3-yl)propanoic acid (0.531 g, 1.774 mmol) dissolved in tert-butanol (10 ml. TEA (0.395 g, 0.544 ml, 3.90 mmol) and diphenylphosphoryl azide (0.59 g, 0.46 ml, 2.1 mmol) were added. Heated at 80° C. for 29 hours. The reaction was poured into H$_2$O (50 mL) and extracted with EA (3×50 mL), the combined org. phases washed with brine, dried over MgSO$_4$, concentrated in vacuo and purified by flash chromatography to yield 49 mg (7%) tert-butyl (2-(1-methyl-1H-pyrazol-4-yl)-2-(6-(trifluoromethyl)pyridin-3-yl)ethyl)carbamate.

LC-MS (m/z) 371.2 (MI-1+), t$_R$ (minutes, Method E)=0.67.

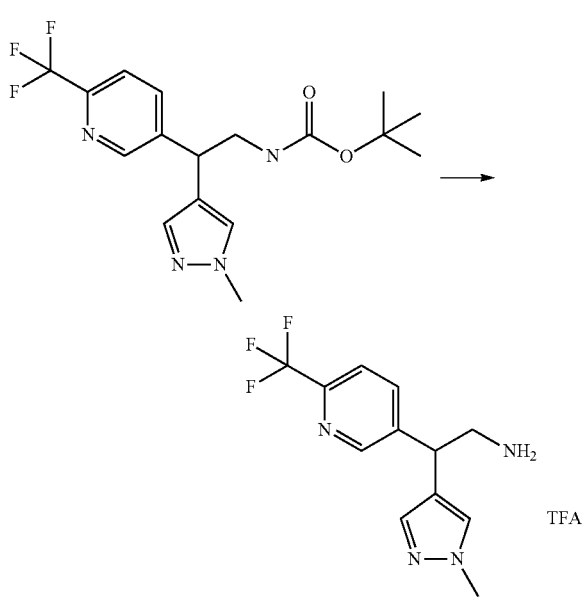

2-(1-Methyl-1H-pyrazol-4-yl)-2-(6-(trifluoromethyl) pyridin-3-yl)ethanamine Tert-butyl (2-(1-methyl-1H-pyrazol-4-yl)-2-(6-(trifluoromethyl)pyridin-3-yl)ethyl)carbamate (49 mg, 0.132 mmol) was dissolved in DCM (5 ml) and cooled at 0° C. TFA (740 mg, 0.5 ml, 6.49 mmol) was added and mixture stirred for 30 min after which cooling was removed and the mixture was stirred for a further 30 minutes. Concentrated in vacuo to yield the crude amine as the trifluoroacetic acid salt.

The following intermediates were prepared in a similar way:

2-(1-methyl-1H-pyrazol-5-yl)-2-(2-(trifluoromethyl)pyrimidin-5-yl)ethanamine;

2-(1-methyl-1H-imidazol-4-yl)-2-(2-(trifluoromethyl)pyrimidin-5-yl)ethanamine;

C-(1-Methyl-4-phenyl-piperidin-4-yl)-methylamine

Prepared according to the ref: Diamond, J. et al. *J. Org. Chem.*, 1965, 1840

C-(1-Pyridin-3-yl-cyclopentyl)-methylamine

Commercially available from Chengdu Chemicals 2-(4-Chloro-phenyl)-2-phenyl-ethylamine Commercially available from Sigma Aldrich Chemicals Compounds of formula I can be prepared by employing standard amide bond forming coupling procedures by the reaction of a carboxylic acid of formula II with an amine of formula III.

Scheme 1.

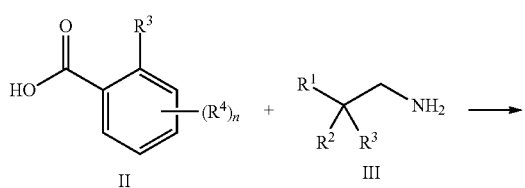

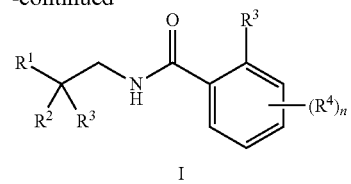

This reaction is typically carried out in a solvent such as THF or DMF, employing peptide coupling reagents exemplified by, but not limited to EDC and HOBt in the presence of a tertiary amine base such as triethylamine or diisopropylethylamine (DIPEA), at a temperature ranging from about 10° C. to about 30° C. Other non-limiting examples of coupling reagents include carbonyl diimidazol e, N,N'-dicyclohexylcarbodiimide or benzotriazol-1-yl-oxytripyrrolidinophosphonium hexafluorophosphate as reported by Coste et al. *Tetrahedron Lett.* (1990) 31 (2): 205. Or Compounds of formula I can be prepared by employing standard amide bond forming coupling procedures by the reaction of a carboxylic acid chloride of formula IV with an amine of formula III.

Scheme 2.

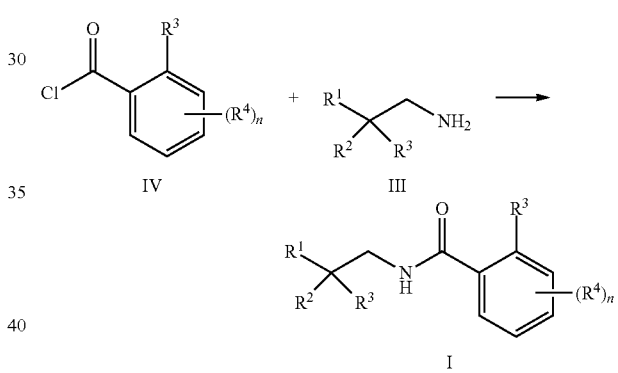

This reaction is typically carried out in a solvent such as THF or DCM in the presence of a tertiary amine base such as triethylamine or diisopropylethylamine (DIPEA), at a temperature ranging from about 10° C. to about 30° C.

Preparation of the Compounds of the Invention

Example 1a

2-Chloro-N-[4-(4-chloro-phenyl)-tetrahydro-pyran-4-ylmethyl]-2,3-dimethyl-benzamide

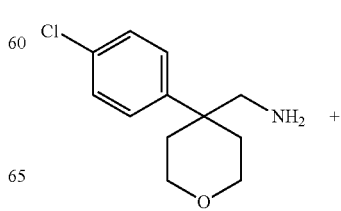

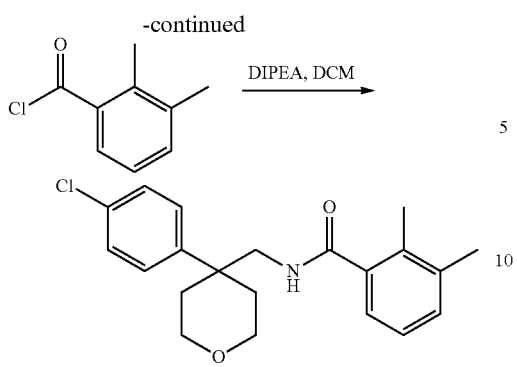

A mixture of [4-(4-chloro-phenyl)-tetrahydro-pyran-4-yl]-methylamine (67.7 mg, 0.3 mmol), 2,3-dimethylbenzoyl chloride (53 mg, 0.315 mmol) and DIPEA (78 mg, 0.60 mmol) in DCM (1.5 mL) was stirred at room temperature for 16 h. The mixture was purified by preparative HPLC to yield the title compound (70.5 mg, yield: 66%). $^1$H NMR (CDCl$_3$ 300 MHz): δ ppm 7.40-6.98 (m, 7H), 5.35 (bs, 1H), 3.95-3.87 (m, 2H), 3.70 (d, 2H), 3.70-3.60 (m, 2H), 2.31 (s, 3H), 2.23 (s, 3H), 2.18-1.92 (m, 4H). LCMS (MH+): m/z=358.0, tR (minutes, Method B)=1.03

The following compounds were synthesised in a similar way as to example 1a:

Example 1b

N-[4-(4-Chloro-phenyl)-tetrahydro-pyran-4-ylmethyl]-2-methoxy-benzamide

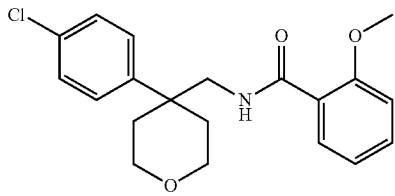 [SMILES: COc1ccccc1C(=O)NCC1(c2ccc(Cl)cc2)CCOCC1]

From 2-methoxybenzoyl chloride and [4-(4-chloro-phenyl)-tetrahydro-pyran-4-yl]-methylamine. LCMS (MH$^+$): m/z=360.0, $t_R$ (minutes, Method B)=1.01

Example 1c 2,3-Dichloro-N-[4-(4-chloro-phenyl)-tetrahydro-pyran-4-ylmethyl]-benzamide

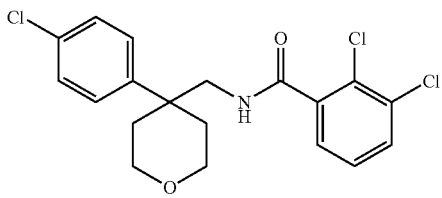 [SMILES: O=C(NCC1(c2ccc(Cl)cc2)CCOCC1)c1cccc(Cl)c1Cl]

From 2,3-dichlorobenzoyl chloride and [4-(4-chloro-phenyl)-tetrahydro-pyran-4-yl]-methylamine. LCMS m/z=399.9, $t_R$ (minutes, Method B)=1.03

Example 1d

N-[4-(4-Chloro-phenyl)-tetrahydro-pyran-4-ylmethyl]-2-methyl-benzamide

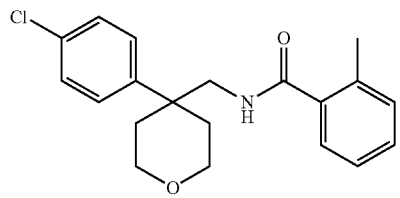 [SMILES: Cc1ccccc1C(=O)NCC1(c2ccc(Cl)cc2)CCOCC1]

From 2-methylbenzoyl chloride and [4-(4-chloro-phenyl)-tetrahydro-pyran-4-yl]-methylamine. LCMS (MH$^+$): m/z=344.0, $t_R$ (minutes, Method A)=1.26

Example 2a

2-Chloro-N-[4-(4-chloro-phenyl)-tetrahydro-pyran-4-ylmethyl]-5-methyl-benzamide

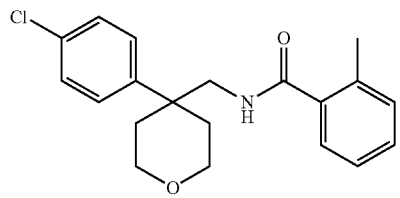 [SMILES: Cc1ccccc1C(=O)NCC1(c2ccc(Cl)cc2)CCOCC1]

A mixture of [4-(4-Chloro-phenyl)-tetrahydro-pyran-4-yl]methylamine (67.7 mg, 0.3 mmol), 2-choloro-5-methylbenzoic acid (54 mg, 0.315 mmol), PyBOP (187 mg, 0.36 mmol) and DIPEA (78 mg, 0.60 mmol) in DCM (1.5 mL) was stirred at room temperature for 16 h. The mixture was purified by preparative HPLC to yield the title compound (35.5 mg, yield: 31%). LCMS (MH$^+$): m/z=378.0, $t_R$ (minutes, Method A)=1.38

The following compounds were synthesised in a similar way as to example 2a:

Example 2b

N-[4-(4-Chloro-phenyl)-tetrahydro-pyran-4-ylmethyl]-2-cyano-benzamide

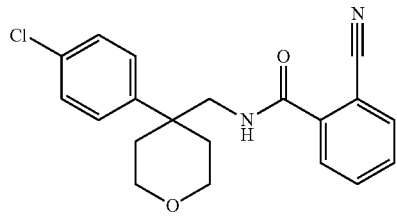 [SMILES: N#Cc1ccccc1C(=O)NCC1(c2ccc(Cl)cc2)CCOCC1]

From 2-cyanobenzoic acid and [4-(4-chloro-phenyl)-tetrahydro-pyran-4-yl]-methylamine. LCMS (MH⁺): m/z=372.0, $t_R$ (minutes, Method B)=0.96

Example 2c 2,3-Dichloro-N-(1-pyridin-3-yl-cyclopentylmethyl)-benzamide

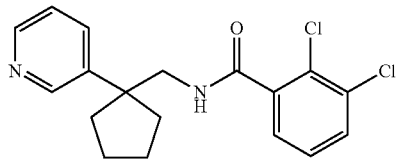 [SMILES: O=C(NCC1(c2cccnc2)CCCC1)c1cccc(Cl)c1Cl]

From 2,3-dichlorobenzoic acid and C-(1-pyridin-3-yl-cyclopentyl)-methylamine. LCMS (MH⁺): m/z=348.9, $t_R$ (minutes, Method A)=1.16

Example 2d 2,3-Dimethyl-N-(1-pyridin-3-yl-cyclopentylmethyl)-benzamide

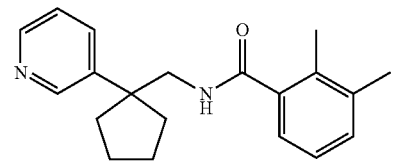 [SMILES: Cc1cccc(C(=O)NCC2(c3cccnc3)CCCC2)c1C]

From 2,3-dimethylbenzoic acid and C-(1-pyridin-3-yl-cyclopentyl)-methylamine. LCMS (MH⁺): m/z=309.1, $t_R$ (minutes, Method A)=1.11

Example 2e

2-Chloro-5-methyl-N-(1-pyridin-3-yl-cyclopentylmethyl)-benzamide

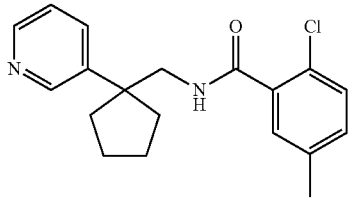 [SMILES: Cc1ccc(Cl)c(C(=O)NCC2(c3cccnc3)CCCC2)c1]

From 2-chloro-5-methylbenzoic acid and C-(1-pyridin-3-yl-cyclopentyl)-methylamine. LCMS (MH⁺): m/z=329.0, $t_R$ (minutes, Method A)=1.14

Example 2f

N-[4-(4-Chloro-phenyl)-tetrahydro-pyran-4-ylmethyl]-2-trifluoromethyl-benzamide

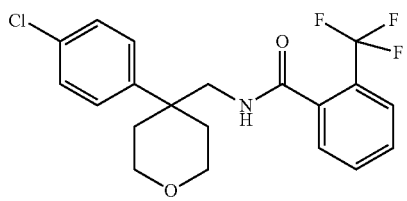 [SMILES: O=C(NCC1(c2ccc(Cl)cc2)CCOCC1)c1ccccc1C(F)(F)F]

From 2-trifluoromethylbenzoic acid and [4-(4-chloro-phenyl)-tetrahydro-pyran-4-yl]-methylamine. LCMS (MH⁺): m/z=397.9, $t_R$ (minutes, Method B)=1.04

Example 2g

2-Methyl-N-(1-pyridin-3-yl-cyclopentylmethyl)-benzamide

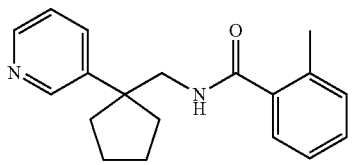 [SMILES: Cc1ccccc1C(=O)NCC1(c2cccnc2)CCCC1]

From 2-methylbenzoic acid and C-(1-pyridin-3-yl-cyclopentyl)-methylamine. LCMS (MH⁺): m/z=357.0, $t_R$ (minutes, Method B)=1.16

Example 2h

N-[4-(4-Chloro-phenyl)-tetrahydro-pyran-4-ylmethyl]-2-fluoro-3-trifluoromethyl-benzamide

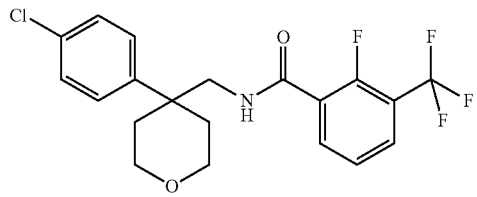 [SMILES: O=C(NCC1(c2ccc(Cl)cc2)CCOCC1)c1cccc(C(F)(F)F)c1F]

From 2-fluoro-3-trifluoromethylbenzoic acid and [4-(4-chloro-phenyl)-tetrahydro-pyran-4-yl]-methylamine. LCMS (MH$^+$): m/z=415.9, $t_R$ (minutes, Method B)=1.19

Example 2i

3-Chloro-N-[4-(4-chloro-phenyl)-tetrahydro-pyran-4-ylmethyl]-2-fluoro-benzamide

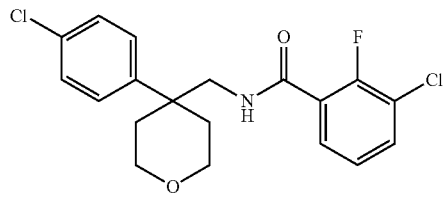

From 3-chloro-2-fluorobenzoic acid and [4-(4-chloro-phenyl)-tetrahydro-pyran-4-yl]-methylamine. LCMS (MH$^+$): m/z=381.9, $t_R$ (minutes, Method B)=1.10

Example 2j

N-[4-(4-Chloro-phenyl)-tetrahydro-pyran-4-ylmethyl]-2,5-difluoro-benzamide

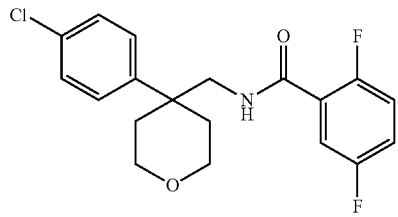 [SMILES: O=C(NCC1(c2ccc(Cl)cc2)CCOCC1)c1cc(F)ccc1F]

From 2,5-difluorobenzoic acid and [4-(4-chloro-phenyl)-tetrahydro-pyran-4-yl]-methylamine. LCMS (MH$^+$): m/z=366.0, $t_R$ (minutes, Method B)=1.05

Example 2k

2-Chloro-N-[1-(4-methoxy-phenyl)-cyclopentylmethyl]-5-methyl-benzamide

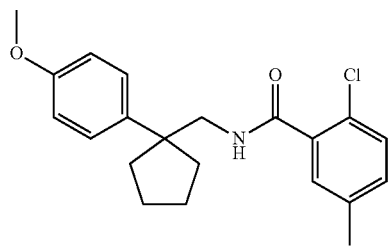 [SMILES: COc1ccc(C2(CNC(=O)c3cc(C)ccc3Cl)CCCC2)cc1]

From 2-chloro-5-methylbenzoic acid and [1-(4-methoxy-phenyl)-cyclopentyl]-methylamine. LCMS (MH$^+$): m/z=358.0, $t_R$ (minutes, Method B)=1.13

Example 2l 2,3-Dichloro-N-[1-(4-methoxy-phenyl)-cyclopentyl-methyl]-benzamide

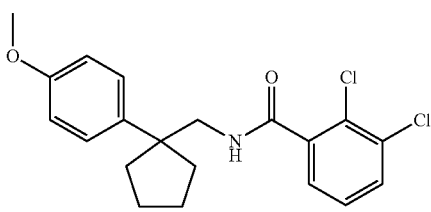 [SMILES: COc1ccc(C2(CNC(=O)c3cccc(Cl)c3Cl)CCCC2)cc1]

From 2,3-dichlorobenzoic acid and [1-(4-methoxyphenyl)-cyclopentyl]-methylamine. LCMS (MH$^+$): m/z=377.9, $t_R$ (minutes, Method B)=1.22

Example 2m

N-[1-(4-Methoxy-phenyl)-cyclopentylmethyl]-2-methyl-benzamide

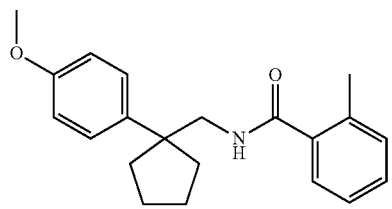 [SMILES: COc1ccc(C2(CNC(=O)c3ccccc3C)CCCC2)cc1]

From 2-methylbenzoic acid and [1-(4-methoxyphenyl)-cyclopentyl]methylamine. LCMS (MH$^+$): m/z=324.0, $t_R$ (minutes, Method B)=1.18

Example 2n

N-[1-(4-Methoxy-phenyl)-cyclopentylmethyl]-2,3-dimethyl-benzamide

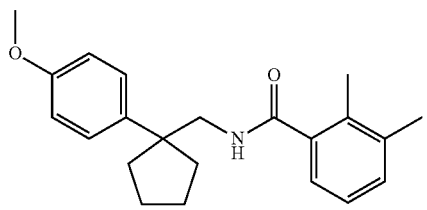 [SMILES: COc1ccc(C2(CNC(=O)c3cccc(C)c3C)CCCC2)cc1]

From 2,3-dimethylbenzoic acid and [1-(4-methoxyphenyl)-cyclopentyl]-methylamine. LCMS (MH$^+$): m/z=338.0, $t_R$ (minutes, Method B)=1.23

Example 2o 2,3-Dichloro-N-(1-methyl-4-phenyl-piperidin-4-ylmethyl)-benzamide

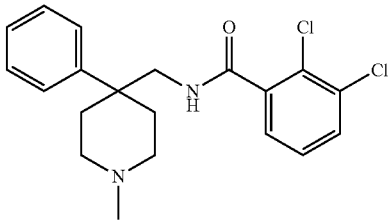 [SMILES: CN1CCC(CNC(=O)c2cccc(Cl)c2Cl)(c2ccccc2)CC1]

From 2,3-dichlorobenzoic acid and C-(1-methyl-4-phenyl-piperidin-4-yl)-methylamine. LCMS (MH$^+$): m/z=376.9, $t_R$ (minutes, Method A)=0.69

Example 2p 2,3-Dimethyl-N-(1-methyl-4-phenyl-piperidin-4-ylmethyl)-benzamide

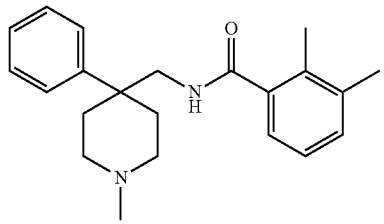 [SMILES: Cc1cccc(C(=O)NCC2(c3ccccc3)CCN(C)CC2)c1C]

From 2,3-dimethylbenzoic acid and C-(1-methyl-4-phenyl-piperidin-4-yl)-methylamine. LCMS (MH$^+$): m/z=337.0, $t_R$ (minutes, Method A)=0.65

Example 2q

2-Chloro-5-methyl-N-(1-methyl-4-phenyl-piperidin-4-ylmethyl)-benzamide

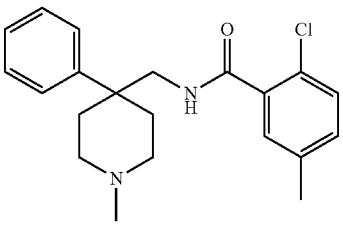 [SMILES: Cc1ccc(Cl)c(C(=O)NCC2(c3ccccc3)CCN(C)CC2)c1]

From 2-chloro-5-methylbenzoic acid and C-(1-methyl-4-phenyl-piperidin-4-yl)-methylamine. LCMS (MI-1): m/z=367.0, $t_R$ (minutes, Method A)=0.68

Example 2r

2-Methyl-N-(1-methyl-4-phenyl-piperidin-4-ylmethyl)-benzamide

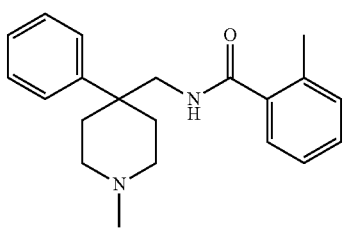 [SMILES: Cc1ccccc1C(=O)NCC1(c2ccccc2)CCN(C)CC1]

From 2-methylbenzoic acid and C-(1-methyl-4-phenyl-piperidin-4-yl)-methylamine. LCMS (MIL): m/z=323.1, $t_R$ (minutes, Method A)=0.56

Example 2s

N-[4-(4-Chloro-phenyl)-tetrahydro-pyran-4-ylmethyl]-2,3,5-trifluoro-benzamide

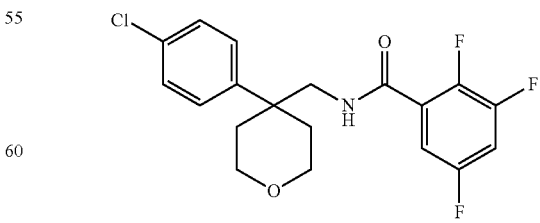

From 2,3,5-trifluorobenzoic acid and [4-(4-chloro-phenyl)-tetrahydro-pyran-4-yl]-methylamine. LCMS (MIL): m/z=384.0, $t_R$ (minutes, Method B)=1.25

Example 2t

N-[2-(4-Chloro-phenyl)-4-dimethylamino-butyl]-2-methyl-benzamide

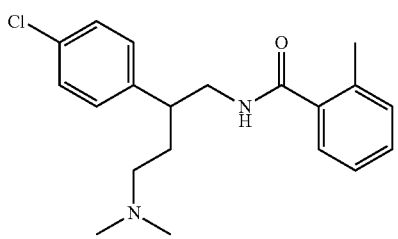 [SMILES: Cc1ccccc1C(=O)NCC(CCN(C)C)c1ccc(Cl)cc1]

From 2-methylbenzoic acid and 3-(4-chloro-phenyl)-N1,N1-dimethyl-butane-1,4-diamine. LCMS (MH+): m/z=345.1, $t_R$ (minutes, Method A)=0.8

Example 2u

2-Chloro-N-[4-(4-chloro-phenyl)-1-methyl-piperidin-4-ylmethyl]-5-methyl-benzamide

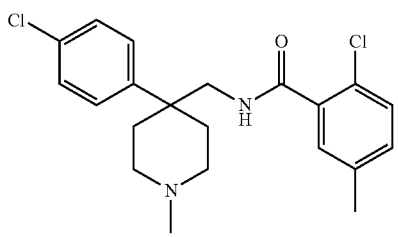 [SMILES: Cc1ccc(Cl)c(C(=O)NCC2(c3ccc(Cl)cc3)CCN(C)CC2)c1]

From 2-chloro-5-methylbenzoic acid and [4-(4-chloro-phenyl)-1-methyl-piperidine-4-yl]-methylamine. LCMS (MIL): m/z=391.0, $t_R$ (minutes, Method B)=0.71

Example 2v

N-[4-(4-Chloro-phenyl)-1-methyl-piperidin-4-ylmethyl]-2-methyl-benzamide

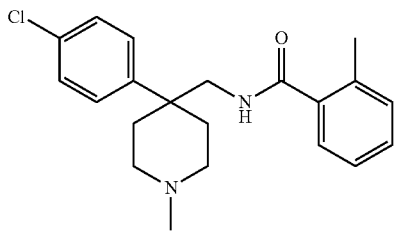 [SMILES: Cc1ccccc1C(=O)NCC1(c2ccc(Cl)cc2)CCN(C)CC1]

From 2-methylbenzoic acid and [4-(4-chloro-phenyl)-1-methyl-piperidine-4-yl]-methylamine. LCMS (MH+): m/z=357.1, $t_R$ (minutes, Method B)=0.61

Example 2w 2,3-Dichloro-N-[4-methyl-2-(6-methyl-pyridin-3-yl)-pentyl]-benzamide

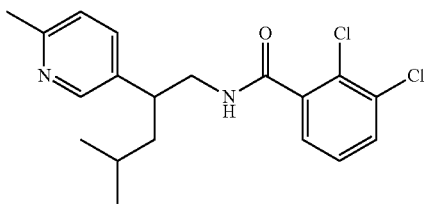 [SMILES: Cc1ccc(C(CNC(=O)c2cccc(Cl)c2Cl)CC(C)C)cn1]

From 2,3-dichlorobenzoic acid and 4-methyl-2-(6-methylpyridin-3-yl)-pentylamine. LCMS (MI-1): m/z=364.9, $t_R$ (minutes, Method A)=1.43

Example 2x 2,3-Dimethyl-N-[4-methyl-2-(6-methyl-pyridin-3-yl)-pentyl-]benzamide

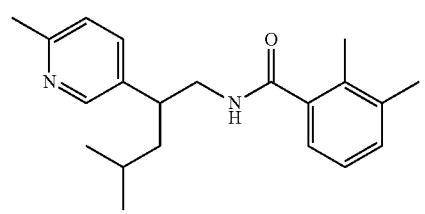

From 2,3-dimethylbenzoic acid and 4-methyl-2-(6-methylpyridin-3-yl)-pentylamine. LCMS (MH+): m/z=325.0, $t_R$ (minutes, Method A)=1.38

Example 2y

2-Methyl-N-[4-methyl-2-(6-methyl-pyridin-3-yl)-pentyl]-benzamide

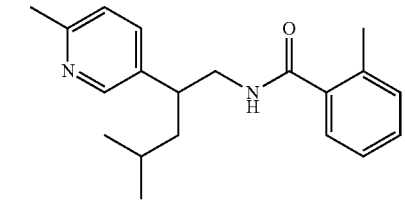 [SMILES: Cc1ccc(C(CNC(=O)c2ccccc2C)CC(C)C)cn1]

From 2-methylbenzoic acid and 4-methyl-2-(6-methyl-pyridin-3-yl)-pentylamine. LCMS (MH+): m/z=311.0, $t_R$ (minutes, Method A)=1.31

Example 2z

2-Chloro-5-methyl-N-[4-(6-methylpyridin-3-yl)-tetrahydro-pyran-4-yl-methyl]-benzamide

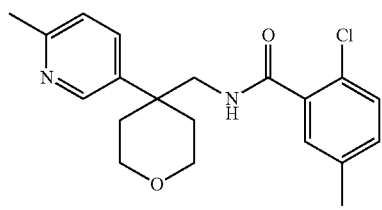 [SMILES: Cc1ccc(Cl)c(C(=O)NCC2(c3ccc(C)nc3)CCOCC2)c1]

From 2-chloro-5-methylbenzoic acid and C-[4-(6-methylpyridin-3-yl)-tetrahydropyran-4-yl]methylamine. LCMS (MH$^+$): m/z=359.0, $t_R$ (minutes, Method B)=0.74

Example 2a1

2-Methyl-N-[4-(6-methyl-pyridin-3-yl)-tetrahydro-pyran-4-ylmethyl]-benzamide

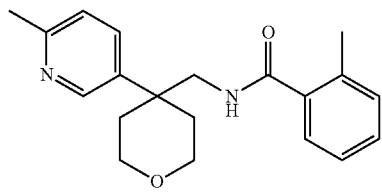 [SMILES: Cc1ccc(C2(CNC(=O)c3ccccc3C)CCOCC2)cn1]

From 2-methylbenzoic acid and C-[4-(6-methylpyridin-3-yl)-tetrahydropyran-4-yl]methylamine. LCMS (MH$^+$): m/z=325.0, $t_R$ (minutes, Method B)=0.60

Example 2b1

5-Bromo-2-chloro-N-[4-(4-chloro-phenyl)-tetrahydro-pyran-4-ylmethyl]-benzamide

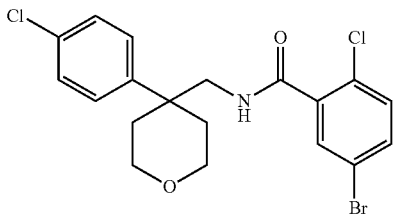

From 5-bromo-2-chlorobenzoic acid and [4-(4-chloro-phenyl)-tetrahydro-pyran-4-yl]-methylamine. LCMS (MH$^+$): m/z=443.7, $t_R$ (minutes, Method A)=1.52

Example 2c1

2-Chloro-N-[4-(4-chloro-phenyl)-tetrahydro-pyran-4-ylmethyl]-benzamide

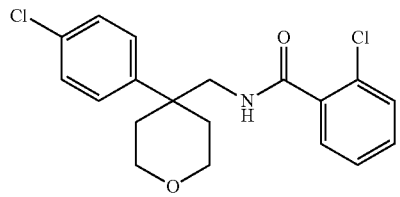

From 2-chlorobenzoic acid and [4-(4-chloro-phenyl)-tetrahydro-pyran-4-yl]methylamine. LCMS (MH$^+$): m/z=363.9, $t_R$ (minutes, Method A)=1.34

Example 3a 2,3-Dichloro-N-[[4,4-difluoro-1-(6-fluoro-3-pyridyl)cyclohexyl]methyl]benzamide

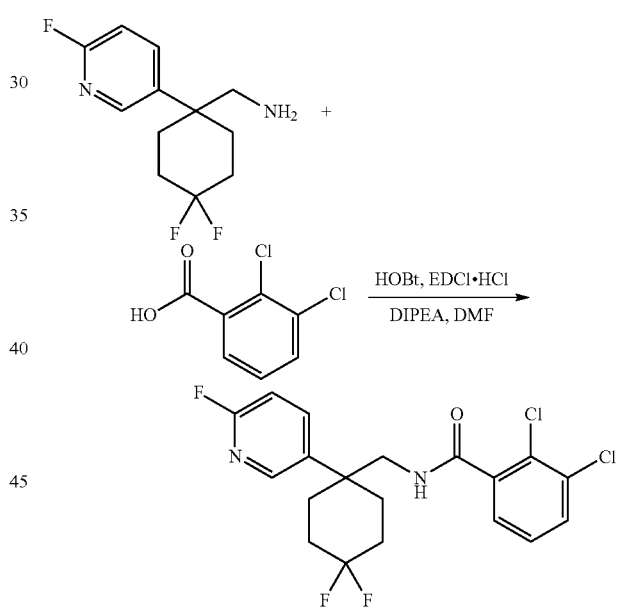

A solution of C-[4,4-difluoro-1-(6-fluoro-pyridin-3-yl)-cyclohexyl]-methylamine (38 mg, 0.157 mmol), 2,3-dichlorobenzoic acid (30 mg, 0.157 mmol), HOBt (25 mg, 0.185 mmol), EDCI.HCl (36 mg, 0.185 mmol) and DIPEA (48 mg, 0.345 mmol) in DMF (2 mL) was stirred at room temperature overnight. Water was added to the solution followed by extraction with EtOAc (3×10 ml). The combined organic layers were dried over Na$_2$SO$_4$, filtered and concentrated. The crude product was purified by Prep. HPLC to give the title compound (25 mg, yield: 38%). $^1$H NMR (CDCl$_3$ 300 MHz): δ ppm 8.18 (d, J=2.8 Hz, 1H), 7.89-7.80 (m, 1H), 7.50 (dd, J=8.0 Hz, 2.0 Hz, 1H), 7.33 (dd, J=7.6 Hz, 1.6 Hz, 1H), 7.28-7.18 (m, 1H), 6.98 (dd, J=8.8 Hz, 3.2 Hz, 1H), 5.85 (t, J=6.8 Hz, 1H), 3.64 (d, J=6.8 Hz, 2H), 2.36-2.00 (m, 6H), 1.87-1.65 (m, 2H). LCMS (MH$^+$): m/z=417.1, $t_R$ (minutes, Method C)=1.11

The following compounds were synthesised in a similar way as to example 3a, purification of the compounds was performed by prep. HPLC or Combiflash:

Example 3b

2-Chloro-N-[[4,4-difluoro-1-(6-fluoro-3-pyridyl)cyclohexyl]methyl]-6-fluoro-benzamide

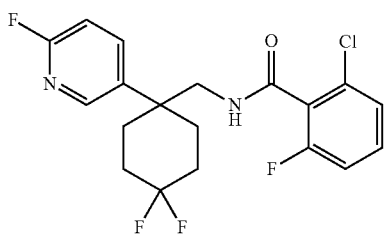 [SMILES: O=C(NCC1(c2ccc(F)nc2)CCC(F)(F)CC1)c1c(F)cccc1Cl]

From 2-chloro-6-fluorobenzoic acid and C-[4,4-difluoro-1-(6-fluoro-pyridin-3-yl)-cyclohexyl]-methylamine. LCMS (MH$^+$): m/z=401.1, $t_R$ (minutes, Method C)=1.07

Example 3c

2-Chloro-N-[[4,4-difluoro-1-(6-fluoro-3-pyridyl)cyclohexyl]methyl]-5-methyl-benzamide

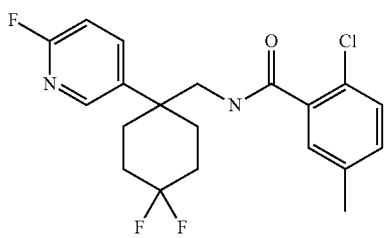 [SMILES: Cc1ccc(Cl)c(C(=O)NCC2(c3ccc(F)nc3)CCC(F)(F)CC2)c1]

From 2-chloro-5-methylbenzoic acid and C-[4,4-difluoro-1-(6-fluoro-pyridin-3-yl)-cyclohexyl]-methylamine. LCMS (MH$^+$): m/z=397.2, $t_R$ (minutes, Method C)=1.11

Example 3d

2-Chloro-N-[[4,4-difluoro-1-(6-fluoro-3-pyridyl)cyclohexyl]methyl]-5-(trifluoromethyl)benzamide

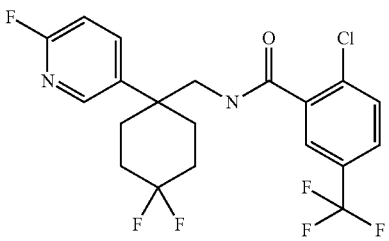 [SMILES: O=C(NCC1(c2ccc(F)nc2)CCC(F)(F)CC1)c1cc(C(F)(F)F)ccc1Cl]

From 2-chloro-5-trifluoromethylbenzoic acid and C-[4,4-difluoro-1-(6-fluoro-pyridin-3-yl)-cyclohexyl]-methylamine. LCMS (MH$^+$): m/z=451.1, $t_R$ (minutes, Method C)=1.15

Example 3e

N-[4,4-Difluoro-1-(6-fluoro-pyridin-3-yl)-cyclohexylmethyl]-2-fluoro-benzamide

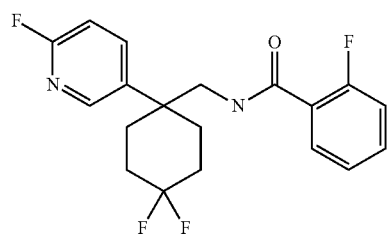 [SMILES: O=C(NCC1(c2ccc(F)nc2)CCC(F)(F)CC1)c1ccccc1F]

From 2-fluorobenzoic acid and C-[4,4-difluoro-1-(6-fluoro-pyridin-3-yl)-cyclohexyl]-methylamine. LCMS (MH$^+$): m/z=367.1, $t_R$ (minutes, Method D)=0.69

Example 3f

4-Cyano-N-[4,4-difluoro-1-(6-fluoro-pyridin-3-yl)-cyclohexylmethyl]-2-fluoro-benzamide

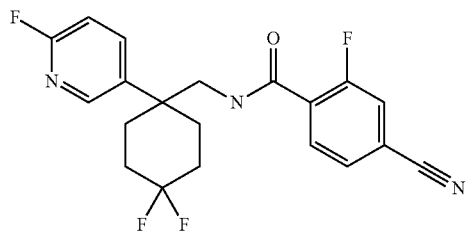 [SMILES: N#Cc1ccc(C(=O)NCC2(c3ccc(F)nc3)CCC(F)(F)CC2)c(F)c1]

From 2-fluoro-4-cyanobenzoic acid and C-[4,4-difluoro-1-(6-fluoro-pyridin-3-yl)-cyclohexyl]-methylamine. LCMS (MH$^+$): m/z=392.1, $t_R$ (minutes, Method D)=0.68

Example 3g

N-[4,4-Difluoro-1-(6-fluoro-pyridin-3-yl)-cyclohexylmethyl]-2-fluoro-3-methoxy-benzamide

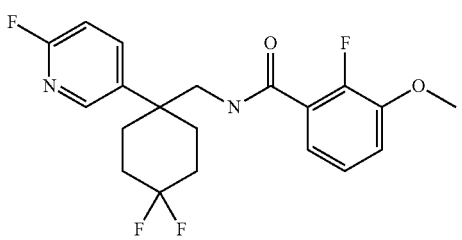 [SMILES: COc1cccc(C(=O)NCC2(c3ccc(F)nc3)CCC(F)(F)CC2)c1F]

From 2-fluoro-3-methoxybenzoic acid and C-[4,4-difluoro-1-(6-fluoro-pyridin-3-yl)-cyclohexyl]-methylamine. LCMS (MH$^+$): m/z=397.2, $t_R$ (minutes, Method D)=0.69

Example 3h

2-Chloro-N-[4,4-difluoro-1-(6-fluoro-pyridin-3-yl)-cyclohexylmethyl]-5-methanesulfonyl-benzamide

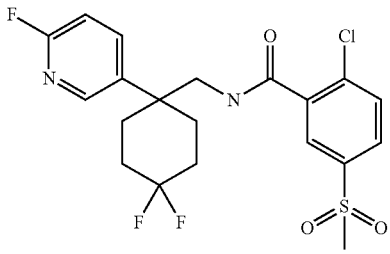 [SMILES: CS(=O)(=O)c1ccc(Cl)c(C(=O)NCC2(c3ccc(F)nc3)CCC(F)(F)CC2)c1]

From 2-chloro-5-methanesulfonylbenzoic acid and C-[4,4-difluoro-1-(6-fluoro-pyridin-3-yl)-cyclohexyl]-methylamine. LCMS (MH$^+$): m/z=461.1, $t_R$ (minutes, Method D)=0.64

Example 3i

2-Chloro-N-[4,4-difluoro-1-(6-fluoro-pyridin-3-yl)-cyclohexylmethyl]-benzamide

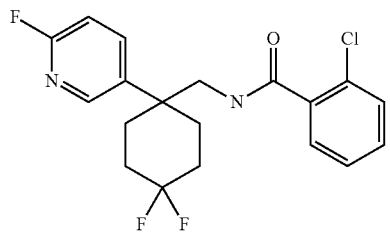 [SMILES: O=C(NCC1(c2ccc(F)nc2)CCC(F)(F)CC1)c1ccccc1Cl]

From 2-chlorobenzoic acid and C-[4,4-difluoro-1-(6-fluoro-pyridin-3-yl)-cyclohexyl]-methylamine. LCMS (MH$^+$): m/z=383.1, $t_R$ (minutes, Method D)=0.69

Example 3j

N-[4,4-Difluoro-1-(6-fluoro-pyridin-3-yl)-cyclohexylmethyl]-2-fluoro-5-methoxy-benzamide

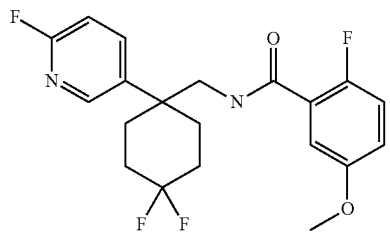 [SMILES: COc1ccc(F)c(C(=O)NCC2(c3ccc(F)nc3)CCC(F)(F)CC2)c1]

From 2-fluoro-5-methoxybenzoic acid and C-[4,4-difluoro-1-(6-fluoro-pyridin-3-yl)-cyclohexyl]methylamine. LCMS (MH$^+$): m/z=397.1, $t_R$ (minutes, Method D)=0.71

Example 3k

N-[4,4-Difluoro-1-(6-fluoro-pyridin-3-yl)-cyclohexylmethyl]-2-fluoro-3-methyl-benzamide

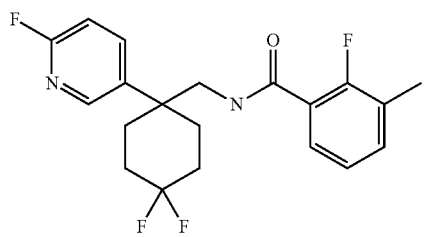 [SMILES: Cc1cccc(C(=O)NCC2(c3ccc(F)nc3)CCC(F)(F)CC2)c1F]

From 2-fluoro-3-methylbenzoic acid and C-[4,4-difluoro-1-(6-fluoro-pyridin-3-yl)-cyclohexyl]-methylamine. LCMS (MH$^+$): m/z=381.1, $t_R$ (minutes, Method D)=0.74

Example 3l

N-[4,4-Difluoro-1-(6-fluoro-pyridin-3-yl)-cyclohexylmethyl]-2,5-difluoro-benzamide

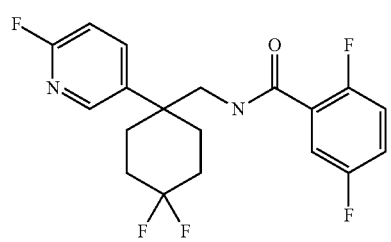 [SMILES: O=C(NCC1(c2ccc(F)nc2)CCC(F)(F)CC1)c1cc(F)ccc1F]

From 2,5-difluorobenzoic acid and C-[4,4-difluoro-1-(6-fluoro-pyridin-3-yl)-cyclohexyl]-methylamine. LCMS (MH$^+$): m/z=385.2, $t_R$ (minutes, Method D)=0.71

Example 3m 2,5-Dichloro-N-[4,4-difluoro-1-(6-fluoro-pyridin-3-yl)-cyclohexylmethyl]-benzamide

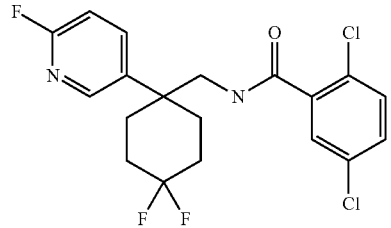 [SMILES: O=C(NCC1(c2ccc(F)nc2)CCC(F)(F)CC1)c1cc(Cl)ccc1Cl]

From 2,5-dichlorobenzoic acid and C-[4,4-difluoro-1-(6-fluoro-pyridin-3-yl)-cyclohexyl]-methylamine. LCMS (MH$^+$): m/z=417.1, $t_R$ (minutes, Method D)=0.76

Example 3n

2-Chloro-N-[4, 4-difluoro-1-(6-fluoro-pyridin-3-yl)-cyclohexylmethyl]-5-methoxy-benzamide

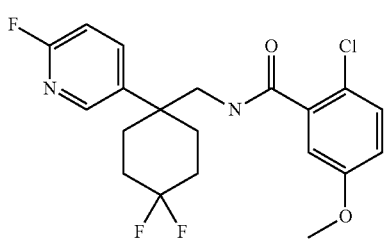 [SMILES: COc1ccc(Cl)c(C(=O)NCC2(c3ccc(F)nc3)CCC(F)(F)CC2)c1]

From 2-chloro-5-methoxybenzoic acid and C-[4,4-difluoro-1-(6-fluoro-pyridin-3-yl)-cyclohexyl]-methylamine. LCMS (MH$^+$): m/z=413.1, t$_R$ (minutes, Method D)=0.72

Example 3o

N-[4,4-Difluoro-1-(6-fluoro-pyridin-3-yl)-cyclohexylmethyl]-2,3-difluoro-benzamide

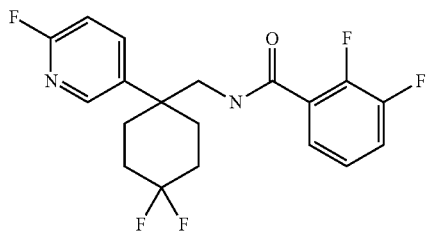 [SMILES: O=C(NCC1(c2ccc(F)nc2)CCC(F)(F)CC1)c1cccc(F)c1F]

From 2,3-difluorobenzoic acid and C-[4,4-difluoro-1-(6-fluoro-pyridin-3-yl)-cyclohexyl]-methylamine. LCMS (MH$^+$): m/z=385.0, t$_R$ (minutes, Method D)=0.71

Example 3p 2,3-Dichloro-N-[4-(4-chloro-phenyl)-tetrahydro-pyran-4-ylmethyl]-benzamide

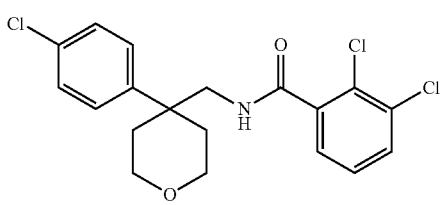 [SMILES: O=C(NCC1(c2ccc(Cl)cc2)CCOCC1)c1cccc(Cl)c1Cl]

From 2,3-dichlorobenzoic acid and [4-(4-chloro-phenyl)-tetrahydro-pyran-4-yl]-methylamine. LCMS (MH$^+$): m/z=398.1, t$_R$ (minutes, Method D)=0.79

Example 3q 2,3-Dichloro-N-[4-(4-trifluoromethyl-phenyl)-tetrahydro-pyran-4-ylmethyl]-benzamide

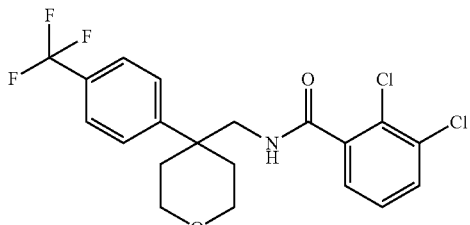

From 2,3-dichlorobenzoic acid and [4-(4-trifluoromethyl-phenyl)-tetrahydro-pyran-4-yl]-methylamine. LCMS (MH$^+$): m/z=432.0, t$_R$ (minutes, Method E)=0.83

Example 3r 2,3-Dichloro-N-[4, 4-difluoro-1-(6-trifluoromethyl-pyridin-3-yl)-cyclohexylmethyl]-benzamide

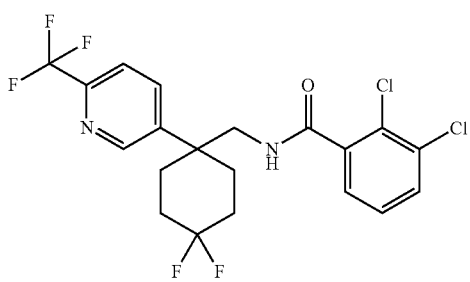 [SMILES: O=C(NCC1(c2ccc(C(F)(F)F)nc2)CCC(F)(F)CC1)c1cccc(Cl)c1Cl]

From 2,3-dichlorobenzoic acid and C-[4,4-difluoro-1-(6-trifluoromethyl-pyridin-3-yl)-cyclohexyl]-methylamine. LCMS (Ma): m/z=467.0, t$_R$ (minutes, Method E)=0.83

Example 3s 2,3-Dichloro-N-[4-(6-trifluoromethyl-pyridin-3-yl)-tetrahydro-pyran-4-ylmethyl]-benzamide

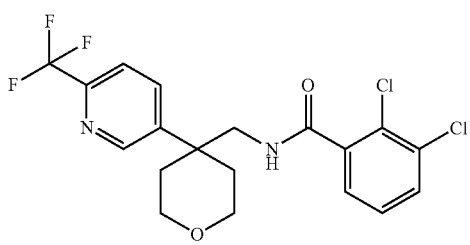 [SMILES: O=C(NCC1(c2ccc(C(F)(F)F)nc2)CCOCC1)c1cccc(Cl)c1Cl]

From 2,3-dichlorobenzoic acid and [4-(6-trifluoromethyl-pyridin-3-yl)-tetrahydro-pyran-4-yl]-methylamine. LCMS (MH$^+$): m/z=433.3, t$_R$ (minutes, Method E)=0.72

Example 3t 2,3-Dichloro-N-[1-(6-cyclopropyl-pyridin-3-yl)-4,4-difluoro-cyclohexylmethyl]-benzamide

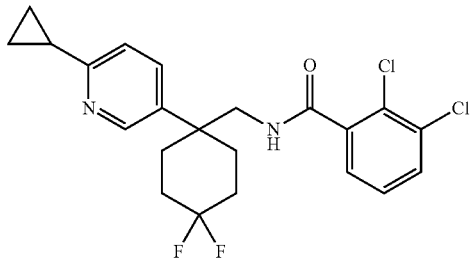 [SMILES: O=C(NCC1(c2ccc(C3CC3)nc2)CCC(F)(F)CC1)c1cccc(Cl)c1Cl]

From 2,3-dichlorobenzoic acid and C-[4,4-difluoro-1-(6-cyclopropyl-pyridin-3-yl)-cyclohexyl]-methylamine. LCMS (MH+): m/z=439.0, $t_R$ (minutes, Method E)=0.55

Example 3u 2,3-Dichloro-N-[4,4-difluoro-1-(6-methoxy-pyridin-3-yl)-cyclohexylmethyl]-benzamide

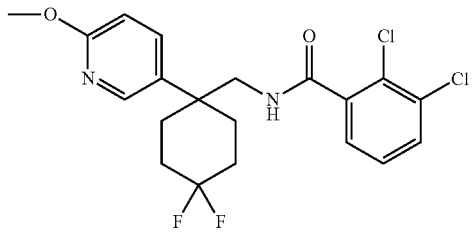 [SMILES: COc1ccc(C2(CNC(=O)c3cccc(Cl)c3Cl)CCC(F)(F)CC2)cn1]

From 2,3-dichlorobenzoic acid and C-[4,4-difluoro-1-(6-methoxy-pyridin-3-yl)-cyclohexyl]-methylamine. LCMS m/z=429.1, $t_R$ (minutes, Method D)=0.67

Example 3v

2-Cyano-N-[4,4-difluoro-1-(6-trifluoromethyl-pyridin-3-yl)-cyclohexylmethyl]-benzamide

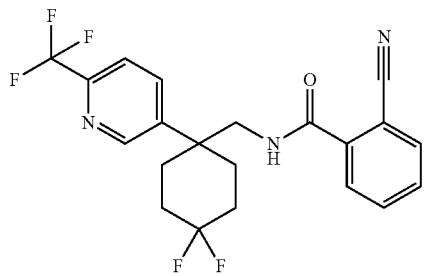 [SMILES: N#Cc1ccccc1C(=O)NCC1(c2ccc(C(F)(F)F)nc2)CCC(F)(F)CC1]

From 2-cyanobenzoic acid and C-[4,4-difluoro-1-(6-trifluoromethyl-pyridin-3-yl)-cyclohexyl]-methylamine. LCMS (ME 1+): m/z=424.2, $t_R$ (minutes, Method D)=0.66

Example 3w

2-Chloro-N-[4,4-difluoro-1-(6-trifluoromethyl-pyridin-3-yl)-cyclohexylmethyl]-4-methanesulfonyl-benzamide

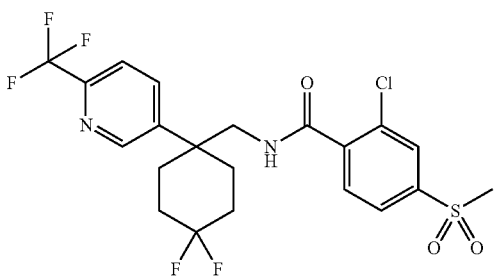 [SMILES: CS(=O)(=O)c1ccc(C(=O)NCC2(c3ccc(C(F)(F)F)nc3)CCC(F)(F)CC2)c(Cl)c1]

From 2-chloro-4-methanesulfonylbenzoic acid and C-[4,4-difluoro-1-(6-trifluoromethyl-pyridin-3-yl)-cyclohexyl]-methylamine. LCMS (MH+): m/z=511.1, $t_R$ (minutes, Method D)=0.68

Example 3x

N-[4,4-Difluoro-1-(6-trifluoromethyl-pyridin-3-yl)-cyclohexylmethyl]-2-methyl-benzamide

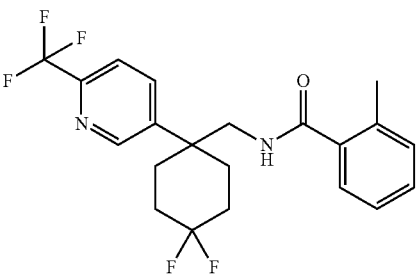 [SMILES: Cc1ccccc1C(=O)NCC1(c2ccc(C(F)(F)F)nc2)CCC(F)(F)CC1]

From 2-methylbenzoic acid and C-[4,4-difluoro-1-(6-trifluoromethyl-pyridin-3-yl)-cyclohexyl]-methylamine. LCMS (MH+): m/z=413.2, $t_R$ (minutes, Method D)=0.74

Example 3y 2,3-Dichloro-N-[2-cyclopropyl-2-(6-trifluoromethyl-pyridin-3-yl)-ethyl]-benzamide

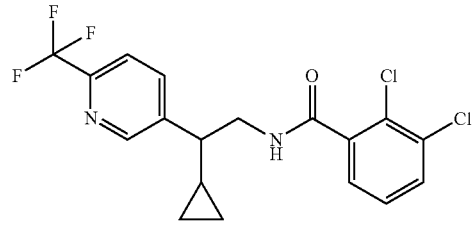 [SMILES: O=C(NCC(c1ccc(C(F)(F)F)nc1)C1CC1)c1cccc(Cl)c1Cl]

From 2,3-dichlorobenzoic acid and 2-cyclopropyl-2-(6-trifluoromethyl-pyridin-3-yl)-ethylamine. LCMS (MH+): m/z=403.1, $t_R$ (minutes, Method D)=0.79

Example 3z

N-[4,4-Difluoro-1-(6-trifluoromethyl-pyridin-3-yl)-cyclohexylmethyl]-2-methanesulfonyl-benzamide

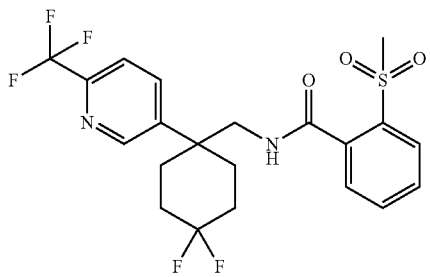 [SMILES: CS(=O)(=O)c1ccccc1C(=O)NCC1(c2ccc(C(F)(F)F)nc2)CCC(F)(F)CC1]

From 2-methanesulfonylbenzoic acid and C-[4,4-difluoro-1-(6-trifluoromethyl-pyridin-3-yl)-cyclohexyl]-methylamine. LCMS (MH+): m/z=413.2, $t_R$ (minutes, Method D)=0.74

Example 3a1

2,3-Dichloro-N-[4,4-difluoro-1-(5-fluoro-pyridin-3-yl)-cyclohexylmethyl]-benzamide

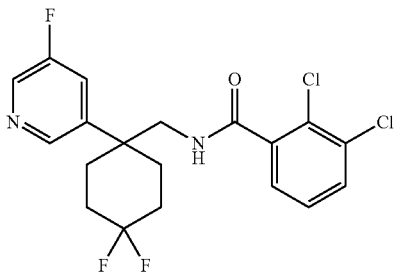 [SMILES: O=C(NCC1(c2cncc(F)c2)CCC(F)(F)CC1)c1cccc(Cl)c1Cl]

From 2,3-dichlorobenzoic acid and C-[4,4-difluoro-1-(5-fluoro-pyridin-3-yl)-cyclohexyl]-methylamine. LCMS (MH+): m/z=417.2, $t_R$ (minutes, Method D)=0.68

Example 3b1

2,3-Dichloro-N-[3-cyclopropyl-2-[6-(trifluoromethyl)-3-pyridyl]propyl]benzamide

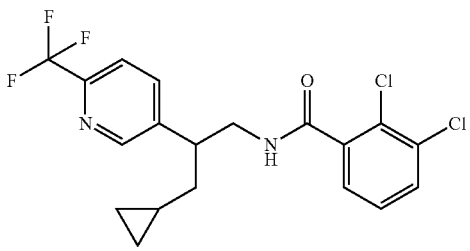 [SMILES: O=C(NCC(CC1CC1)c1ccc(C(F)(F)F)nc1)c1cccc(Cl)c1Cl]

From 2,3-dichlorobenzoic acid and 3-cyclopropyl-2-(6-trifluoromethyl-pyridin-3-yl)-propylamine. LCMS (MH+): m/z=416.9, $t_R$ (minutes, Method C)=1.29

Example 3c1

2-Chloro-N-[3-cyclopropyl-2-[6-(trifluoromethyl)-3-pyridyl]propyl]benzamide

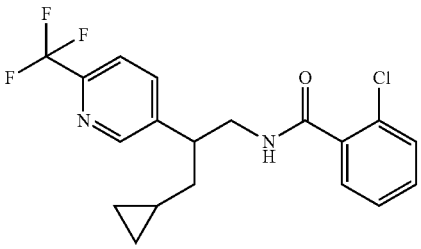 [SMILES: O=C(NCC(CC1CC1)c1ccc(C(F)(F)F)nc1)c1ccccc1Cl]

From 2-chlorobenzoic acid and 3-cyclopropyl-2-(6-trifluoromethyl-pyridin-3-yl)-propylamine. LCMS (MH+): m/z=382.9, $t_R$ (minutes, Method C)=1.24

Example 3d1

N-[4,4-Difluoro-1-(6-trifluoromethyl-pyridin-3-yl)-cyclohexylmethyl]-3-fluoro-2-methyl-benzamide

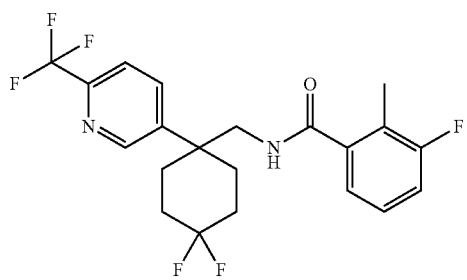 [SMILES: Cc1c(F)cccc1C(=O)NCC1(c2ccc(C(F)(F)F)nc2)CCC(F)(F)CC1]

From 3-fluoro-2-methylbenzoic acid and C-[4,4-difluoro-1-(6-trifluoromethyl-pyridin-3-yl)-cyclohexyl]-methylamine. LCMS (MH+): m/z=431.2, $t_R$ (minutes, Method D)=0.79

Example 3e1

N-[4,4-Difluoro-1-(6-trifluoromethyl-pyridin-3-yl)-cyclohexylmethyl]-3-methoxy-2-methyl-benzamide

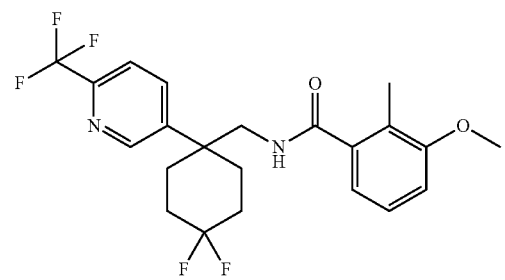 [SMILES: COc1cccc(C(=O)NCC2(c3ccc(C(F)(F)F)nc3)CCC(F)(F)CC2)c1C]

From 3-methoxy-2-methylbenzoic acid and C-[4,4-difluoro-1-(6-trifluoromethyl-pyridin-3-yl)-cyclohexyl]-methylamine. LCMS m/z=443.2, $t_R$ (minutes, Method D)=0.78

Example 3f1

N-[4,4-Difluoro-1-(6-trifluoromethyl-pyridin-3-yl)-cyclohexylmethyl]-5-fluoro-2-methyl-benzamide

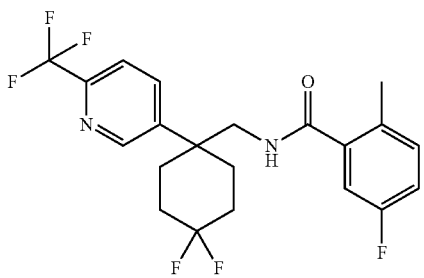

From 5-fluoro-2-methylbenzoic acid and C-[4,4-difluoro-1-(6-trifluoromethyl-pyridin-3-yl)-cyclohexyl]-methylamine. LCMS m/z=431.2, $t_R$ (minutes, Method D)=0.79

Example 3g1

N-[4,4-Difluoro-1-(6-trifluoromethyl-pyridin-3-yl)-cyclohexylmethyl]-2-methyl-5-trifluoromethyl-benzamide

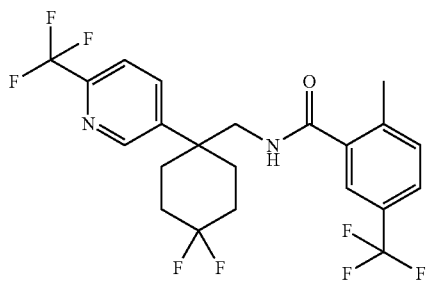 [SMILES: Cc1ccc(C(F)(F)F)cc1C(=O)NCC1(c2ccc(C(F)(F)F)nc2)CCC(F)(F)CC1]

From 5-trifluoromethyl-2-methylbenzoic acid and C-[4,4-difluoro-1-(6-trifluoromethyl-pyridin-3-yl)-cyclohexyl]-methylamine. LCMS (MH+): m/z=481.1, $t_R$ (minutes, Method D)=0.86

Example 3h1

3-Bromo-N-[4,4-difluoro-1-(6-trifluoromethyl-pyridin-3-yl)-cyclohexylmethyl]-2-methyl-benzamide

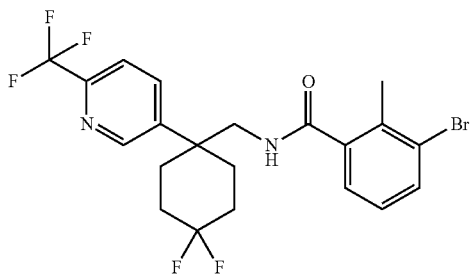 [SMILES: Cc1c(Br)cccc1C(=O)NCC1(c2ccc(C(F)(F)F)nc2)CCC(F)(F)CC1]

From 3-bromo-2-methylbenzoic acid and C-[4,4-difluoro-1-(6-trifluoromethyl-pyridin-3-yl)-cyclohexyl]-methylamine. LCMS (MH+): m/z=491.1, $t_R$ (minutes, Method D)=0.84

Example 3i1

2-Chloro-N-[4, 4-difluoro-1-(6-trifluoromethyl-pyridin-3-yl)-cyclohexylmethyl]-3-methyl-benzamide

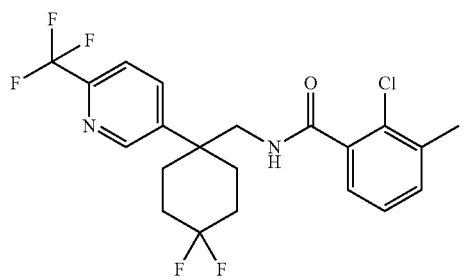 [SMILES: Cc1cccc(C(=O)NCC2(c3ccc(C(F)(F)F)nc3)CCC(F)(F)CC2)c1Cl]

From 2-chloro-3-methylbenzoic acid and C-[4,4-difluoro-1-(6-trifluoromethyl-pyridin-3-yl)-cyclohexyl]-methylamine. LCMS (MH+): m/z=447.1, $t_R$ (minutes, Method D)=0.80

Example 3j1

3-Cyano-N-[4,4-difluoro-1-(6-trifluoromethyl-pyridin-3-yl)-cyclohexylmethyl]-2-methyl-benzamide

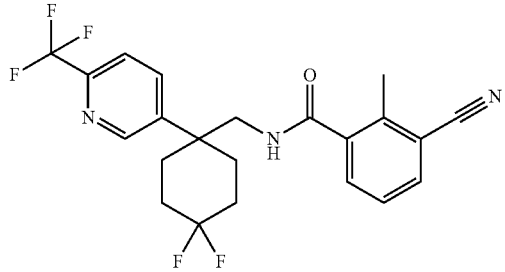 [SMILES: Cc1c(C#N)cccc1C(=O)NCC1(c2ccc(C(F)(F)F)nc2)CCC(F)(F)CC1]

From 3-cyano-2-methylbenzoic acid and C-[4,4-difluoro-1-(6-trifluoromethyl-pyridin-3-yl)-cyclohexyl]-methylamine. LCMS (MH+): m/z=438.2, $t_R$ (minutes, Method D)=0.75

Example 3k1

2,3-Dichloro-N-[2-(5-chloro-pyridin-3-yl)-3-cyclopropyl-propyl]-benzamide

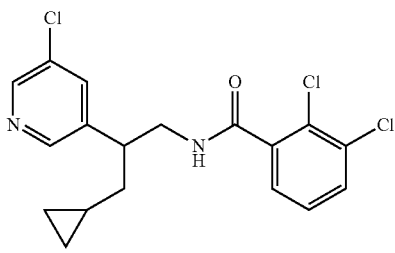 [SMILES: O=C(NCC(CC1CC1)c1cncc(Cl)c1)c1cccc(Cl)c1Cl]

From 2,3-dichlorobenzoic acid and 3-cyclopropyl-2-(5-chloro-pyridin-3-yl)-propylamine. LCMS (MH+): m/z=383.0, $t_R$ (minutes, Method D)=0.74

Example 3l1

2,3-Dichloro-N-[2-(4-chloro-phenyl)-2-phenyl-ethyl]-benzamide

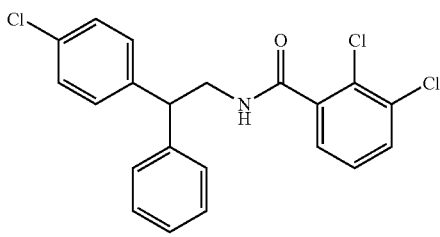 [SMILES: O=C(NCC(c1ccccc1)c1ccc(Cl)cc1)c1cccc(Cl)c1Cl]

From 2,3-dichlorobenzoic acid and 2-(4-chloro-phenyl)-2-phenyl-ethylamine. LCMS (MH+): m/z=404.0, $t_R$ (minutes, Method D)=0.91

Example 3m1

2,3-Dichloro-N-[3-cyclopropyl-2-(2,6-dimethyl-3-pyridyl)propyl]benzamide

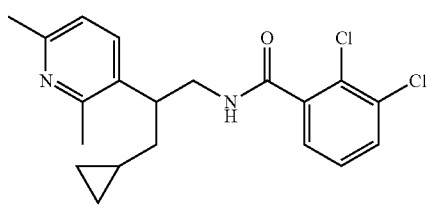 [SMILES: Cc1ccc(C(CNC(=O)c2cccc(Cl)c2Cl)CC2CC2)c(C)n1]

From 2,3-dichlorobenzoic acid and 3-cyclopropyl-2-(2,6-dimethyl-pyridin-3-yl)-propylamine. LCMS (MH+): m/z=377.1, $t_R$ (minutes, Method G)=1.68

Example 3n1

2,3-Dichloro-N-[2-(2-methylpyrimidin-5-yl)-3-[1-(trifluoromethyl)cyclopropyl]propyl]benzamide

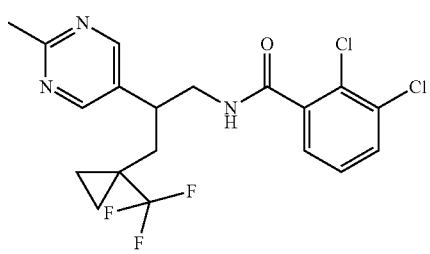 [SMILES: Cc1ncc(C(CNC(=O)c2cccc(Cl)c2Cl)CC2(C(F)(F)F)CC2)cn1]

From 2,3-dichlorobenzoic acid and 2-(2-methyl-pyrimidin-5-yl)-3-(1-trifluoromethyl-cyclopropyl)-propylamine. LCMS (MH+): m/z=377.1, $t_R$ (minutes, Method F)=1.68

Example 3o1

2,3-Dichloro-N-[3-[1-(trifluoromethyl)cyclopropyl]-2-[6-(trifluoromethyl)-3-pyridyl]propyl]benzamide

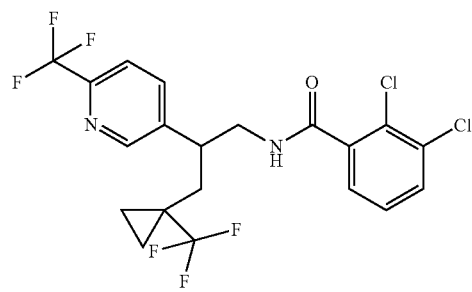 [SMILES: O=C(NCC(CC1(C(F)(F)F)CC1)c1ccc(C(F)(F)F)nc1)c1cccc(Cl)c1Cl]

From 2,3-dichlorobenzoic acid and 3-(1-trifluoromethyl-cyclopropyl)-2-(6-trifluoromethyl-pyridin-3-yl)-propylamine. LCMS (MH+): m/z=485.1, $t_R$ (minutes, Method G)=2.74

Example 3p1

2,3-Dichloro-N-[2-(6-cyclopropyl-3-pyridyl)-3-[1-(trifluoromethyl)cyclopropyl]propyl]benzamide

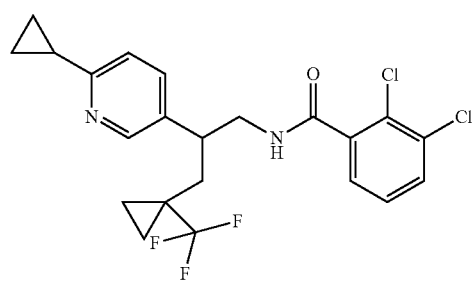 [SMILES: O=C(NCC(CC1(C(F)(F)F)CC1)c1ccc(C2CC2)nc1)c1cccc(Cl)c1Cl]

From 2,3-dichlorobenzoic acid and 2-(6-cyclopropyl-pyridin-3-yl)-3-(1-trifluoromethyl-cyclopropyl)-propylamine. LCMS (MH+): m/z=457.1, $t_R$ (minutes, Method G)=1.96

Example 3q1

2,3-Dichloro-N-[2-(6-cyclopropyl-3-pyridyl)-3-[1-(difluoromethyl)cyclopropyl]propyl]benzamide

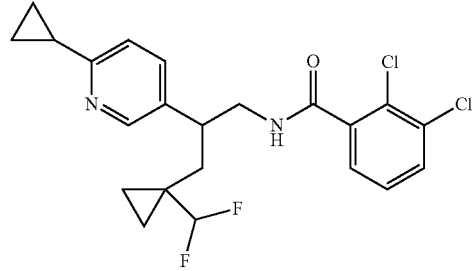 [SMILES: O=C(NCC(CC1(C(F)F)CC1)c1ccc(C2CC2)nc1)c1cccc(Cl)c1Cl]

From 2,3-dichlorobenzoic acid and 2-(6-cyclopropyl-pyridin-3-yl)-3-(1-difluoromethyl-cyclopropyl)-propylamine. LCMS (MH+): m/z=439.1, $t_R$ (minutes, Method G)=2.09

Example 3r1

2,3-Dichloro-N-[3-[1-(difluoromethyl)cyclopropyl]-2-[6-(trifluoromethyl)-3-pyridyl]propyl]benzamide

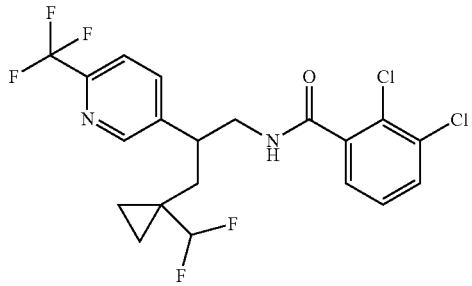 [SMILES: O=C(NCC(CC1(C(F)F)CC1)c1ccc(C(F)(F)F)nc1)c1cccc(Cl)c1Cl]

From 2,3-dichlorobenzoic acid and 2-(6-trifluoromethyl-pyridin-3-yl)-3-(1-difluoromethyl-cyclopropyl)-propylamine. LCMS (MH+): m/z=467.1, $t_R$ (minutes, Method G)=2.62

Example 3s1

2-Chloro-N-[2-(6-cyclopropyl-3-pyridyl)-3-[1-(trifluoromethyl)cyclopropyl]propyl]benzamide

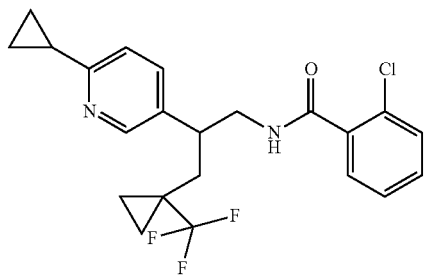 [SMILES: O=C(NCC(CC1(C(F)(F)F)CC1)c1ccc(C2CC2)nc1)c1ccccc1Cl]

From 2-chlorobenzoic acid and 2-(6-cyclopropyl-pyridin-3-yl)-3-(1-trifluoromethyl-cyclopropyl)-propylamine. LCMS (MH+): m/z=423.1, $t_R$ (minutes, Method G)=2.04

Example 3t1

N-[2-(6-Cyclopropyl-3-pyridyl)-3-[1-(trifluoromethyl)cyclopropyl]propyl]-2-fluoro-benzamide

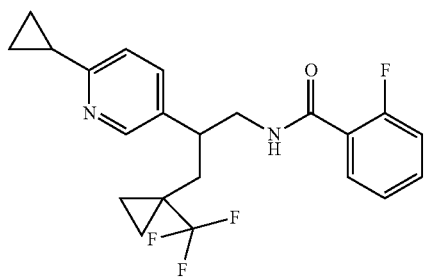 [SMILES: O=C(NCC(CC1(C(F)(F)F)CC1)c1ccc(C2CC2)nc1)c1ccccc1F]

From 2-fluorobenzoic acid and 2-(6-cyclopropyl-pyridin-3-yl)-3-(1-trifluoromethyl-cyclopropyl)-propylamine. LCMS (MH+): m/z=407.1, $t_R$ (minutes, Method G)=2.01

Example 3u1

2-Chloro-N-[3-cyclopropyl-2-(2-methylpyrimidin-5-yl)propyl]benzamide

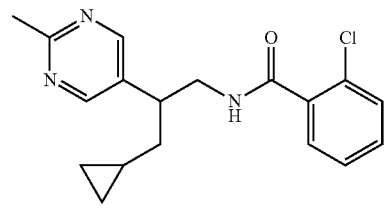 [SMILES: Cc1ncc(C(CNC(=O)c2ccccc2Cl)CC2CC2)cn1]

From 2-chlorobenzoic acid and 2-(2-methyl-pyrimidin-5-yl)-3-cyclopropyl-propylamine. LCMS (MH+): m/z=330.1, $t_R$ (minutes, Method F)=2.32

Example 3v1

2,3-Dichloro-N-[3-cyclopropyl-2-(2-methylpyrimidin-5-yl)propyl]benzamide

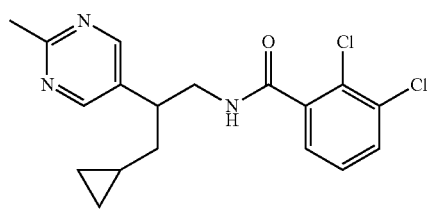 [SMILES: Cc1ncc(C(CNC(=O)c2cccc(Cl)c2Cl)CC2CC2)cn1]

From 2,3-dichlorobenzoic acid and 2-(2-methyl-pyrimidin-5-yl)-3-cyclopropyl-propylamine. LCMS (MH+): m/z=364.1, $t_R$ (minutes, Method F)=2.52

Example 3w1

2-Chloro-N-[3-[1-(trifluoromethyl)cyclopropyl]-2-[6-(trifluoromethyl)-3-pyridyl]propyl]benzamide

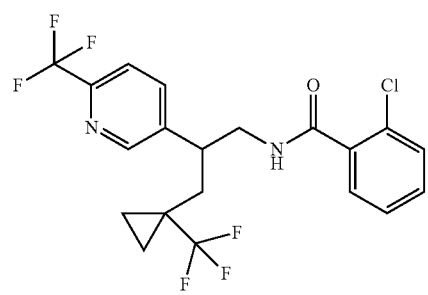 [SMILES: O=C(NCC(CC1(C(F)(F)F)CC1)c1ccc(C(F)(F)F)nc1)c1ccccc1Cl]

From 2-chlorobenzoic acid and 3-(1-trifluoromethyl-cyclopropyl)-2-(6-trifluoromethyl-pyridin-3-yl)-propylamine. LCMS (MH+): m/z=451.1, $t_R$ (minutes, Method G)=2.58

Example 3x1

2-Fluoro-N-[3-[1-(trifluoromethyl)cyclopropyl]-2-[6-(trifluoromethyl)-3-pyridyl]propyl]benzamide

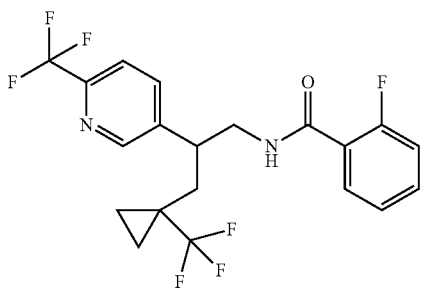 [SMILES: O=C(NCC(CC1(C(F)(F)F)CC1)c1ccc(C(F)(F)F)nc1)c1ccccc1F]

From 2-fluorobenzoic acid and 3-(1-trifluoromethyl-cyclopropyl)-2-(6-trifluoromethyl-pyridin-3-yl)-propylamine. LCMS (MH+): m/z=435.1, $t_R$ (minutes, Method G)=2.58

Example 3y1

2-Chloro-N-[[4,4-difluoro-1-(2-methylpyrimidin-5-yl)cyclohexyl]methyl]benzamide

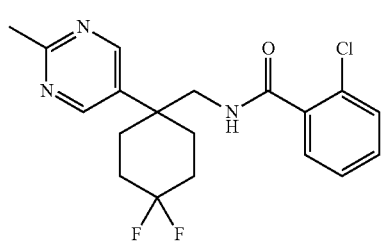 [SMILES: Cc1ncc(C2(CNC(=O)c3ccccc3Cl)CCC(F)(F)CC2)cn1]

From 2-chlorobenzoic acid and C-[4,4-difluoro-1-(2-methyl-pyrimidin-5-yl)-cyclohexyl]-methylamine. LCMS (MH+): m/z=380.1, $t_R$ (minutes, Method F)=2.37

Example 3z1

2,3-Dichloro-N-[[4,4-difluoro-1-(2-methylpyrimidin-5-yl)cyclohexyl]methyl]benzamide

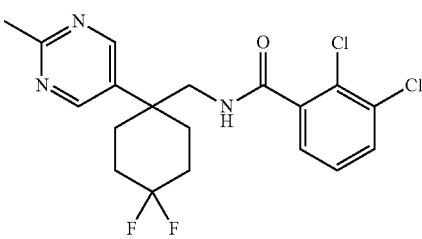 [SMILES: Cc1ncc(C2(CNC(=O)c3cccc(Cl)c3Cl)CCC(F)(F)CC2)cn1]

From 2,3-dichlorobenzoic acid and C-[4,4-difluoro-1-(2-methyl-pyrimidin-5-yl)-cyclohexyl]-methylamine. LCMS (MH+): m/z=414.1, $t_R$ (minutes, Method F)=2.57

Example 3a2

2,3-Dichloro-N-[3-cyclopropyl-2-[2-(trifluoromethyl)pyrimidin-5-yl]propyl]benzamide

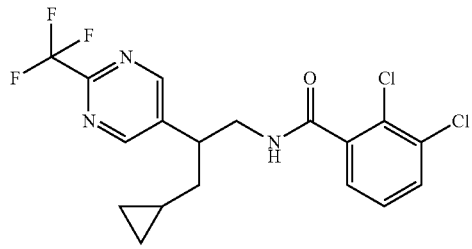 [SMILES: O=C(NCC(CC1CC1)c1cnc(C(F)(F)F)nc1)c1cccc(Cl)c1Cl]

From 2,3-dichlorobenzoic acid and 2-(2-trifluoromethyl-pyrimidin-5-yl)-3-cyclopropyl-propylamine. LCMS (MH+): m/z=418.1, $t_R$ (minutes, Method G)=2.55

Example 3b2

2,3-Dichloro-N-[[4,4-difluoro-1-[6-(1-hydroxy-1-methyl-ethyl)-3-pyridyl]cyclohexyl]methyl]benzamide

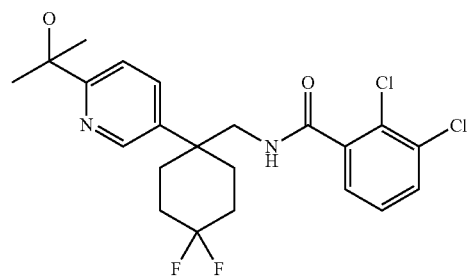 [SMILES: CC(C)(O)c1ccc(C2(CNC(=O)c3cccc(Cl)c3Cl)CCC(F)(F)CC2)cn1]

From 2,3-dichlorobenzoic acid and 2-[5-(1-aminomethyl-4,4-difluoro-cyclohexyl)-pyridin-2-yl]-propan-2-ol. LCMS (MH+): m/z=457.1, $t_R$ (minutes, Method F)=1.97

Example 3c2

2-Chloro-N-[[4,4-difluoro-1-[6-(1-hydroxy-1-methyl-ethyl)-3-pyridyl]cyclohexyl]methyl]benzamide

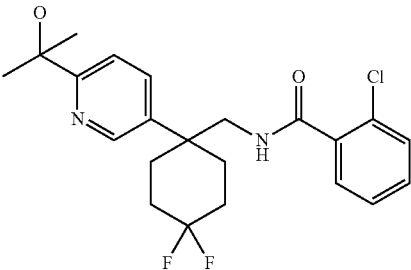 [SMILES: CC(C)(O)c1ccc(C2(CNC(=O)c3ccccc3Cl)CCC(F)(F)CC2)cn1]

From 2-chlorobenzoic acid and 2-[5-(1-aminomethyl-4,4-difluoro-cyclohexyl)-pyridin-2-yl]-propan-2-ol. LCMS (MH+): m/z=423.2, $t_R$ (minutes, Method F)=1.78

Example 3d2

2-chloro-N-[3-cyclopropyl-2-[6-(trifluoromethyl)-3-pyridyl]propyl]-3-methoxybenzamide

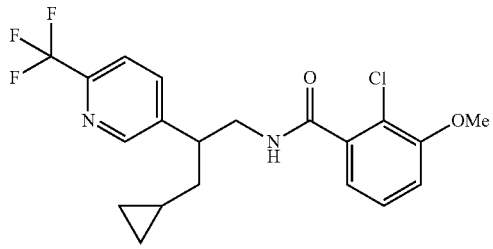

From 2-chloro-3-methoxybenzoic acid and 3-cyclopropyl-2-(6-(trifluoromethyl)pyridin-3-yl)propan-1-amine. LCMS (MH+): m/z=413.1, $t_R$ (minutes, Method G)=2.84

Example 3e2

2-chloro-N-(3-cyclopropyl-2-(6-(trifluoromethyl)pyridin-3-yl)propyl)-6-fluorobenzamide

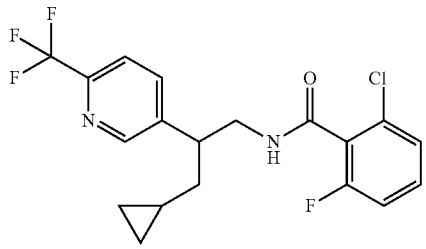

From 2-chloro-6-fluorobenzoic acid and 3-cyclopropyl-2-(6-(trifluoromethyl)pyridin-3-yl)propan-1-amine. LCMS (MH+): m/z=401.1, $t_R$ (minutes, Method G)=2.88

Example 3f2

N-(3-cyclopropyl-2-(6-(trifluoromethyl)pyridin-3-yl)propyl)-2-methoxybenzamide

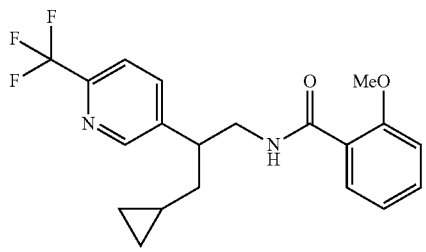

From 2-methoxybenzoic acid and 3-cyclopropyl-2-(6-(trifluoromethyl)pyridin-3-yl)propan-1-amine. LCMS (MH+): m/z=379.1, $t_R$ (minutes, Method G)=2.91

Example 3g2

N-(3-cyclopropyl-2-(6-(trifluoromethyl)pyridin-3-yl)propyl)-2,6-difluorobenzamide

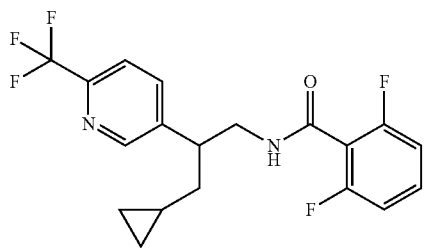

From 2,6-difluorobenzoic acid and 3-cyclopropyl-2-(6-(trifluoromethyl)pyridin-3-yl)propan-1-amine. LCMS (MH+): m/z=385.1, $t_R$ (minutes, Method G)=2.82

Example 3h2

2-chloro-N-(3-cyclopropyl-2-(6-(trifluoromethyl)pyridin-3-yl)propyl)-5-(methyl sulfonyl)benzamide

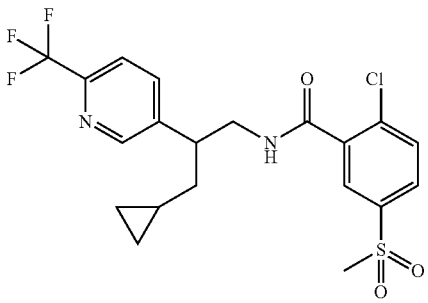 [SMILES: CS(=O)(=O)c1ccc(Cl)c(C(=O)NCC(CC2CC2)c2ccc(C(F)(F)F)nc2)c1]

From 2-chloro-5-(methylsulfonyl)benzoic acid and 3-cyclopropyl-2-(6-(trifluoromethyl)pyridin-3-yl)propan-1-amine. LCMS (MH+): m/z=461.1, $t_R$ (minutes, Method G)=2.88

Example 3i2

2-chloro-N-(3-cyclopropyl-2-(6-(trifluoromethyl)pyridin-3-yl)propyl)-3-fluorobenzamide

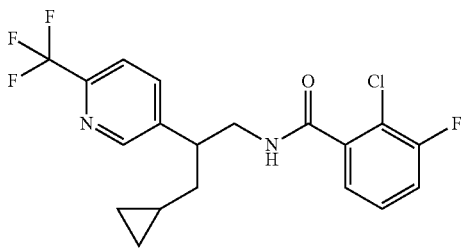

From 2-chloro-3-fluorobenzoic acid and 3-cyclopropyl-2-(6-(trifluoromethyl)pyridin-3-yl)propan-1-amine. LCMS (MH+): m/z=401.1, $t_R$ (minutes, Method G)=2.51

Example 3j2

2-chloro-N-(3-cyclopropyl-2-(6-fluoropyridin-3-yl)propyl)benzamide

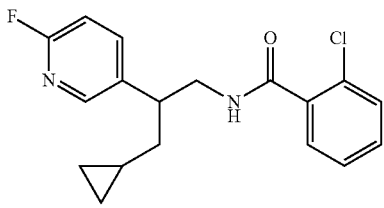 [SMILES: O=C(NCC(CC1CC1)c1ccc(F)nc1)c1ccccc1Cl]

From 2-chlorobenzoic acid and 3-cyclopropyl-2-(6-fluoropyridin-3-yl)propan-1-amine. LCMS (MH+): m/z=333.1, $t_R$ (minutes, Method F)=2.43

Example 3k2

2,3-dichloro N-(3-cyclopropyl-2-(2-methylpyrimidin-5-yl)propyl)benzamide

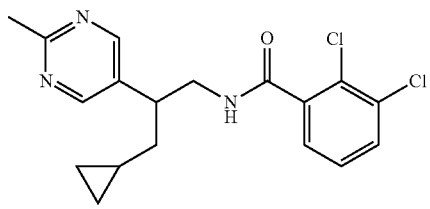 [SMILES: Cc1ncc(C(CNC(=O)c2cccc(Cl)c2Cl)CC2CC2)cn1]

From 2,3-dichlorobenzoic acid and 3-cyclopropyl-2-(2-methylpyrimidin-5-yl)propan-1-amine. LCMS (MH+): m/z=364.1, $t_R$ (minutes, Method F)=2.52

Example 3l2

2-chloro-N-(3-cyclopropyl-2-methyl-2-(2-(trifluoromethyl)pyrimidin-5-yl)propyl)benzamide

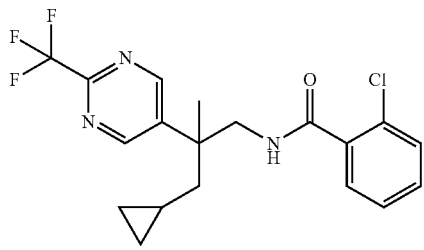

From 2-chlorobenzoic acid and 3-cyclopropyl-2-methyl-2-(2-(trifluoromethyl)pyrimidin-5-yl)propan-1-amine. LCMS (MH+): m/z=398.1, $t_R$ (minutes, Method F)=2.64

Example 3m2

2-chloro-N-(3-cyclopropyl-2-methyl-2-(2-(trifluoromethyl)pyrimidin-5-yl)propyl)-3-fluorobenzamide

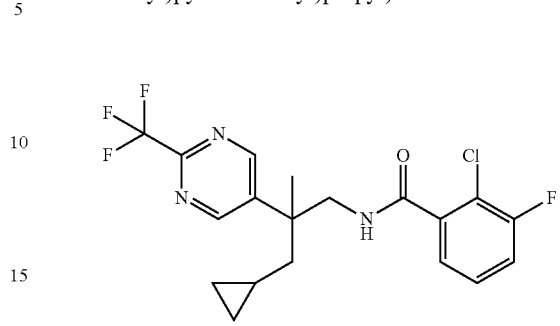

From 2-chloro-3-fluorobenzoic acid and 3-cyclopropyl-2-methyl-2-(2-(trifluoromethyl)pyrimidin-5-yl)propan-1-amine. LCMS (MH+): m/z=416.1, $t_R$ (minutes, Method G)=2.49

Example 3n2

2,3-dichloro-N-(3-cyclopropyl-2-(2-(trifluoromethyl)pyrimidin-5-yl)propyl)benzamide

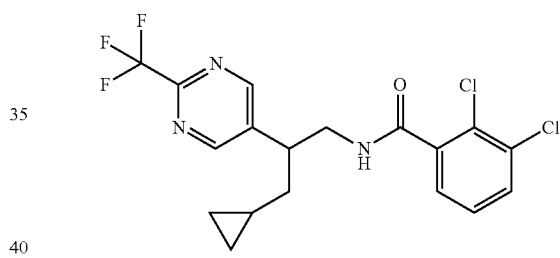

From 2,3-dichlorobenzoic acid and 3-cyclopropyl-2-(6-(trifluoromethyl)pyridin-3-yl)propan-1-amine. LCMS (MH+): m/z=418.1, $t_R$ (minutes, Method G)=2.48

Example 3o2

2-chloro-N-(3-cyclopropyl-2-(2-(trifluoromethyl)pyrimidin-5-yl)propyl)benzamide

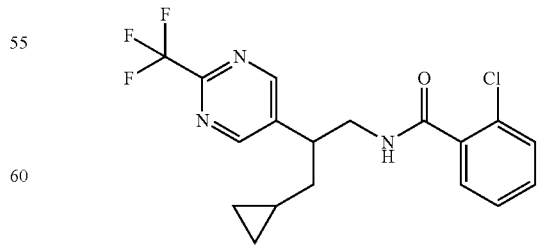

From 2-chlorobenzoic acid and 3-cyclopropyl-2-(6-(trifluoromethyl)pyridin-3-yl)propan-1-amine. LCMS (MH+): m/z=384.1, $t_R$ (minutes, Method F)=2.55

Example 3p2

2-chloro-N-(3-cyclopropyl-2-(2-(trifluoromethyl)pyrimidin-5-yl)propyl)-3-fluorobenzamide

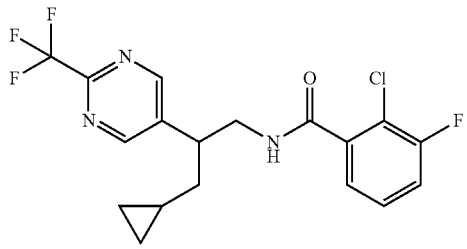 [SMILES: O=C(NCC(CC1CC1)c1cnc(C(F)(F)F)nc1)c1cccc(F)c1Cl]

From 2-chloro-3-fluorobenzoic acid and 3-cyclopropyl-2-(6-(trifluoromethyl)pyrimidin-3-yl)propan-1-amine. LCMS (MH+): m/z=402.1, $t_R$ (minutes, Method F)=2.61

Example 3q2

2-chloro-N-(3-cyclopropyl-2-(2-(trifluoromethyl)pyrimidin-5-yl)propyl)-6-fluorobenzamide

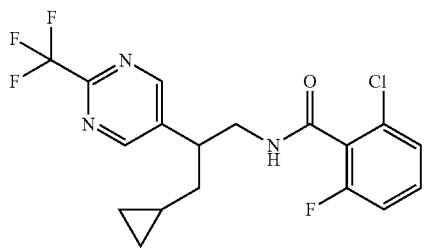

From 2-chloro-6-fluorobenzoic acid and 3-cyclopropyl-2-(6-(trifluoromethyl)pyrimidin-3-yl)propan-1-amine. LCMS (MH+): m/z=402.1, $t_R$ (minutes, Method F)=2.59

Example 3h2

2,3-dichloro-N-(2-(4-chlorophenyl)-2-(tetrahydro-2H-pyran-4-yl)ethyl)benzamide

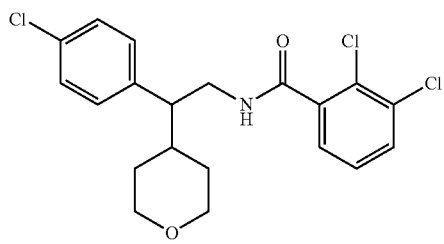 [SMILES: O=C(NCC(c1ccc(Cl)cc1)C1CCOCC1)c1cccc(Cl)c1Cl]

From 2,3-dichlorobenzoic acid and 2-(4-chlorophenyl)-2-(tetrahydro-2H-pyran-4-yl)ethanamine. LCMS (MH+): m/z=412.1, $t_R$ (minutes, Method G)=2.49

Example 3i2

2-chloro-N-(2-(4-chlorophenyl)-2-(tetrahydro-2H-pyran-4-yl)ethyl)benzamide

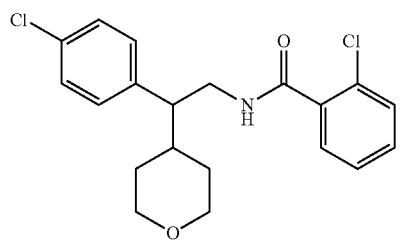 [SMILES: O=C(NCC(c1ccc(Cl)cc1)C1CCOCC1)c1ccccc1Cl]

From 2-chlorobenzoic acid and 2-(4-chlorophenyl)-2-(tetrahydro-2H-pyran-4-yl)ethanamine. LCMS (MH+): m/z=378.1, $t_R$ (minutes, Method G)=2.34

Example 3i2

2-chloro-6-fluoro-N-(2-(4-chlorophenyl)-2-(tetrahydro-2H-pyran-4-yl)ethyl)benzamide

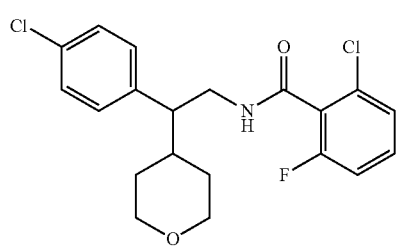 [SMILES: O=C(NCC(c1ccc(Cl)cc1)C1CCOCC1)c1c(F)cccc1Cl]

From 2-chloro-6-fluorobenzoic acid and 2-(4-chlorophenyl)-2-(tetrahydro-2H-pyran-4-yl)ethanamine. LCMS (MH+): m/z=396.1, $t_R$ (minutes, Method G)=2.36

Example 3i2

2-chloro-3-fluoro-N-(2-(4-chlorophenyl)-2-(tetrahydro-2H-pyran-4-yl)ethyl)benzamide

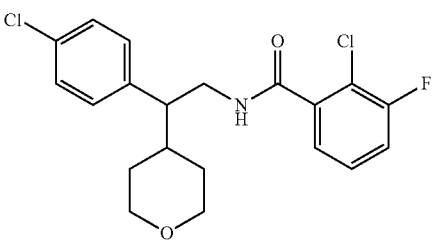 [SMILES: O=C(NCC(c1ccc(Cl)cc1)C1CCOCC1)c1cccc(F)c1Cl]

From 2-chloro-3-fluorobenzoic acid and 2-(4-chlorophenyl)-2-(tetrahydro-2H-pyran-4-yl)ethanamine. LCMS (MH+) m/z=396.1, $t_R$ (minutes, Method G)=2.36

Example 3j2

2,3-dichloro-N4(4-(2-methylpyrimidin-5-yl)tetra-hydro-2H-pyran-4-yl)methyl)benzamide

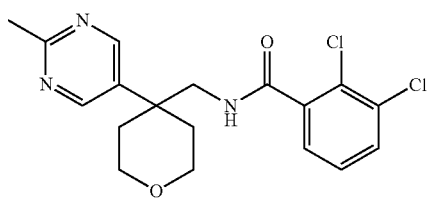 [SMILES: Cc1ncc(C2(CNC(=O)c3cccc(Cl)c3Cl)CCOCC2)cn1]

From 2,3-dichlorobenzoic acid and (4-(2-methylpyrimidin-5-yl)tetrahydro-2H-pyran-4-yl)methanamine. LCMS (MH+): m/z=380.1, $t_R$ (minutes, Method F)=1.80

Example 3k2

2-chloro-N-((4-(2-methylpyrimidin-5-yl)tetrahydro-2H-pyran-4-yl)methyl)benzamide

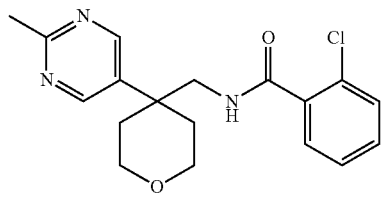 [SMILES: Cc1ncc(C2(CNC(=O)c3ccccc3Cl)CCOCC2)cn1]

From 2-chlorobenzoic acid and (4-(2-methylpyrimidin-5-yl)tetrahydro-2H-pyran-4-yl)methanamine. LCMS (MH+): m/z=346.1, $t_R$ (minutes, Method F)=1.55

Example 3l2

2-chloro-6-fluoro-N-((4-(2-methylpyrimidin-5-yl)tetrahydro-2H-pyran-4-yl)methyl)benzamide

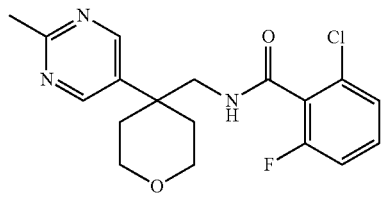 [SMILES: Cc1ncc(C2(CNC(=O)c3c(F)cccc3Cl)CCOCC2)cn1]

From 2-chloro-6-fluorobenzoic acid and (4-(2-methylpyrimidin-5-yl)tetrahydro-2H-pyran-4-yl)methanamine. LCMS (MH+): m/z=364.1, $t_R$ (minutes, Method F)=1.57

Example 3m2

2-chloro-3-fluoro-N-((4-(2-methylpyrimidin-5-yl)tetrahydro-2H-pyran-4-yl)methyl)benzamide

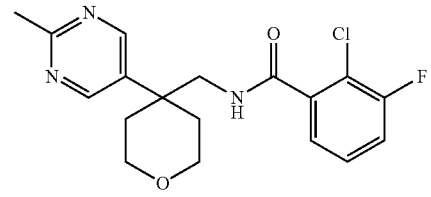 [SMILES: Cc1ncc(C2(CNC(=O)c3cccc(F)c3Cl)CCOCC2)cn1]

From 2-chloro-3-fluorobenzoic acid and (4-(2-methylpyrimidin-5-yl)tetrahydro-2H-pyran-4-yl)methanamine. LCMS (MH+): m/z=364.1, $t_R$ (minutes, Method F)=1.95

Example 3n2

2,3-dichloro-N-((4-(2-(trifluoromethyl)pyrimidin-5-yl)tetrahydro-2H-pyran-4-yl)methyl)benzamide

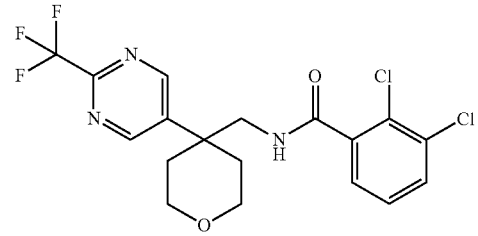 [SMILES: O=C(NCC1(c2cnc(C(F)(F)F)nc2)CCOCC1)c1cccc(Cl)c1Cl]

From 2,3-dichlorobenzoic acid and (4-(2-(trifluoromethyl)pyrimidin-5-yl)tetrahydro-2H-pyran-4-yl)methanamine. LCMS (MH+): m/z=434.1, $t_R$ (minutes, Method F)=2.34

Example 3o2

2-chloro-N-((4-(2-(trifluoromethyl)pyrimidin-5-yl)tetrahydro-2H-pyran-4-yl)methyl)benzamide

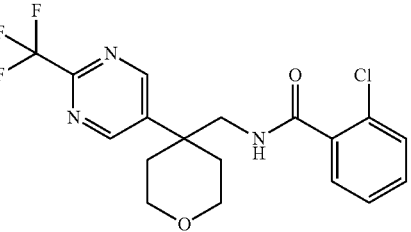

From 2-chlorobenzoic acid and (4-(2-(trifluoromethyl)pyrimidin-5-yl)tetrahydro-2H-pyran-4-yl)methanamine. LCMS (MH+): m/z=400.1, $t_R$ (minutes, Method F)=2.15

Example 3p2

2-chloro-6-fluoro-N-((4-(2-(trifluoromethyl)pyrimidin-5-yl)tetrahydro-2H-pyran-4-yl)methyl)benzamide

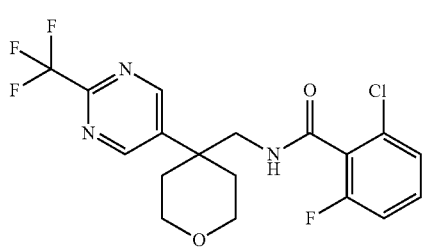 [SMILES: O=C(NCC1(c2cnc(C(F)(F)F)nc2)CCOCC1)c1c(F)cccc1Cl]

From 2-chloro-6-fluorobenzoic acid and (4-(2-(trifluoromethyl)pyrimidin-5-yl)tetrahydro-2H-pyran-4-yl)methanamine. LCMS (MH+): m/z=418.1, $t_R$ (minutes, Method F)=2.17

Example 3q2

2-chloro-3-fluoro-N-((4-(2-(trifluoromethyl)pyrimidin-5-yl)tetrahydro-2H-pyran-4-yl)methyl)benzamide

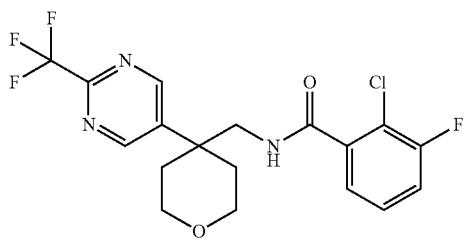 [SMILES: O=C(NCC1(c2cnc(C(F)(F)F)nc2)CCOCC1)c1cccc(F)c1Cl]

From 2-chloro-3-fluorobenzoic acid and (4-(2-(trifluoromethyl)pyrimidin-5-yl)tetrahydro-2H-pyran-4-yl)methanamine. LCMS (MH+): m/z=418.1, $t_R$ (minutes, Method F)=2.24

Example 3q2

2,3-dichloro N-(3-cyclopropyl-2-(6-(2-hydroxypropan-2-yl) pyridin-3-yl)propyl)benzamide

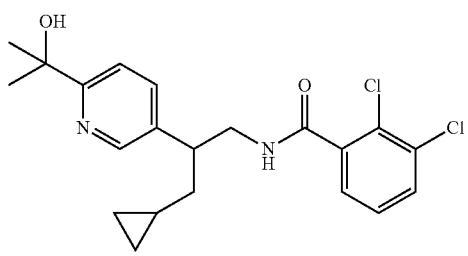 [SMILES: CC(C)(O)c1ccc(C(CNC(=O)c2cccc(Cl)c2Cl)CC2CC2)cn1]

From 2,3-dichlorobenzoic acid and 2-(5-(1-amino-3-cyclopropylpropan-2-yl)pyridin-2-yl)propan-2-ol. LCMS (MH+): m/z=407.1, $t_R$ (minutes, Method F)=1.98

Example 3r2

2-chloro-N-(3-cyclopropyl-2-(2-(trifluoromethyl)pyrimidin-5-yl)propyl)-3-methoxybenzamide

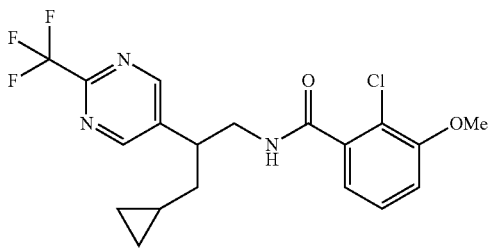

From 2-chloro-3-methoxybenzoic acid and 3-cyclopropyl-2-(2-(trifluoromethyl)pyrimidin-5-yl)propan-1-amine. LCMS (MH+): m/z=414.0, $t_R$ (minutes, Method F)=2.53

Example 3s2

2-methyl-N-(3-cyclopropyl-2-(2-(trifluoromethyl)pyrimidin-5-yl)propyl)-3-methoxybenzamide

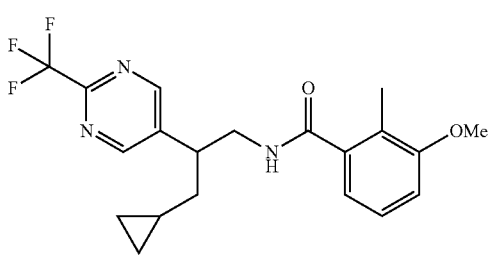

From 2-methyl-3-methoxybenzoic acid and 3-cyclopropyl-2-(2-(trifluoromethyl)pyrimidin-5-yl)propan-1-amine. LCMS (MH+): m/z=394.0, $t_R$ (minutes, Method F)=2.59

Example 3t2

2,3-dichloro-N-(3-(1-fluorocyclopropyl)-2-(6-(trifluoromethyl)pyridin-3-yl)propyl)benzamide

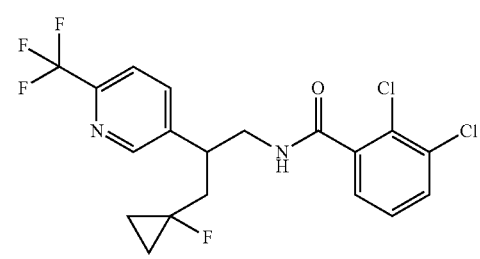 [SMILES: O=C(NCC(CC1(F)CC1)c1ccc(C(F)(F)F)nc1)c1cccc(Cl)c1Cl]

From 2,3-dichlorobenzoic acid and 3-(1-fluorocyclopropyl)-2-(6-(trifluoromethyl)pyridin-3-yl)propan-1-amine. LCMS (MH+): m/z=435.1, $t_R$ (minutes, Method G)=2.46

Example 3u2

2,6-dichloro-N-(3-cyclopropyl-2-(2-(trifluoromethyl)pyrimidin-5-yl)propyl)benzamide

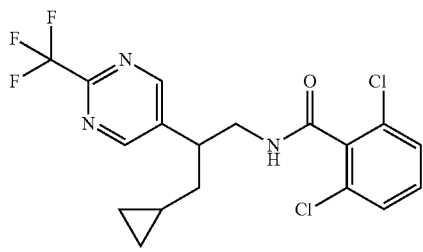 [SMILES: O=C(NCC(CC1CC1)c1cnc(C(F)(F)F)nc1)c1c(Cl)cccc1Cl]

From 2,6-dichlorobenzoic acid and 3-cyclopropyl-2-(2-(trifluoromethyl)pyrimidin-5-yl)propan-1-amine. LCMS (MH+): m/z=418.1, $t_R$ (minutes, Method G)=2.62

Example 3v2

2,6-dichloro-N-(3-cyclopropyl-2-(2-(trifluoromethyl)pyridin-5-yl)propyl)benzamide

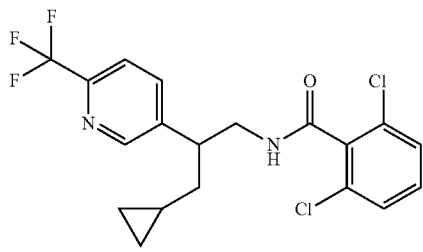 [SMILES: O=C(NCC(CC1CC1)c1ccc(C(F)(F)F)nc1)c1c(Cl)cccc1Cl]

From 2,6-dichlorobenzoic acid and 3-cyclopropyl-2-(2-(trifluoromethyl)pyridin-5-yl)propan-1-amine. LCMS (MH+): m/z=417.1, $t_R$ (minutes, Method F)=2.50

Example 3x2

2,6-dichloro N-(3-cyclopropyl-2-(2-methylpyrimidin-5-yl)propyl)benzamide

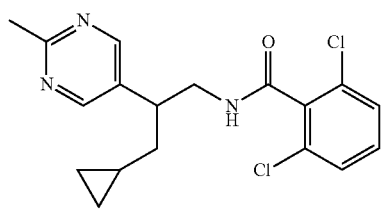 [SMILES: Cc1ncc(C(CNC(=O)c2c(Cl)cccc2Cl)CC2CC2)cn1]

From 2,6-dichlorobenzoic acid and 3-cyclopropyl-2-(2-methylpyrimidin-5-yl)propan-1-amine. LCMS (MH+): m/z=364.1, $t_R$ (minutes, Method G)=2.43

Example 3y2

2,3-dichloro-N-(3-(1-fluorocyclopropyl)-2-(6-(trifluoromethyl)pyrimidin-3-yl)propyl)benzamide

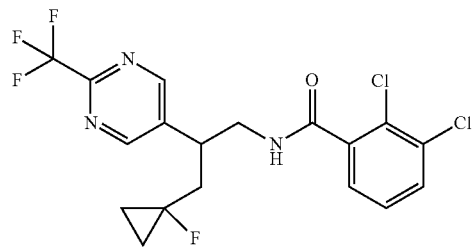

From 2,3-dichlorobenzoic acid and 3-(1-fluorocyclopropyl)-2-(6-(trifluoromethyl)pyrimidin-3-yl)propan-1-amine. LCMS (MH+): m/z=436.1, $t_R$ (minutes, Method G)=2.61

Example 3z2

2,3-dichloro-N-((4,4-difluoro-1-(2-(trifluoromethyl)pyrimidin-5-yl)cyclohexyl)methyl)benzamide

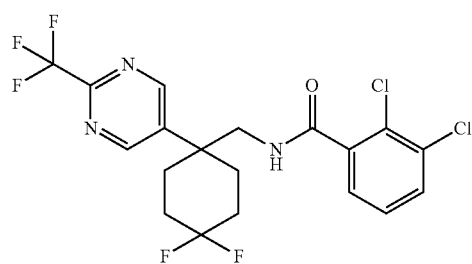 [SMILES: O=C(NCC1(c2cnc(C(F)(F)F)nc2)CCC(F)(F)CC1)c1cccc(Cl)c1Cl]

From 2,3-dichlorobenzoic acid and (4,4-difluoro-1-(2-(trifluoromethyl)pyrimidin-5-yl)cyclohexyl)methanamine. LCMS (MH+): m/z=468.1, $t_R$ (minutes, Method G)=2.48

Example 3a3

2,3-dichloro N-(2-(2-methylpyrimidin-5-yl)-2-(pyridin-4-yl)ethyl)benzamide

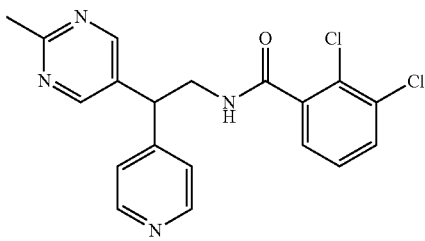 [SMILES: Cc1ncc(C(CNC(=O)c2cccc(Cl)c2Cl)c2ccncc2)cn1]

From 2,3-dichlorobenzoic acid and 2-(2-methylpyrimidin-5-yl)-2-(pyridin-4-yl)ethanamine. LCMS (MH+): m/z=387.1, $t_R$ (minutes, Method F)=1.56

Example 3b3

2-chloro-N-(2-(2-methylpyrimidin-5-yl)-2-(pyridin-4-yl)ethyl)benzamide

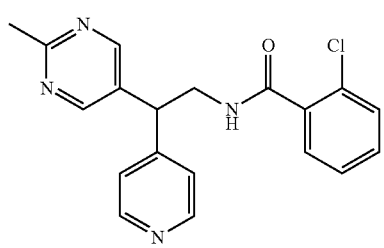 [SMILES: Cc1ncc(C(CNC(=O)c2ccccc2Cl)c2ccncc2)cn1]

From 2-chlorobenzoic acid and 2-(2-methylpyrimidin-5-yl)-2-(pyridin-4-yl)ethanamine. LCMS (MH+): m/z=353.1, $t_R$ (minutes, Method F)=1.62

Example 3c3

2-chloro-6-fluoro-N-(2-(2-methylpyrimidin-5-yl)-2-(pyridin-4-yl)ethyl)benzamide

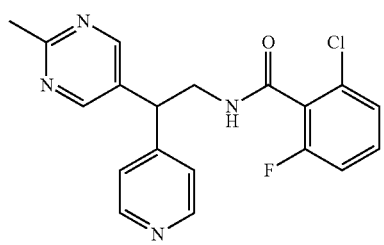 [SMILES: Cc1ncc(C(CNC(=O)c2c(F)cccc2Cl)c2ccncc2)cn1]

From 2-chloro-6-fluorobenzoic acid and 2-(2-methylpyrimidin-5-yl)-2-(pyridin-4-yl)ethanamine. LCMS (MH+): m/z=371.1, $t_R$ (minutes, Method F)=1.65

Example 3d3

2-chloro-3-fluoro-N-(2-(2-methylpyrimidin-5-yl)-2-(pyridin-4-yl)ethyl)benzamide

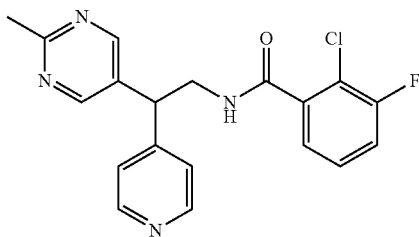 [SMILES: Cc1ncc(C(CNC(=O)c2cccc(F)c2Cl)c2ccncc2)cn1]

From 2-chloro-3-fluorobenzoic acid and 2-(2-methylpyrimidin-5-yl)-2-(pyridin-4-yl)ethanamine. LCMS (MIFF): m/z=371.1, $t_R$ (minutes, Method F)=1.73

Example 3e3

2-chloro-N-(3-cyclopropyl-2-methyl-2-(2-(trifluoromethyl)pyrimidin-5-yl)propyl)benzamide

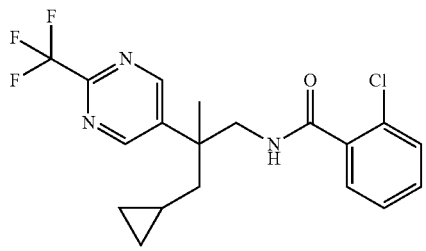 [SMILES: CC(CNC(=O)c1ccccc1Cl)(CC1CC1)c1cnc(C(F)(F)F)nc1]

From 2-chlorobenzoic acid and 3-cyclopropyl-2-methyl-2-(2-(trifluoromethyl)pyrimidin-5-yl)propan-1-amine. LCMS (MH+): m/z=398.1, $t_R$ (minutes, Method F)=2.62

Example 3f3

2-chloro-3-fluoro-N-(3-cyclopropyl-2-methyl-2-(2-(trifluoromethyl)pyrimidin-5-yl)propyl)benzamide

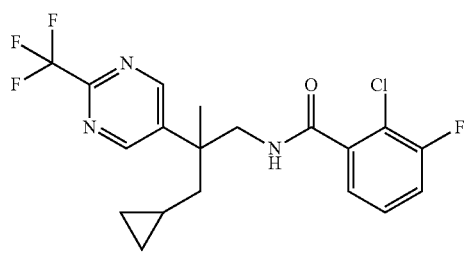 [SMILES: CC(CNC(=O)c1cccc(F)c1Cl)(CC1CC1)c1cnc(C(F)(F)F)nc1]

From 2-chloro-3-fluorobenzoic acid and 3-cyclopropyl-2-methyl-2-(2-(trifluoromethyl)pyrimidin-5-yl)propan-1-amine. LCMS (MH+): m/z=416.1, $t_R$ (minutes, Method G)=2.48

Example 3g3

2,3-dichloro-N-(3-cyclopropyl-2-methyl-2-(2-(trifluoromethyl)pyrimidin-5-yl)propyl)benzamide

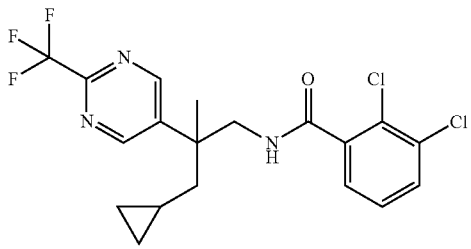

From 2,3-dichlorobenzoic acid and 3-cyclopropyl-2-methyl-2-(2-(trifluoromethyl)pyrimidin-5-yl)propan-1-amine. LCMS (MH+): m/z=432.1, $t_R$ (minutes, Method G)=2.58

Example 3h3

2-chloro-N-(2-(2-methylpyrimidin-5-yl)-2-(tetrahydro-2H-pyran-4-yl)ethyl)benzamide

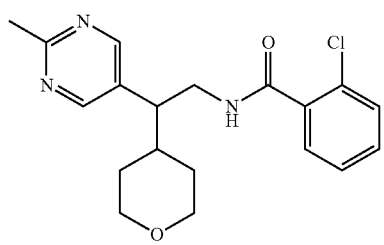 [SMILES: Cc1ncc(C(CNC(=O)c2ccccc2Cl)C2CCOCC2)cn1]

From 2-chlorobenzoic acid and 2-(2-methylpyrimidin-5-yl)-2-(tetrahydro-2H-pyran-4-yl)ethanamine. LCMS (MH+): m/z=360.1, $t_R$ (minutes, Method F)=1.97

Example 3i3

2,3-dichloro N-(2-(2-methylpyrimidin-5-yl)-2-(tetrahydro-2H-pyran-4-yl)ethyl)benzamide

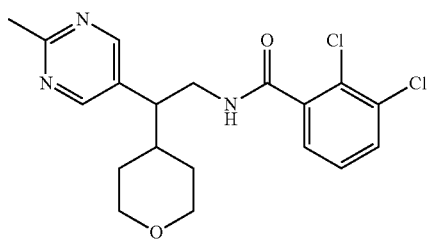 [SMILES: Cc1ncc(C(CNC(=O)c2cccc(Cl)c2Cl)C2CCOCC2)cn1]

From 2,3-dichlorobenzoic acid and 2-(2-methylpyrimidin-5-yl)-2-(tetrahydro-2H-pyran-4-yl)ethanamine. LCMS (MH+): m/z=394.1, $t_R$ (minutes, Method F)=1.88

Example 3j3

2-chloro-3-fluoro-N-(2-(2-methylpyrimidin-5-yl)-2-(tetrahydro-2H-pyran-4-yl)ethyl)benzamide

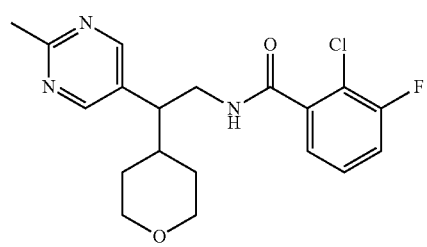 [SMILES: Cc1ncc(C(CNC(=O)c2cccc(F)c2Cl)C2CCOCC2)cn1]

From 2-chloro-3-fluorobenzoic acid and 2-(2-methylpyrimidin-5-yl)-2-(tetrahydro-2H-pyran-4-yl)ethanamine. LCMS (MH+): m/z=378.1, $t_R$ (minutes, Method F)=2.00

Example 3k3

2-chloro-6-fluoro-N-(2-(2-methylpyrimidin-5-yl)-2-(tetrahydro-2H-pyran-4-yl)ethyl)benzamide

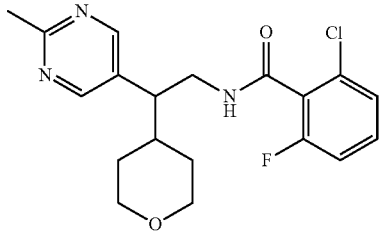 [SMILES: Cc1ncc(C(CNC(=O)c2c(F)cccc2Cl)C2CCOCC2)cn1]

From 2-chloro-6-fluorobenzoic acid and 2-(2-methylpyrimidin-5-yl)-2-(tetrahydro-2H-pyran-4-yl)ethanamine. LCMS (MH+): m/z=378.1, $t_R$ (minutes, Method F)=2.06

Example 3l3

2,3-dichloro-N-(2-(4,4-difluorocyclohexyl)-2-(2-methylpyrimidin-5-yl)ethyl)benzamide

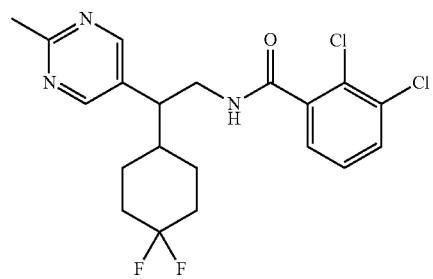 [SMILES: Cc1ncc(C(CNC(=O)c2cccc(Cl)c2Cl)C2CCC(F)(F)CC2)cn1]

From 2,3-dichlorobenzoic acid and 2-(4,4-difluorocyclohexyl)-2-(2-methylpyrimidin-5-yl)ethanamine. LCMS (MH+): m/z=428.1, $t_R$ (minutes, Method G)=2.04

Example 3m3

2-chloro-N-(2-(4,4-difluorocyclohexyl)-2-(2-methylpyrimidin-5-yl)ethyl)benzamide

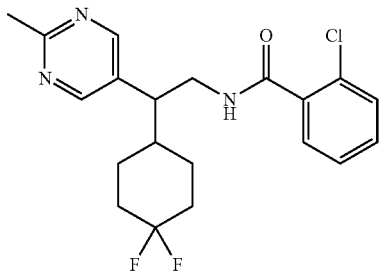 [SMILES: Cc1ncc(C(CNC(=O)c2ccccc2Cl)C2CCC(F)(F)CC2)cn1]

From 2-chlorobenzoic acid and 2-(4,4-difluorocyclohexyl)-2-(2-methylpyrimidin-5-yl)ethanamine. LCMS (MH+): m/z=394.1, $t_R$ (minutes, Method F)=2.1

Example 3n3

2-chloro-6-fluoroN-(2-(4,4-difluorocyclohexyl)-2-(2-methylpyrimidin-5-yl)ethyl)benzamide

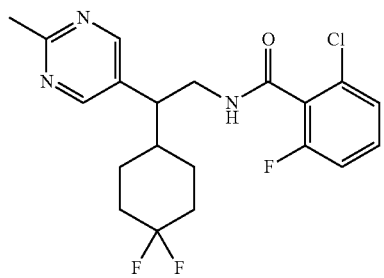 [SMILES: Cc1ncc(C(CNC(=O)c2c(F)cccc2Cl)C2CCC(F)(F)CC2)cn1]

From 2-chloro-6-fluorobenzoic acid and 2-(4,4-difluorocyclohexyl)-2-(2-methylpyrimidin-5-yl)ethanamine. LCMS (MH+): m/z=412.1, $t_R$ (minutes, Method F)=2.14

Example 3o3

2-chloro-3-fluoro-N-(2-(4,4-difluorocyclohexyl)-2-(2-methylpyrimidin-5-yl)ethyl)benzamide

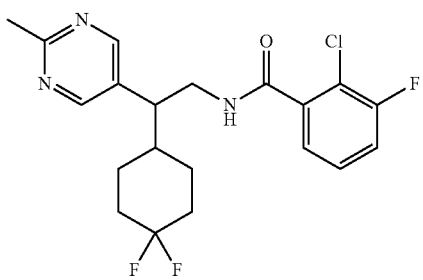 [SMILES: Cc1ncc(C(CNC(=O)c2cccc(F)c2Cl)C2CCC(F)(F)CC2)cn1]

From 2-chloro-3-fluorobenzoic acid and 2-(4,4-difluorocyclohexyl)-2-(2-methylpyrimidin-5-yl)ethanamine. LCMS (MH+): m/z=412.1, $t_R$ (minutes, Method F)=2.18

Example 3p3

2-chloro-N-(3-(1-(trifluoromethyl)cyclopropyl)-2-(2-(trifluoromethyl)pyrimidin-5-yl)propyl)benzamide

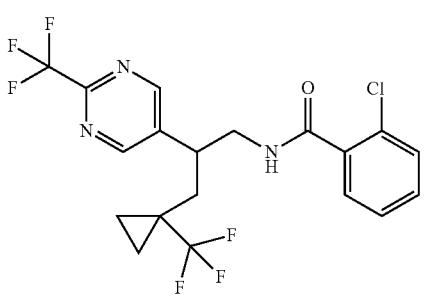 [SMILES: O=C(NCC(CC1(C(F)(F)F)CC1)c1cnc(C(F)(F)F)nc1)c1ccccc1Cl]

From 2-chlorobenzoic acid and 3-(1-(trifluoromethyl)cyclopropyl)-2-(2-(frifluoromethyl)pyrimidin-5-yl)propan-1-amine. LCMS (MH+): m/z=452.0, $t_R$ (minutes, Method F)=3.03

Example 3q3

2,3-dichloro-N-(3-(1-(trifluoromethyl)cyclopropyl)-2-(2-(trifluoromethyl)pyrimidin-5-yl)propyl)benzamide

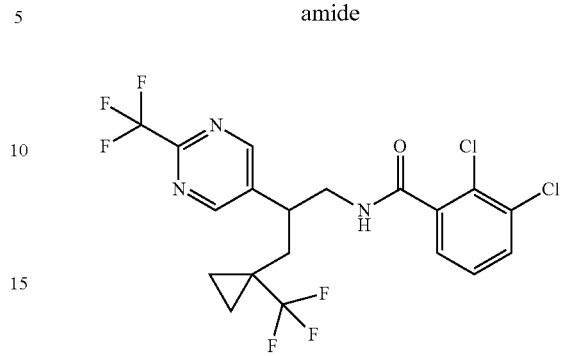

From 2,3-dichlorobenzoic acid and 3-(1-(trifluoromethyl)cyclopropyl)-2-(2-(trifluoromethyl)pyrimidin-5-yl)propan-1-amine. LCMS (1\4H+): m/z=486.1, $t_R$ (minutes, Method F)=2.77

Example 3r3

2-chloro-3-fluoro-N-(3-(1-(trifluoromethyl)cyclopropyl)-2-(2-(trifluoromethyl)pyrimidin-5-yl)propyl)benzamide

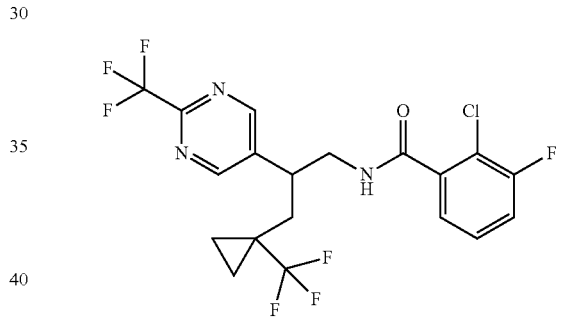

From 2-chloro-3-fluorobenzoic acid and 3-(1-(trifluoromethyl)cyclopropyl)-2-(2-(trifluoromethyl)pyrimidin-5-yl)propan-1-amine. LCMS (MH+): m/z=470.0, $t_R$ (minutes, Method F)=3.07

Example 3s3

2-chloro-N-(3-(1-(trifluoromethyl)cyclopropyl)-2-(2-(trifluoromethyl)pyridin-5-yl)propyl)benzamide

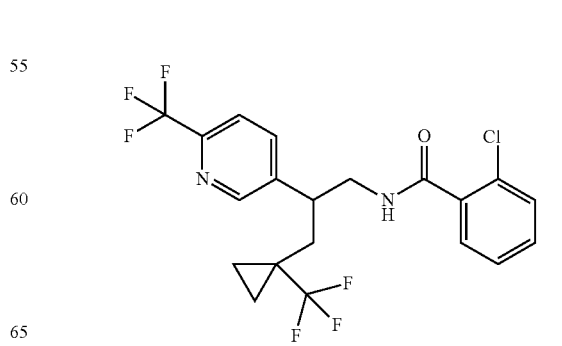

From 2-chlorobenzoic acid and 3-(1-(trifluoromethyl)cyclopropyl)-2-(2-(trifluoromethyl)pyridin-5-yl)propan-1-amine. LCMS (MH+): m/z=451.1, $t_R$ (minutes, Method G)=2.50

Example 3t3

2,3-dichloro-N-(3-(1-(trifluoromethyl)cyclopropyl)-2-(2-(trifluoromethyl)pyridin-5-yl)propyl)benzamide

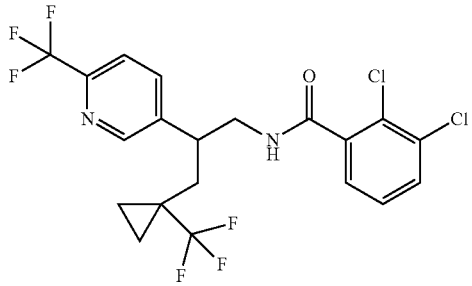 [SMILES: O=C(NCC(CC1(C(F)(F)F)CC1)c1ccc(C(F)(F)F)nc1)c1cccc(Cl)c1Cl]

From 2,3-dichlorobenzoic acid and 3-(1-(trifluoromethyl)cyclopropyl)-2-(2-(trifluoromethyl)pyridin-5-yl)propan-1-amine. LCMS (MH+): m/z=485.1, $t_R$ (minutes, Method G)=2.63

Example 3u3

2-chloro-3-fluoro-N-(3-(1-(trifluoromethyl)cyclopropyl)-2-(2-(trifluoromethyl)pyridin-5-yl)propyl)benzamide

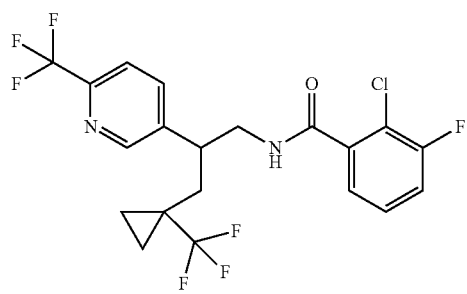 [SMILES: O=C(NCC(CC1(C(F)(F)F)CC1)c1ccc(C(F)(F)F)nc1)c1cccc(F)c1Cl]

From 2-chloro-3-fluorobenzoic acid and 3-(1-(trifluoromethyl)cyclopropyl)-2-(2-(trifluoromethyl)pyridin-5-yl)propan-1-amine. LCMS (MH+): m/z=469.1, $t_R$ (minutes, Method G)=2.54

Example 3v3

2,3-dichloro-N-(2-(tetrahydro-2H-pyran-4-yl)-2-(2-(trifluoromethyl)pyrimidin-5-yl)ethyl)benzamide

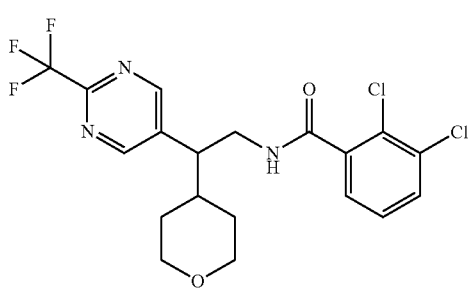 [SMILES: O=C(NCC(c1cnc(C(F)(F)F)nc1)C1CCOCC1)c1cccc(Cl)c1Cl]

From 2,3-dichlorobenzoic acid and 2-(tetrahydro-2H-pyran-4-yl)-2-(2-(trifluoromethyl)pyrimidin-5-yl)ethanamine. LCMS (MH+): m/z=448.0, $t_R$ (minutes, Method F)=2.72

Example 3x3

2-chloro-N-(2-(tetrahydro-2H-pyran-4-yl)-2-(2-(trifluoromethyl)pyrimidin-5-yl)ethyl)benzamide

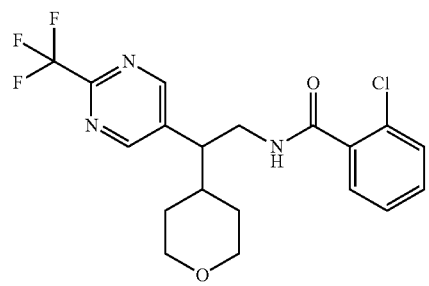 [SMILES: O=C(NCC(c1cnc(C(F)(F)F)nc1)C1CCOCC1)c1ccccc1Cl]

From 2-chlorobenzoic acid and 2-(tetrahydro-2H-pyran-4-yl)-2-(2-(trifluoromethyl)pyrimidin-5-yl)ethanamine. LCMS (MH+): m/z=414.1, $t_R$ (minutes, Method F)=2.54

Example 3y3

2-chloro-3-fluoro-N-(2-(tetrahydro-2H-pyran-4-yl)-2-(2-(trifluoromethyl)pyrimidin-5-yl)ethyl)benzamide

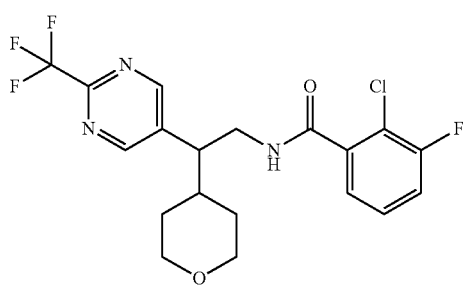 [SMILES: O=C(NCC(c1cnc(C(F)(F)F)nc1)C1CCOCC1)c1cccc(F)c1Cl]

From 2-chloro-3-fluorobenzoic acid and 2-(tetrahydro-2H-pyran-4-yl)-2-(2-(trifluoromethyl)pyrimidin-5-yl)ethanamine. LCMS (MH+): m/z=432.1, $t_R$ (minutes, Method F)=2.48

Example 3z3

2-chloro-6-fluoro-N-(2-(tetrahydro-2H-pyran-4-yl)-2-(2-(trifluoromethyl)pyrimidin-5-yl)ethyl)benzamide

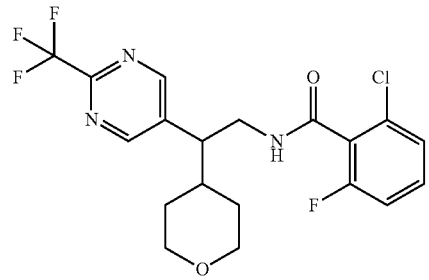 [SMILES: O=C(NCC(c1cnc(C(F)(F)F)nc1)C1CCOCC1)c1c(F)cccc1Cl]

From 2-chloro-6-fluorobenzoic acid and 2-(tetrahydro-2H-pyran-4-yl)-2-(2-(trifluoromethyl)pyrimidin-5-yl)ethanamine. LCMS (MH+): m/z=432.1, $t_R$ (minutes, Method F)=2.6

Example 3a4

2,3-dichloro-N-(2-(4-fluorophenyl)-2-(6-(trifluoromethyl)pyridin-3-yl)ethyl)benzamide

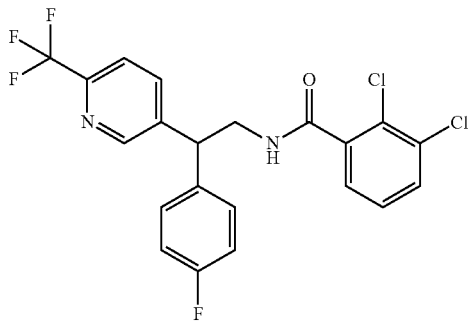

From 2,3-dichlorobenzoic acid and 2-(4-fluorophenyl)-2-(6-(trifluoromethyl)pyridin-3-yl)ethanamine. LCMS (MH+): m/z=457.0, $t_R$ (minutes, Method G)=3.02

Example 3b4

2-chloro-N-(2-(4-fluorophenyl)-2-(6-(trifluoromethyl)pyridin-3-yl)ethyl)benzamide

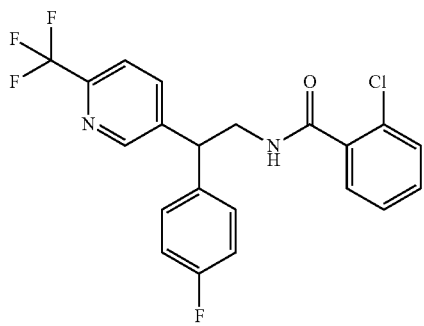 [SMILES: O=C(NCC(c1ccc(F)cc1)c1ccc(C(F)(F)F)nc1)c1ccccc1Cl]

From 2-chlorobenzoic acid and 2-(4-fluorophenyl)-2-(6-(trifluoromethyl)pyridin-3-yl)ethanamine. LCMS (M+): m/z=423.1, $t_R$ (minutes, Method G)=2.58

Example 3c4

2-chloro-3-fluoro-N-(2-(4-fluorophenyl)-2-(6-(trifluoromethyl)pyridin-3-yl)ethyl)benzamide

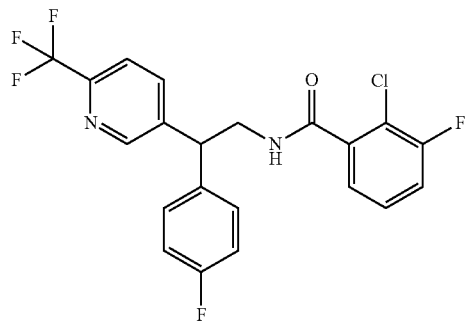 [SMILES: O=C(NCC(c1ccc(F)cc1)c1ccc(C(F)(F)F)nc1)c1cccc(F)c1Cl]

From 2-chloro-3-fluorobenzoic acid and 2-(4-fluorophenyl)-2-(6-(trifluoromethyl)pyridin-3-yl)ethanamine. LCMS (MH+): m/z=441.1, $t_R$ (minutes, Method G)=2.63

Example 3d4

2-chloro-6-fluoro-N-(2-(4-fluorophenyl)-2-(6-(trifluoromethyl)pyridin-3-yl)ethyl)benzamide

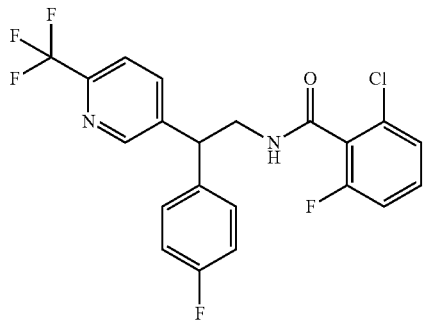 [SMILES: O=C(NCC(c1ccc(F)cc1)c1ccc(C(F)(F)F)nc1)c1c(F)cccc1Cl]

From 2-chloro-6-fluorobenzoic acid and 2-(4-fluorophenyl)-2-(6-(trifluoromethyl)pyridin-3-yl)ethanamine. LCMS (MH+): m/z=441.0, $t_R$ (minutes, Method G)=2.86

Example 3e4

2-chloro-N-(2-(pyridin-4-yl)-2-(2-(trifluoromethyl)pyrimidin-5-yl)ethyl)benzamide

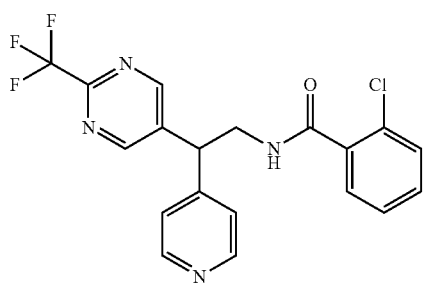 [SMILES: O=C(NCC(c1ccncc1)c1cnc(C(F)(F)F)nc1)c1ccccc1Cl]

From 2-chlor° benzoic acid and 2-(pyridin-4-yl)-2-(2-(trifluoromethyl)pyrimidin-5-yl)ethanamine. LCMS (MH+): m/z=407.1, $t_R$ (minutes, Method F)=2.25

Example 3f4

2,3-dichloro-N-(2-(pyridin-4-yl)-2-(2-(trifluoromethyl)pyrimidin-5-yl)ethyl)benzamide

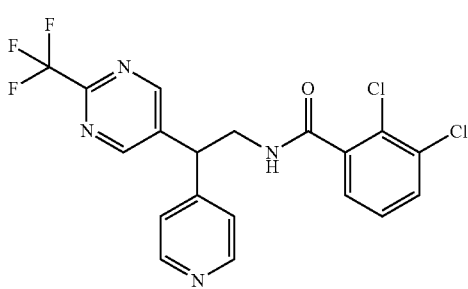 [SMILES: O=C(NCC(c1ccncc1)c1cnc(C(F)(F)F)nc1)c1cccc(Cl)c1Cl]

From 2,3-dichlorobenzoic acid and 2-(pyridin-4-yl)-2-(2-(trifluoromethyl)pyrimidin-5-yl)ethanamine. LCMS (MH+): m/z=441.1, $t_R$ (minutes, Method F)=2.43

Example 3g4

2-chloro-N-(2-(pyridin-4-yl)-2-(2-(trifluoromethyl)pyridin-5-yl)ethyl)benzamide

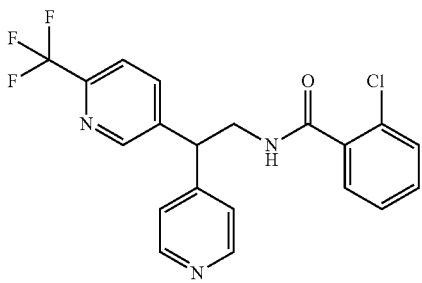 [SMILES: O=C(NCC(c1ccncc1)c1ccc(C(F)(F)F)nc1)c1ccccc1Cl]

From 2-chlorobenzoic acid and 2-(pyridin-4-yl)-2-(2-(trifluoromethyl)pyridin-5-yl)ethanamine. LCMS (MH+): m/z=406.1, $t_R$ (minutes, Method F)=2.27

Example 3h4

2,3-dichloro-N-(2-(pyridin-4-yl)-2-(2-(trifluoromethyl)pyridin-5-yl)ethyl)benzamide

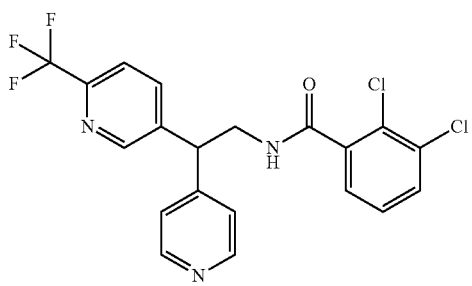 [SMILES: O=C(NCC(c1ccncc1)c1ccc(C(F)(F)F)nc1)c1cccc(Cl)c1Cl]

From 2,3-dichlorobenzoic acid and 2-(pyridin-4-yl)-2-(2-(trifluoromethyl)pyridin-5-yl)ethanamine. LCMS (MH+): m/z=440.0, $t_R$ (minutes, Method F)=2.43

Example 3i4

2,3-dichloro-N-(2-(4-fluorophenyl)-2-(2-(trifluoromethyl)pyrimidin-5-yl)ethyl)benzamide

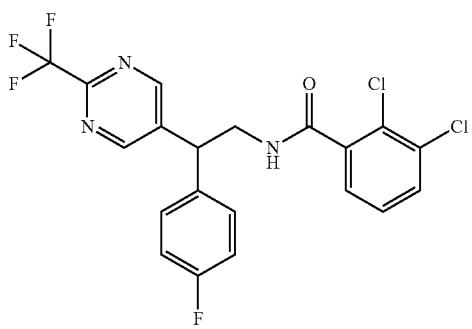

From 2,3-dichlorobenzoic acid and 2-(4-fluorophenyl)-2-(2-(trifluoromethyl)pyrimidin-5-yl)ethanamine. LCMS (MH+): m/z=458.0, $t_R$ (minutes, Method G)=2.91

Example 3j4

2-chloro-N-(2-(4-fluorophenyl)-2-(2-(trifluoromethyl)pyrimidin-5-yl)ethyl)benzamide

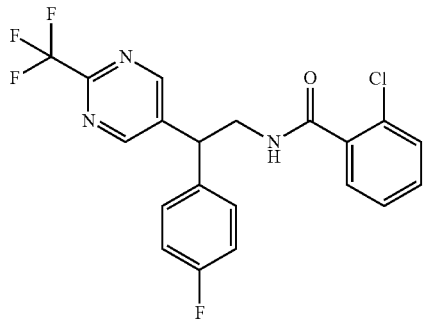 [SMILES: O=C(NCC(c1ccc(F)cc1)c1cnc(C(F)(F)F)nc1)c1ccccc1Cl]

From 2-chlorobenzoic acid and 2-(4-fluorophenyl)-2-(2-(trifluoromethyl)pyrimidin-5-yl)ethanamine. LCMS (MH+): m/z=424.1, $t_R$ (minutes, Method F)=3.19

Example 3k4

2-chloro-3-fluoro-N-(2-(4-fluorophenyl)-2-(2-(trifluoromethyl)pyrimidin-5-yl)ethyl)benzamide

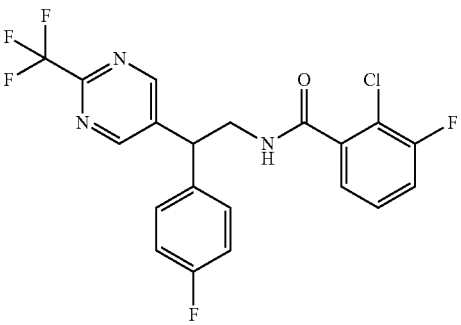 [SMILES: O=C(NCC(c1ccc(F)cc1)c1cnc(C(F)(F)F)nc1)c1cccc(F)c1Cl]

From 2-chloro-3-fluorobenzoic acid and 2-(4-fluorophenyl)-2-(2-(trifluoromethyl)pyrimidin-5-yl)ethanamine. LCMS (MH+) m/z=442.1, $t_R$ (minutes, Method F)=3.24

Example 3l4

2-chloro-6-fluoro-N-(2-(4-fluorophenyl)-2-(2-(trifluoromethyl)pyrimidin-5-yl)ethyl)benzamide

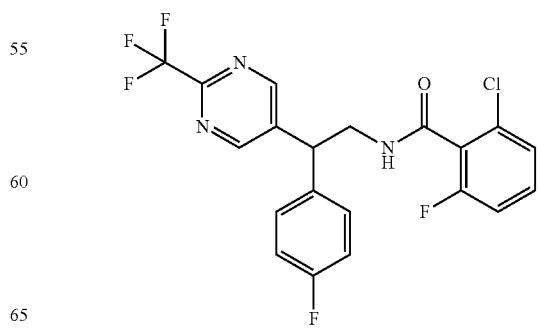

From 2-chloro-6-fluorobenzoic acid and 2-(4-fluorophenyl)-2-(2-(trifluoromethyl)pyrimidin-5-yl)ethanamine. LCMS (MH+) m/z=442.0, $t_R$ (minutes, Method F)=2.99

Example 3m4

2-chloro-N-(2-(4,4-difluorocyclohexyl)-2-(2-(trifluoromethyl)pyrimidin-5-yl)ethyl)benzamide

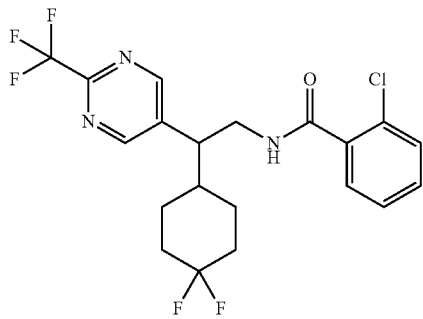 [SMILES: O=C(NCC(c1cnc(C(F)(F)F)nc1)C1CCC(F)(F)CC1)c1ccccc1Cl]

From 2-chlorobenzoic acid and 2-(4,4-difluorocyclohexyl)-2-(2-(trifluoromethyl)pyrimidin-5-yl)ethanamine. LCMS (MH+): m/z=448.1, $t_R$ (minutes, Method F)=2.95

Example 3n4

2,3-dichloro-N-(2-(4,4-difluorocyclohexyl)-2-(2-(trifluoromethyl)pyrimidin-5-yl)ethyl)benzamide

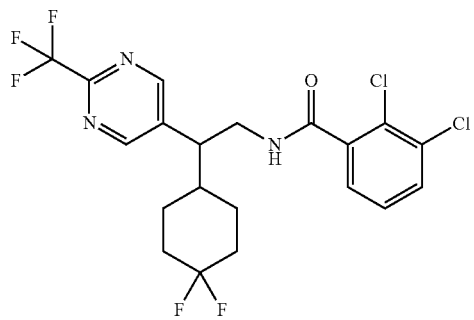 [SMILES: O=C(NCC(c1cnc(C(F)(F)F)nc1)C1CCC(F)(F)CC1)c1cccc(Cl)c1Cl]

From 2,3-dichlorobenzoic acid and 2-(4,4-difluorocyclohexyl)-2-(2-(trifluoromethyl)pyrimidin-5-yl)ethanamine. LCMS (MH+): m/z=482.1, $t_R$ (minutes, Method G)=2.76

Example 3o4

2-chloro-6-fluoro-N-(2-(4,4-difluorocyclohexyl)-2-(2-(trifluoromethyl)pyrimidin-5-yl)ethyl)benzamide

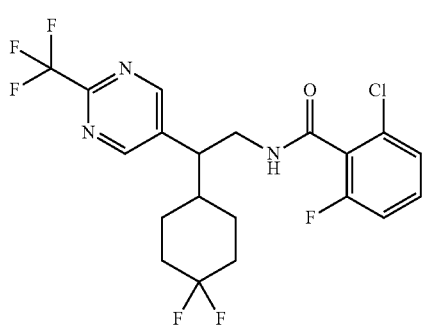 [SMILES: O=C(NCC(c1cnc(C(F)(F)F)nc1)C1CCC(F)(F)CC1)c1c(F)cccc1Cl]

From 2-chloro-6-fluorobenzoic acid and 2-(4,4-difluorocyclohexyl)-2-(2-(trifluoromethyl)pyrimidin-5-yl)ethanamine. LCMS (MH+): m/z=466.1, $t_R$ (minutes, Method F)=2.97

Example 3p4

2-chloro-3-fluoro-N-(2-(4,4-difluorocyclohexyl)-2-(2-(trifluoromethyl)pyrimidin-5-yl)ethyl)benzamide

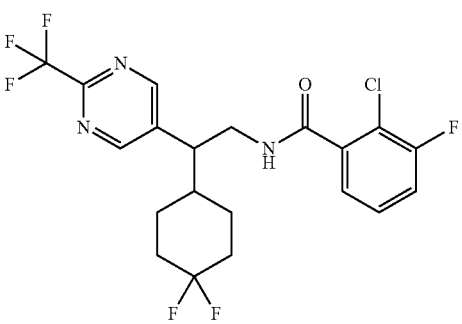 [SMILES: O=C(NCC(c1cnc(C(F)(F)F)nc1)C1CCC(F)(F)CC1)c1cccc(F)c1Cl]

From 2-chloro-3-fluorobenzoic acid and 2-(4,4-difluorocyclohexyl)-2-(2-(trifluoromethyl)pyrimidin-5-yl)ethanamine. LCMS (MH+): m/z=466.1, $t_R$ (minutes, Method F)=2.67

Example 3q4

2,3-dichloro N-(2-(4,4-difluorocyclohexyl)-2-(2-methylpyrimidin-5-yl)ethyl)benzamide

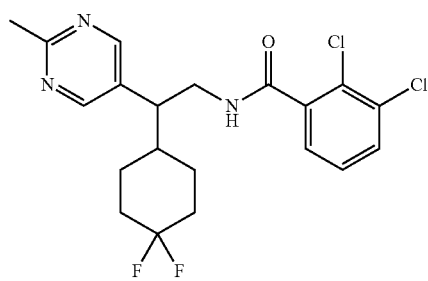 [SMILES: Cc1ncc(C(CNC(=O)c2cccc(Cl)c2Cl)C2CCC(F)(F)CC2)cn1]

From 2,3-dichlorobenzoic acid and 2-(4,4-difluorocyclohexyl)-2-(2-methylpyrimidin-5-yl)ethanamine. LCMS (M11-1+): m/z=448.1, $t_R$ (minutes, Method F)=2.95

Example 3r4

2,3-dichloro N-(4-methoxy-2-(2-(trifluoromethyl)pyrimidin-5-yl)butyl)benzamide

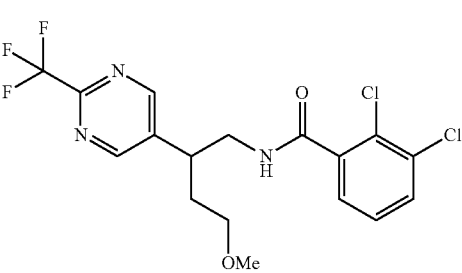 [SMILES: COCCC(CNC(=O)c1cccc(Cl)c1Cl)c1cnc(C(F)(F)F)nc1]

From 2,3-dichlorobenzoic acid and 4-methoxy-2-(2-(trifluoromethyl)pyrimidin-5-yl)butan-1-amine. LCMS (MH+): m/z=422.0, $t_R$ (minutes, Method F)=2.73

Example 3s4

2,3-dichloro-N-(2-phenyl-2-(pyridazin-4-yl)ethyl)benzamide

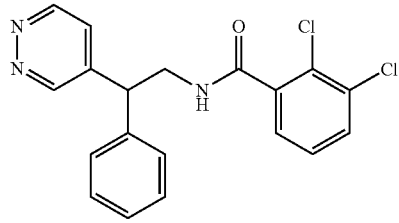 [SMILES: O=C(NCC(c1ccccc1)c1ccnnc1)c1cccc(Cl)c1Cl]

From 2,3-dichlorobenzoic acid and 2-phenyl-2-(pyridazin-4-yl)ethanamine. LCMS (MH+): m/z=372.1, $t_R$ (minutes, Method G)=2.05

Example 3t4

2,4-dichloro-N-(2-phenyl-2-(pyridazin-4-yl)ethyl)benzamide

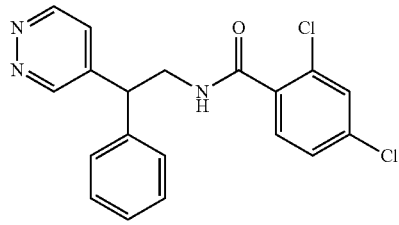 [SMILES: O=C(NCC(c1ccccc1)c1ccnnc1)c1ccc(Cl)cc1Cl]

From 2,4-dichlorobenzoic acid and 2-phenyl-2-(pyridazin-4-yl)ethanamine. LCMS (MH+): m/z=372.1, $t_R$ (minutes, Method G)=2.09

Example 3u4

2-chloro-N-(3-cyclopropyl-2-(6-(difluoromethyl)pyridin-3-yl)propyl)benzamide

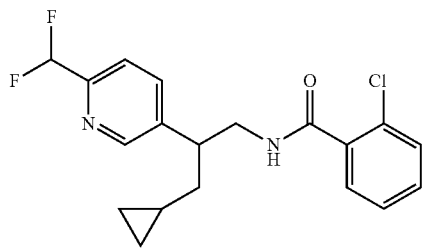 [SMILES: O=C(NCC(CC1CC1)c1ccc(C(F)F)nc1)c1ccccc1Cl]

From 2-chlorobenzoic acid and 3-cyclopropyl-2-(6-(difluoromethyl)pyridin-3-yl)propan-1-amine. LCMS (MH+): m/z=365.1, $t_R$ (minutes, Method F)=2.97

Example 3v4

2,3-dichloro-N-(3-cyclopropyl-2-(6-(difluoromethyl)pyridin-3-yl)propyl)benzamide

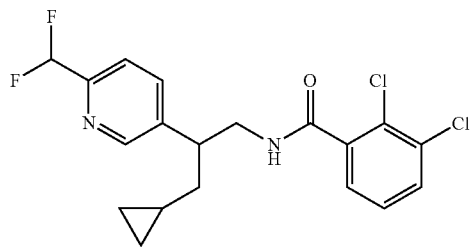 [SMILES: O=C(NCC(CC1CC1)c1ccc(C(F)F)nc1)c1cccc(Cl)c1Cl]

From 2,3-dichlorobenzoic acid and 3-cyclopropyl-2-(6-(difluoromethyl)pyridin-3-yl)propan-1-amine. LCMS (MH+): m/z=399.1, $t_R$ (minutes, Method G)=2.57

Example 3w4

2-chloro-3-fluoro-N-(3-cyclopropyl-2-(6-(difluoromethyl)pyridin-3-yl)propyl)benzamide

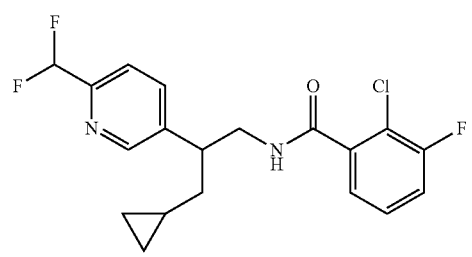 [SMILES: O=C(NCC(CC1CC1)c1ccc(C(F)F)nc1)c1cccc(F)c1Cl]

From 2-chloro-3-fluorobenzoic acid and 3-cyclopropyl-2-(6-(difluoromethyl)pyridin-3-yl)propan-1-amine. LCMS (MH+): m/z=383.1, $t_R$ (minutes, Method F)=3.02

Example 3x4

2-chloro-3-methoxy-N-(3-cyclopropyl-2-(6-(difluoromethyl)pyridin-3-yl)propyl)benzamide

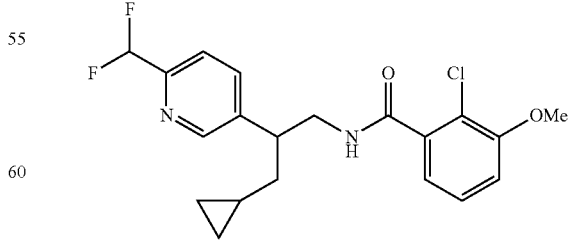

From 2-chloro-3-methoxybenzoic acid and 3-cyclopropyl-2-(6-(difluoromethyl)pyridin-3-yl)propan-1-amine. LCMS (MH+): m/z=395.1, $t_R$ (minutes, Method F)=2.96

Example 3y4

2,4-dichloro-N-(3-cyclopropyl-2-(6-(difluoromethyl)pyridin-3-yl)propyl)benzamide

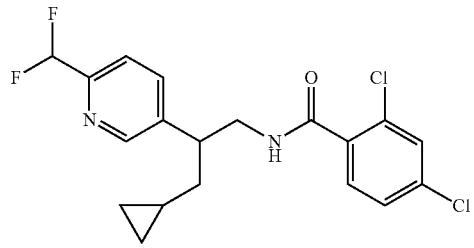 [SMILES: O=C(NCC(CC1CC1)c1ccc(C(F)F)nc1)c1ccc(Cl)cc1Cl]

From 2,4-dichlorobenzoic acid and 3-cyclopropyl-2-(6-(difluoromethyl)pyridin-3-yl)propan-1-amine. LCMS (MH+): m/z=399.1, $t_R$ (minutes, Method G)=2.61

Example 3z4

2,6-dichloro-N-(3-cyclopropyl-2-(6-(difluoromethyl)pyridin-3-yl)propyl)benzamide

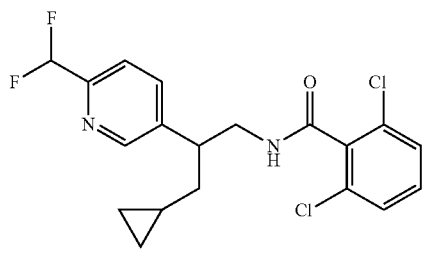 [SMILES: O=C(NCC(CC1CC1)c1ccc(C(F)F)nc1)c1c(Cl)cccc1Cl]

From 2,6-dichlorobenzoic acid and 3-cyclopropyl-2-(6-(difluoromethyl)pyridin-3-yl)propan-1-amine. LCMS (MH+): m/z=399.1, $t_R$ (minutes, Method F)=3.06

Example 3a5

2-chloro-N-(3-cyclopropyl-2-(2-(difluoromethyl)pyrimidin-5-yl)propyl)benzamide

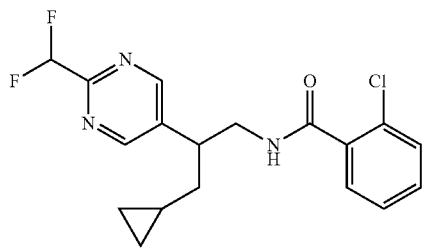 [SMILES: O=C(NCC(CC1CC1)c1cnc(C(F)F)nc1)c1ccccc1Cl]

From 2-chlorobenzoic acid and 3-cyclopropyl-2-(6-(difluoromethyl)pyrimidin-3-yl)propan-1-amine. LCMS (ML-1+): m/z=366.1, $t_R$ (minutes, Method F)=2.84

Example 3b5

2,3-dichloro-N-(3-cyclopropyl-2-(2-(difluoromethyl)pyrimidin-5-yl)propyl)benzamide

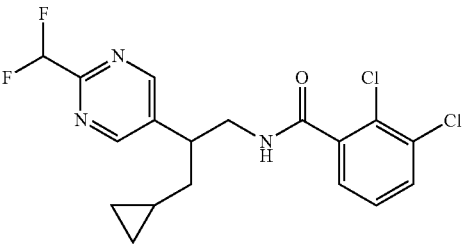 [SMILES: O=C(NCC(CC1CC1)c1cnc(C(F)F)nc1)c1cccc(Cl)c1Cl]

From 2,3-dichlorobenzoic acid and 3-cyclopropyl-2-(6-(difluoromethyl)pyrimidin-3-yl)propan-1-amine. LCMS (MH+): m/z=400.1, $t_R$ (minutes, Method F)=3.00

Example 3c5

2-chloro-3-fluoro-N-(3-cyclopropyl-2-(2-(difluoromethyl)pyrimidin-5-yl)propyl)benzamide

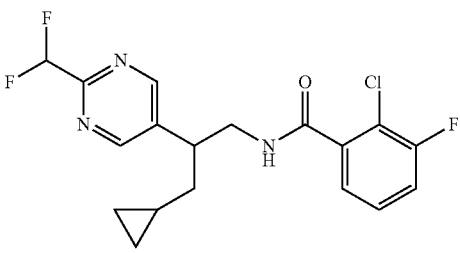 [SMILES: O=C(NCC(CC1CC1)c1cnc(C(F)F)nc1)c1cccc(F)c1Cl]

From 2-chloro-3-fluorobenzoic acid and 3-cyclopropyl-2-(6-(difluoromethyl)pyrimidin-3-yl)propan-1-amine. LCMS (MH+): m/z=384.1, $t_R$ (minutes, Method F)=2.90

Example 3d5

2-chloro-3-methoxy-N-(3-cyclopropyl-2-(2-(difluoromethyl)pyrimidin-5-yl)propyl)benzamide

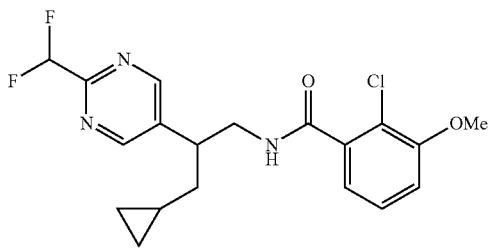 [SMILES: COc1cccc(C(=O)NCC(CC2CC2)c2cnc(C(F)F)nc2)c1Cl]

From 2-chloro-3-methoxybenzoic acid and 3-cyclopropyl-2-(6-(difluoromethyl)pyrimidin-3-yl)propan-1-amine. LCMS (MH+): m/z=396.1, $t_R$ (minutes, Method F)=2.84

Example 3e5

2,4-dichloro-N-(3-cyclopropyl-2-(2-(difluoromethyl)pyrimidin-5-yl)propyl)benzamide

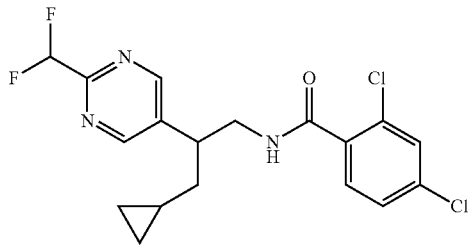 [SMILES: O=C(NCC(CC1CC1)c1cnc(C(F)F)nc1)c1ccc(Cl)cc1Cl]

From 2,4-dichlorobenzoic acid and 3-cyclopropyl-2-(6-(difluoromethyl)pyrimidin-3-yl)propan-1-amine. LCMS (MH+): m/z=400.1, $t_R$ (minutes, Method F)=3.04

Example 3f5

2,6-dichloro-N-(3-cyclopropyl-2-(2-(difluoromethyl)pyrimidin-5-yl)propyl)benzamide

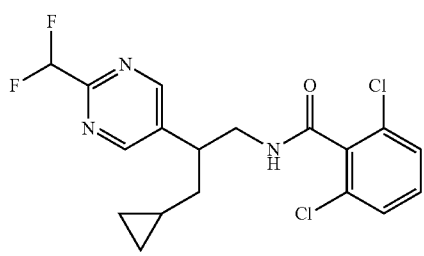

From 2,6-dichlorobenzoic acid and 3-cyclopropyl-2-(6-(difluoromethyl)pyrimidin-3-yl)propan-1-amine. LCMS (MH+): m/z=400.1, $t_R$ (minutes, Method F)=2.93

Example 3g5

2,3-dichloro-N-((4,4-difluoro-1-(4-methyl-1H-imidazol-1-yl)cyclohexyl)methyl)benzamide

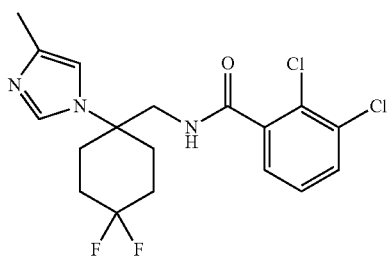 [SMILES: Cc1cn(C2(CNC(=O)c3cccc(Cl)c3Cl)CCC(F)(F)CC2)cn1]

From 2,3-dichlorobenzoic acid and (4,4-difluoro-1-(4-methyl-1H-imidazol-1-yl)cyclohexyl)methanamine. LCMS (MH+): m/z=402.0, $t_R$ (minutes, Method E)=0.45

Example 3h5

N-(1-(1-(6-bromopyridin-3-yl)-4,4-difluorocyclohexyl)ethyl)-2,3-dichlorobenzamide

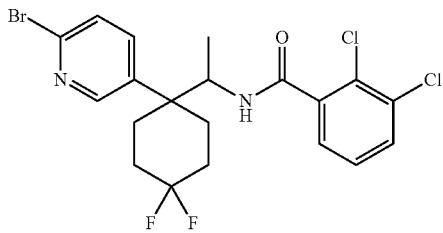 [SMILES: CC(NC(=O)c1cccc(Cl)c1Cl)C1(c2ccc(Br)nc2)CCC(F)(F)CC1]

From 2,3-dichlorobenzoic acid and 1-(1-(6-bromopyridin-3-yl)-4,4-difluorocyclohexyl)ethanamine. LCMS (MH+): m/z=493.1, $t_R$ (minutes, Method D)=0.83

Example 3i5

2,3-dichloro-N((4,4-difluoro-1-(6-methylpyridin-3-yl)cyclohexyl)methyl)benzamide

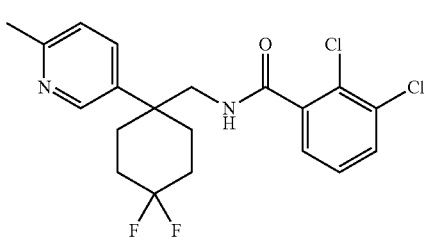 [SMILES: Cc1ccc(C2(CNC(=O)c3cccc(Cl)c3Cl)CCC(F)(F)CC2)cn1]

From 2,3-dichlorobenzoic acid and (4,4-difluoro-1-(6-methylpyridin-3-yl)cyclohexyl)methanamine. LCMS (MH+): m/z=413.2, $t_R$ (minutes, Method D)=0.51

Example 3j5

2-chloro-3-fluoro-N-((4,4-difluoro-1-(6-fluoropyridin-3-yl)cyclohexyl)methyl)benzamide

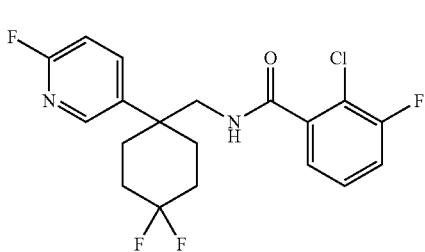 [SMILES: O=C(NCC1(c2ccc(F)nc2)CCC(F)(F)CC1)c1cccc(F)c1Cl]

From 2-chloro-3-fluorobenzoic acid and (4,4-difluoro-1-(6-fluoropyridin-3-yl)cyclohexyl)methanamine. LCMS (MH+): m/z=401.2, $t_R$ (minutes, Method D)=0.72

Example 3l5

3-chloro-N-((4,4-difluoro-1-(6-fluoropyridin-3-yl)cyclohexyl)methyl)-2-fluorobenzamide

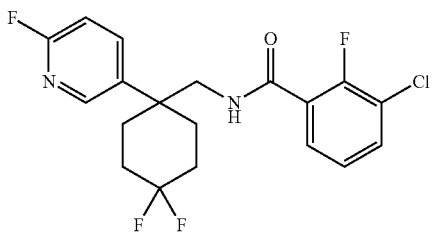 [SMILES: O=C(NCC1(c2ccc(F)nc2)CCC(F)(F)CC1)c1cccc(Cl)c1F]

From 3-chloro-2-fluorobenzoic acid and (4,4-difluoro-1-(6-fluoropyridin-3-yl)cyclohexyl)methanamine. LCMS (MH+): m/z=401.2, $t_R$ (minutes, Method D)=0.75

Example 3l5

2-chloro-N-((4,4-difluoro-1-(6-(trifluoromethyl)pyridin-3-yl)cyclohexyl)methyl)benzamide

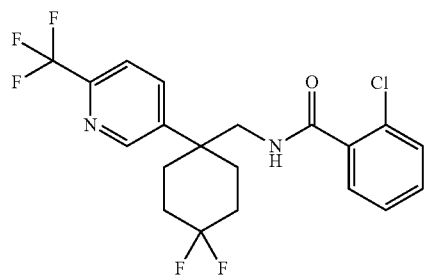 [SMILES: O=C(NCC1(c2ccc(C(F)(F)F)nc2)CCC(F)(F)CC1)c1ccccc1Cl]

From 2-chlorobenzoic acid and (4,4-difluoro-1-(6-(trifluoromethyl)pyridin-3-yl)cyclohexyl)methanamine. LCMS (MH+): m/z=433.2, $t_R$ (minutes, Method D)=0.78

Example 3m5

2-chloro-3-methoxy-N-(0,4-difluoro-1-(6-(trifluoromethyl)pyridin-3-yl)cyclohexyl)methyl)benzamide

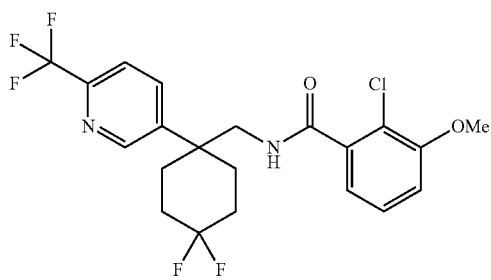 [SMILES: COc1cccc(C(=O)NCC2(c3ccc(C(F)(F)F)nc3)CCC(F)(F)CC2)c1Cl]

From 2-chloro-3-methoxybenzoic acid and (4,4-difluoro-1-(6-(trifluoromethyl)pyridin-3-yl)cyclohexyl)methanamine. LCMS (MH+): m/z=463.2, $t_R$ (minutes, Method D)=0.77

Example 3n5

2-chloro-3-fluoro-N-((4,4-difluoro-1-(6-(trifluoromethyl)pyridin-3-yl)cyclohexyl)methyl)benzamide

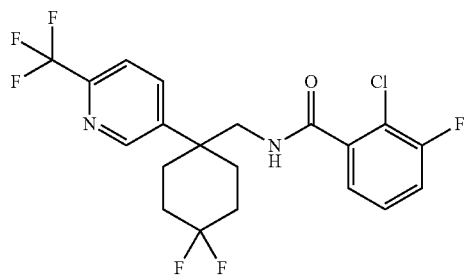 [SMILES: O=C(NCC1(c2ccc(C(F)(F)F)nc2)CCC(F)(F)CC1)c1cccc(F)c1Cl]

From 2-chloro-3-fluorobenzoic acid and (4,4-difluoro-1-(6-(trifluoromethyl)pyridin-3-yl)cyclohexyl)methanamine. LCMS (MH+): in z=451.2, $t_R$ (minutes, Method D)=0.79

Example 3o5

3-chloro-N-((4,4-difluoro-1-(6-(trifluoromethyl)pyridin-3-yl)cyclohexyl)methyl)-2-fluorobenzamide

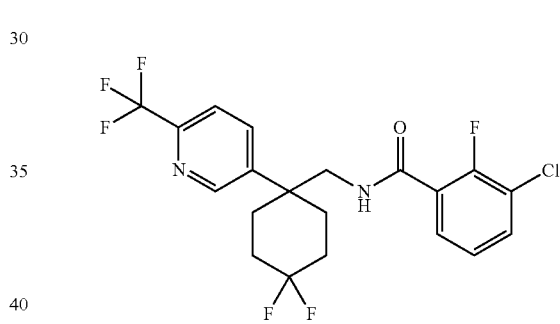

From 3-chloro-2-fluorobenzoic acid and (4,4-difluoro-1-(6-(trifluoromethyl)pyridin-3-yl)cyclohexyl)methanamine. LCMS (MH+): m/z=433.2, $t_R$ (minutes, Method D)=0.83

Example 3p5

3-chloro-N-(3-cyclopropyl-2-(6-(trifluoromethyl)pyridin-3-yl)propyl)-2-fluorobenzamide

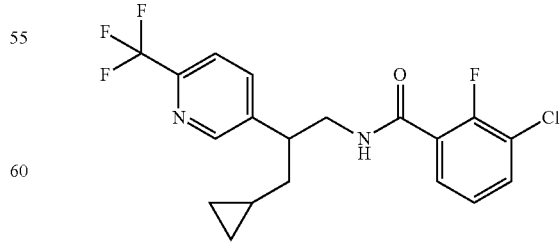

From 3-chloro-2-fluorobenzoic acid and 3-cyclopropyl-2-(6-(trifluoromethyl)pyridin-3-yl)propan-1-amine. LCMS (MH+): m/z=401.2, $t_R$ (minutes, Method D)=0.84

Example 3q5

2-chloro-4-fluoro-N-(3-cyclopropyl-2-(6-(trifluoromethyl)pyridin-3-yl)propyl)benzamide

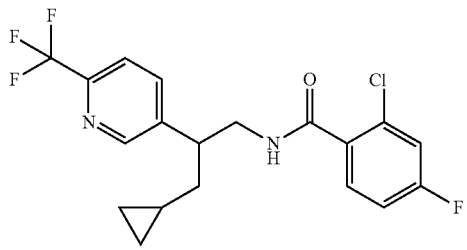 [SMILES: O=C(NCC(CC1CC1)c1ccc(C(F)(F)F)nc1)c1ccc(F)cc1Cl]

From 2-chloro-4-fluorobenzoic acid and 3-cyclopropyl-2-(6-(trifluoromethyl)pyridin-3-yl)propan-1-amine. LCMS (MH+): m/z=401.0, $t_R$ (minutes, Method D)=0.79

Example 3r5

2,6-dichloro-N-(3-cyclopropyl-2-(6-(trifluoromethyl)pyridin-3-yl)propyl)benzamide

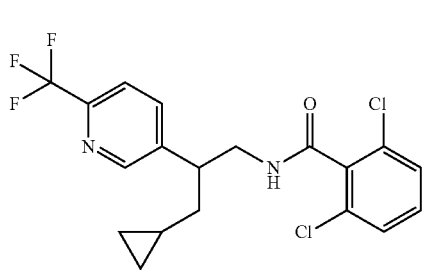

From 2,6-dichlorobenzoic acid and 3-cyclopropyl-2-(6-(trifluoromethyl)pyridin-3-yl)propan-1-amine. LCMS (MH+): m/z=417.2, $t_R$ (minutes, Method f))=0.89

Example 3s5

2,6-dichloro-N-(3-cyclopropyl-2-(6-(trifluoromethyl)pyrimidin-3-yl)propyl)benzamide

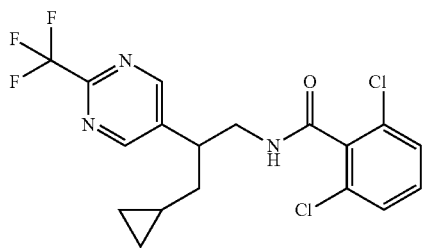

From 2,6-dichlorobenzoic acid and 3-cyclopropyl-2-(6-(trifluoromethyl)pyrimidin-3-yl)propan-1-amine. LCMS (MH+): m/z=418.1, $t_R$ (minutes, Method D)=0.79

Example 3t5

2-chloro-N-(3-cyclopropyl-2-(6-(trifluoromethyl)pyrimidin-3-yl)propyl)benzamide

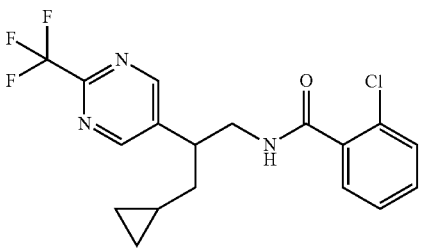 [SMILES: O=C(NCC(CC1CC1)c1cnc(C(F)(F)F)nc1)c1ccccc1Cl]

From 2-chlorobenzoic acid and 3-cyclopropyl-2-(6-(trifluoromethyl)pyrimidin-3-yl)propan-1-amine. LCMS (MH+): m/z=384.1, $t_R$ (minutes, Method D)=0.76

Example 3u5

2-chloro-3-fluoro-N-(3-cyclopropyl-2-(6-(trifluoromethyl)pyrimidin-3-yl)propyl)benzamide

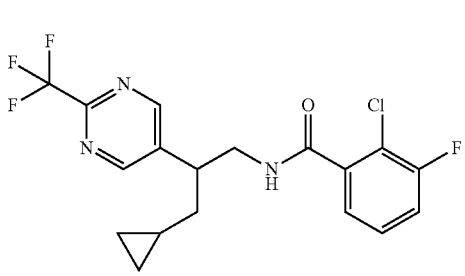 [SMILES: O=C(NCC(CC1CC1)c1cnc(C(F)(F)F)nc1)c1cccc(F)c1Cl]

From 2-chloro-3-fluorobenzoic acid and 3-cyclopropyl-2-(6-(trifluoromethyl)pyrimidin-3-yl)propan-1-amine. LCMS (MH+): m/z=402.1, $t_R$ (minutes, Method D)=0.78

Example 3v5

2-chloro-6-fluoro-N-(3-cyclopropyl-2-(6-(trifluoromethyl)pyrimidin-3-yl)propyl)benzamide

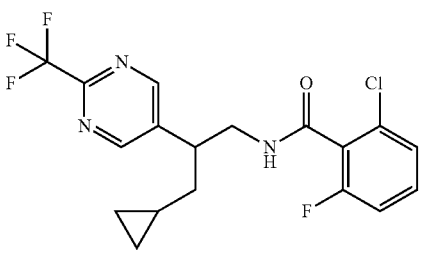

From 2-chloro-6-fluorobenzoic acid and 3-cyclopropyl-2-(6-(trifluoromethyl)pyrimidin-3-yl)propan-1-amine. LCMS (MH+): m/z=402.1, $t_R$ (minutes, Method D)=0.77

Example 3w5

2,4-dichloro-N-(2-phenyl-2-(6-(trifluoromethyl)pyridin-3-yl)ethyl)benzamide

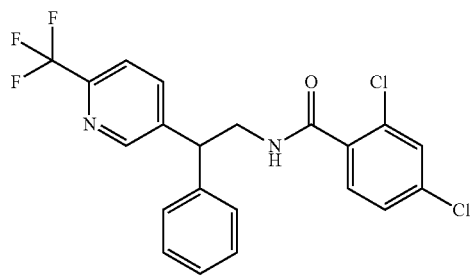 [SMILES: O=C(NCC(c1ccccc1)c1ccc(C(F)(F)F)nc1)c1ccc(Cl)cc1Cl]

From 2,4-dichlorobenzoic acid and 2-phenyl-2-(6-(trifluoromethyl)pyridin-3-yl)ethanamine. LCMS (MH+): m/z=439.0, $t_R$ (minutes, Method E)=0.81

Example 3x5

2,3-dichloro-N-((3-(2-methylpyrimidin-5-yl)tetrahydrofuran-3-yl)methyl)benzamide

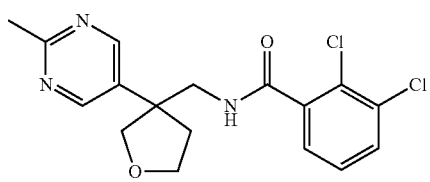 [SMILES: Cc1ncc(C2(CNC(=O)c3cccc(Cl)c3Cl)CCOC2)cn1]

From 2,3-dichlorobenzoic acid and (3-(2-methylpyrimidin-5-yl)tetrahydrofuran-3-yl)methanamine. LCMS (MH+): m/z=366.0, $t_R$ (minutes, Method E)=0.45

Example 3y5

2-Chloro-N-(2-phenyl-2-(6-(trifluoromethyl)pyridin-3-yl)ethyl)benzamide

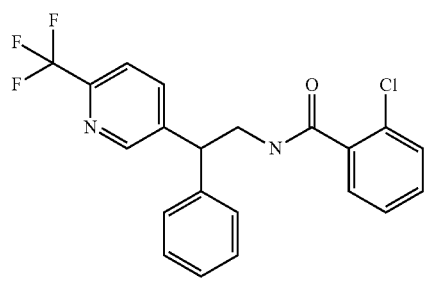 [SMILES: O=C(NCC(c1ccccc1)c1ccc(C(F)(F)F)nc1)c1ccccc1Cl]

From 2-chlorobenzoic acid and 2-phenyl-2-(6-(trifluoromethyl)pyridin-3-yl)ethanamine. LCMS (MH+): m/z=405.2, $t_R$ (minutes, Method D)=0.79

Example 3z5

2-chloro-6-fluoro-N-(2-phenyl-2-(6-(trifluoromethyl)pyridin-3-yl)ethyl)benzamide

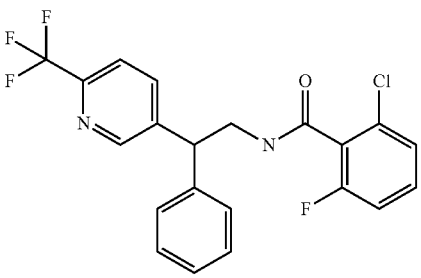 [SMILES: O=C(NCC(c1ccccc1)c1ccc(C(F)(F)F)nc1)c1c(F)cccc1Cl]

From 2-chloro-6-fluorobenzoic acid and 2-phenyl-2-(6-(trifluoromethyl)pyridin-3-yl)ethanamine. LCMS (MIFF): m/z=423.1, $t_R$ (minutes, Method D)=0.80

Example 3a6

2-chloro-3-fluoro-N-(2-phenyl-2-(6-(trifluoromethyl)pyridin-3-yl)ethyl)benzamide

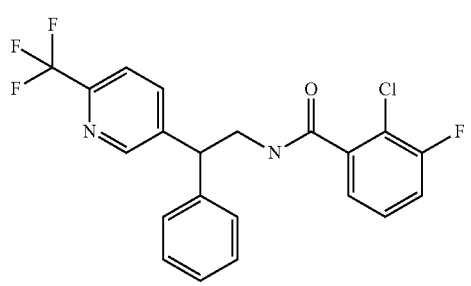 [SMILES: O=C(NCC(c1ccccc1)c1ccc(C(F)(F)F)nc1)c1cccc(F)c1Cl]

From 2-chloro-3-fluorobenzoic acid and 2-phenyl-2-(6-(trifluoromethyl)pyridin-3-yl)ethanamine. LCMS (MH+): m/z=423.1, $t_R$ (minutes, Method D)=0.81

Example 3b6

2,3-dichloro-N-(2-phenyl-2-(6-(trifluoromethyl)pyridin-3-yl)ethyl)benzamide

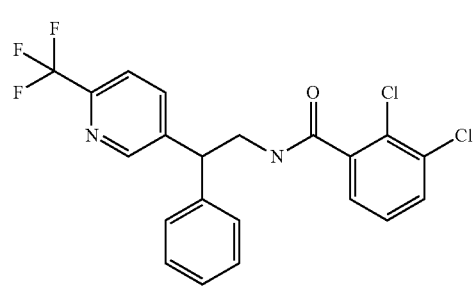 [SMILES: O=C(NCC(c1ccccc1)c1ccc(C(F)(F)F)nc1)c1cccc(Cl)c1Cl]

From 2,3-dichlorobenzoic acid and 2-phenyl-2-(6-(trifluoromethyl)pyridin-3-yl)ethanamine. LCMS (MH+): m/z=439.2, $t_R$ (minutes, Method D)=0.84

Example 3c6

2-Chloro-N-(3-cyclopropyl-2-(5-methylpyrazin-2-yl)propyl)benzamide

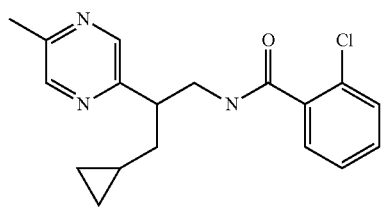 [SMILES: Cc1cnc(C(CNC(=O)c2ccccc2Cl)CC2CC2)cn1]

From 2-chlorobenzoic acid and 3-cyclopropyl-2-(5-methylpyrazin-2-yl)propylamine. LCMS (MH+): m/z=330.0, $t_R$ (minutes, Method E)=0.61

Example 3d6

2-Chloro-N-(2-(tetrahydro-2H-pyran-4-yl)-2-(6-(trifluoromethyl)pyridin-3-yl)ethyl)benzamide

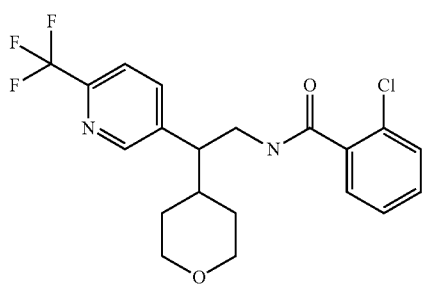 [SMILES: O=C(NCC(c1ccc(C(F)(F)F)nc1)C1CCOCC1)c1ccccc1Cl]

From 2-chlorobenzoic acid and 2-(tetrahydro-2H-pyran-4-yl)-2-(6-(trifluoromethyl)pyridin-3-yl)ethanamine. LCMS (MH+): m/z=413.0, $t_R$ (minutes, Method E)=0.64

Example 3e6

2-Chloro-3-fluoro-N-(2-(tetrahydro-2H-pyran-4-yl)-2-(6-(trifluoromethyl)pyridin-3-yl)ethyl)benzamide

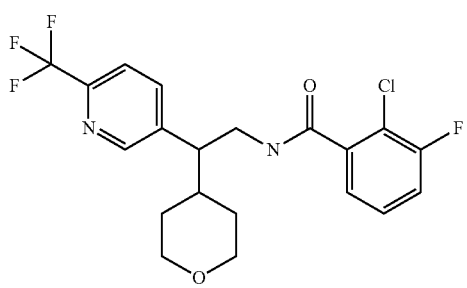 [SMILES: O=C(NCC(c1ccc(C(F)(F)F)nc1)C1CCOCC1)c1cccc(F)c1Cl]

From 2-chloro-3-fluorobenzoic acid and 2-(tetrahydro-2H-pyran-4-yl)-2-(6-(trifluoromethyl)pyridin-3-yl)ethanamine. LCMS (MIFF): m/z=431.2, $t_R$ (minutes, Method D)=0.69

Example 3f6

2,3-Dichloro-N-(2-(tetrahydro-2H-pyran-4-yl)-2-(6-(trifluoromethyl)pyridin-3-yl)ethyl)benzamide

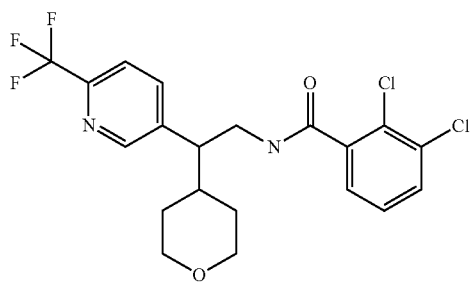 [SMILES: O=C(NCC(c1ccc(C(F)(F)F)nc1)C1CCOCC1)c1cccc(Cl)c1Cl]

From 2,3-dichlorobenzoic acid and 2-(tetrahydro-2H-pyran-4-yl)-2-(6-(trifluoromethyl)pyridin-3-yl)ethanamine. LCMS (MH+): m/z=447.0, $t_R$ (minutes, Method E)=0.70

Example 3g6

2-Chloro-6-fluoro-N-(2-(tetrahydro-2H-pyran-4-yl)-2-(6-(trifluoromethyl)pyridin-3-yl)ethyl)benzamide

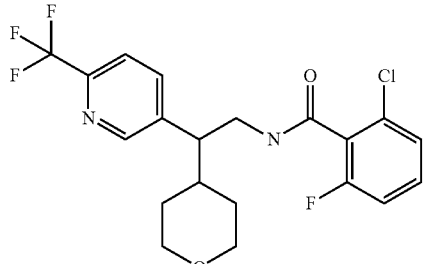

From 2-chloro-6-fluorobenzoic acid and 2-(tetrahydro-2H-pyran-4-yl)-2-(6-(trifluoromethyl)pyridin-3-yl)ethanamine. LCMS (MH+): m/z=431.0, $t_R$ (minutes, Method E)=0.64

Example 3h6

2-Chloro-N-(2-isopropoxy-2-(2-methylpyrimidin-5-yl)ethyl)benzamide

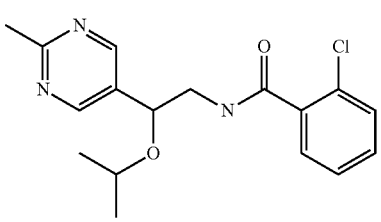 [SMILES: Cc1ncc(C(CNC(=O)c2ccccc2Cl)OC(C)C)cn1]

From 2-chlorobenzoic acid and 2-isopropoxy-2-(2-methylpyrimidin-5-yl)ethanamine. LCMS (MH+): m/z=334.0, $t_R$ (minutes, Method E)=0.52

Example 3i6

2,3-Dichloro-N-(2-isopropoxy-2-(2-methylpyrimidin-5-yl)ethyl)benzamide

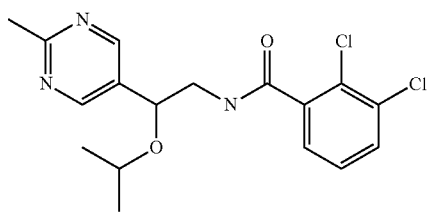 [SMILES: Cc1ncc(C(CNC(=O)c2cccc(Cl)c2Cl)OC(C)C)cn1]

From 2,3-dichlorobenzoic acid and 2-isopropoxy-2-(2-methylpyrimidin-5-yl)ethanamine. LCMS (MH+): m/z=368.1, $t_R$ (minutes, Method D)=0.64

Example 3j6

2,3-Dichloro-N-(2-(1-methyl-1H-pyrazol-4-yl)-2-(tetrahydro-2H-pyran-4-yl)ethyl)benzamide

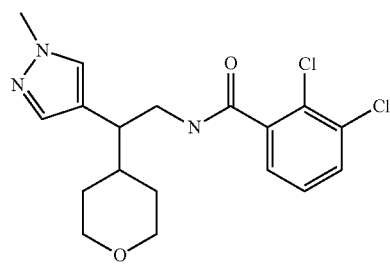 [SMILES: Cn1cc(C(CNC(=O)c2cccc(Cl)c2Cl)C2CCOCC2)cn1]

From 2,3-dichlorobenzoic acid and 2-(1-methyl-1H-pyrazol-4-yl)-2-(tetrahydro-2H-pyran-4-yl)ethanamine. LCMS (MH+): m/z=382.0, $t_R$ (minutes, Method E)=0.52

Example 3k6

2,3-Dichloro-N-((2-(2-methylpyrimidin-5-yl)tetrahydrofuran-2-yl)methyl)benzamide

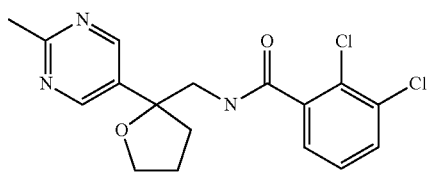 [SMILES: Cc1ncc(C2(CNC(=O)c3cccc(Cl)c3Cl)CCCO2)cn1]

From 2,3-dichlorobenzoic acid and (2-(2-methylpyrimidin-5-yl)tetrahydrofuran-2-yl)methanamine. LCMS (MH+): m/z=366.0, $t_R$ (minutes, Method E)=0.52

Example 3l6

2,3-Dichloro-N-(2-(1-methyl-1H-pyrazol-4-yl)-2-(6-(trifluoromethyl)pyridin-3-yl)ethyl)benzamide

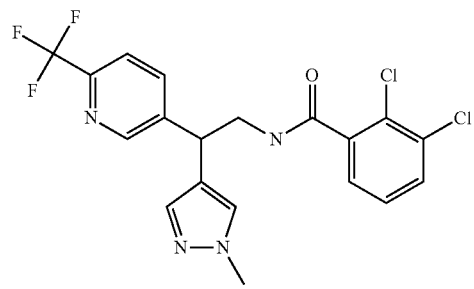 [SMILES: Cn1cc(C(CNC(=O)c2cccc(Cl)c2Cl)c2ccc(C(F)(F)F)nc2)cn1]

From 2,3-dichlorobenzoic acid and 2-(1-methyl-1H-pyrazol-4-yl)-2-(6-(trifluoromethyl)pyridin-3-yl)ethanamine. LCMS (MH+): m/z=443.2, $t_R$ (minutes, Method D)=0.67

Example 3m6

2,3-Dichloro-N-[2-(1-methylpyrazol-4-yl)-2-[2-(trifluoromethyl)pyrimidin-5-yl]ethyl]benzamide

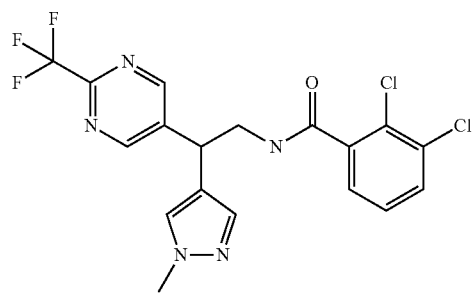 [SMILES: Cn1cc(C(CNC(=O)c2cccc(Cl)c2Cl)c2cnc(C(F)(F)F)nc2)cn1]

From 2,3-dichlorobenzoic acid and 2-(1-methyl-1H-pyrazol-4-yl)-2-(6-(trifluoromethyl)pyrimidin-5-yl)ethanamine. LCMS (MH+): m/z=444.1, $t_R$ (minutes, Method F)=2.73

Example 3n6

2,3-dichloro-N-[2-(1-methylpyrazol-3-yl)-2-[2-(trifluoromethyl)pyrimidin-5-yl]ethyl]benzamide

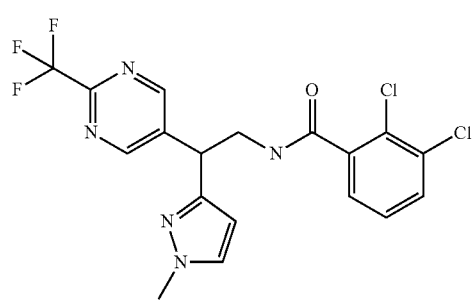 [SMILES: Cn1ccc(C(CNC(=O)c2cccc(Cl)c2Cl)c2cnc(C(F)(F)F)nc2)n1]

From 2,3-dichlorobenzoic acid and 2-(1-methyl-1H-pyrazol-3-yl)-2-(6-(trifluoromethyl)pyrimidin-5-yl)ethanamine. LCMS (MH+): m/z=444.1, $t_R$ (minutes, Method F)=2.87

Example 3o6

2,3-Dichloro-N-[2-(1-methyl-1H-imidazol-4-yl)-2-(2-trifluoromethyl-pyrimidin-5-yl)-ethyl]-benzamide

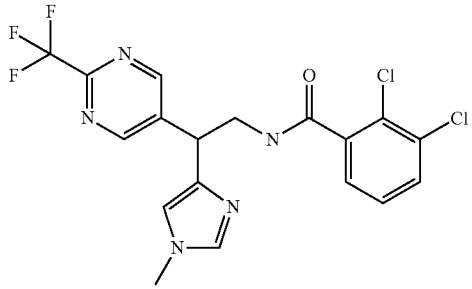 [SMILES: Cn1cnc(C(CNC(=O)c2cccc(Cl)c2Cl)c2cnc(C(F)(F)F)nc2)c1]

From 2,3-dichlorobenzoic acid and 2-(1-methyl-1H-imidazol-4-yl)-2-(6-(trifluoromethyl)pyrimidin-5-yl)ethanamine. LCMS (MH+): m/z=443.8, $t_R$ (minutes, Method F)=1.97

Example 3p6

2-Chloro-N-((4,4-difluoro-1-(2-(trifluoromethyl)pyrimidin-5-yl)cyclohexyl)methyl)-3-methoxybenzamide

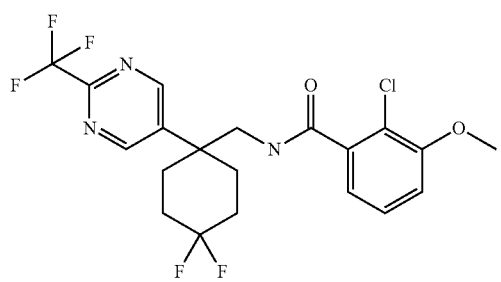

From 2-chloro-3-methoxybenzoic acid and [4,4-Difluoro-1-(2-(trifluoromethyl)pyrimidin-5-yl)cyclohexyl]methanamine. LCMS (MH+): m/z=464.1, $t_R$ (minutes, Method F)=3.02

Example 3q6

2-Chloro-N-[[4,4-difluoro-1-[2-(trifluoromethyl)pyrimidin-5-yl]cyclohexyl]methyl]benzamide

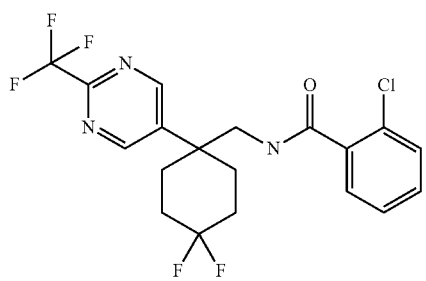 [SMILES: O=C(NCC1(c2cnc(C(F)(F)F)nc2)CCC(F)(F)CC1)c1ccccc1Cl]

From 2-chlorobenzoic acid and [4,4-Difluoro-1-(2-(trifluoromethyl)pyrimidin-5-yl)cyclohexyl]methanamine. LCMS (MH+): m/z=434.1, $t_R$ (minutes, Method F)=3.04

Example 3r6

2-Chloro-N-((4,4-difluoro-1-(2-(trifluoromethyl)pyrimidin-5-yl)cyclohexyl)methyl)-3-fluorobenzamide

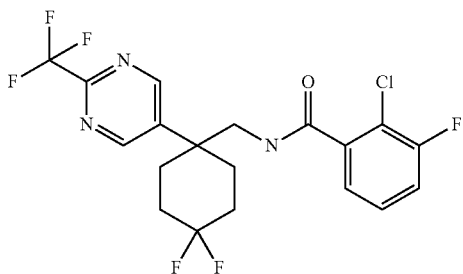 [SMILES: O=C(NCC1(c2cnc(C(F)(F)F)nc2)CCC(F)(F)CC1)c1cccc(F)c1Cl]

From 2-chloro-3-fluorobenzoic acid and [4,4-Difluoro-1-(2-(trifluoromethyl)pyrimidin-5-yl)cyclohexyl]methanamine. LCMS (MH+): m/z=452.1, $t_R$ (minutes, Method F)=3.08

Example 3s6

2-Chloro-N-((4,4-difluoro-1-(2-(trifluoromethyl)pyrimidin-5-yl)cyclohexyl)methyl)-3-(trifluoromethyl)benzamide

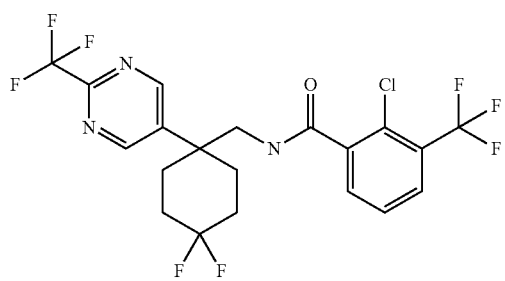 [SMILES: O=C(NCC1(c2cnc(C(F)(F)F)nc2)CCC(F)(F)CC1)c1cccc(C(F)(F)F)c1Cl]

From 2-chloro-3-trifluoromethylbenzoic acid and [4,4-Difluoro-1-(2-(trifluoromethyl)pyrimidin-5-yl)cyclohexyl]methanamine. LCMS (MH+): m/z=502.1, $t_R$ (minutes, Method F)=3.25

Example 3t6

2-Chloro-N-((4,4-difluoro-1-(2-(difluoromethyl)pyrimidin-5-yl)cyclohexyl)methyl)-3-methoxybenzamide

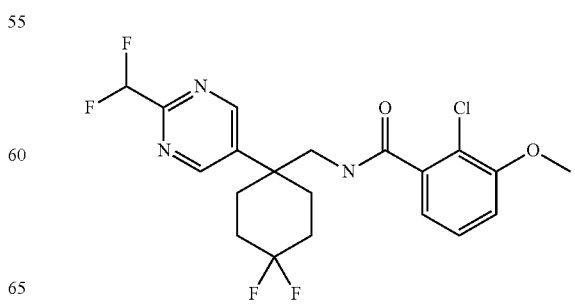

From 2-chloro-3-methoxybenzoic acid and (1-(2-(difluoromethyl)pyrimidin-5-yl)-4,4-difluorocyclohexyl)methanamine. LCMS (MH+): m/z=446.1, $t_R$ (minutes, Method F)=2.82

Example 3u6

2-Chloro-N-((4,4-difluoro-1-(2-(difluoromethyl)pyrimidin-5-yl)cyclohexyl)methyl)benzamide

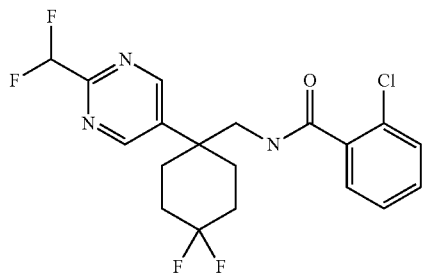 [SMILES: O=C(NCC1(c2cnc(C(F)F)nc2)CCC(F)(F)CC1)c1ccccc1Cl]

From 2-chloro benzoic acid and (1-(2-(difluoromethyl)pyrimidin-5-yl)-4,4-difluorocyclohexyl)methanamine. LCMS (MH+): m/z=416.1, $t_R$ (minutes, Method F)=2.83

Example 3v6

2,3-dichloro-N-((4,4-difluoro-1-(2-(difluoromethyl)pyrimidin-5-yl)cyclohexyl)methyl)benzamide

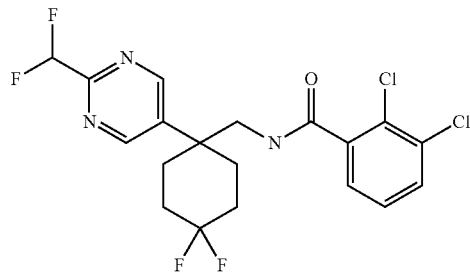 [SMILES: O=C(NCC1(c2cnc(C(F)F)nc2)CCC(F)(F)CC1)c1cccc(Cl)c1Cl]

From 2,3-dichlorobenzoic acid and (1-(2-(difluoromethyl)pyrimidin-5-yl)-4,4-difluorocyclohexyl)methanamine. LCMS (MH+): m/z=450.1, $t_R$ (minutes, Method F)=2.98

Example 3w6

2-Chloro-N-((4,4-difluoro-1-(2-(difluoromethyl)pyrimidin-5-yl)cyclohexyl)methyl)-3-fluorobenzamide

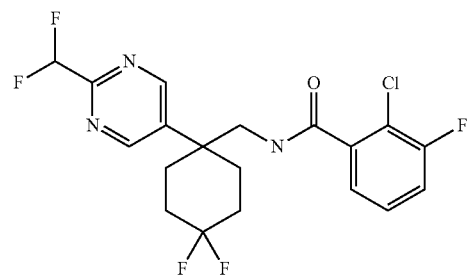 [SMILES: O=C(NCC1(c2cnc(C(F)F)nc2)CCC(F)(F)CC1)c1cccc(F)c1Cl]

From 2-chloro-3-fluorobenzoic acid (1-(2-(difluoromethyl)pyrimidin-5-yl)-4,4-difluorocyclohexyl)methanamine. LCMS (MH+): m/z=434.1, $t_R$ (minutes, Method F)=2.88

Example 3x6

2-Chloro-N-((4,4-difluoro-1-(2-(difluoromethyl)pyrimidin-5-yl)cyclohexyl)methyl)-3-(trifluoromethyl)benzamide

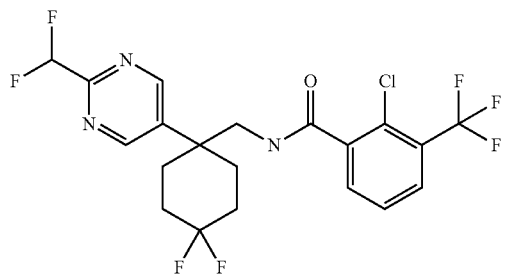 [SMILES: O=C(NCC1(c2cnc(C(F)F)nc2)CCC(F)(F)CC1)c1cccc(C(F)(F)F)c1Cl]

From 2-chloro-3-trifluoromethylbenzoic (1-(2-(difluoromethyl)pyrimidin-5-yl)-4,4-difluorocyclohexyl)methanamine. LCMS (MH+): m/z=484.0, $t_R$ (minutes, Method F)=3.07

Example 3y6

2,6-dichloro-N-((4,4-difluoro-1-(2-(difluoromethyl)pyrimidin-5-yl)cyclohexyl)methyl)benzamide

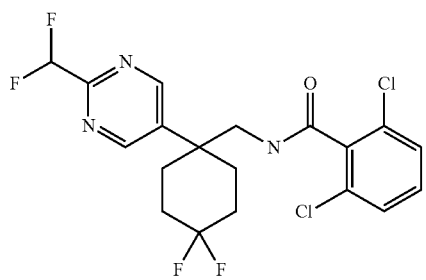 [SMILES: O=C(NCC1(c2cnc(C(F)F)nc2)CCC(F)(F)CC1)c1c(Cl)cccc1Cl]

From 2,6-dichlorobenzoic acid and (1-(2-(difluoromethyl)pyrimidin-5-yl)-4,4-difluorocyclohexyl)methanamine. LCMS (MH+): m/z=450.1, $t_R$ (minutes, Method F)=2.93

Example 4a (+)-2-Chloro-N-[3-cyclopropyl-2-[6-(trifluoromethyl)-3-pyridyl]propyl]benzamide

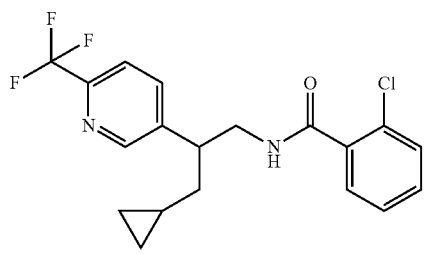 [SMILES: O=C(NCC(CC1CC1)c1ccc(C(F)(F)F)nc1)c1ccccc1Cl]

The racemic mixture which was prepared as described for example 3c1 was separated into the two enantiomers by preparative SFC to yield the title compound. LCMS (MH+): m/z=383.1, $t_R$ (minutes, Method G)=2.5. $[\alpha]_D^{20}$=+13.66 (c=3.0 mg/mL, $CHCl_3$)

And the corresponding enantiomer

Example 4b (−)-2-Chloro-N-[3-cyclopropyl-2-[6-(trifluoromethyl)-3-pyridyl]propyl]benzamide LCMS (MH+): m/z=383.1, $t_R$ (minutes, Method G)=2.5. $[\alpha]_D^{20}$=−13.0 (c=3.0 mg/mL, $CHCl_3$)

Example 4c (+)-2,3-Dichloro-N-[3-cyclopropyl-2-[6-(trifluoromethyl)-3-pyridyl]propyl]benzamide

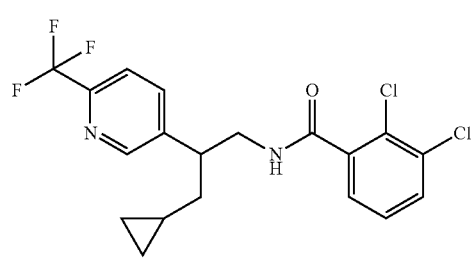 [SMILES: O=C(NCC(CC1CC1)c1ccc(C(F)(F)F)nc1)c1cccc(Cl)c1Cl]

The racemic mixture which was prepared as described for example 3a was separated into the two enantiomers by preparative SFC to yield the title compound. LCMS (MH+): m/z=417.1, $t_R$ (minutes, Method G)=2.64. $[\alpha]_D^{20}$=+15.0 (c=3.0 mg/mL, $CHCl_3$)

And the corresponding enantiomer

Example 4d (+2,3-Dichloro-N-[3-cyclopropyl-2-[6-(trifluoromethyl)-3-pyridyl]propyl]benzamide LCMS (MIFF): m/z=417.1, $t_R$ (minutes, Method G)=2.64. $[\alpha]_D^{20}$=−12.0 (c=3.0 mg/mL, $CHCl_3$)

Example 4e (+)-2-Chloro-N-[3-cyclopropyl-2-[6-(trifluoromethyl)-3-pyridyl]propyl]-3-(trifluoromethyl)benzamide

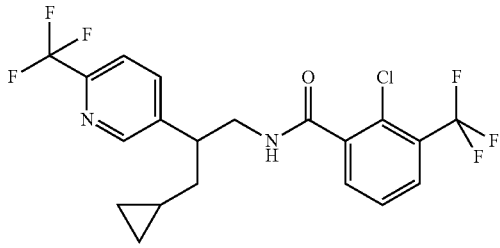 [SMILES: O=C(NCC(CC1CC1)c1ccc(C(F)(F)F)nc1)c1cccc(C(F)(F)F)c1Cl]

The racemic mixture which was prepared in a similar manner to example 3a from 2-chloro-3-trifluoromethylbenzoic acid and 3-cyclopropyl-2-(6-trifluoromethyl-pyridin-3-yl)-propylamine was separated into the two enantiomers by preparative SFC to yield the title compound. LCMS (M11+): m/z=451.1, $t_R$ (minutes, Method G)=3.11. $[\alpha]_D^{20}$=+26.0 (c=2.0 mg/mL, $CHCl_3$)

And the corresponding enantiomer

Example 4f (−)-2-Chloro-N-[3-cyclopropyl-2-[6-(trifluoromethyl)-3-pyridyl]propyl]-3-(trifluoromethyl)benzamide LCMS (MH+): m/z=451.1, $t_R$ (minutes, Method G)=3.11. $[\alpha]_D^{20}$=−25.0 (c=2.0 mg/mL, $CHCl_3$)

Example 4g (−)-2,3-Dichloro-N-[2-(2-methylpyrimidin-5-yl)-3-[1-(trifluoromethyl)cyclopropyl]propyl]benzamide

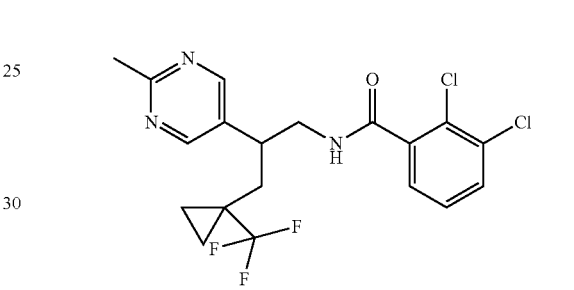

The racemic mixture which was prepared as described for example 3a was separated into the two enantiomers by preparative SFC to yield the title compound. LCMS (MH+): m/z=432.0, $t_R$ (minutes, Method F)=2.72. $[\alpha]_D^{20}$=−34.0 (c=4.5 mg/mL, $CHCl_3$)

And the corresponding enantiomer

Example 4h (+)-2,3-Dichloro-N-[2-(2-methylpyrimidin-5-yl)-3-[1-(trifluoromethyl)cyclopropyl]propyl]benzamide LCMS (MH+): m/z=432.0, $t_R$ (minutes, Method F)=2.72. $[\alpha]_D^{20}$=35.7 (c=4.7 mg/mL, $CHCl_3$)

Example 4i (−)-2-Chloro-N-[2-(2-methylpyrimidin-5-yl)-3-[1-(trifluoromethyl)cyclopropyl]propyl]benzamide

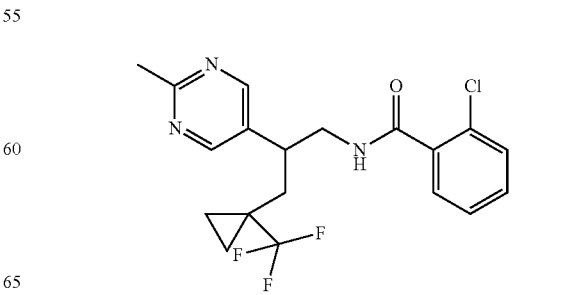

The racemic mixture which was prepared in a similar manner to example 3a from 2-chlorobenzoic acid and 2-(2-methyl-pyrimidin-5-yl)-3-(1-trifluoromethyl-cyclopropyl)-propylamine was separated into the two enantiomers by preparative SFC to yield the title compound. LCMS (MH+): m/z=398.1, $t_R$ (minutes, Method F)=2.55. $[\alpha]_D^{20}$=−25.5 (c=5.1 mg/mL, CHCl$_3$)

And the corresponding enantiomer

Example 4j (+)-2-Chloro-N-[2-(2-methylpyrimidin-5-yl)-3-[1-(trifluoromethyl)cyclopropyl]propyl]benzamide LCMS (MH+): m/z=398.1, $t_R$ (minutes, Method F)=2.55. $[\alpha]_D^{20}$=27.1 (c=5.5 mg/mL, CHCl$_3$)

Example 4k (+)-2-Chloro-N-[3-cyclopropyl-2-[6-(trifluoromethyl)-3-pyridyl]propyl]-3-methoxybenzamide

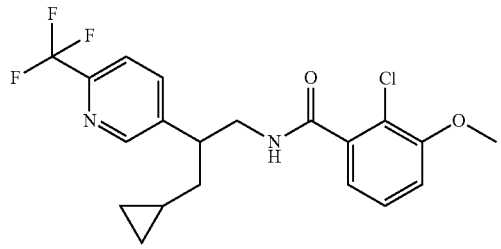 [SMILES: COc1cccc(C(=O)NCC(CC2CC2)c2ccc(C(F)(F)F)nc2)c1Cl]

The racemic mixture which was prepared in a similar manner to example 3a from 2-chloro-3-methoxybenzoic acid and 3-cyclopropyl-2-(6-trifluoromethyl-pyridin-3-yl)-propylamine was separated into the two enantiomers by preparative SFC to yield the title compound. LCMS (MH+): m/z=413.1, $t_R$ (minutes, Method G)=2.84. $[\alpha]_D^{20}$=+20.9 (c=0.86 mg/mL, CHCl$_3$)

Example 4l (−)-2-Chloro-N-[3-cyclopropyl-2-[6-(trifluoromethyl)-3-pyridyl]propyl]-3-methoxybenzamide LCMS (MH+): m/z=413.1, $t_R$ (minutes, Method G)=2.84. $[\alpha]_D^{20}$=−22.09 (c=0.86 mg/mL, CHCl$_3$)

Example 4m (−)-2-chloro-N-(3-cyclopropyl-2-(6-(trifluoromethyl)pyridin-3-yl)propyl)-6-fluorobenzamide

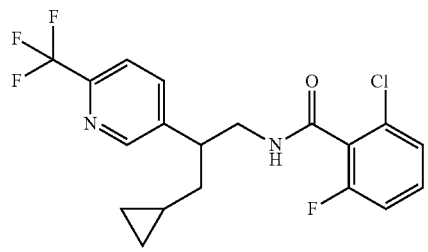

The racemic mixture which was prepared in a similar manner to example 3a from 2-chloro-6-fluorobenzoic acid and 3-cyclopropyl-2-(6-(trifluoromethyl)pyridin-3-yl)propan-1-amine was separated into the two enantiomers by preparative SFC to yield the title compound. LCMS (MH+): m/z=401.1, $t_R$ (minutes, Method G)=2.88. $[\alpha]_D^{20}$=−25.9 (c=0.81 mg/mL, CHCl$_3$)

And the corresponding enantiomer

Example 4n (+)-2-chloro-N-(3-cyclopropyl-2-(6-(trifluoromethyl)pyridin-3-yl)propyl)-6-fluorobenzamide LCMS (MH+): m/z=401.1, $t_R$ (minutes, Method G)=2.88. $[\alpha]_D^{20}$=25.9 (c=0.81 mg/mL, CHCl$_3$)

Example 4o (−)-N-(3-cyclopropyl-2-(6-(trifluoromethyl)pyridin-3-yl)propyl)-2-methoxybenzamide

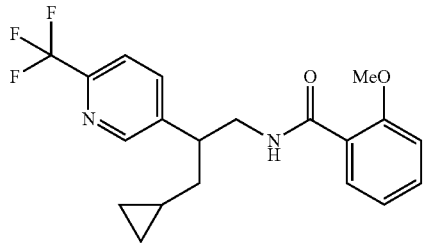 [SMILES: COc1ccccc1C(=O)NCC(CC1CC1)c1ccc(C(F)(F)F)nc1]

The racemic mixture which was prepared in a similar manner to example 3a from 2-methoxybenzoic acid and 3-cyclopropyl-2-(6-(trifluoromethyl)pyridin-3-yl)propan-1-amine was separated into the two enantiomers by preparative SFC to yield the title compound. LCMS (MH+): m/z=379.1, $t_R$ (minutes, Method G)=3.01. $[\alpha]_D^{20}$=−6.67 (c=3.9 mg/mL, CHCl$_3$)

And the corresponding enantiomer

Example 4p (+)-N-(3-cyclopropyl-2-(6-(trifluoromethyl)pyridin-3-yl)propyl)-2-methoxybenzamide LCMS (MH+): m/z=379.1, $t_R$ (minutes, Method G)=3.01. $[\alpha]_D^{20}$=6.89 (c=4.5 mg/mL, CHCl$_3$)

Example 4q (−)-N-(3-cyclopropyl-2-(6-(trifluoromethyl)pyridin-3-yl)propyl)-2,6-difluorobenzamide

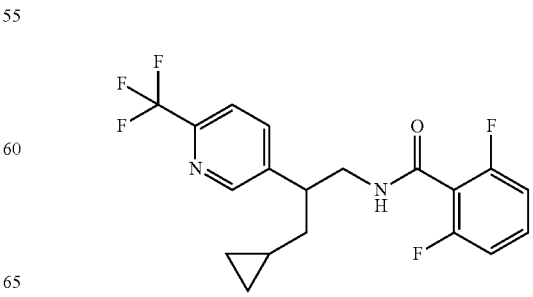

The racemic mixture which was prepared in a similar manner to example 3a from 2,6-difluorobenzoic acid and 3-cyclopropyl-2-(6-(trifluoromethyl)pyridin-3-yl)propan-1-amine was separated into the two enantiomers by preparative SFC to yield the title compound. LCMS (MH+): m/z=385.1, $t_R$ (minutes, Method G)=2.92. $[\alpha]_D^{20}$=−35.71 (c=0.84 mg/mL, CHCl$_3$)

And the corresponding enantiomer

Example 4r (+)-N-(3-cyclopropyl-2-(6-(trifluoromethyl)pyridin-3-yl)propyl)-2,6-difluorobenzamide LCMS (MH+): m/z=385.1, $t_R$ (minutes, Method G)=2.92. $[\alpha]_D^{20}$=36.9 (c=0.84 mg/mL, CHCl$_3$)

Example 4s (+)-2-chloro-N-(3-cyclopropyl-2-(6-(trifluoromethyl)pyridin-3-yl)propyl)-5-(methylsulfonyl)benzamide

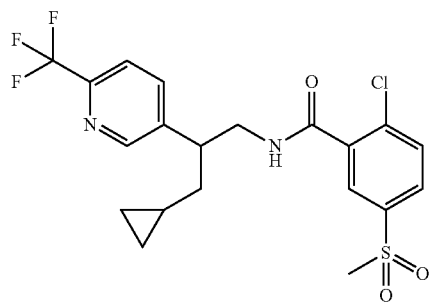 [SMILES: CS(=O)(=O)c1ccc(Cl)c(C(=O)NCC(CC2CC2)c2ccc(C(F)(F)F)nc2)c1]

The racemic mixture which was prepared in a similar manner to example 3a from 2-chloro-5-(methylsulfonyl)benzoic acid and 3-cyclopropyl-2-(6-(trifluoromethyl)pyridin-3-yl)propan-1-amine was separated into the two enantiomers by preparative SFC to yield the title compound.

LCMS (MH+): m/z=461.1, $t_R$ (minutes, Method F)=2.98. $[\alpha]_D^{20}$=+28.75 (c=0.8 mg/mL, CHCl$_3$)

And the corresponding enantiomer

Example 4t (−)-2-chloro-N-(3-cyclopropyl-2-(6-(trifluoromethyl)pyridin-3-yl)propyl)-5-(methyl sulfonyl)benzamide LCMS (MH+): m/z=461.1, $t_R$ (minutes, Method F)=2.98. $[\alpha]_D^{20}$=−27.0 (c=1.0 mg/mL, CHCl$_3$)

Example 4u (+)-2-chloro-N-(3-cyclopropyl-2-(6-(trifluoromethyl)pyridin-3-yl)propyl)-3-fluorobenzamide

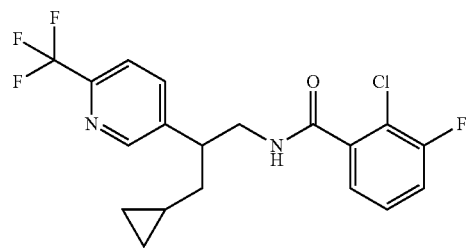 [SMILES: O=C(NCC(CC1CC1)c1ccc(C(F)(F)F)nc1)c1cccc(F)c1Cl]

The racemic mixture which was prepared in a similar manner to example 3a from 2-chloro-3-fluorobenzoic acid and 3-cyclopropyl-2-(6-(trifluoromethyl)pyridin-3-yl)propan-1-amine was separated into the two enantiomers by preparative SFC to yield the title compound. LCMS (MH+): m/z=401.1, $t_R$ (minutes, Method G)=2.61. $[\alpha]_D^{20}$=+28.13 (c=1.6 mg/mL, CHCl$_3$)

And the corresponding enantiomer

Example 4v (−)-2-chloro-N-(3-cyclopropyl-2-(6-(trifluoromethyl)pyridin-3-yl)propyl)-3-fluorobenzamide LCMS (MH+): m/z=401.1, $t_R$ (minutes, Method G)=2.61. $[\alpha]_D^{20}$=−26.25 (c=1.6 mg/mL, CHCl$_3$)

Example 4w (+)-2-chloro-N-(3-cyclopropyl-2-(6-fluoropyridin-3-yl)propyl)benzamide

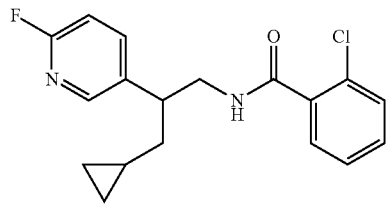 [SMILES: O=C(NCC(CC1CC1)c1ccc(F)nc1)c1ccccc1Cl]

The racemic mixture which was prepared in a similar manner to example 3a from 2-chlorobenzoic acid and 3-cyclopropyl-2-(6-fluoropyridin-3-yl)propan-1-amine was separated into the two enantiomers by preparative SFC to yield the title compound. LCMS (MH+): m/z=333.1, $t_R$ (minutes, Method F)=2.53. $[\alpha]_D^{20}$=+29.0 (c=2.0 mg/mL, CHCl$_3$)

And the corresponding enantiomer

Example 4x (−)-2-chloro-N-(3-cyclopropyl-2-(6-fluoropyridin-3-yl)propyl)benzamide LCMS (MH+): m/z=333.1, $t_R$ (minutes, Method F)=2.53. $[\alpha]_D^{20}$=−24.5 (c=2.0 mg/mL, CHCl$_3$)

Example 4y (+)-2,3-dichloro-N-(3-cyclopropyl-2-(2-methylpyrimidin-5-yl)propyl)benzamide

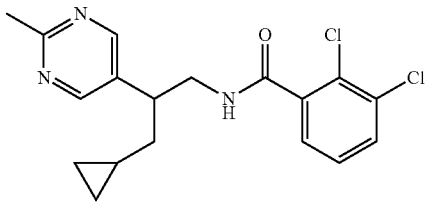 [SMILES: Cc1ncc(C(CNC(=O)c2cccc(Cl)c2Cl)CC2CC2)cn1]

The racemic mixture which was prepared in a similar manner to example 3a from 2,3-dichlorobenzoic acid and 3-cyclopropyl-2-(2-methylpyrimidin-5-yl)propan-1-amine was separated into the two enantiomers by preparative SFC to yield the title compound LCMS (MH+): m/z=364.1, $t_R$ (minutes, Method F)=2.64. $[\alpha]_D^{20}$=+41.3 (c=1.5 mg/mL, CHCl$_3$)
And the corresponding enantiomer

Example 4z (+2,3-dichloro-N-(3-cyclopropyl-2-(2-methylpyrimidin-5-yl)propyl)benzamide LCMS (MH+): m/z=364.1, $t_R$ (minutes, Method F)=2.64. $[\alpha]_D^{20}$=−40.7 (c=1.5 mg/mL, CHCl$_3$)

Example 4a1

(+)-2,3-dichloro-N-(3-cyclopropyl-2-(2-(trifluoromethyl)pyrimidin-5-yl)propyl)benzamide

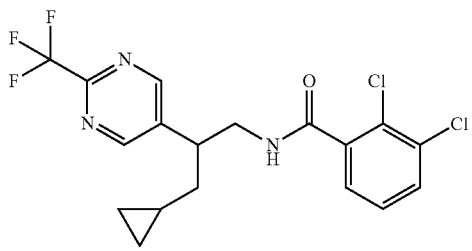 [SMILES: O=C(NCC(CC1CC1)c1cnc(C(F)(F)F)nc1)c1cccc(Cl)c1Cl]

The racemic mixture which was prepared in a similar manner to example 3a from 2,3-dichlorobenzoic acid and 3-cyclopropyl-2-(6-(trifluoromethyl)pyrimidin-3-yl)propan-1-amine was separated into the two enantiomers by preparative SFC to yield the title compound. LCMS (MH+): m/z=418.1, $t_R$ (minutes, Method G)=2.59. $[\alpha]_D^{20}$=+21.41 (c=3.27 mg/mL, CHCl$_3$)
And the corresponding enantiomer

Example 4b1

(+2,3-dichloro-N-(3-cyclopropyl-2-(2-(trifluoromethyl)pyrimidin-5-yl)propyl)benzamide LCMS (MH+): m/z=418.1, $t_R$ (minutes, Method G)=2.59. $[\alpha]_D^{20}$=−22.00 (c=3.0 mg/mL, CHCl$_3$)

Example 4c1

(+)-2-chloro-N-(3-cyclopropyl-2-(2-(trifluoromethyl)pyrimidin-5-yl)propyl)benzamide

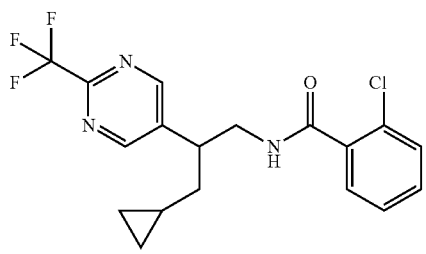 [SMILES: O=C(NCC(CC1CC1)c1cnc(C(F)(F)F)nc1)c1ccccc1Cl]

The racemic mixture which was prepared in a similar manner to example 3a from 2-chlorobenzoic acid and 3-cyclopropyl-2-(6-(trifluoromethyl)pyrimidin-3-yl)propan-1-amine was separated into the two enantiomers by preparative SFC to yield the title compound. LCMS (MH+): m/z=384.1, $t_R$ (minutes, Method F)=2.66. $[\alpha]_D^{20}$=+23.68 (c=5.49 mg/mL, CHCl$_3$)
And the corresponding enantiomer

Example 4d1

(−)-2-chloro-N-(3-cyclopropyl-2-(2-(trifluoromethyl)pyrimidin-5-yl)propyl)benzamide LCMS (MH+): m/z=384.1, $t_R$ (minutes, Method F)=2.66. $[\alpha]_D^{20}$=−21.63 (c=5.27 mg/mL, CHCl$_3$)

Example 4e1

(+)-2-chloro-N-(3-cyclopropyl-2-(2-(trifluoromethyl)pyrimidin-5-yl)propyl)-3-fluorobenzamide

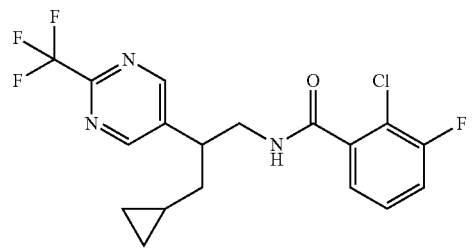 [SMILES: O=C(NCC(CC1CC1)c1cnc(C(F)(F)F)nc1)c1cccc(F)c1Cl]

The racemic mixture which was prepared in a similar manner to example 3a from 2-chloro-3-fluorobenzoic acid and 3-cyclopropyl-2-(6-(trifluoromethyl)pyrimidin-3-yl) propan-1-amine was separated into the two enantiomers by preparative SFC to yield the title compound. LCMS (MH+): m/z=402.1, $t_R$ (minutes, Method F)=2.71. $[\alpha]_D^{20}$=+24.77 (c=4.44 mg/mL, CHCl$_3$)
And the corresponding enantiomer

Example 4f1

(−)-2-chloro-N-(3-cyclopropyl-2-(2-(trifluoromethyl)pyrimidin-5-yl)propyl)-3-fluorobenzamide LCMS (MH+): m/z=402.1, $t_R$ (minutes, Method F)=2.71. $[\alpha]_D^{20}$=−21.77 (c=4.50 mg/mL, CHCl$_3$)

Example 4g1

(+)-2-chloro-N-(3-cyclopropyl-2-(2-(trifluoromethyl)pyrimidin-5-yl)propyl)-6-fluorobenzamide

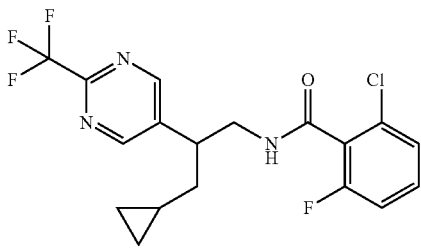 [SMILES: O=C(NCC(CC1CC1)c1cnc(C(F)(F)F)nc1)c1c(F)cccc1Cl]

The racemic mixture which was prepared in a similar manner to example 3a from 2-chloro-6-fluorobenzoic acid and 3-cyclopropyl-2-(6-(trifluoromethyl)pyrimidin-3-yl)propan-1-amine was separated into the two enantiomers by preparative SFC to yield the title compound. LCMS (MH+): m/z=402.1, $t_R$ (minutes, Method F)=2.69. $[\alpha]_D^{20}$=+35.56 (c=2.25 mg/mL, CHCl$_3$)
And the corresponding enantiomer

Example 4h1

(−)-2-chloro-N-(3-cyclopropyl-2-(2-(trifluoromethyl)pyrimidin-5-yl)propyl)-6-fluorobenzamide LCMS (MH+): m/z=402.1, $t_R$ (minutes, Method F)=2.69. $[\alpha]_D^{20}$=−34.27 (c=2.48 mg/mL, CHCl$_3$)

Example 4i1

(+)-2,3-dichloro-N-(3-cyclopropyl-2-(6-(2-hydroxypropan-2-yl)pyridin-3-yl)propyl)benzamide

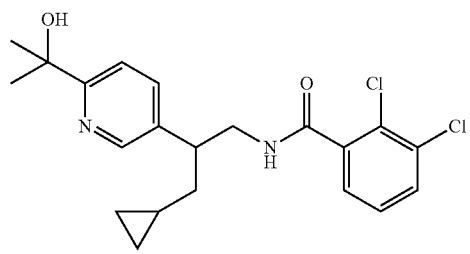 [SMILES: CC(C)(O)c1ccc(C(CNC(=O)c2cccc(Cl)c2Cl)CC2CC2)cn1]

The racemic mixture which was prepared in a similar manner to example 3a from 2,3-dichlorobenzoic acid and 2-(5-(1-amino-3-cyclopropylpropan-2-yl)pyridin-2-yl)propan-2-ol was separated into the two enantiomers by preparative SFC to yield the title compound. LCMS (MH+): m/z=407.1, $t_R$ (minutes, Method F)=1.98. $[\alpha]_D^{20}$=+23.89 (c=3.0 mg/mL, CHCl$_3$)
And the corresponding enantiomer

Example 4j1

(−)-2,3-dichloro-N-(3-cyclopropyl-2-(6-(2-hydroxypropan-2-yl)pyridin-3-yl)propyl)benzamide LCMS (MH+): m/z=407.1, $t_R$ (minutes, Method F)=1.98. $[\alpha]_D^{20}$=−28.17 (c=3.1 mg/mL, CHCl$_3$)

Example 4k1

(+)-2-chloro-N-(3-cyclopropyl-2-(2-(trifluoromethyl)pyrimidin-5-yl)propyl)-3-methoxybenzamide

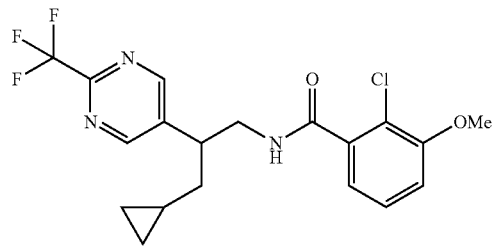 [SMILES: COc1cccc(C(=O)NCC(CC2CC2)c2cnc(C(F)(F)F)nc2)c1Cl]

The racemic mixture which was prepared in a similar manner to example 3a from 2-chloro-3-methoxybenzoic acid and 3-cyclopropyl-2-(2-(trifluoromethyl)pyrimidin-5-yl)propan-1-amine was separated into the two enantiomers by preparative SFC to yield the title compound. LCMS (MH+): m/z=414.0, $t_R$ (minutes, Method F)=2.53. $[\alpha]_D^{20}$=+26.3 (c=4.0 mg/mL, CHCl$_3$)
And the corresponding enantiomer

Example 4l1

(−)-2-chloro-N-(3-cyclopropyl-2-(2-(trifluoromethyl)pyrimidin-5-yl)propyl)-3-methoxybenzamide LCMS (MH+): m/z=414.0, $t_R$ (minutes, Method F)=2.53. $[\alpha]_D^{20}$=−29.5 (c=3.7 mg/mL, CHCl$_3$)

Example 4 m1

(+)-2-methyl-N-(3-cyclopropyl-2-(2-(trifluoromethyl)pyrimidin-5-yl)propyl)-3-methoxybenzamide

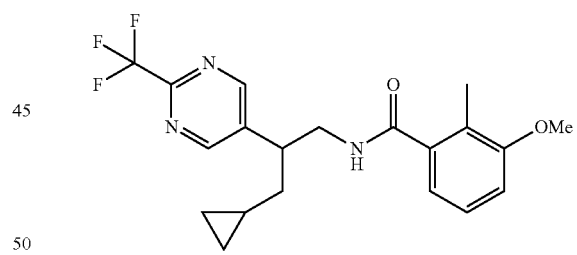

The racemic mixture which was prepared in a similar manner to example 3a from 2-methyl-3-methoxybenzoic acid and 3-cyclopropyl-2-(2-(trifluoromethyl)pyrimidin-5-yl)propan-1-amine was separated into the two enantiomers by preparative SFC to yield the title compound. LCMS (MH+): m/z=394.0, $t_R$ (minutes, Method F)=2.59. $[\alpha]_D^{20}$=+26.8 (c=3.90 mg/mL, CHCl$_3$)
And the corresponding enantiomer

Example 4n1

(−)-2-methyl-N-(3-cyclopropyl-2-(2-(trifluoromethyl)pyrimidin-5-yl)propyl)-3-methoxybenzamide LCMS (MH+): m/z=394.0, $t_R$ (minutes, Method F)=2.59. $[\alpha]_D^{20}$=−26.9 (c=3.40 mg/mL, CHCl$_3$)

Example 4o1

(+)-2,6-dichloro-N-(3-cyclopropyl-2-(2-(trifluoromethyl)pyrimidin-5-yl)propyl)benzamide

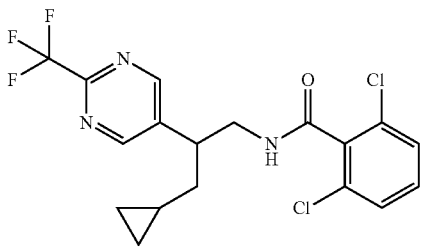 [SMILES: O=C(NCC(CC1CC1)c1cnc(C(F)(F)F)nc1)c1c(Cl)cccc1Cl]

The racemic mixture which was prepared in a similar manner to example 3a from 2,6-dichlorobenzoic acid and 3-cyclopropyl-2-(2-(trifluoromethyl)pyrimidin-5-yl)propan-1-amine was separated into the two enantiomers by preparative SFC to yield the title compound. LCMS (MH+): m/z=418.1, $t_R$ (minutes, Method F)=2.62. $[\alpha]_D^{20}$=+21.87 (c=3.2 mg/mL, CHCl$_3$)

And the corresponding enantiomer

Example 4p1

(−)-2,6-dichloro-N-(3-cyclopropyl-2-(2-(trifluoromethyl)pyrimidin-5-yl)propyl)benzamide LCMS (MH+): m/z=418.1, $t_R$ (minutes, Method F)=2.62. $[\alpha]_D^{20}$=−21.43 (c=2.8 mg/mL, CHCl$_3$)

Example 4q1

(+)-2,6-dichloro-N-(3-cyclopropyl-2-(2-(trifluoromethyl)pyridin-5-yl)propyl)benzamide

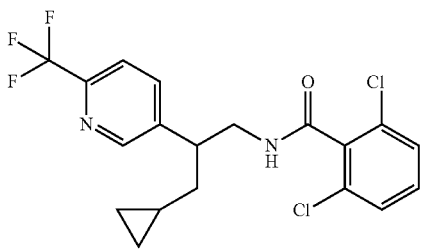 [SMILES: O=C(NCC(CC1CC1)c1ccc(C(F)(F)F)nc1)c1c(Cl)cccc1Cl]

The racemic mixture which was prepared in a similar manner to example 3a from 2,6-dichlorobenzoic acid and 3-cyclopropyl-2-(2-(trifluoromethyl)pyridin-5-yl)propan-1-amine was separated into the two enantiomers by preparative SFC to yield the title compound LCMS (MH+): m/z=417.1, $t_R$ (minutes, Method G)=2.50. $[\alpha]_D^{20}$=+20.64 (c=4.7 mg/mL, CHCl$_3$)

And the corresponding enantiomer

Example 4r1

(−)-2,6-dichloro-N-(3-cyclopropyl-2-(2-(trifluoromethyl)pyridin-5-yl)propyl)benzamide LCMS (MH+): m/z=417.1, $t_R$ (minutes, Method G)=2.50. $[\alpha]_D^{20}$=−20.3 (c=3.5 mg/mL, CHCl$_3$)

Example 4s1

(+)-2,6-dichloro-N-(3-cyclopropyl-2-(2-methylpyrimidin-5-yl)propyl)benzamide

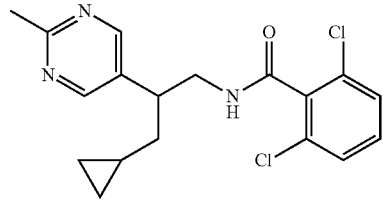 [SMILES: Cc1ncc(C(CNC(=O)c2c(Cl)cccc2Cl)CC2CC2)cn1]

The racemic mixture which was prepared in a similar manner to example 3a from 2,6-dichlorobenzoic acid and 3-cyclopropyl-2-(2-methylpyrimidin-5-yl)propan-1-amine was separated into the two enantiomers by preparative SFC to yield the title compound. LCMS (MH+): m/z=364.1, $t_R$ (minutes, Method F)=2.43. $[\alpha]_D^{20}$=+15.42 (c=2.4 mg/mL, CHCl$_3$)

And the corresponding enantiomer

Example 4t1

(−)-2,6-dichloro-N-(3-cyclopropyl-2-(2-methylpyrimidin-5-yl)propyl)benzamide

LCMS (MH+): m/z=364.1, $t_R$ (minutes, Method F)=2.43. $[\alpha]_D^{20}$=−11.51 (c=1.87 mg/mL, CHCl$_3$)

Example 4u1

(+)-2-chloro-N-(3-cyclopropyl-2-methyl-2-(2-(trifluoromethyl)pyrimidin-5-yl)propyl)benzamide

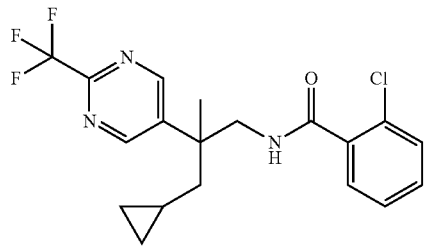 [SMILES: CC(CNC(=O)c1ccccc1Cl)(CC1CC1)c1cnc(C(F)(F)F)nc1]

The racemic mixture which was prepared in a similar manner to example 3a from 2-chlorobenzoic acid and 3-cyclopropyl-2-methyl-2-(2-(trifluoromethyl)pyrimidin-5-yl)propan-1-amine was separated into the two enantiomers by preparative SFC to yield the title compound. LCMS (MH+): m/z=398.1, $t_R$ (minutes, Method F)=2.62. $[\alpha]_D^{20}$=+13.77 (c=5.30 mg/mL, CHCl$_3$)

And the corresponding enantiomer

Example 4v1

(−)-2-chloro-N-(3-cyclopropyl-2-methyl-2-(2-(trifluoromethyl)pyrimidin-5-yl)propyl)benzamide LCMS (M11+): m/z=398.1, $t_R$ (minutes, Method F)=2.62. $[\alpha]_D^{20}$=−14.16 (c=5.86 mg/mL, CHCl$_3$)

Example 4x1

(+)-2-chloro-3-fluoro-N-(3-cyclopropyl-2-methyl-2-(2-(trifluoromethyl)pyrimidin-5-yl)propyl)benzamide

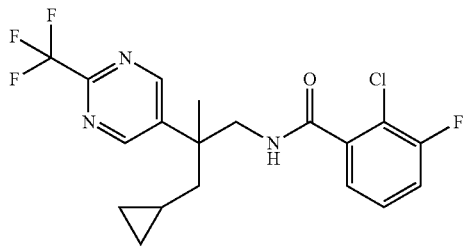

The racemic mixture which was prepared in a similar manner to example 3a from 2-chloro-3-fluorobenzoic acid and 3-cyclopropyl-2-methyl-2-(2-(trifluoromethyl)pyrimidin-5-yl)propan-1-amine was separated into the two enantiomers by preparative SFC to yield the title compound.

LCMS (MH+): m/z=416.1, $t_R$ (minutes, Method G)=2.48. $[\alpha]_D^{20}$=+13.80 (c=5.87 mg/mL, CHCl$_3$)

And the corresponding enantiomer

Example 4y1

(−)-2-chloro-3-fluoro-N-(3-cyclopropyl-2-methyl-2-(2-(trifluoromethyl)pyrimidin-5-yl)propyl)benzamide LCMS (MH+): m/z=416.1, $t_R$ (minutes, Method G)=2.48. $[\alpha]_D^{20}$=−13.85 (c=5.63 mg/mL, CHCl$_3$)

Example 4z1

(+)-2,3-dichloro-N-(3-cyclopropyl-2-methyl-2-(2-(trifluoromethyl)pyrimidin-5-yl)propyl)benzamide

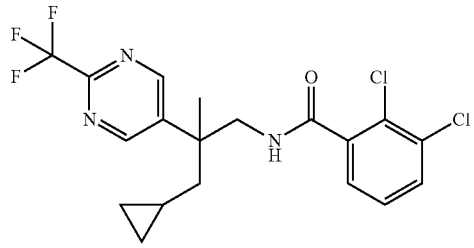 [SMILES: CC(CNC(=O)c1cccc(Cl)c1Cl)(CC1CC1)c1cnc(C(F)(F)F)nc1]

The racemic mixture which was prepared in a similar manner to example 3a from 2,3-dichlorobenzoic acid and 3-cyclopropyl-2-methyl-2-(2-(trifluoromethyl)pyrimidin-5-yl)propan-1-amine was separated into the two enantiomers by preparative SFC to yield the title compound. LCMS (MH+): m/z=432.1, $t_R$ (minutes, Method G)=2.58. $[\alpha]_D^{20}$=+17.42 (c=6.6 mg/mL, CHCl$_3$)

And the corresponding enantiomer

Example 4a2

(−)-2,3-dichloro-N-(3-cyclopropyl-2-methyl-2-(2-(trifluoromethyl)pyrimidin-5-yl)propyl)benzamide LCMS (MH+): m/z=432.1, $t_R$ (minutes, Method G)=2.58. $[\alpha]_D^{20}$=−17.32 (c=6.6 mg/mL, CHCl$_3$)

Example 4b2

(+)-2-chloro-N-(2-(2-methylpyrimidin-5-yl)-2-(tetrahydro-2H-pyran-4-yl)ethyl)benzamide

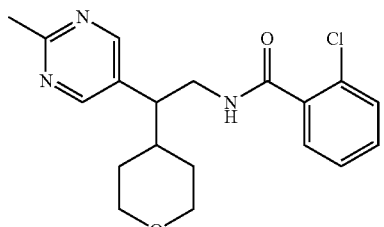

The racemic mixture which was prepared in a similar manner to example 3a from 2-chlorobenzoic acid and 2-(2-methylpyrimidin-5-yl)-2-(tetrahydro-2H-pyran-4-yl)ethanamine was separated into the two enantiomers by preparative SFC to yield the title compound. LCMS (MH+): m/z=360.1, $t_R$ (minutes, Method F)=1.97/1.65. $[\alpha]_D^{20}$=+43.43 (c=1.75 mg/mL, CHCl$_3$)

And the corresponding enantiomer

Example 4c2

(−)-2-chloro-N-(2-(2-methylpyrimidin-5-yl)-2-(tetrahydro-2H-pyran-4-yl)ethyl)benzamide LCMS (MH+): m/z=360.1, $t_R$ (minutes, Method F)=1.97. $[\alpha]_D^{20}$=−38.00 (c=1.5 mg/mL, CHCl$_3$)

Example 4d2

(+)-2,3-dichloro-N-(2-(2-methylpyrimidin-5-yl)-2-(tetrahydro-2H-pyran-4-yl)ethyl)benzamide

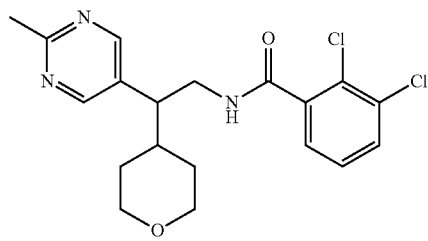 [SMILES: Cc1ncc(C(CNC(=O)c2cccc(Cl)c2Cl)C2CCOCC2)cn1]

The racemic mixture which was prepared in a similar manner to example 3a from 2,3-dichlorobenzoic acid and 2-(2-methylpyrimidin-5-yl)-2-(tetrahydro-2H-pyran-4-yl)ethanamine was separated into the two enantiomers by preparative SFC to yield the title compound LCMS (MH+): m/z=394.1, $t_R$ (minutes, Method F)=1.88. $[\alpha]_D^{20}$=+57.50 (c=2.0 mg/mL, CHCl$_3$)

And the corresponding enantiomer

Example 4e2

(−)-2,3-dichloro-N-(2-(2-methylpyrimidin-5-yl)-2-(tetrahydro-2H-pyran-4-yl)ethyl)benzamide LCMS (MH+): m/z=394.1, $t_R$ (minutes, Method F)=1.88. $[\alpha]_D^{20}$=−57.89 (c=1.9 mg/mL, CHCl$_3$)

Example 4f2

(+)-2-chloro-N-(3-(1-(trifluoromethyl)cyclopropyl)-2-(2-(trifluoromethyl)pyrimidin-5-yl)propyl)benzamide

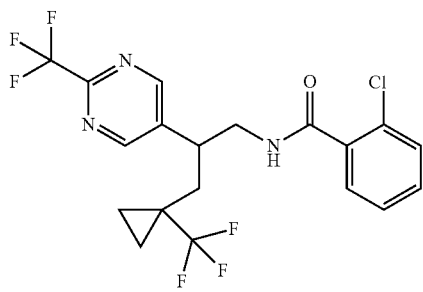 [SMILES: O=C(NCC(CC1(C(F)(F)F)CC1)c1cnc(C(F)(F)F)nc1)c1ccccc1Cl]

The racemic mixture which was prepared in a similar manner to example 3a from 2-chlorobenzoic acid and 3-(1-(trifluoromethyl)cyclopropyl)-2-(2-(trifluoromethyl)pyrimidin-5-yl)propan-1-amine was separated into the two enantiomers by preparative SFC to yield the title compound. LCMS (MH+): m/z=452.0, $t_R$ (minutes, Method F)=3.03. $[\alpha]_D^{20}$=+27.50 (c=4.80 mg/mL, CHCl$_3$)
And the corresponding enantiomer

Example 4g2

(−)-2-chloro-N-(3-(1-(trifluoromethyl)cyclopropyl)-2-(2-(trifluoromethyl)pyrimidin-5-yl)propyl)benzamide LCMS (MH+): m/z=452.0, $t_R$ (minutes, Method F)=3.03. $[\alpha]_D^{20}$=−27.32 (c=3.88 mg/mL, CHCl$_3$)

Example 4h2

(+)-2,3-dichloro-N-(3-(1-(trifluoromethyl)cyclopropyl)-2-(2-(trifluoromethyl)pyrimidin-5-yl)propyl)benzamide

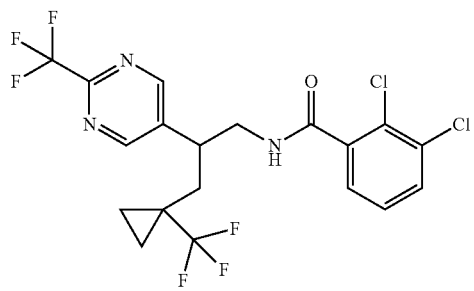 [SMILES: O=C(NCC(CC1(C(F)(F)F)CC1)c1cnc(C(F)(F)F)nc1)c1cccc(Cl)c1Cl]

The racemic mixture which was prepared in a similar manner to example 3a from 2,3-dichlorobenzoic acid and 3-(1-(trifluoromethyl)cyclopropyl)-2-(2-(trifluoromethyl)pyrimidin-5-yl)propan-1-amine was separated into the two enantiomers by preparative SFC to yield the title compound. LCMS (MH+): m/z=486.1, $t_R$ (minutes, Method F)=2.77. $[\alpha]_D^{20}$=+31.03 (c=5.80 mg/mL, CHCl$_3$)
And the corresponding enantiomer

Example 4i2

(−)-2,3-dichloro-N-(3-(1-(trifluoro methyl)cyclopropyl)-2-(2-(trifluoromethyl)pyrimidin-5-yl)propyl)benzamide LCMS (MH+): m/z=486.1, $t_R$ (minutes, Method F)=2.77. $[\alpha]_D^{20}$=−31.87 (c=5.02 mg/mL, CHCl$_3$)

Example 4j2

(+)-2-chloro-3-fluoro-N-(3-(1-(trifluoromethyl)cyclopropyl)-2-(2-(trifluoromethyl)pyrimidin-5-yl)propyl)benzamide

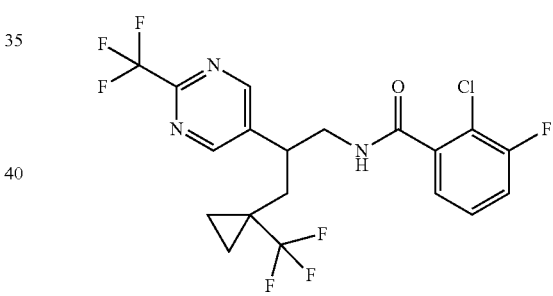

The racemic mixture which was prepared in a similar manner to example 3a from 2-chloro-3-fluorobenzoic acid and 3-(1-(trifluoromethyl)cyclopropyl)-2-(2-(trifluoromethyl)pyrimidin-5-yl)propan-1-amine was separated into the two enantiomers by preparative SFC to yield the title compound. LCMS (MH+): m/z=470.0, $t_R$ (minutes, Method F)=3.07. $[\alpha]_D^{20}$=+28.85 (c=3.05 mg/mL, CHCl$_3$)
And the corresponding enantiomer

Example 4k2

(−)-2-chloro-3-fluoro-N-(3-(1-(trifluoromethyl)cyclopropyl)-2-(2-(trifluoromethyl)pyrimidin-5-yl)propyl)benzamide LCMS (MH+): m/z=470.0, $t_R$ (minutes, Method F)=3.07. $[\alpha]_D^{20}$=−28.97 (c=3.21 mg/mL, CHCl$_3$)

Example 4l2

(+)-2-chloro-N-(3-(1-(trifluoromethyl)cyclopropyl)-2-(2-trifluoromethyl)pyridin-5-yl)propyl)benzamide

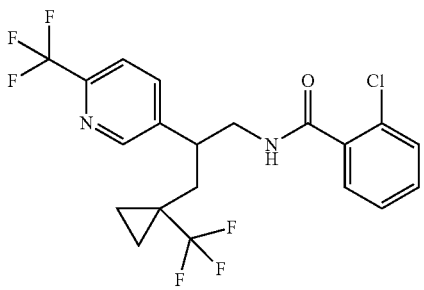 [SMILES: O=C(NCC(CC1(C(F)(F)F)CC1)c1ccc(C(F)(F)F)nc1)c1ccccc1Cl]

The racemic mixture which was prepared in a similar manner to example 3a from 2-chlorobenzoic acid and 3-(1-(trifluoromethyl)cyclopropyl)-2-(2-(trifluoromethyl)pyridin-5-yl)propan-1-amine was separated into the two enantiomers by preparative SFC to yield the title compound. LCMS (MH+): m/z=451.1, $t_R$ (minutes, Method G)=2.50. $[\alpha]_D^{20}$=+33.55 (c=3.07 mg/mL, CHCl$_3$)

And the corresponding enantiomer

Example 4m2

(−)-2-chloro-N-(3-(1-(trifluoromethyl)cyclopropyl)-2-(2-(trifluoromethyl)pyridin-5-yl)propyl)benzamide LCMS (MH+): m/z=451.1, $t_R$ (minutes, Method G)=2.50. $[\alpha]_D^{20}$=−32.98 (c=3.20 mg/mL, CHCl$_3$)

Example 4n2

(+)-2,3-dichloro-N-(3-(1-(trifluoromethyl)cyclopropyl)-2-(2-(trifluoromethyl)pyridin-5-yl)propyl)benzamide

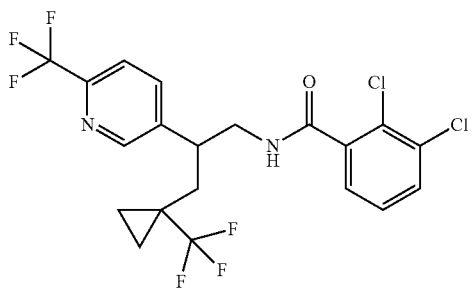 [SMILES: O=C(NCC(CC1(C(F)(F)F)CC1)c1ccc(C(F)(F)F)nc1)c1cccc(Cl)c1Cl]

The racemic mixture which was prepared in a similar manner to example 3a from 2,3-dichlorobenzoic acid and 3-(1-(trifluoromethyl)cyclopropyl)-2-(2-(trifluoromethyl)pyridin-5-yl)propan-1-amine was separated into the two enantiomers by preparative SFC to yield the title compound. LCMS (MH+): m/z=485.1, $t_R$ (minutes, Method G)=2.63. $[\alpha]_D^{20}$=+27.63 (c=1.52 mg/mL, CHCl$_3$)

And the corresponding enantiomer

Example 4o2

(−)-2,3-dichloro-N-(3-(1-(trifluoromethyl)cyclopropyl)-2-(2-(trifluoromethyl)pyridin-5-yl)propyl)benzamide LCMS (MH+): m/z=485.1, $t_R$ (minutes, Method G)=2.63. $[\alpha]_D^{20}$=−26.67 (c=1.50 mg/mL, CHCl$_3$)

Example 4p2

(+)-2-chloro-3-fluoro-N-(3-(1-(trifluoromethyl)cyclopropyl)-2-(2-(trifluoromethyl)pyridin-5-yl)propyl)benzamide

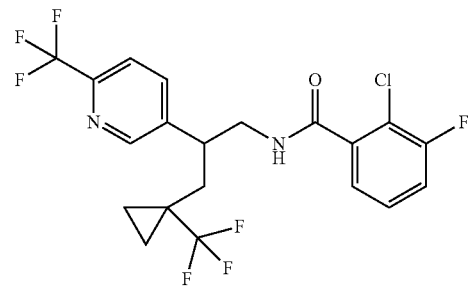 [SMILES: O=C(NCC(CC1(C(F)(F)F)CC1)c1ccc(C(F)(F)F)nc1)c1cccc(F)c1Cl]

The racemic mixture which was prepared in a similar manner to example 3a from 2-chloro-3-fluorobenzoic acid and 3-(1-(trifluoromethyl)cyclopropyl)-2-(2-(trifluoromethyl)pyridin-5-yl)propan-1-amine was separated into the two enantiomers by preparative SFC to yield the title compound. LCMS (MH+): m/z=469.1, $t_R$ (minutes, Method G)=2.54. $[\alpha]_D^{20}$=+27.60 (c=3.20 mg/mL, CHCl$_3$)

And the corresponding enantiomer

Example 4q2

(−)-2-chloro-3-fluoro-N-(3-(1-(trifluoromethyl)cyclopropyl)-2-(2-(trifluoromethyl)pyridin-5-yl)propyl)benzamide LCMS (MH+): m/z=469.1, $t_R$ (minutes, Method G)=2.54. $[\alpha]_D^{20}$=−27.55 (c=3.40 mg/mL, CHCl$_3$)

Example 4r2

(+)-2,3-dichloro-N-(2-(tetrahydro-2H-pyran-4-yl)-2-(2-(trifluoromethyl)pyrimidin-5-yl)ethyl)benzamide

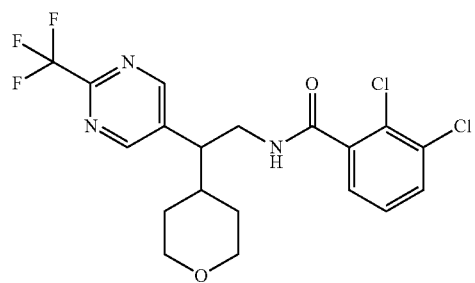 [SMILES: O=C(NCC(c1cnc(C(F)(F)F)nc1)C1CCOCC1)c1cccc(Cl)c1Cl]

The racemic mixture which was prepared in a similar manner to example 3a from 2,3-dichlorobenzoic acid and 2-(tetrahydro-2H-pyran-4-yl)-2-(2-(trifluoromethyl)pyrimidin-5-yl)ethanamine was separated into the two enantiomers by preparative SFC to yield the title compound. LCMS (M11+): m/z=448.0, $t_R$ (minutes, Method F)=2.72. $[\alpha]_D^{20}$=+42.52 (c=3.8 mg/mL, CHCl$_3$)

And the corresponding enantiomer

Example 4s2

(−)-2,3-dichloro-N-(2-(tetrahydro-2H-pyran-4-yl)-2-(2-(trifluoromethyl)pyrimidin-5-yl)ethyl)benzamide LCMS (MH+): m/z=448.0, $t_R$ (minutes, Method F)=2.72. $[\alpha]_D^{20}$=−42.62 (c=3.66 mg/mL, CHCl$_3$)

Example 4t2

(+)-2-chloro-N-(2-(tetrahydro-2H-pyran-4-yl)-2-(2-(trifluoromethyl)pyrimidin-5-yl)ethyl)benzamide

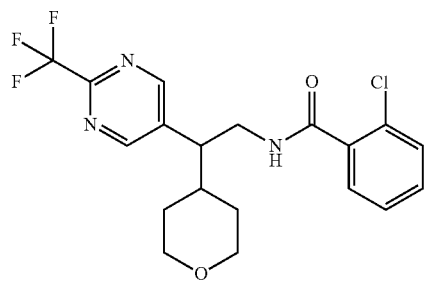 [SMILES: O=C(NCC(c1cnc(C(F)(F)F)nc1)C1CCOCC1)c1ccccc1Cl]

The racemic mixture which was prepared in a similar manner to example 3a from 2-chlorobenzoic acid and 2-(tetrahydro-2H-pyran-4-yl)-2-(2-(trifluoromethyl)pyrimidin-5-yl)ethanamine was separated into the two enantiomers by preparative SFC to yield the title compound. LCMS (MH+): m/z=414.1, $t_R$ (minutes, Method F)=2.54. $[\alpha]_D^{20}$=+38.57 (c=2.80 mg/mL, CHCl$_3$)

And the corresponding enantiomer

Example 4u2

(−)-2-chloro-N-(2-(tetrahydro-2H-pyran-4-yl)-2-(2-(trifluoromethyl)pyrimidin-5-yl)ethyl)benzamide LCMS (MH+): m/z=414.1, $t_R$ (minutes, Method F)=2.54. $[\alpha]_D^{20}$=−38.13 (c=3.20 mg/mL, CHCl$_3$)

Example 4v2

(+)-2-chloro-3-fluoro-N-(2-(tetrahydro-2H-pyran-4-yl)-2-(2-(trifluoromethyl)pyrimidin-5-yl)ethyl)benzamide

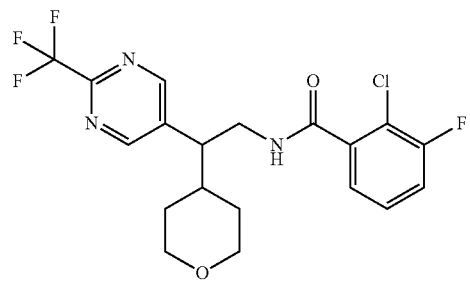 [SMILES: O=C(NCC(c1cnc(C(F)(F)F)nc1)C1CCOCC1)c1cccc(F)c1Cl]

The racemic mixture which was prepared in a similar manner to example 3a from 2-chloro-3-fluorobenzoic acid and 2-(tetrahydro-2H-pyran-4-yl)-2-(2-(trifluoromethyl)pyrimidin-5-yl)ethanamine was separated into the two enantiomers by preparative SFC to yield the title compound. LCMS (MH+): m/z=432.1, $t_R$ (minutes, Method F)=2.48. $[\alpha]_D^{20}$=+32.38 (c=3.27 mg/mL, CHCl$_3$)

And the corresponding enantiomer

Example 4x2

(−)-2-chloro-3-fluoro-N-(2-(tetrahydro-2H-pyran-4-yl)-2-(2-(trifluoromethyl)pyrimidin-5-yl)ethyl)benzamide LCMS (MH+): m/z=432.1, $t_R$ (minutes, Method F)=2.48. $[\alpha]_D^{20}$=−35.64 (c=3.18 mg/mL, CHCl$_3$)

Example 4y2

(+)-2-chloro-6-fluoro-N-(2-(tetrahydro-2H-pyran-4-yl)-2-(2-(trifluoromethyl)pyrimidin-5-yl)ethyl)benzamide

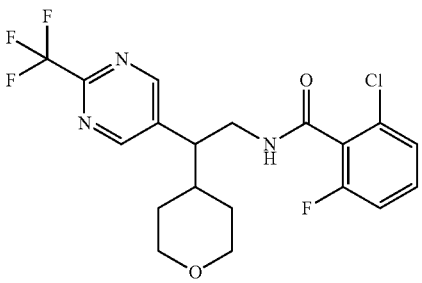 [SMILES: O=C(NCC(c1cnc(C(F)(F)F)nc1)C1CCOCC1)c1c(F)cccc1Cl]

The racemic mixture which was prepared in a similar manner to example 3a from 2-chloro-6-fluorobenzoic acid and 2-(tetrahydro-2H-pyran-4-yl)-2-(2-(trifluoromethyl)pyrimidin-5-yl)ethanamine was separated into the two enantiomers by preparative SFC to yield the title compound. LCMS (MH+): m/z=432.1, $t_R$ (minutes, Method F)=2.6. $[\alpha]_D^{20}$=+37.86 (c=4.20 mg/mL, CHCl$_3$)

And the corresponding enantiomer

Example 4z2

(−)-2-chloro-6-fluoro-N-(2-(tetrahydro-2H-pyran-4-yl)-2-(2-(trifluoro methyl)pyrimidin-5-yl)ethyl)benzamide LCMS (MH+): m/z=432.1, $t_R$ (minutes, Method F)=2.6. $[\alpha]_D^{20}$=−37.86 (c=3.83 mg/mL, CHCl$_3$)

Example 4a3

(+)-2,6-dichloro-N-(2-phenyl-2-(6-(trifluoromethyl)pyrid-yl)ethyl)benzamide

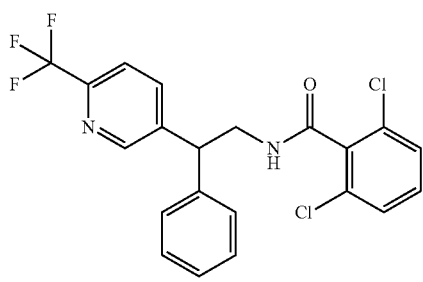 [SMILES: O=C(NCC(c1ccccc1)c1ccc(C(F)(F)F)nc1)c1c(Cl)cccc1Cl]

The racemic mixture which was prepared in a similar manner to example 3a from 2,6-dichlorobenzoic acid and 2-phenyl-2-(6-(trifluoromethyl)pyridin-3-yl)ethanamine was separated into the two enantiomers by preparative SFC to yield the title compound. LCMS (MH+): m/z=439.1, $t_R$ (minutes, Method G)=2.76. $[\alpha]_D^{20}$=+3.18 (c=6.38 mg/mL, CHCl$_3$)

And the corresponding enantiomer

Example 4b3

(−)-2,6-dichloro-N-(2-phenyl-2-(6-(trifluoromethyl)pyridin-3-yl)ethyl)benzamide

LCMS (MH+): m/z=439.1, $t_R$ (minutes, Method G)=2.76. $[\alpha]_D^{20}$=−4.19 (c=7.8 mg/mL, CHCl$_3$)

Example 4c3

(+)-2,3-dichloro-N-(2-(4-fluorophenyl)-2-(6-(trifluoromethyl)pyridin-3-yl)ethyl)benzamide

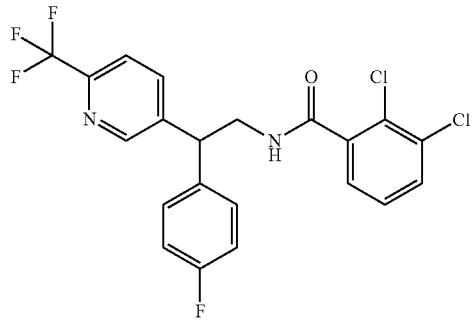 [SMILES: O=C(NCC(c1ccc(F)cc1)c1ccc(C(F)(F)F)nc1)c1cccc(Cl)c1Cl]

The racemic mixture which was prepared in a similar manner to example 3a from 2,3-dichlorobenzoic acid and 2-(4-fluorophenyl)-2-(6-(trifluoromethyl)pyridin-3-yl) ethanamine was separated into the two enantiomers by preparative SFC to yield the title compound. LCMS (MH+): m/z=457.0, $t_R$ (minutes, Method G)=3.02. $[\alpha]_D^{20}$=+4.17 (c=3.04 mg/mL, CHCl$_3$) And the corresponding enantiomer

Example 4d3

(−)-2,3-dichloro-N-(2-(4-fluorophenyl)-2-(6-(trifluoromethyl)pyridin-3-yl)ethyl)benzamide LCMS (MH+): m/z=457.0, $t_R$ (minutes, Method G)=3.02. $[\alpha]_D^{20}$=−4.31 (c=3.64 mg/mL, CHCl$_3$)

Example 4e3

(+)-2-chloro-N-(2-(4-fluoro phenyl)-2-(6-(trifluoromethyl)pyridin-3-yl)ethyl)benzamide

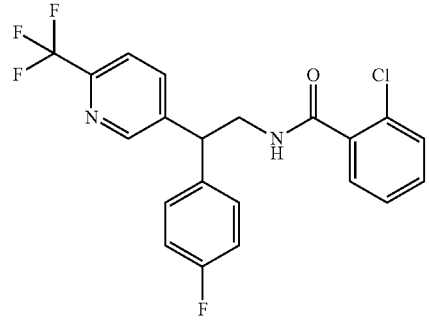 [SMILES: O=C(NCC(c1ccc(F)cc1)c1ccc(C(F)(F)F)nc1)c1ccccc1Cl]

The racemic mixture which was prepared in a similar manner to example 3a from 2-chlorobenzoic acid and 2-(4-fluorophenyl)-2-(6-(trifluoromethyl)pyridin-3-yl)ethanamine was separated into the two enantiomers by preparative SFC to yield the title compound. LCMS (MH+): m/z=423.1, $t_R$ (minutes, Method G)=2.58. $[\alpha]_D^{20}$=+18.1 (c=5.22 mg/mL, CHCl$_3$)

And the corresponding enantiomer

Example 4f3

(−)-2-chloro-N-(2-(4-fluorophenyl)-2-(6-(trifluoromethyl)pyridin-3-yl)ethyl)benzamide LCMS (MH+): m/z=423.1, $t_R$ (minutes, Method G)=2.58. $[\alpha]_D^{20}$=−16.1 (c=5.26 mg/mL, CHCl$_3$)

Example 4g3

(+)-2-chloro-3-fluoro-N-(2-(4-fluorophenyl)-2-(6-(trifluoromethyl)pyridin-3-yl)ethyl)benzamide

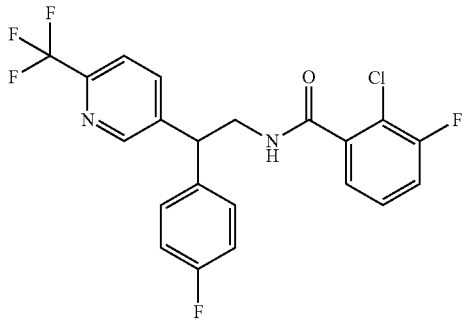 [SMILES: O=C(NCC(c1ccc(F)cc1)c1ccc(C(F)(F)F)nc1)c1cccc(F)c1Cl]

The racemic mixture which was prepared in a similar manner to example 3a from 2-chloro-3-fluorobenzoic acid and 2-(4-fluorophenyl)-2-(6-(trifluoromethyl)pyridin-3-yl)ethanamine was separated into the two enantiomers by preparative SFC to yield the title compound. LCMS (MH+): m/z=441.1, $t_R$ (minutes, Method G)=2.63. $[\alpha]_D^{20}$=+10.60 (c=5.6 mg/mL, CHCl$_3$)

And the corresponding enantiomer

Example 4h3

(−)-2-chloro-3-fluoro-N-(2-(4-fluorophenyl)-2-(6-(trifluoro methyl)pyridin-3-yl)ethyl)benzamide LCMS (MH+): m/z=441.1, $t_R$ (minutes, Method G)=2.63. $[\alpha]_D^{20}$=−10.96 (c=5.2 mg/mL, CHCl$_3$)

Example 4I3

(+)-2-chloro-6-fluoro-N-(2-(4-fluorophenyl)-2-(6-(trifluoromethyl)pyridin-3-yl)ethyl)benzamide

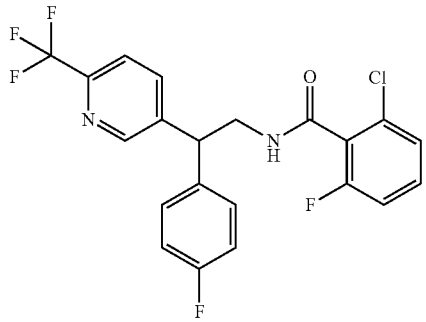 [SMILES: O=C(NCC(c1ccc(F)cc1)c1ccc(C(F)(F)F)nc1)c1c(F)cccc1Cl]

The racemic mixture which was prepared in a similar manner to example 3a from 2-chloro-6-fluorobenzoic acid and 2-(4-fluorophenyl)-2-(6-(trifluoromethyl)pyridin-3-yl)ethanamine was separated into the two enantiomers by preparative SFC to yield the title compound LCMS (MH+): m/z=441.0, $t_R$ (minutes, Method G)=2.86. $[\alpha]_D^{20}$=+17.1 (c=4.44 mg/mL, CHCl$_3$)

And the corresponding enantiomer

Example 4j3

(−)-2-chloro-6-fluoro-N-(2-(4-fluorophenyl)-2-(6-(trifluoromethyl)pyridin-3-yl)ethyl)benzamide LCMS (MH+): m/z=441.0, $t_R$ (minutes, Method G)=2.86. $[\alpha]_D^{20}$=−15.7 (c=4.58 mg/mL, CHCl$_3$)

Example 4k3

(+)-2,3-dichloro-N-(2-(4-fluorophenyl)-2-(2-(trifluoromethyl)pyrimidin-5-yl)ethyl)benzamide

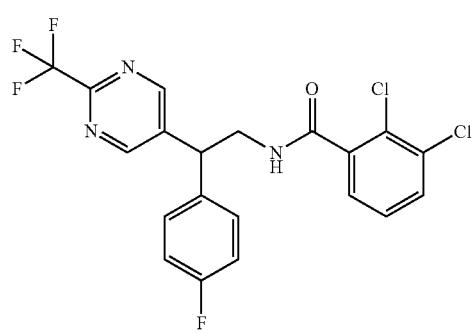 [SMILES: O=C(NCC(c1ccc(F)cc1)c1cnc(C(F)(F)F)nc1)c1cccc(Cl)c1Cl]

The racemic mixture which was prepared in a similar manner to example 3a from 2,3-dichlorobenzoic acid and 2-(4-fluorophenyl)-2-(2-(trifluoromethyl)pyrimidin-5-yl)ethanamine was separated into the two enantiomers by preparative SFC to yield the title compound. LCMS (MH+): m/z=458.0, $t_R$ (minutes, Method G)=2.91. $[\alpha]_D^{20}$=+14.2 (c=8.50 mg/mL, CHCl$_3$)

And the corresponding enantiomer

Example 4i3

(−)-2,3-dichloro-N-(2-(4-fluorophenyl)-2-(2-(trifluoromethyl)pyrimidin-5-yl)ethyl)benzamide LCMS (MH+): m/z=458.0, $t_R$ (minutes, Method G)=2.91. $[\alpha]_D^{20}$=−14.3 (c=7.90 mg/mL, CHCl$_3$)

Example 4m3

(+)-2-chloro-N-(2-(4-fluoro phenyl)-2-(2-(trifluoromethyl)pyrimidin-5-yl)ethyl)benzamide

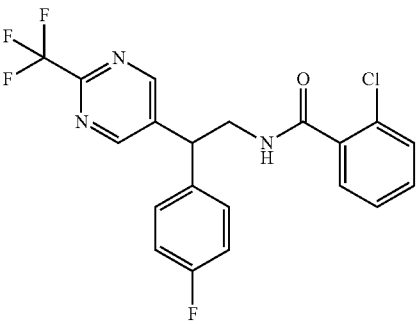 [SMILES: O=C(NCC(c1ccc(F)cc1)c1cnc(C(F)(F)F)nc1)c1ccccc1Cl]

The racemic mixture which was prepared in a similar manner to example 3a from 2-chlorobenzoic acid and 2-(4-fluorophenyl)-2-(2-(trifluoromethyl)pyrimidin-5-yl)ethanamine was separated into the two enantiomers by preparative SFC to yield the title compound. LCMS (MH+): m/z=424.1, $t_R$ (minutes, Method F)=3.19. $[\alpha]_D^{20}$=+16.4 (c=6.80 mg/mL, CHCl$_3$)

And the corresponding enantiomer

Example 4n3

(−)-2-chloro-N-(2-(4-fluorophenyl)-2-(2-(trifluoromethyl)pyrimidin-5-yl)ethyl)benzamide LCMS (MH+): m/z=424.1, $t_R$ (minutes, Method F)=3.19. $[\alpha]_D^{20}$=−14.3 (c=6.40 mg/mL, CHCl$_3$)

Example 4o3

(+)-2-chloro-3-fluoro-N-(2-(4-fluorophenyl)-2-(2-(trifluoromethyl)pyrimidin-5-yl)ethyl)benzamide

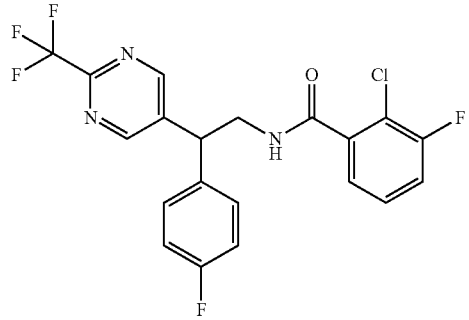 [SMILES: O=C(NCC(c1ccc(F)cc1)c1cnc(C(F)(F)F)nc1)c1cccc(F)c1Cl]

The racemic mixture which was prepared in a similar manner to example 3a from 2-chloro-3-fluorobenzoic acid and 2-(4-fluorophenyl)-2-(2-(trifluoromethyl)pyrimidin-5-yl)ethanamine was separated into the two enantiomers by preparative SFC to yield the title compound. LCMS (MH+): m/z=442.1, $t_R$ (minutes, Method F)=3.24. $[\alpha]_D^{20}$=+12.8 (c=6.8 mg/mL, CHCl$_3$)

And the corresponding enantiomer

Example 4p3

(−)-2-chloro-3-fluoro-N-(2-(4-fluorophenyl)-2-(2-(trifluoromethyl)pyrimidin-5-yl)ethyl)benzamide LCMS (MH+): m/z=442.1, $t_R$ (minutes, Method F)=3.24. $[\alpha]_D^{20}$=−12.3 (c=7.0 mg/mL, CHCl$_3$)

Example 4q3

(+)-2-chloro-6-fluoro-N-(2-(4-fluorophenyl)-2-(2-(trifluoromethyl)pyrimidin-5-yl)ethyl)benzamide

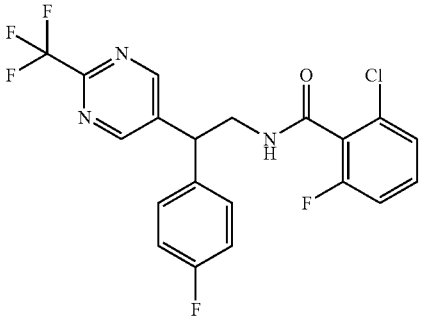 [SMILES: O=C(NCC(c1ccc(F)cc1)c1cnc(C(F)(F)F)nc1)c1c(F)cccc1Cl]

The racemic mixture which was prepared in a similar manner to example 3a from 2-chloro-6-fluorobenzoic acid and 2-(4-fluorophenyl)-2-(2-(trifluoromethyl)pyrimidin-5-yl)ethanamine was separated into the two enantiomers by preparative SFC to yield the title compound. LCMS (MH+): m/z=442.0, $t_R$ (minutes, Method F)=2.99. $[\alpha]_D^{20}$=+18.1 (c=4.0 mg/mL, CHCl$_3$)

And the corresponding enantiomer

Example 4r3

(−)-2-chloro-6-fluoro-N-(2-(4-fluorophenyl)-2-(2-(trifluoromethyl)pyrimidin-5-yl)ethyl)benzamide LCMS (MIFF): m/z=442.0, $t_R$ (minutes, Method F)=2.99. $[\alpha]_D^{20}$=−16.1 (c=4.0 mg/mL, CHCl$_3$)

Example 4s3

(+)-2-chloro-N-(2-(4,4-difluorocyclohexyl)-2-(2-(trifluoromethyl)pyrimidin-5-yl)ethyl)benzamide

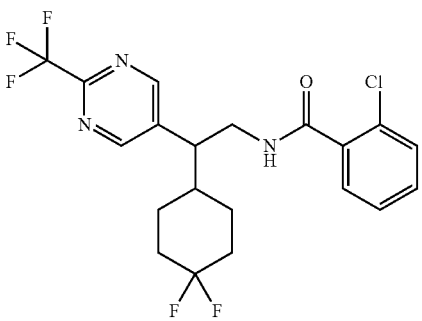 [SMILES: O=C(NCC(c1cnc(C(F)(F)F)nc1)C1CCC(F)(F)CC1)c1ccccc1Cl]

The racemic mixture which was prepared in a similar manner to example 3a from 2-chlorobenzoic acid and 2-(4,4-difluorocyclohexyl)-2-(2-(trifluoromethyl)pyrimidin-5-yl)ethanamine was separated into the two enantiomers by preparative SFC to yield the title compound. LCMS (M11+): m/z=448.1, $t_R$ (minutes, Method F)=2.95. $[\alpha]_D^{20}$=+28.00 (c=1.5 mg/mL, CHCl$_3$)

And the corresponding enantiomer

Example 4t3

(−)-2-chloro-N-(2-(4,4-difluorocyclohexyl)-2-(2-(trifluoromethyl)pyrimidin-5-yl)ethyl)benzamide LCMS (M11+): m/z=448.1, $t_R$ (minutes, Method F)=2.95. $[\alpha]_D^{20}$=−28.83 (c=1.63 mg/mL, CHCl$_3$)

Example 4u3

(+)-2,3-dichloro-N-(2-(4,4-difluorocyclohexyl)-2-(2-(trifluoromethyl)pyrimidin-5-yl)ethyl)benzamide

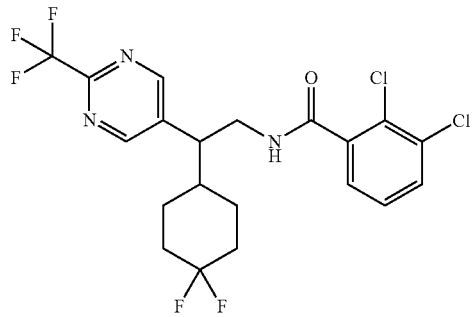 [SMILES: O=C(NCC(c1cnc(C(F)(F)F)nc1)C1CCC(F)(F)CC1)c1cccc(Cl)c1Cl]

The racemic mixture which was prepared in a similar manner to example 3a from 2,3-dichlorobenzoic acid and 2-(4,4-difluorocyclohexyl)-2-(2-(trifluoromethyl)pyrimidin-5-yl)ethanamine was separated into the two enantiomers by preparative SFC to yield the title compound. LCMS (MH+): m/z=482.1, $t_R$ (minutes, Method G)=2.76. $[\alpha]_D^{20}$=+24.29 (c=0.70 mg/mL, CHCl$_3$)

And the corresponding enantiomer

Example 4v3

(−)-2,3-dichloro-N-(2-(4,4-difluorocyclohexyl)-2-(2-(trifluoromethyl)pyrimidin-5-yl)ethyl)benzamide LCMS (MH+): m/z=482.1, $t_R$ (minutes, Method G)=2.76. $[\alpha]_D^{20}$=−23.46 (c=0.81 mg/mL, CHCl$_3$)

Example 4x3

(+)-2-chloro-6-fluoro-N-(2-(4,4-difluorocyclohexyl)-2-(2-(trifluoromethyl)pyrimidin-5-yl)ethyl)benzamide

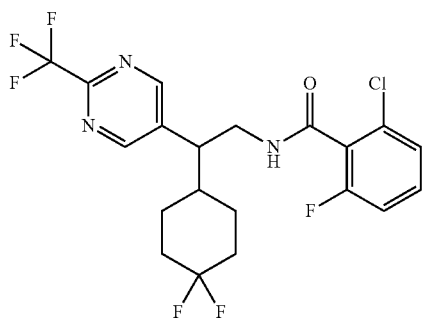 [SMILES: O=C(NCC(c1cnc(C(F)(F)F)nc1)C1CCC(F)(F)CC1)c1c(F)cccc1Cl]

The racemic mixture which was prepared in a similar manner to example 3a from 2-chloro-6-fluorobenzoic acid and 2-(4,4-difluorocyclohexyl)-2-(2-(trifluoromethyl)pyrimidin-5-yl)ethanamine was separated into the two enantiomers by preparative SFC to yield the title compound. LCMS (MH+): m/z=466.1, $t_R$ (minutes, Method F)=2.97. $[\alpha]_D^{20}$=+36.00 (c=1.50 mg/mL, CHCl$_3$)

And the corresponding enantiomer

Example 4y3

(−)-2-chloro-6-fluoro-N-(2-(4,4-difluorocyclohexyl)-2-(2-(trifluoromethyl)pyrimidin-5-yl)ethyl)benzamide LCMS (MH+): m/z=466.1, $t_R$ (minutes, Method F)=2.97. $[\alpha]_D^{20}$=−34.89 (c=1.50 mg/mL, CHCl$_3$)

Example 4z3

(+)-2-chloro-3-fluoro-N-(2-(4,4-difluorocyclohexyl)-2-(2-(trifluoromethyl)pyrimidin-5-yl)ethyl)benzamide

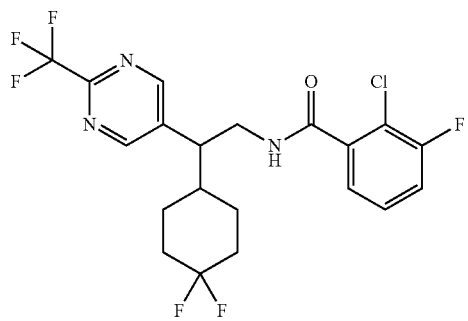 [SMILES: O=C(NCC(c1cnc(C(F)(F)F)nc1)C1CCC(F)(F)CC1)c1cccc(F)c1Cl]

The racemic mixture which was prepared in a similar manner to example 3a from 2-chloro-3-fluorobenzoic acid and 2-(4,4-difluorocyclohexyl)-2-(2-(trifluoromethyl)pyrimidin-5-yl)ethanamine was separated into the two enantiomers by preparative SFC to yield the title compound. LCMS (MH+): m/z=466.1, $t_R$ (minutes, Method F)=2.67. $[\alpha]_D^{20}$=+28.57 (c=0.56 mg/mL, CHCl$_3$)

And the corresponding enantiomer

Example 4a4

(−)-2-chloro-3-fluoro-N-(2-(4,4-difluorocyclohexyl)-2-(2-(trifluoromethyl)pyrimidin-5-yl)ethyl)benzamide LCMS (MH+): m/z=466.1, $t_R$ (minutes, Method F)=2.67. $[\alpha]_D^{20}$=−28.83 (c=0.61 mg/mL, CHCl$_3$)

Example 4b4

(+)-2,3-dichloro-N-(2-(4,4-difluorocyclohexyl)-2-(2-methylpyrimidin-5-yl)ethyl)benzamide

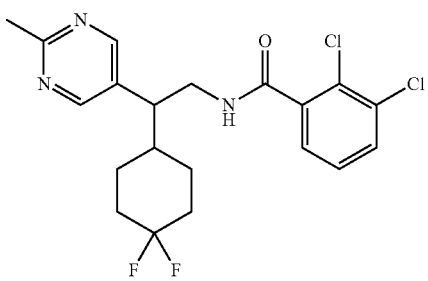 [SMILES: Cc1ncc(C(CNC(=O)c2cccc(Cl)c2Cl)C2CCC(F)(F)CC2)cn1]

The racemic mixture which was prepared in a similar manner to example 3a from 2,3-dichlorobenzoic acid and 2-(4,4-difluorocyclohexyl)-2-(2-methylpyrimidin-5-yl)ethanamine was separated into the two enantiomers by preparative SFC to yield the title compound. LCMS (MH+): m/z=448.1, $t_R$ (minutes, Method F)=2.95. $[\alpha]_D^{20}$=+49.6 (c=4.8 mg/mL, CHCl$_3$)

And the corresponding enantiomer

Example 4c4

(+)-2,3-dichloro-N-(2-(4,4-difluorocyclohexyl)-2-(2-methylpyrimidin-5-yl)ethyl)benzamide LCMS (MH+): m/z=448.1, $t_R$ (minutes, Method F)=2.95. $[\alpha]_D^{20}$=−47.0 (c=5.20 mg/mL, CHCl$_3$)

Example 4d4

(+)-2-chloro-N-(3-cyclopropyl-2-(6-(difluoromethyl)pyridin-3-yl)propyl)benzamide

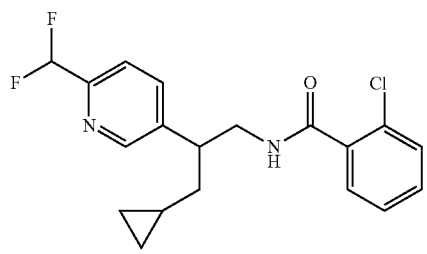 [SMILES: O=C(NCC(CC1CC1)c1ccc(C(F)F)nc1)c1ccccc1Cl]

The racemic mixture which was prepared in a similar manner to example 3a from 2-chlorobenzoic acid and 3-cyclopropyl-2-(6-(difluoromethyl)pyridin-3-yl)propan-1-amine was separated into the two enantiomers by preparative SFC to yield the title compound. LCMS (MH+): m/z=365.1, $t_R$ (minutes, Method F)=2.97. $[\alpha]_D^{20}$=+21.00 (c=3.00 mg/mL, CHCl$_3$)

And the corresponding enantiomer

Example 4e4

(−)-2-chloro-N-(3-cyclopropyl-2-(6-(difluoromethyl)pyridin-3-yl)propyl)benzamide LCMS (MH+): m/z=365.1, $t_R$ (minutes, Method F)=2.97. $[\alpha]_D^{20}$=−20.00 (c=2.90 mg/mL, CHCl$_3$)

Example 4f4

(+)-2,3-dichloro-N-(3-cyclopropyl-2-(6-(difluoromethyl)pyridin-3-yl)propyl)benzamide

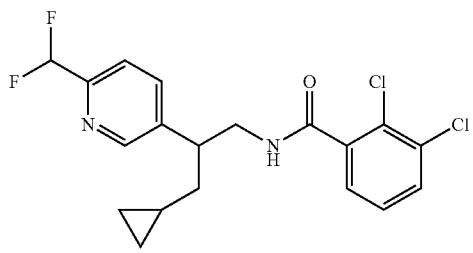 [SMILES: O=C(NCC(CC1CC1)c1ccc(C(F)F)nc1)c1cccc(Cl)c1Cl]

The racemic mixture which was prepared in a similar manner to example 3a from 2,3-dichlorobenzoic acid and 3-cyclopropyl-2-(6-(difluoromethyl)pyridin-3-yl)propan-1-amine was separated into the two enantiomers by preparative SFC to yield the title compound. LCMS (MH+): m/z=399.1, $t_R$ (minutes, Method G)=2.57. $[\alpha]_D^{20}$=+20.45 (c=2.20 mg/mL, CHCl$_3$)

And the corresponding enantiomer

Example 4g4

(−)-2,3-dichloro-N-(3-cyclopropyl-2-(6-(difluoromethyl)pyridin-3-yl)propyl)benzamide LCMS (MH+): m/z=399.1, $t_R$ (minutes, Method G)=2.57. $[\alpha]_D^{20}$=−19.43 (c=2.11 mg/mL, CHCl$_3$)

Example 4h4

(+)-2-chloro-3-fluoro-N-(3-cyclopropyl-2-(6-(difluoromethyl)pyridin-3-yl)propyl)benzamide

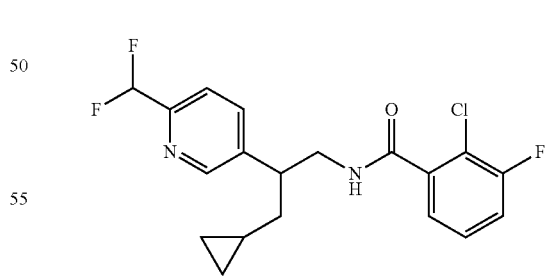

The racemic mixture which was prepared in a similar manner to example 3a from 2-chloro-3-fluorobenzoic acid and 3-cyclopropyl-2-(6-(difluoromethyl)pyridin-3-yl)propan-1-amine was separated into the two enantiomers by preparative SFC to yield the title compound. LCMS (MH+): m/z=383.1, $t_R$ (minutes, Method F)=3.02. $[\alpha]_D^{20}$=+21.03 (c=2.90 mg/mL, CHCl$_3$)

And the corresponding enantiomer

Example 4i4

(−)-2-chloro-N-(3-cyclopropyl-2-(2-(trifluoromethyl)pyridin-5-yl)propyl)-6-fluorobenzamide LCMS (MH+): m/z=383.1, $t_R$ (minutes, Method F)=3.02. $[\alpha]_D^{20}$=−20.40 (c=2.50 mg/mL, CHCl$_3$)

Example 4j4

(+)-2-chloro-3-methoxy-N-(3-cyclopropyl-2-(6-(difluoromethyl)pyridin-3-yl)propyl)benzamide

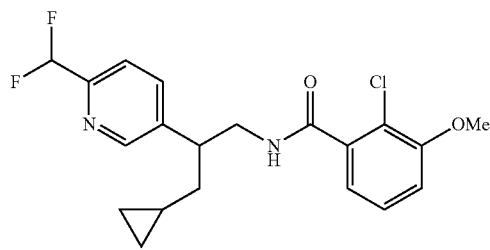 [SMILES: COc1cccc(C(=O)NCC(CC2CC2)c2ccc(C(F)F)nc2)c1Cl]

The racemic mixture which was prepared in a similar manner to example 3a from 2-chloro-3-methoxybenzoic acid and 3-cyclopropyl-2-(6-(difluoromethyl)pyridin-3-yl) propan-1-amine was separated into the two enantiomers by preparative SFC to yield the title compound. LCMS (MH+): m/z=395.1, $t_R$ (minutes, Method F)=2.96. $[\alpha]_D^{20}$=+28.21 (c=2.80 mg/mL, CHCl$_3$)

And the corresponding enantiomer

Example 4k4

(−)-2-chloro-3-methoxy-N-(3-cyclopropyl-2-(6-(difluoromethyl)pyridin-3-yl)propyl)benzamide LCMS (MH+): m/z=395.1, $t_R$ (minutes, Method F)=2.96. $[\alpha]_D^{20}$=−28.21 (c=2.80 mg/mL, CHCl$_3$)

Example 4l4

(+)-2,4-dichloro-N-(3-cyclopropyl-2-(6-(difluoromethyl)pyridin-3-yl)propyl)benzamide

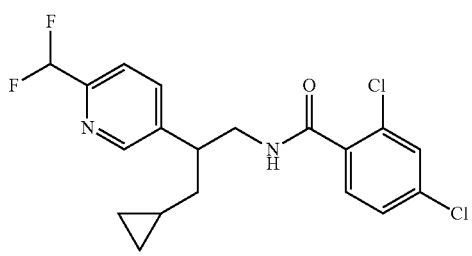 [SMILES: O=C(NCC(CC1CC1)c1ccc(C(F)F)nc1)c1ccc(Cl)cc1Cl]

The racemic mixture which was prepared in a similar manner to example 3a from 2,4-dichlorobenzoic acid and 3-cyclopropyl-2-(6-(difluoromethyl)pyridin-3-yl)propan-1-amine was separated into the two enantiomers by preparative SFC to yield the title compound. LCMS (MH+): m/z=399.1, $t_R$ (minutes, Method G)=2.61. $[\alpha]_D^{20}$=+29.58 (c=2.40 mg/mL, CHCl$_3$)

And the corresponding enantiomer

Example 4m4

(−)-2,4-dichloro-N-(3-cyclopropyl-2-(6-(difluoromethyl)pyridin-3-yl)propyl)benzamide LCMS (MH+): m/z=399.1, $t_R$ (minutes, Method G)=2.61. $[\alpha]_D^{20}$=−30.22 (c=2.78 mg/mL, CHCl$_3$)

Example 4n4

(+)-2,6-dichloro-N-(3-cyclopropyl-2-(6-(difluoromethyl)pyridin-3-yl)propyl)benzamide

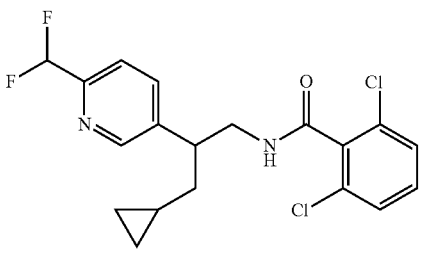 [SMILES: O=C(NCC(CC1CC1)c1ccc(C(F)F)nc1)c1c(Cl)cccc1Cl]

The racemic mixture which was prepared in a similar manner to example 3a from 2,6-dichlorobenzoic acid and 3-cyclopropyl-2-(6-(difluoromethyl)pyridin-3-yl)propan-1-amine was separated into the two enantiomers by preparative SFC to yield the title compound. LCMS (MH+): m/z=399.1, $t_R$ (minutes, Method F)=3.06. $[\alpha]_D^{20}$=+31.97 (c=1.22 mg/mL, CHCl$_3$)

And the corresponding enantiomer

Example 4o4

(+2,6-dichloro-N-(3-cyclopropyl-2-(6-(difluoromethyl)pyridin-3-yl)propyl)benzamide LCMS (MH+): m/z=399.1, $t_R$ (minutes, Method F)=3.06. $[\alpha]_D^{20}$=−30.25 (c=1.62 mg/mL, CHCl$_3$)

Example 4p4

(+)-2-chloro-N-(3-cyclopropyl-2-(2-(difluoromethyl)pyrimidin-5-yl)propyl)benzamide

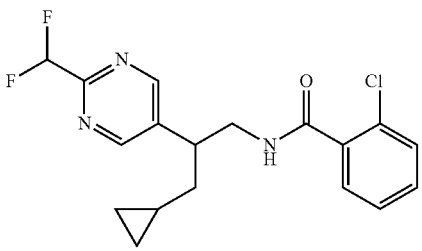

The racemic mixture which was prepared in a similar manner to example 3a from 2-chlorobenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=366.1, $t_R$ (minutes, Method F)=2.84. $[\alpha]_D^{20}$=+26.75 (c=2.43 mg/mL, CHCl$_3$)

And the corresponding enantiomer

Example 4q4

(−)-2-chloro-N-(3-cyclopropyl-2-(2-(difluoromethyl)pyrimidin-5-yl)propyl)benzamide LCMS (MH+): m/z=366.1, $t_R$ (minutes, Method F)=2.84 $[\alpha]_D^{20}$=−24.52 (c=2.08 mg/mL, CHCl$_3$)

Example 4r4

(+)-2,3-dichloro-N-(3-cyclopropyl-2-(2-(difluoromethyl)pyrimidin-5-yl)propyl)benzamide

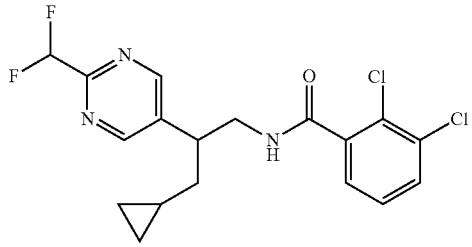

The racemic mixture which was prepared in a similar manner to example 3a from 2,3-dichlorobenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=400.1, $t_R$ (minutes, Method F)=3.00. $[\alpha]_D^{20}$=+24.20 (c=2.81 mg/mL, CHCl$_3$)

And the corresponding enantiomer

Example 4s4

(−)-2,3-dichloro-N-(3-cyclopropyl-2-(2-(difluoromethyl)pyrimidin-5-yl)propyl)benzamide LCMS (MH+): m/z=400.1, $t_R$ (minutes, Method F)=3.00. $[\alpha]_D^{20}$=−27.31 (c=2.38 mg/mL, CHCl$_3$)

Example 4t4

(+)-2-chloro-3-fluoro-N-(3-cyclopropyl-2-(2-(difluoromethyl)pyrimidin-5-yl)propyl)benzamide The racemic mixture which was prepared in a similar manner to example 3a from 2-chloro-3-fluorobenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=384.1, $t_R$ (minutes, Method F)=2.90. $[\alpha]_D^{20}$=+20.59 (c=4.08 mg/mL, CHCl$_3$)

And the Corresponding enantiomer

Example 4u4

(−)-2-chloro-3-fluoro-N-(3-cyclopropyl-2-(2-(difluoromethyl)pyrimidin-5-yl)propyl)benzamide LCMS (M11+): m/z=384.1, $t_R$ (minutes, Method F)=2.90. $[\alpha]_D^{20}$=−20.87 (c=4.12 mg/mL, CHCl$_3$)

Example 4v4

(+)-2-chloro-3-methoxy-N-(3-cyclopropyl-2-(2-(difluoromethyl)pyrimidin-5-yl)propyl)benzamide

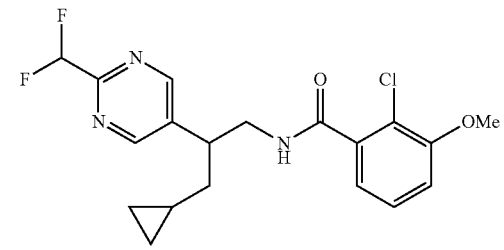

The racemic mixture which was prepared in a similar manner to example 3a from 2-chloro-3-methoxybenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=396.1, $t_R$ (minutes, Method F)=2.84. $[\alpha]_D^{20}$=+24.50 (c=4.98 mg/mL, CHCl$_3$)

And the corresponding enantiomer

Example 4x4

(−)-2-chloro-3-methoxy-N-(3-cyclopropyl-2-(2-(difluoromethyl)pyrimidin-5-yl)propyl)benzamide LCMS (MH+): in z=396.1, $t_R$ (minutes, Method F)=2.84. $[\alpha]_D^{20}$=−25.19 (c=5.16 mg/mL, CHCl$_3$)

Example 4y4

(+)-2,4-dichloro-N-(3-cyclopropyl-2-(2-(difluoromethyl)pyrimidin-5-yl)propyl)benzamide

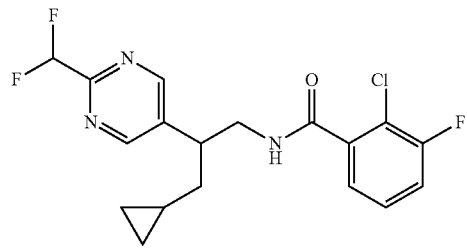 [SMILES: O=C(NCC(CC1CC1)c1cnc(C(F)F)nc1)c1cccc(F)c1Cl]

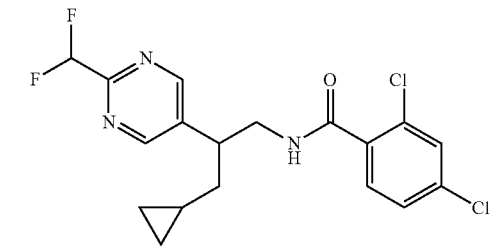 [SMILES: O=C(NCC(CC1CC1)c1cnc(C(F)F)nc1)c1ccc(Cl)cc1Cl]

The racemic mixture which was prepared in a similar manner to example 3a from 2,4-dichlorobenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=400.1, $t_R$ (minutes, Method F)=3.04. $[\alpha]_D^{20}$=+28.45 (c=4.64 mg/mL, CHCl$_3$)

And the corresponding enantiomer

Example 4z4

(−)-2,4-dichloro-N-(3-cyclopropyl-2-(2-(difluoromethyl)pyrimidin-5-yl) propyl)benzamide LCMS (MH+): m/z=400.1, $t_R$ (minutes, Method F)=3.04. $[\alpha]_D^{20}$=−28.60 (c=4.79 mg/mL, CHCl$_3$)

Example 4a5

(+)-2,6-dichloro-N-(3-cyclopropyl-2-(2-(difluoromethyl)pyrimidin-5-yl)propyl)benzamide

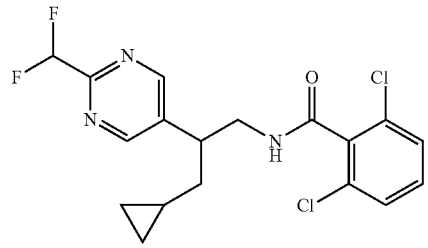

The racemic mixture which was prepared in a similar manner to example 3a from 2,6-dichlorobenzoic acid and 3-cyclopropyl-2-(6-(difluoromethyl)pyrimidin-3-yl)propan-1-amine was separated into the two enantiomers by preparative SFC to yield the title compound. LCMS (MH+): m/z=400.1, $t_R$ (minutes, Method F)=2.93. $[\alpha]_D^{20}$=+18.43 (c=3.58 mg/mL, CHCl$_3$)

And the corresponding enantiomer

Example 4b5

(−)-2,6-dichloro-N-(3-cyclopropyl-2-(2-(difluoromethyl)pyrimidin-5-yl)propyl)benzamide LCMS (MH+): m/z=400.1, $t_R$ (minutes, Method F)=2.93. $[\alpha]_D^{20}$=−18.51 (c=4.16 mg/mL, CHCl$_3$)

Example 4c5

(+)-2-chloro-N-[(3-cyclopropyl-2-[2-(difluoromethyl)pyrimidin-5-yl]-2-methyl-propyl]benzamide

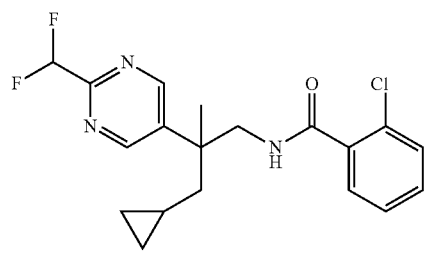

The racemic mixture which was prepared in a similar manner to example 3a from 2-chlorobenzoic acid and 3-cyclopropyl-2-(6-(difluoromethyl)pyrimidin-3-yl)-2-methyl-propan-1-amine was separated into the two enantiomers by preparative SFC to yield the title compound. LCMS (MH+): m/z=380.1, $t_R$ (minutes, Method F)=2.82. $[\alpha]_D^{20}$=+11.73 (c=5.20 mg/mL, CHCl$_3$)

And the corresponding enantiomer

Example 4d5

(−)-2-chloro-N-[(3-cyclopropyl-2-[2-(difluoromethyl)pyrimidin-5-yl]-2-methyl-propyl]benzamide LCMS (MH+): m/z=380.1, $t_R$ (minutes, Method F)=2.82. $[\alpha]_D^{20}$=−13.47 (c=5.27 mg/mL, CHCl$_3$)

Example 4e5

(+)-2,4-Dichloro-N-[(3-cyclopropyl-2-[2-(difluoromethyl)pyrimidin-5-yl]-2-methyl-propyl]benzamide

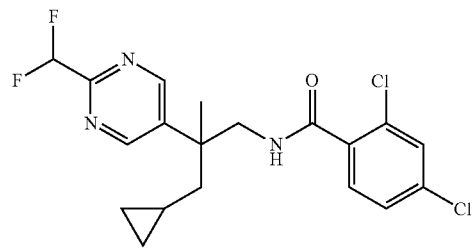 [SMILES: CC(CNC(=O)c1ccc(Cl)cc1Cl)(CC1CC1)c1cnc(C(F)F)nc1]

The racemic mixture which was prepared in a similar manner to example 3a from 2,4-dichlorobenzoic acid and 3-cyclopropyl-2-(6-(difluoromethyl)pyrimidin-3-yl)-2-methyl-propan-1-amine was separated into the two enantiomers by preparative SFC to yield the title compound. LCMS (MH+): m/z=414.1, $t_R$ (minutes, Method F)=2.99. $[\alpha]_D^{20}$=+17.16 (c=5.07 mg/mL, CHCl$_3$)

And the corresponding enantiomer

Example 4f5

(−)-2,4-Dichloro-N-[(3-cyclopropyl-2-[2-(difluoromethyl)pyrimidin-5-yl]-2-methyl-propyl]benzamide LCMS (MH+): m/z=414.1, $t_R$ (minutes, Method F)=2.99. $[\alpha]_D^{20}$=−17.55 (c=5.30 mg/mL, CHCl$_3$)

Example 4g5

(+)-2,3-Dichloro-N-[(3-cyclopropyl-2-[2-(difluoromethyl)pyrimidin-5-yl]-2-methyl-propyl]benzamide

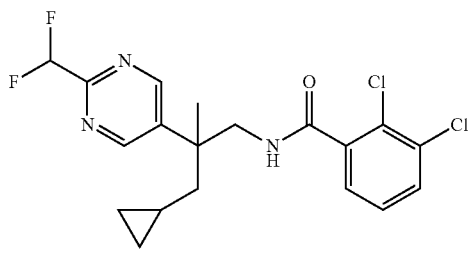 [SMILES: CC(CNC(=O)c1cccc(Cl)c1Cl)(CC1CC1)c1cnc(C(F)F)nc1]

The racemic mixture which was prepared in a similar manner to example 3a from 2,3-dichlorobenzoic acid and 3-cyclopropyl-2-(6-(difluoromethyl)pyrimidin-3-yl)-2-methyl-propan-1-amine was separated into the two enantiomers by preparative SFC to yield the title compound. LCMS (MH+): m/z=414.1, $t_R$ (minutes, Method F)=2.96. $[\alpha]_D^{20}$=+18.40 (c=6.63 mg/mL, CHCl$_3$)

And the corresponding enantiomer

Example 4h5

(−)-2,3-Dichloro-N-[(3-cyclopropyl-2-[2-(difluoromethyl)pyrimidin-5-yl]-2-methyl-propyl]benzamide LCMS (MH+): m/z=414.1, $t_R$ (minutes, Method F)=2.96. $[\alpha]_D^{20}$=−20.13 (c=5.91 mg/mL, CHCl$_3$)

Example 4i5

(+)-2-chloro-N-(2-(2-(difluoromethyl)pyrimidin-5-yl)-3-(1-fluorocyclopropyl)propyl)benzamide

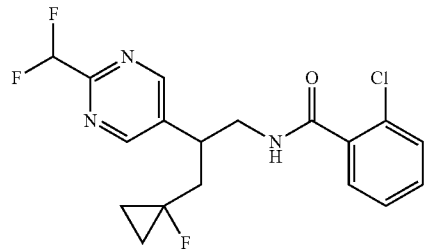 [SMILES: O=C(NCC(CC1(F)CC1)c1cnc(C(F)F)nc1)c1ccccc1Cl]

The racemic mixture which was prepared in a similar manner to example 3a from 2-chlorobenzoic acid and 2-(2-(difluoromethyl)pyrimidin-5-yl)-3-(1-fluorocyclopropyl)propan-1-amine was separated into the two enantiomers by preparative SFC to yield the title compound. LCMS (MH+): m/z=384.1, $t_R$ (minutes, Method F)=2.72. $[\alpha]_D^{20}$=+21.30 (c=2.39 mg/mL, CHCl$_3$)

And the corresponding enantiomer

Example 4j5

(−)-2-chloro-N-(2-(2-(difluoromethyl)pyrimidin-5-yl)-3-(1-fluorocyclopropyl)propyl)benzamide LCMS (MH+): m/z=384.1, $t_R$ (minutes, Method F)=2.72. $[\alpha]_D^{20}$=−20.80 (c=2.02 mg/mL, CHCl$_3$)

Example 4k5

(+)-2,4-Dichloro-N-(2-(2-(difluoromethyl)pyrimidin-5-yl)-3-(1-fluorocyclopropyl)propyl)benzamide

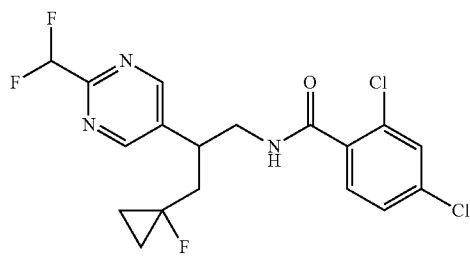 [SMILES: O=C(NCC(CC1(F)CC1)c1cnc(C(F)F)nc1)c1ccc(Cl)cc1Cl]

The racemic mixture which was prepared in a similar manner to example 3a from 2,4-dichlorobenzoic acid and 2-(2-(difluoromethyl)pyrimidin-5-yl)-3-(1-fluorocyclopropyl)propan-1-amine was separated into the two enantiomers by preparative SFC to yield the title compound. LCMS (MH+): m/z=418.1, $t_R$ (minutes, Method F)=2.93. $[\alpha]_D^{20}$=+25.40 (c=3.42 mg/mL, CHCl$_3$)

And the corresponding enantiomer

Example 4l5

(−)-2,4-Dichloro-N-(2-(2-(difluoromethyl)pyrimidin-5-yl)-3-(1-fluorocyclopropyl)propyl)benzamide LCMS (MH+): m/z=418.1, $t_R$ (minutes, Method F)=2.93. $[\alpha]_D^{20}$=−29.5 (c=2.71 mg/mL, CHCl$_3$)

Example 4m5

(+)-2,3-Dichloro-N-(2-(2-(difluoromethyl)pyrimidin-5-yl)-3-(1-fluorocyclopropyl)propyl)benzamide

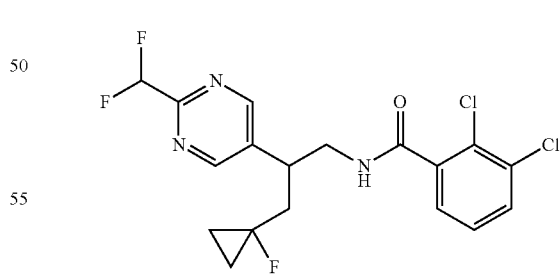

The racemic mixture which was prepared in a similar manner to example 3a from 2,3-dichlorobenzoic acid and 2-(2-(difluoromethyl)pyrimidin-5-yl)-3-(1-fluorocyclopropyl)propan-1-amine was separated into the two enantiomers by preparative SFC to yield the title compound. LCMS (MH+): m/z=418.1, $t_R$ (minutes, Method F)=2.89. $[\alpha]_D^{20}$=+21.70 (c=3.00 mg/mL, CHCl$_3$)

And the corresponding enantiomer

Example 4n5

(−)-2,3-Dichloro-N-(2-(2-(difluoromethyl)pyrimidin-5-yl)-3-(1-fluorocyclopropyl)propyl)benzamide LCMS (MH+): m/z=418.1, $t_R$ (minutes, Method F)=2.89. $[\alpha]_D^{20}$=−23.7 (c=3.20 mg/mL, CHCl$_3$)

Example 4o5

(+)-2-Chloro-N-(2-(2-(difluoromethyl)pyrimidin-5-yl)-3-(1-(trifluoromethyl)cyclopropyl)propyl)benzamide

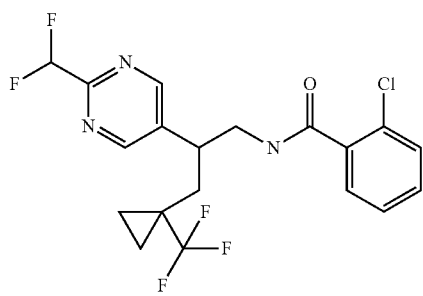 [SMILES: O=C(NCC(CC1(C(F)(F)F)CC1)c1cnc(C(F)F)nc1)c1ccccc1Cl]

The racemic mixture which was prepared in a similar manner to example 3a from 2-chlorobenzoic acid and 2-(2-(difluoromethyl)pyrimidin-5-yl)-3-(1-(trifluoromethyl)cyclopropyl)propan-1-amine was separated into the two enantiomers by preparative SFC to yield the title compound. LCMS (MH+): m/z=434.0, $t_R$ (minutes, Method F)=2.42. $[\alpha]_D^{20}$=+25.30 (c=3.75 mg/mL, CHCl$_3$)

And the corresponding enantiomer

Example 4p5

(−)-2-Chloro-N-(2-(2-(difluoromethyl)pyrimidin-5-yl)-3-(1-(trifluoromethyl)cyclopropyl)propyl)benzamide LCMS (1\411+): m/z=434.0, $t_R$ (minutes, Method F)=2.72. $[\alpha]_D^{20}$=−28.50 (c=3.86 mg/mL, CHCl$_3$)

Example 4q5

(+)-2,4-Dichloro-N-(2-(2-(difluoromethyl)pyrimidin-5-yl)-3-(1-(trifluoromethyl)cyclopropyl)propyl)benzamide

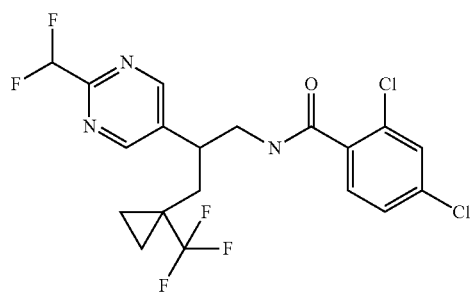 [SMILES: O=C(NCC(CC1(C(F)(F)F)CC1)c1cnc(C(F)F)nc1)c1ccc(Cl)cc1Cl]

The racemic mixture which was prepared in a similar manner to example 3a from 2,4-dichlorobenzoic acid and 2-(2-(difluoromethyl)pyrimidin-5-yl)-3-(1-(trifluoromethyl)cyclopropyl)propan-1-amine was separated into the two enantiomers by preparative SFC to yield the title compound. LCMS (MH+): m/z=468.0, $t_R$ (minutes, Method F)=3.14. $[\alpha]_D^{20}$=+32.40 (c=3.15 mg/mL, CHCl$_3$)

And the corresponding enantiomer

Example 4r5

(−)-2,4-Dichloro-N-(2-(2-(difluoromethyl)pyrimidin-5-yl)-3-(1-(trifluoromethyl)cyclopropyl)propyl)benzamide LCMS (1\411+): m/z=468.0, $t_R$ (minutes, Method F)=3.14. $[\alpha]_D^{20}$=−45.3 (c=2.76 mg/mL, CHCl$_3$)

Example 4s5

(+)-2,3-Dichloro-N-(2-(2-(difluoromethyl)pyrimidin-5-yl)-3-(1-(trifluoromethyl)cyclopropyl)propyl)benzamide

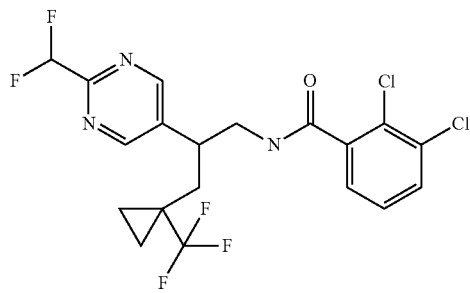 [SMILES: O=C(NCC(CC1(C(F)(F)F)CC1)c1cnc(C(F)F)nc1)c1cccc(Cl)c1Cl]

The racemic mixture which was prepared in a similar manner to example 3a from 2,3-dichlorobenzoic acid and 2-(2-(difluoromethyl)pyrimidin-5-yl)-3-(1-(trifluoromethyl)cyclopropyl)propan-1-amine was separated into the two enantiomers by preparative SFC to yield the title compound. LCMS (MH+): m/z=468.0, $t_R$ (minutes, Method F)=2.84. $[\alpha]_D^{20}$=+27.80 (c=3.41 mg/mL, CHCl$_3$)

And the corresponding enantiomer

Example 4t5

(−)-2,3-Dichloro-N-(2-(2-(difluoromethyl)pyrimidin-5-yl)-3-(1-(trifluoromethyl)cyclopropyl)propyl)benzamide LCMS (MIFF): m/z=468.0, $t_R$ (minutes, Method F)=2.57. $[\alpha]_D^{20}$=−35.8 (c=2.37 mg/mL, CHCl$_3$)

Example 5 P2X$_7$ Binding Assay

This example illustrates representative assays for use in evaluating the test compounds for antagonist activity. Compounds of the present invention were tested in vitro for their ability to act as antagonists to the P2X$_7$ receptor.

Screening assays to determine P2X$_7$ receptor antagonism are well known to the person skilled in the art. Functional assays, such as second messenger assays, and cytokine measurement assays done in vitro are also well known in the art and may be used to assess the specific binding and cellular activity of P2X$_7$ receptor compounds.

In Vitro Assay Example

Cell culture: 293 HEK cells, stably transfected with plasmids capable of expressing human P2X$_7$ receptor, were cultured by standard methods. Cells were plated to cell density of approximately 15,000 cells/well in 384-well assay plates (50 μl/well) with 1.5% low serum media (DMEM, 1.5% BCS, 1% L-glut (2 mM), 1% P/S).

293 HEK cells, stably transfected with plasmids capable of expressing rat or mouse P2X$_7$ receptor, were cultured by standard methods. Cells were plated to cell density of approximately 15,000 cells/well in 384-well assay plates (50 μl/well) with 1.5% low serum media (DMEM, 1.5% FBS, 1% L-glut (2 mM), 10 mM HEPES, 1% P/S). Cells were plated 24 hours prior to assay. Cells expressing human, rat or mouse P2X$_7$ receptor were assayed in the following manner.

Fluorescent Imaging Plate Reader (FLIPR) assay: Briefly, 293-human or mouse P2X$_7$ stable cells were incubated in sucrose buffer, pH 7.4 [KCl (5 mM), NaH$_2$PO$_4$.2H$_2$O (9.6 mM), HEPES (25 mM), sucrose (280 mM), glucose (5 mM), CaCl$_2$ (0.5 mM), and probenecid (0.1425 g in 3 mL 1N NaOH was added for 500 mL solution)] in 384-well plates.

293-rat P2X$_7$ stable cells were incubated in HHPB (pH 7.4) [consisting of Hank's BSS (1×); HEPES (pH 7.4) (20 mM) (Sigma); probenecid (0.710 g/5 mL 1N NaOH) (Sigma); and BSA (0.05%) (Roche) which was added after the pH had been adjusted] in 384-well plates. Fluo-4 NW dye mix (Molecular Probes, Inc., Eugene, Oreg., USA) was prepared in buffer (see manufacturer's instructions). Cell plates were removed from the 37° C. incubator, the media discarded and then 30 μL of dye was added to each well. Plates were placed in the 37° C., non-CO$_2$ incubator for 30 minutes and then room temperature for 30 minutes.

Two sets of drug plates were prepared: A) Mixtures of compound plus agonist were prepared as follows, in order to determine dose response: BzATP: 11 point ½ log, diluted in buffer, starting from 1 mM. Testing compounds: 11 point ½ log, diluted in 2% DMSO buffer starting from 10 μM. B) Agonist only mixture was prepared with BzATP at a single concentration in buffer (concentration determined by dose response).

Compound mixtures (A) were added to assay plates containing cells and placed at room temperature for 30 minutes, then BzATP (B) was added. Fluorescence was read using the Tetra FLIPR® (Molecular Devices, Inc., Sunnyvale, Calif., USA) and IC$_{50}$ values were calculated by standard methods to determine antagonist activity.

Assay for stimulating IL1β release from THP-1 cells: THP-1 cells (The Global Bioresource Center; ATCC #: TIB-202™) were differentiated by incubation with 10 ng/mL IFN-gamma (Sigma, Cat#: I3265) in T150 plates, at a cell density of 0.5 E$^6$ cells/mL, in RPMI1640 media (ATCC, Cat#30-2001) with 10% FBS and 1% P/S for 48 hours. The cells then were stimulated with 100 ng/mL LPS (Sigma, Cat#: L4516) in serum free CTL Test media (Sigma Cat#: CTLT-005), without L-glutamine and antibiotics, for 3 hours. Test compounds (antagonists) were added and incubated for 30 minutes. BzATP (at final concentration of 1 mM) was added and incubated for 30 minutes.

Cell plates were centrifuged at 3000 rpm for 5 minutes and the supernatants were immediately collected for AlphaLISA® immunoassay (PerkinElmer Inc., Waltham, Mass., USN Catalog No. AL220C) or aliquoted and stored at <−20° C. The AlphaLISA® immunoassay was performed according to the manufacturer's instructions.

TABLE 1

Exemplified IC$_{50}$ values of compounds of the invention:

| Chemical name | IC50 (nM) |
| --- | --- |
| 2-Chloro-N-[4-(4-chloro-phenyl)-tetrahydro-pyran-4-ylmethyl]-5-methyl-benzamide | 62 |
| 2-Chloro-N-[4-(4-chloro-phenyl)-tetrahydro-pyran-4-ylmethyl]-5-methyl-benzamide | 62 |
| N-[4-(4-Chloro-phenyl)-tetrahydro-pyran-4-ylmethyl]-2,3-dimethyl-benzamide | 170 |
| N-[4-(4-Chloro-phenyl)-tetrahydro-pyran-4-ylmethyl]-2-methoxy-benzamide | 620 |
| 2,6-Dichloro-N-[4-(4-chloro-phenyl)-tetrahydro-pyran-4-ylmethyl]-benzamide | 360 |
| N-[4-(4-Chloro-phenyl)-tetrahydro-pyran-4-ylmethyl]-2-methyl-benzamide | 2100 |
| 2,3-Dichloro-N-(1-pyridin-3-yl-cyclopentylmethyl)-benzamide | 2200 |
| 2-Chloro-5-methyl-N-(1-pyridin-3-yl-cyclopentylmethyl)-benzamide | 2900 |
| N-[4-(4-Chloro-phenyl)-tetrahydro-pyran-4-ylmethyl]-2-trifluoromethyl-benzamide | 1200 |
| 2-Methyl-N-(1-pyridin-3-yl-cyclopentylmethyl)-benzamide | 3600 |
| N-[4-(4-Chloro-phenyl)-tetrahydro-pyran-4-ylmethyl]-2-fluoro-3-trifluoromethyl-benzamide | 4300 |
| 3-Chloro-N-[4-(4-chloro-phenyl)-tetrahydro-pyran-4-ylmethyl]-2-fluoro-benzamide | 890 |
| N-[4-(4-Chloro-phenyl)-tetrahydro-pyran-4-ylmethyl]-2,5-difluoro-benzamide | 3000 |
| 2-Chloro-N-[1-(4-methoxy-phenyl)-cyclopentylmethyl]-5-methyl-benzamide | 190 |
| 2,3-Dichloro-N-[1-(4-methoxy-phenyl)-cyclopentylmethyl]-benzamide | 260 |
| N-[1-(4-Methoxy-phenyl)-cyclopentylmethyl]-2-methyl-benzamide | 1400 |
| N-[1-(4-Methoxy-phenyl)-cyclopentylmethyl]-2,3-dimethyl-benzamide | 600 |
| 2-Chloro-5-methyl-N-(1-methyl-4-phenyl-piperidin-4-ylmethyl)-benzamide | 2.4 |
| 2-Methyl-N-(1-methyl-4-phenyl-piperidin-4-ylmethyl)-benzamide | 64 |
| N-[4-(4-Chloro-phenyl)-tetrahydro-pyran-4-ylmethyl]-2,3,5-trifluoro-benzamide | 3600 |
| N-[4-(4-Chloro-phenyl)-1-methyl-piperidin-4-ylmethyl]-2-methyl-benzamide | 60 |
| 2,3-Dichloro-N-[4-methyl-2-(6-methyl-pyridin-3-yl)-pentyl]-benzamide | 1 |
| 2,3-Dimethyl-N-[4-methyl-2-(6-methyl-pyridin-3-yl)-pentyl]-benzamide | 4.4 |
| 2-Methyl-N-[4-methyl-2-(6-methyl-pyridin-3-yl)-pentyl]-benzamide | 29 |
| 2-Chloro-5-methyl-N-[4-(6-methyl-pyridin-3-yl)-tetrahydro-pyran-4-ylmethyl]-benzamide | 3400 |
| 5-Bromo-2-chloro-N-[4-(4-chloro-phenyl)-tetrahydro-pyran-4-ylmethyl]-benzamide | 130 |
| 2-Chloro-N-[4-(4-chloro-phenyl)-tetrahydro-pyran-4-ylmethyl]-benzamide | 800 |
| 2,3-dichloro-N-[[4,4-difluoro-1-(6-fluoro-3-pyridyl)cyclohexyl]methyl]benzamide | 0.28 |
| 2,3-dichloro-N[[4,4-difluoro-1-(6-fluoro-3-pyridyl)cyclohexyl]methyl]benzamide | 0.28 |
| 2-chloro-N-[[4,4-difluoro-1-(6-fluoro-3-pyridyl)cyclohexyl]methyl]-6-fluoro-benzamide | 14 |
| 2-chloro-N-[[4,4-difluoro-1-(6-fluoro-3-pyridyl)cyclohexylimethyl]-5-methyl-benzamide | 0.76 |
| 2-chloro-N-[[4,4-difluoro-1-(6-fluoro-3-pyridyl)cyclohexyl]methyl]-5-(trifluoromethyl)benzamide | 1.2 |
| N-((4,4-difluoro-1-(6-fluoropyridin-3-yl)cyclohexyl)methyl)-2-fluorobenzamide | 190 |
| N-((4,4-difluoro-1-(6-fluoropyridin-3-yl)cyclohexyl)methyl)-2-fluoro-3-methoxybenzamide | 100 |
| 2-chloro-N-((4,4-difluoro-1-(6-fluoropyridin-3-yl)cyclohexyl)methyl)-5-(methylsulfonyl)benzamide | 8.7 |

TABLE 1-continued

Exemplified IC$_{50}$ values of compounds of the invention:

| Chemical name | IC50 (nM) |
|---|---|
| 2-chloro-N-((4,4-difluoro-1-(6-fluoropyridin-3-yl)cyclohexyl)methyl)benzamide | 25 |
| N-((4,4-difluoro-1-(6-fluoropyridin-3-yl)cyclohexyl)methyl)-2-fluoro-5-methoxybenzamide | 65 |
| N-((4,4-difluoro-1-(6-fluoropyridin-3-yl)cyclohexyl)methyl)-2-fluoro-3-methylbenzamide | 78 |
| N-((4,4-difluoro-1-(6-fluoropyridin-3-yl)cyclohexyl)methyl)-2,5-difluorobenzamide | 1500 |
| 2,5-dichloro-N-((4,4-ditluoro-1-(6-fluoropyridin-3-yl)cyclohexyl)methyl)benzamide | 2.3 |
| 2-chloro-N-((4,4-difluoro-1-(6-fluoropyridin-3-yl)cyclohexyl)methyl)-5-methoxybenzamide | 0.83 |
| N-((4,4-difluoro-1-(6-fluoropyridin-3-yl)cyclohexyl)methyl)-2,3-difluorobenzamide | 290 |
| 2,3-dichloro-N-((4-(4-chlorophenyl)tetrahydro-2H-pyran-4-yl)methyl)benzamide | 43 |
| 2,3-dichloro-N-((4-(4-(trifluoromethyl)phenyl)tetrahydro-2H-pyran-4-yl)methyl)benzamide | 41 |
| 2,3-dichloro-N-((4,4-difluoro-1-(6-(trifluoromethyl)pyridin-3-yl)cyclohexyl)methyl)benzamide | 1.2 |
| 2,3-dichloro-N-((4-(6-(trifluoromethyl)pyridin-3-yl)tetrahydro-2H-pyran-4-yl)methyl)benzamide | 52 |
| 2,3-dichloro-N-((1-(6-cyclopropylpyridin-3-yl)-4,4-difluorocyclohexyl)methyl)benzamide | 1.3 |
| 2,3-dichloro-N-((4,4-difluoro-1-(6-methoxypyridin-3-yl)cyclohexyl)methyl)benzamide | 0.96 |
| 2-cyano-N-((4,4-difluoro-1-(6-(trifluoromethyl)pyridin-3-yl)cyclohexyl)methyl)benzamide | 150 |
| 2-chloro-N-((4,4-difluoro-1-(6-(trifluoromethyl)pyridin-3-yl)cyclohexyl)methyl)-4-(methylsulfonyl)benzamide | 1800 |
| N-((4,4-difluoro-1-(6-(trifluoromethyl)pyridin-3-yl)cyclohexyl)methyl)-2-methylbenzamide | 2.6 |
| 2,3-dichloro-N-(2-cyclopropyl-2-(6-(trifluoromethyl)pyridin-3-yl)ethyl)benzamide | 120 |
| N-((4,4-difluoro-1-(6-(trifluoromethyl)pyridin-3-yl)cyclohexyl)methyl)-2-(methylsulfonyl)benzamide | 480 |
| 2,3-dichloro-N-((4,4-difluoro-1-(5-fluoropyridin-3-yl)cyclohexyl)methyl)benzamide | 1.2 |
| 2,3-dichloro-N-[3-cyclopropyl-2-[6-(trifluoromethyl)-3-pyridyl]propyl]benzamide | 0.55 |
| 2-chloro-N-[3-cyclopropyl-2-[6-(trifluoromethyl)-3-pyridyl]propyl]benzamide | 3.4 |
| N-((4,4-difluoro-1-(6-(trifluoromethyl)pyridin-3-yl)cyclohexyl)methyl)-3-fluoro-2-methylbenzamide | 4 |
| N-((4,4-difluoro-1-(6-(trifluoromethyl)pyridin-3-yl)cyclohexyl)methyl)-3-methoxy-2-methylbenzamide | 1.6 |
| N-((4,4-difluoro-1-(6-(trifluoromethyl)pyridin-3-yl)cyclohexyl)methyl)-5-fluoro-2-methylbenzamide | 9.1 |
| N-((4,4-difluoro-1-(6-(trifluoromethyl)pyridin-3-yl)cyclohexyl)methyl)-2-methyl-5-(trifluoromethyl)benzamide | 39 |
| 3-bromo-N-((4,4-difluoro-1-(6-(trifluoromethyl)pyridin-3-yl)cyclohexyl)methyl)-2-methylbenzamide | 0.71 |
| 2-chloro-N-((4,4-difluoro-1-(6-(trifluoromethyl)pyridin-3-yl)cyclohexyl)methyl)-3-methylbenzamide | 0.54 |
| 3-cyano-N-((4,4-difluoro-1-(6-(trifluoromethyl)pyridin-3-yl)cyclohexyl)methyl)-2-methylbenzamide | 45 |
| 2,3-dichloro-N-(2-(5-chloropyridin-3-yl)-3-cyclopropylpropyl)benzamide | 5.5 |
| 2,3-dichloro-N-(2-(4-chlorophenyl)-2-phenylethyl)benzamide | 120 |
| 2,3-dichloro-N-[3-cyclopropyl-2-(2,6-dimethyl-3-pyridyl)propyl]benzamide | 1300 |
| 2,3-dichloro-N-[2-(2-methylpyrimidin-5-yl)-3-[1-(trifluoromethyl)cyclopropyl]propyl]benzamide | 7.1 |
| (+)2-chloro-N-[3-cyclopropyl-2-[6-(trifluoromethyl)-3-pyridyl]propyl]benzamide | 63 |
| (−)2-chloro-N-[3-cyclopropyl-2-[6-(trifluoromethyl)-3-pyridyl]propyl]benzamide | 2.3 |
| (+)2,3-dichloro-N-[3-cyclopropyl-2-[6-(trifluoromethyl)-3-pyridyl]propyl]benzamide | 2.6 |
| (−)2,3-dichloro-N-[3-cyclopropyl-2-[6-(trifluoromethyl)-3-pyridyl]propyl]benzamide | 0.31 |
| 2,3-dichloro-N-[3-[1-(trifluoromethyl)cyclopropyl]-2-[6-(trifluoromethyl)-3-pyridyl]propyl]benzamide | 19 |
| 2,3-dichloro-N-[2-(6-cyclopropyl-3-pyridyl)-3-[1-(trifluoromethyl)cyclopropyl]propyl]benzamide | 15 |
| 2,3-dichloro-N-[2-(6-cyclopropyl-3-pyridyl)-3-[1-(difluoromethyl)cyclopropyl]propyl]benzamide | 0.76 |
| (+)2-chloro-N-[3-cyclopropyl-2-[6-(trifluoromethyl)-3-pyridyl]propyl]-3-(trifluoromethyl)benzamide | 1100 |
| (−)2-chloro-N-[3-cyclopropyl-2-[6-(trifluoromethyl)-3-pyridyl]propyl]-3-(trifluoromethyl)benzamide | 110 |
| 2,3-dichloro-N-[3-[1-(difluoromethyl)cyclopropyl]-2-[6-(trifluoromethyl)-3-pyridyl]propyl]benzamide | 1.6 |
| (−)2,3-dichloro-N-[2-(2-methylpyrimidin-5-yl)-3-[1-(trifluoromethyl)cyclopropyl]propyl]benzamide | 64 |
| (+)2,3-dichloro-N-[2-(2-methylpyrimidin-5-yl)-3-[1-(trifluoromethyl)cyclopropyl]propyl]benzamide | 1.5 |
| (−)2-chloro-N-[2-(2-methylpyrimidin-5-yl)-3-[1-(trifluoromethyl)cyclopropyl]propyl]benzamide | 650 |
| (+)2-chloro-N-[2-(2-methylpyrimidin-5-yl)-3-[1-(trifluoromethyl)cyclopropyl]propyl]benzamide | 130 |
| 2-chloro-N-[2-(6-cyclopropyl-3-pyridyl)-3-[1-(trifluoromethyl)cyclopropyl]propyl]benzamide | 94 |
| N-[2-(6-cyclopropyl-3-pyridyl)-3-[1-(trifluoromethyl)cyclopropyl]propyl]-2-fluoro-benzamide | 1700 |
| 2-chloro-N-[3-cyclopropyl-2-(2-methylpyrimidin-5-yl)propyl]benzamide | 1200 |
| 2,3-dichloro-N-[3-cyclopropyl-2-(2-methylpyrimidin-5-yl)propyl]benzamide | 60 |
| 2-chloro-N-[3-[1-(trifluoromethyl)cyclopropyl]-2-[6-(trifluoromethyl)-3-pyridyl]propyl]benzamide | 2.1 |
| 2-fluoro-N-[3-[1-(trifluoromethyl)cyclopropyl]-2-[6-(trifluoromethyl)-3-pyridyl]propyl]benzamide | 430 |
| 2-chloro-N-[[4,4-difluoro-1-(2-methylpyrimidin-5-yl)cyclohexyl]methyl]benzamide | 120 |
| 2,3-dichloro-N-[[4,4-difluoro-1-(2-methylpyrimidin-5-yl)cyclohexyl]methyl]benzamide | 8.6 |
| 2,3-dichloro-N-[3-cyclopropyl-2-[2-(trifluoromethyl)pyrimidin-5-yl]propyl]benzamide | 0.88 |
| 2,3-dichloro-N-[[4,4-difluoro-1-[6-(1-hydroxy-1-methyl-ethyl)-3-pyridyl]cyclohexyl]methyl]benzamide | 23 |
| 2-chloro-N-[[4,4-difluoro-1-[6-(1-hydroxy-1-methyl-ethyl)-3-pyridyl]cyclohexyl]methyl]benzamide | 380 |
| (+)2-chloro-N-[3-cyclopropyl-2-[6-(trifluoromethyl)-3-pyridyl]propyl]-3-methoxybenzamide | 12 |

TABLE 1-continued

Exemplified IC$_{50}$ values of compounds of the invention:

| Chemical name | IC50 (nM) |
|---|---|
| (−)2-chloro-N-[3-cyclopropyl-2-[6-(trifluoromethyl)-3-pyridyl]propyl]-3-methoxy-benzamide | 4.2 |
| (+)2-chloro-N-[3-cyclopropyl-2-[6-(trifluoromethyl)-3-pyridyl]propyl]-6-fluoro-benzamide | 50 |
| (−)2-chloro-N-[3-cyclopropyl-2-[6-(trifluoromethyl)-3-pyridyl]propyl]-6-fluoro-benzamide | 2.1 |
| (+)N-[3-cyclopropyl-2-[6-(trifluoromethyl)-3-pyridyl]propyl]-2-methoxy-benzamide | 990 |
| (−)N-[3-cyclopropyl-2-[6-(trifluoromethyl)-3-pyridyl]propyl]-2-methoxy-benzamide | 53 |
| (+)N-[3-cyclopropyl-2-[6-(trifluoromethyl)-3-pyridyl]propyl]-2,6-difluoro-benzamide | 740 |
| (−)N-[3-cyclopropyl-2-[6-(trifluoromethyl)-3-pyridyl]propyl]-2,6-difluoro-benzamide | 130 |
| (+)2-chloro-N-[3-cyclopropyl-2[6-(trifluoromethyl)-3-pyridyl]propyl]-5-methylsulfonyl-benzamide | 560 |
| (−)2-chloro-N-[3-cyclopropyl-2-[6-(trifluoromethyl)-3-pyridyl]propyl]-5-methylsulfonyl-benzamide | 8.1 |
| 2,3-dichloro-N-((4,4-difluoro-1-(4-methyl-1H-imidazol-1-yl)cyclohexyl)methyl)benzamide | 90 |
| (+)2-chloro-N-[3-cyclopropyl-2-[6-(trifluoromethyl)-3-pyridyl]propyl]-3-fluoro-benzamide | 11 |
| 2(−)chloro-N-[3-cyclopropyl-2-[6-(trifluoromethyl)-3-pyridyl]propyl]-3-fluoro-benzamide | 2.9 |
| (−)2-chloro-N-[3-cyclopropyl-2-(6-fluoro-3-pyridyl)propyl]benzamide | 16 |
| (+)2-chloro-N-[3-cyclopropyl-2-(6-fluoro-3-pyridyl)propyl]benzamide | 510 |
| N-(1-(1-(6-bromopyridin-3-yl)-4,4-difluorocyclohexyl)ethyl)-2,3-dichlorobenzamide | 43 |
| (−)2,3-dichloro-N-[3-cyclopropyl-2-(2-methylpyrimidin-5-yl)propyl]benzamide | 39 |
| (+)2,3-dichloro-N-[3-cyclopropyl-2-(2-methylpyrimidin-5-yl)propyl]benzamide | 260 |
| 2-chloro-N-((4,4-difluoro-1-(6-(trifluoromethyl)pyridin-3-yl)cyclohexyl)methyl)benzamide | 2 |
| 2,3-dichloro-N-((4,4-difluoro-1-(6-methylpyridin-3-yl)cyclohexyl)methyl)benzamide | 7.3 |
| 2-chloro-N-((4,4-difluoro-1-(6-(trifluoromethyl)pyridin-3-yl)cyclohexyl)methyl)-3-methoxybenzamide | 7.1 |
| 2-chloro-N-((4,4-difluoro-1-(6-(trifluoromethyl)pyridin-3-yl)cyclohexyl)methyl)-3-fluorobenzamide | 1.4 |
| 2-chloro-N-((4,4-difluoro-1-(6-fluoropyridin-3-yl)cyclohexyl)methyl)-3-fluorobenzamide | 5.3 |
| 3-chloro-N-((4,4-difluoro-1-(6-(trifluoromethyl)pyridin-3-yl)cyclohexyl)methyl)-2-fluorobenzamide | 3.2 |
| 3-chloro-N-((4,4-difluoro-1-(6-fluoropyridin-3-yl)cyclohexyl)methyl)-2-fluorobenzamide | 11 |
| 3-chloro-N-(3-cyclopropyl-2-(6-(trifluoromethyl)pyridin-3-yl)propyl)-2-fluorobenzamide | 660 |
| 2-chloro-N-(3-cyclopropyl-2-(6-(trifluoromethyl)pyridin-3-yl)propyl)-4-fluorobenzamide | 310 |
| 2,6-dichloro-N-(3-cyclopropyl-2-(6-(trifluoromethyl)pyridin-3-yl)propyl)benzamide | 0.71 |
| 2-chloro-N-[3-cyclopropyl-2-methyl-2-[2-(trifluoromethyl)pyrimidin-5-yl]propyl]benzamide | 21 |
| 2-chloro-N-[3-cyclopropyl-2-methyl-2-[2-(trifluoromethyl)pyrimidin-5-yl]propyl]-3-fluoro-benzamide | 16 |
| (−)2,3-dichloro-N-[3-cyclopropyl-2-[2-(trifluoromethyl)pyrimidin-5-yl]propyl]benzamide | 0.86 |
| (+)2,3-dichloro-N-[3-cyclopropyl-2-[2-(trifluoromethyl)pyrimidin-5-yl]propyl]benzamide | 3.9 |
| (+)2-chloro-N-[3-cyclopropyl-2-[2-(trifluoromethyl)pyrimidin-5-yl]propyl]benzamide | 38 |
| (−)2-chloro-N-[3-cyclopropyl-2-[2-(trifluoromethyl)pyrimidin-5-yl]propyl]benzamide | 3.2 |
| (+)2-chloro-N-[3-cyclopropyl-2-[2-(trifluoromethyl)pyrimidin-5-yl]propyl]-3-fluoro-benzamide | 50 |
| (−)2-chloro-N-[3-cyclopropyl-2-[2-(trifluoromethyl)pyrimidin-5-yl]propyl]-3-fluoro-benzamide | 4.7 |
| (+)2-chloro-N-[3-cyclopropyl-2-[2-(trifluoromethyl)pyrimidin-5-yl]propyl]-6-fluoro-benzamide | 41 |
| 2,3-dichloro-N-[2-(4-chlorophenyl)-2-tetrahydropyran-4-yl-ethyl]benzamide | 1.6 |
| 2-chloro-N-[2-(4-chlorophenyl)-2-tetrahydropyran-4-yl-ethyl]benzamide | 14 |
| 2-chloro-N-[2-(4-chlorophenyl)-2-tetrahydropyran-4-yl-ethyl]-6-fluoro-benzamide | 30 |
| 2-chloro-N-[2-(4-chlorophenyl)-2-tetrahydropyran-4-yl-ethyl]-3-fluoro-benzamide | 15 |
| 2,6-dichloro-N-(3-cyclopropyl-2-(2-(trifluoromethyl)pyrimidin-5-yl)propyl)benzamide | 5.1 |
| 2-chloro-N-(3-cyclopropyl-2-(2-(trifluoromethyl)pyrimidin-5-yl)propyl)benzamide | 13 |
| 2-chloro-N-(3-cyclopropyl-2-(2-(trifluoromethyl)pyrimidin-5-yl)propyl)-3-fluorobenzamide | 14 |
| 2-chloro-N-(3-cyclopropyl-2-(2-(trifluoromethyl)pyrimidin-5-yl)propyl)-6-fluorobenzamide | 22 |
| 2,3-dichloro-N-[[4-[2-(trifluoromethyl)pyrimidin-5-yl]tetrahydropyran-4-yl]methyl]benzamide | 250 |
| 2-chloro-N-[[4-[2-(trifluoromethyl)pyrimidin-5-yl]tetrahydropyran-4-yl]methyl]benzamide | 4400 |
| 2-chloro-6-fluoro-N-[[4-[2-(trifluoromethyl)pyrimidin-5-yl]tetrahydropyran-4-yl]methyl]benzamide | 1600 |
| (−)2-chloro-N-[3-cyclopropyl-2-[2-(trifluoromethyl)pyrimidin-5-yl]propyl]-3-methoxy-benzamide | 3.4 |
| (+)2-chloro-N-[3-cyclopropyl-2-[2-(trifluoromethyl)pyrimidin-5-yl]propyl]-3-methoxy-benzamide | 14 |
| (−)N-[3-cyclopropyl-2-[2-(trifluoromethyl)pyrimidin-5-yl]propyl]-3-methoxy-2-methyl-benzamide | 1.4 |
| (+)N-[3-cyclopropyl-2-[2-(trifluoromethyl)pyrimidin-5-yl]propyl]-3-methoxy-2-methyl-benzamide | 9 |
| 2,3-dichloro-N-[3-(1-fluorocyclopropyl)-2-[6-(trifluoromethyl)-3-pyridyl]propyl]benzamide | 3.7 |
| (−)2,6-dichloro-N-[3-cyclopropyl-2-[6-(trifluoromethyl)-3-pyridyl]propyl]benzamide | 1.2 |
| (+)2,6-dichloro-N-[3-cyclopropyl-2-[6-(trifluoromethyl)-3-pyridyl]propyl]benzamide | 0.89 |
| (−)2,6-dichloro-N-[3-cyclopropyl-2-[2-(trifluoromethyl)pyrimidin-5-yl]propyl]benzamide | 0.82 |
| (+)2,6-dichloro-N-[3-cyclopropyl-2-[2-(trifluoromethyl)pyrimidin-5-yl]propyl]benzamide | 3.8 |
| 2,3-dichloro-N-[3-(1-fluorocyclopropyl)-2-[2-(trifluoromethyl)pyrimidin-5-yl]propyl]benzamide | 9.3 |

TABLE 1-continued

Exemplified IC$_{50}$ values of compounds of the invention:

| Chemical name | IC50 (nM) |
|---|---|
| 2,3-dichloro-N-[2-(2-methylpyrimidin-5-yl)-2-(4-pyridyl)ethyl]benzamide | 50 |
| 2-chloro-N-[2-(2-methylpyrimidin-5-yl)-2-(4-pyridyl)ethyl]benzamide | 1300 |
| 2-chloro-6-fluoro-N-[2-(2-methylpyrimidin-5-yl)-2-(4-pyridyl)ethyl]benzamide | 640 |
| 2-chloro-3-fluoro-N-[2-(2-methylpyrimidin-5-yl)-2-(4-pyridyl)ethyl]benzamide | 860 |
| (−)2,6-dichloro-N-[3-cyclopropyl-2-(2-methylpyrimidin-5-yl)propyl]benzamide | 9.9 |
| (+)2,6-dichloro-N-[3-cyclopropyl-2-(2-methylpyrimidin-5-yl)propyl]benzamide | 220 |
| (+)2-chloro-N-[3-cyclopropyl-2-methyl-2-[2-(trifluoromethyl)pyrimidin-5-yl]propyl]benzamide | 460 |
| (−)2-chloro-N-[3-cyclopropyl-2-methyl-2-[2-(trifluoromethyl)pyrimidin-5-yl]propyl]benzamide | 17 |
| 2,3-dichloro-N-[[4,4-difluoro-1-[2-(trifluoromethyl)pyrimidin-5-yl]cyclohexyl]methyl]benzamide | 0.95 |
| (+)2-chloro-N-[3-cyclopropyl-2-methyl-2-[2-(trifluoromethyl)pyrimidin-5-yl]propyl]-3-fluoro-benzamide | 360 |
| (−)2-chloro-N-[3-cyclopropyl-2-methyl-2-[2-(trifluoromethyl)pyrimidin-5-yl]propyl]-3-fluoro-benzamide | 34 |
| (+)2,3-dichloro-N-[3-cyclopropyl-2-methyl-2-[2-(trifluoromethyl)pyrimidin-5-yl]propyl]benzamide | 74 |
| (−)2,3-dichloro-N-[2-(2-methylpyrimidin-5-yl)-2-tetrahydropyran-4-yl-ethyl]benzamide | 58 |
| (+)2,3-dichloro-N-[2-(2-methylpyrimidin-5-yl)-2-tetrahydropyran-4-yl-ethyl]benzamide | 28 |
| (−)2-chloro-N-[2-(2-methylpyrimidin-5-yl)-2-tetrahydropyran-4-yl-ethyl]benzamide | 570 |
| (+)2-chloro-N-[2-(2-methylpyrimidin-5-yl)-2-tetrahydropyran-4-yl-ethyl]benzamide | 970 |
| 2,3-dichloro-N-[2-(4,4-difluorocyclohexyl)-2-(2-methylpyrimidin-5-yl)ethyl]benzamide | 6.2 |
| 2-chloro-N-[2-(4,4-difluorocyclohexyl)-2-(2-methylpyrimidin-5-yl)ethyl]benzamide | 90 |
| (+)2-chloro-N-[3-[1-(trifluoromethyl)cyclopropyl]-2-[2-(trifluoromethyl)pyrimidin-5-yl]propyl]benzamide | 2.4 |
| 2-chloro-6-fluoro-N-[2-(2-methylpyrimidin-5-yl)-2-tetrahydropyran-4-yl-ethyl]benzamide | 1900 |
| 2-chloro-3-fluoro-N-[2-(2-methylpyrimidin-5-yl)-2-tetrahydropyran-4-yl-ethyl]benzamide | 210 |
| 2-chloro-N-[2-(4,4-difluorocyclohexyl)-2-(2-methylpyrimidin-5-yl)ethyl]-6-fluoro-benzamide | 150 |
| 2-chloro-N-[2-(4,4-difluorocyclohexyl)-2-(2-methylpyrimidin-5-yl)ethyl]-3-fluoro-benzamide | 83 |
| (+)2-chloro-N-[3-[1-(trifluoromethyl)cyclopropyl]-2-[6-(trifluoromethyl)-3-pyridyl]propyl]benzamide | 0.09 |
| (−)2-chloro-N-[3-[1-(trifluoromethyl)cyclopropyl]-2-[6-(hifluoromethyl)-3-pyridyl]propyl]benzamide | 32 |
| (+)2,3-dichloro-N-[3-[1-(trifluoromethyl)cyclopropyl]-2-[6-(trifluoromethyl)-3-pyridyl]propyl]benzamide | 12 |
| (−)2,3-dichloro-N-[3-[1-(trifluoromethyl)cyclopropyl]-2-[6-(trifluoromethyl)-3-pyridyl]propyl]benzamide | 25 |
| (+)2-chloro-3-fluoro-N-[3-[1-(trifluoromethyl)cyclopropyl]-2-[2-(trifluoromethyl)pyrimidin-5-yl]propyl]benzamide | 4.5 |
| (−)2-chloro-3-fluoro-N-[3-[1-(trifluoromethyl)cyclopropyl]-2-[2-(trifluoromethyl)pyrimidin-5-yl]propyl]benzamide | 29 |
| (+)2,3-dichloro-N-[3-[1-(trifluoromethyl)cyclopropyl]-2-[2-(trifluoromethyl)pyrimidin-5-yl]propyl]benzamide | 1.6 |
| (−)2,3-dichloro-N-[3-[1-(trifluoromethyl)cyclopropyl]-2-[2-(trifluoromethyl)pyrimidin-5-yl]propyl]benzamide | 21 |
| (+)2-chloro-3-fluoro-N-[3-[1-(trifluoromethyl)cyclopropyl]-2-[6-(trifluoromethyl)-3-pyridyl]propyl]benzamide | 7.2 |
| (−)2-chloro-3-fluoro-N-[3-[1-(trifluoromethyl)cyclopropyl]-2-[6-(trifluoromethyl)-3-pyridyl]propyl]benzamide | 16 |
| (+)2,3-dichloro-N-[3-cyclopropyl-2-[6-(1-hydroxy-1-methyl-ethyl)-3-pyridyl]propyl]benzamide | 740 |
| (−)2,3-dichloro-N-[3-cyclopropyl-2-[6-(1-hydroxy-1-methyl-ethyl)-3-pyridyl]propyl]benzamide | 30 |
| (+)2,3-dichloro-N-[2-tetrahydropyran-4-yl-2-[2-(trifluoromethyl)pyrimidin-5-yl]ethyl]benzamide | 4.1 |
| (−)2,3-dichloro-N-[2-tetrahydropyran-4-yl-2-[2-(trifluoromethyl)pyrimidin-5-yl]ethyl]benzamide | 11 |
| (+)2-chloro-N-[2-tetrahydropyran-4-yl-2-[2-(trifluoromethyl)pyrimidin-5-yl]ethyl]benzamide | 51 |
| (−)2-chloro-N-[2-tetrahydropyran-4-yl-2-[2-(trifluoromethyl)pyrimidin-5-yl]ethyl]benzamide | 56 |
| (+)2-chloro-6-fluoro-N-[2-tetrahydropyran-4-yl-2-[2-(trifluoromethyl)pyrimidin-5-yl]ethyl]benzamide | 56 |
| (−)2-chloro-6-fluoro-N-[2-tetrahydropyran-4-yl-2-[2-(trifluoromethyl)pyrimidin-5-yl]ethyl]benzamide | 68 |
| (+)2-chloro-3-fluoro-N-[2-tetrahydropyran-4-yl-2-[2-(trifluoromethyl)pyrimidin-5-yl[ethyl]benzamide | 32 |
| (−)2-chloro-3-fluoro-N-[2-tetrahydropyran-4-yl-2-[2-(trifluoromethyl)pyrimidin-5-yl]ethyl]benzamide | 64 |
| (+)2,6-dichloro-N-[2-phenyl-2-[6-(trifluoromethyl)-3-pyridyl]ethyl]benzamide | 12 |
| (−)2,6-dichloro-N[2-phenyl-2-[6-(trifluoromethyl)-3-pyridyl]ethyl]benzamide | 18 |
| 2,4-dichloro-N-(2-phenyl-2-(6-(trifluoromethyl)pyridin-3-yl)ethyl)benzamide | 25 |
| 2-chloro-6-fluoro-N-[1-[4-(2-methylpyrimidin-5-yl)tetrahydropyran-4-yl]ethyl]benzamide | 55 |
| 2-chloro-3-fluoro-N-[1-[4-(2-methylpyrimidin-5-yl)tetrahydropyran-4-yl]ethyl]benzamide | 15 |
| 2,3-dichloro-N-((3-(2-methylpyrimidin-5-yl)tetrahydrofuran-3-yl)methyl)benzamide | 15 |
| (+)2,3-dichloro-N-[2-(4-fluorophenyl)-2-[6-(trifluoromethyl)-3-pyridyl]ethyl]benzamide | 12 |
| (−)2,3-dichloro-N-[2-(4-fluorophenyl)-2-[6-(trifluoromethyl)-3-pyridyl]ethyl]benzamide | 9.4 |
| (+)2-chloro-6-fluoro-N-[2-(4-fluorophenyl)-2-[6-(trifluoromethyl)-3-pyridyl]ethyl]benzamide | 15 |
| (−)2-chloro-6-fluoro-N-[2-(4-fluorophenyl)-2-[6-(trifluoromethyl)-3-pyridyl]ethyl]benzamide | 8.5 |
| (+)2-chloro-3-fluoro-N-[2-(4-fluorophenyl)-2-[6-(trifluoromethyl)-3-pyridyl]ethyl]benzamide | 4.6 |
| (−)2-chloro-3-fluoro-N-[2-(4-fluorophenyl)-2-[6-(trifluoromethyl)-3-pyridyl]ethyl]benzamide | 7 |
| (+)2-chloro-N-[2-(4-fluorophenyl)-2-[6-(trifluoromethyl)-3-pyridyl]ethyl]benzamide | 2.2 |
| (−)2-chloro-N-[2-(4-fluorophenyl)-2-[6-(trifluoromethyl)-3-pyridyl]ethyl]benzamide | 3.1 |
| 2-chloro-N-[2-(4-pyridyl)-2-[2-(trifluoromethyl)pyrimidin-5-yl]ethyl]benzamide | 30 |

TABLE 1-continued

Exemplified IC$_{50}$ values of compounds of the invention:

| Chemical name | IC50 (nM) |
|---|---|
| 2,3-dichloro-N-[2-(4-pyridyl)-2-[2-(trifluoromethyl)pyrimidin-5-yl]ethyl]benzamide | 6.2 |
| 2-chloro-N-[2-(4-pyridyl)-2-[6-(trifluoromethyl)-3-pyridyl]ethyl]benzamide | 11 |
| 2,3-dichloro-N-[2-(4-pyridyl)-2-[6-(trifluoromethyl)-3-pyridyl]ethyl]benzamide | 200 |
| (+)2,3-dichloro-N-[2-(4-fluorophenyl)-2-[2-(trifluoromethyl)pyrimidin-5-yl]ethyl]benzamide | 1.1 |
| (−)2,3-dichloro-N-[2-(4-fluorophenyl)-2-[2-(trifluoromethyl)pyrimidin-5-yl]ethyl]benzamide | 1.2 |
| (+)2-chloro-N-[2-(4-fluorophenyl)-2-[2-(trifluoromethyl)pyrimidin-5-yl]ethyl]benzamide | 4.4 |
| (−)2-chloro-N-[2-(4-fluorophenyl)-2-[2-(trifluoromethyl)pyrimidin-5-yl]ethyl]benzamide | 2 |
| 2,3-dichloro-N-[1-[4,4-difluoro-1-(2-methylpyrimidin-5-yl)cyclohexyl]ethyl]benzamide | 960 |
| 2-chloro-N-[1[4,4-difluoro-1-(2-methylpyrimidin-5-yl)cyclohexyl]ethyl]benzamide | 1600 |
| (+)2-chloro-6-fluoro-N-[2-(4-fluorophenyl)-2-[2-(trifluoromethyl)pyrimidin-5-yl]ethyl]benzamide | 6.7 |
| (−)2-chloro-6-fluoro-N-[2-(4-fluorophenyl)-2-[2-(trifluoromethyl)pyrimidin-5-yl]ethyl]benzamide | 2.6 |
| (+)2-chloro-3-fluoro-N-[2-(4-fluorophenyl)-2-[2-(trifluoromethyl)pyrimidin-5-yl]ethyl]benzamide | 4.8 |
| (−)2-chloro-3-fluoro-N-[2-(4-fluorophenyl)-2-[2-(trifluoromethyl)pyrimidin-5-yl]ethyl]benzamide | 1.8 |
| 2-chloro-N-[1-[4,4-difluoro-1-(2-methylpyrimidin-5-yl)cyclohexyl]ethyl]-6-fluoro-benzamide | 1400 |
| 2-chloro-N-[1-[4,4-difluoro-1-(2-methylpyrimidin-5-yl)cyclohexyl]ethyl]-3-fluoro-benzamide | 2000 |
| (−)2,3-dichloro-N-[2-(4,4-difluorocyclohexyl)-2-(2-methylpyrimidin-5-yl)ethyl]benzamide | 16 |
| (+)2,3-dichloro-N-[2-(4,4-difluorocyclohexyl)-2-(2-methylpyrimidin-5-yl)ethyl]benzamide | 8.4 |
| (+)2-chloro-N-[2-(4,4-difluorocyclohexyl)-2-[2-(trifluoromethyppyrimidin-5-yl]ethyl]-3-fluoro-benzamide | 45 |
| (−)2-chloro-N-[2-(4,4-difluorocyclohexyl)-2-[2-(trifluoromethyl)pyrimidin-5-yl]ethyl]-3-fluoro-benzamide | 44 |
| (+)2-chloro-N-[2-(4,4-difluorocyclohexyl)-2-[2-(trifluoromethyl)pyrimidin-5-yl]ethyl]benzamide | 32 |
| (−)2-chloro-N-[2-(4,4-difluorocyclohexyl)-2-[2-(trifluoromethyl)pyrimidin-5-yl]ethyl]benzamide | 6.4 |
| (+)2,3-dichloro-N-[2-(4,4-difluorocyclohexyl)-2-[2-(trifluoromethyl)pyrimidin-5-yl]ethyl]benzamide | 5.7 |
| (−)2,3-dichloro-N-[2-(4,4-difluorocyclohexyl)-2-[2-(trifluoromethyl)pyrimidin-5-yl]ethyl]benzamide | 4.3 |
| (+)2-chloro-N-[2-(4,4-difluorocyclohexyl)-2-[2-(trifluoromethyl)pyrimidin-5-yl]ethyl]-6-fluoro-benzamide | 75 |
| (−)2-chloro-N-[2-(4,4-difluorocyclohexyl)-2-[2-(trifluoromethyl)pyrimidin-5-yl]ethyl]-6-fluoro-benzamide | 61 |
| 2,3-dichloro-N-[4-methoxy-2-[2-(trifluoromethyl)pyrimidin-5-yl]butyl]benzamide | 2200 |
| 2,3-dichloro-N-(2-phenyl-2-pyridazin-4-yl-ethyl)benzamide | 94 |
| 2,4-dichloro-N-(2-phenyl-2-pyridazin-4-yl-ethyl)benzamide | 720 |
| (+)2,3-dichloro-N-[3-cyclopropyl-2-[2-(difluoromethyl)pyrimidin-5-yl]propyl]benzamide | 23 |
| (−)2,3-dichloro-N-[3-cyclopropyl-2-[2-(difluoromethyl)pyrimidin-5-yl]propyl]benzamide | 1.9 |
| (+)2-chloro-N-[3-cyclopropyl-2-[6-(difluoromethyl)-3-pyridyl]propyl]benzamide | 640 |
| (−)2-chloro-N-[3-cyclopropyl-2-[6-(difluoromethyl)-3-pyridyl]propyl]benzamide | 17 |
| (+)2,3-dichloro-N-[3-cyclopropyl-2-[6-(difluoromethyl)-3-pyridyl]propyl]benzamide | 24 |
| (−)2,3-dichloro-N-[3-cyclopropyl-2-[6-(difluoromethyl)-3-pyridyl]propyl]benzamide | 1.9 |
| (+)2-chloro-N-[3-cyclopropyl-2-[6-(difluoromethyl)-3-pyridyl]propyl]-3-fluoro-benzamide | 800 |
| (−)2-chloro-N-[3-cyclopropyl-2-[6-(difluoromethyl)-3-pyridyl]propyl]-3-fluoro-benzamide | 19 |
| (+)2-chloro-N-[3-cyclopropyl-2-[6-(difluoromethyl)-3-pyridyl]propyl]-3-methoxy-benzamide | 4.4 |
| N-[4,4-Difluoro-1-(6-fluoro-pyridin-3-yl)-cyclohexylmethyl]-2-fluoro-benzamide | 14 |

What is claimed is:

1. A method of treating seizures mediated by P2X7 comprising administering a therapeutically P2X7 inhibiting effective amount of at least one compound of formula I

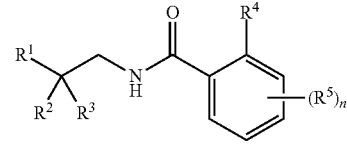

wherein $R^1$ is pyridyl, pyrazinyl, pyridazinyl, or pyrimidyl, each of which is optionally substituted with one or more $C_{1-6}$ alkyl, halogen, hydroxy, $C_{1-6}$ hydroxyalkyl, $C_{1-4}$ fluoroalkyl, $C_{3-6}$ cycloalkyl, $C_{1-4}$ alkoxy, $C_{1-4}$ fluoroalkoxy, cyano or $—SO_2R^8$;

wherein $R^2$ is $C_{3-6}$ cycloalkyl, $C_{3-6}$ cyclohetalkyl, $C_{1-4}$ fluoroalkyl, $C_{1-4}$ fluoroalkoxy, $C_{1-4}$ alkoxy, $C_{1-6}$ alkenyl, $C_{1-6}$ alkynyl, 6 membered heteroaryl, phenyl or $C_{1-4}$ alkyl optionally substituted with one or more $R^9$;

wherein $R^3$ is hydrogen, fluorine, $C_{1-4}$ alkyl or $C_{1-4}$ fluoroalkyl; or wherein $R^2$ and $R^3$ combine with the carbon to which they are attached to form cyclohexyl, tetrahydropyranyl, piperazinyl, piperidinyl, morpholinyl, pyrrolidinyl, pyrrolo, imidazo, azetidinyl, homomorpholinyl, homopiperidinyl or homopiperazinyl each of which is optionally substituted with one or more $C_{1-6}$ alkyl, $C_{1-6}$ alkenyl, $C_{3-6}$-cycloalkyl, $C_{1-6}$ alkoxy, oxo, $—NR^6R^7$ or fluorine;

wherein $R^4$ is halogen, $C_{1-4}$ fluoroalkyl, cyano, cyclopropyl, $C_{1-4}$alkyloxy, $C_{1-4}$ fluoroalkyloxy, $—SO_2R^8$, $—NR^6R^7$ or $C_{1-6}$ alkyl;

wherein $R^5$ is halogen, $C_{1-6}$ alkyl, $C_{1-4}$ fluoroalkyl, cyano, $—SO_2R^8$, $—NR^6R^7$, $C_{1-6}$ alkoxy, $C_{1-4}$ fluoroalkoxy or $C_{3-6}$ cycloalkyl;

wherein $R^6$ and $R^7$ independently of each other are hydrogen or $C_{1-6}$ alkyl;

wherein $R^8$ is $C_{1-6}$ alkyl, $C_{3-6}$ cycloalkyl or $C_{1-4}$ fluoroalkyl;

wherein $R^9$ is $C_{1-6}$ alkyl, $C_{3-6}$ cycloalkyl, —$NR^{10}C_{1-4}$ fluoroalkyl or 3 to 7 membered heterocyclyl which is optionally substituted with one or more $C_{1-6}$ alkyl, halogen, hydroxy, $C_{1-4}$ fluoroalkyl, $C_{3-6}$ cycloalkyl, $C_{1-4}$ alkoxy, $C_{1-4}$ fluoroalkoxy or cyano;

wherein $R^{10}$ and $R^{11}$ independently of each other are hydrogen or $C_{1-6}$ alkyl; or wherein $R^{10}$ and $R^{11}$ combine with the nitrogen to which they are attached to form piperazinyl, piperidinyl, morpholinyl, pyrrolidinyl, azetidinyl, homomorpholinyl, homopiperidinyl or homopiperazinyl each of which is optionally substituted with one or more $C_{1-6}$ alkyl, $C_{1-6}$ alkoxy, oxo or fluorine; and wherein n is 0-3; or a pharmaceutically acceptable salt thereof;

to a subject in need thereof.

2. The method of claim 1, wherein the compound is (−)2-chloro-N-[3-cyclopropyl-2-[2-(trifluoromethyl)pyrimidin-5-yl]propyl]benzamide or a pharmaceutically acceptable salt thereof.

3. The method of claim 1, wherein the compound is (−)-2-chloro-N-(3-cyclopropyl-2-(2-(trifluoromethyl)pyrimidin-5-yl)propyl)-6-fluorobenzamide or a pharmaceutically acceptable salt thereof.

4. The method of claim 1, wherein the compound is (−)2,3-dichloro-N-[3-cyclopropyl-2-[2-(trifluoromethyl)pyrimidin-5-yl]propyl]benzamide or a pharmaceutically acceptable salt thereof.

5. The method of claim 1, wherein the compound is(−) 2,6-dichloro-N-[3-cyclopropyl-2-[2-(trifluoromethyl)pyrimidin-5-yl]propyl]benzamide or a pharmaceutically acceptable salt thereof.

6. The method of claim 1, wherein the compound is (+)2-chloro-N-[3-cyclopropyl-2-[2-(trifluoromethyl)pyrimidin-5-yl]propyl]-3-fluoro-benzamide or a pharmaceutically acceptable salt thereof.

7. The method of claim 1, wherein the compound is (+)-2-chloro-N-(3-(1-(trifluoromethyl)cyclopropyl)-2-(2-(trifluoromethyl)pyrimidin-5-yl)propyl)benzamide or a pharmaceutically acceptable salt thereof.

8. The method of claim 1, wherein the compound is (+)2-chloro-N-[3-[1-(trifluoromethyl)cyclopropyl]-2-[2-(trifluoromethyl)pyrimidin-5-yl]propyl]benzamide or a pharmaceutically acceptable salt thereof.

9. The method of claim 1, wherein the compound is (+)-2,3-Dichloro-N-(2-(2-(difluoromethyl)pyrimidin-5-yl)-3-(1-(trifluoromethyl)cyclopropyl)propyl)benzamide or a pharmaceutically acceptable salt thereof.

10. The method of claim 1, wherein the compound is (−)2,3-dichloro-N-[3-cyclopropyl-2-[2-(difluoromethyl)pyrimidin-5-yl]propyl]benzamide or a pharmaceutically acceptable salt thereof.

11. The method of claim 1, wherein the compound is (+)2,3-dichloro-N-[3-[1-(trifluoromethyl)cyclopropyl]-2-[2-(trifluoromethyl)pyrimidin-5-yl]propyl]benzamide or a pharmaceutically acceptable salt thereof.

12. The method of claim 1, wherein the compound is (−)-2,6-dichloro-N-(3-cyclopropyl-2-(2-(difluoromethyl)pyrimidin-5-yl)propyl)benzamide or a pharmaceutically acceptable salt thereof.

13. The method of claim 1, wherein the compound is (−)2-chloro-N-[3-cyclopropyl-2-[2-(trifluoromethyl)pyrimidin-5-yl]propyl]-3-fluoro-benzamide or a pharmaceutically acceptable salt thereof.

14. The method of claim 1, wherein the compound is (−)-2,3-Dichloro-N-(2-(2-(difluoromethyl)pyrimidin-5-yl)-3-(1-(trifluoromethyl)cyclopropyl)propyl)benzamide or a pharmaceutically acceptable salt thereof.

15. The method of claim 1, wherein the compound is (−)2,3-dichloro-N-[3-[1-(trifluoromethyl)cyclopropyl]-2-[2-(trifluoromethyl)pyrimidin-5-yl]propyl]benzamide or a pharmaceutically acceptable salt thereof.

16. The method of claim 1, wherein the compound is (−)-2,3-dichloro-N-(3-cyclopropyl-2-methyl-2-(2-(trifluoromethyl)pyrimidin-5-yl)propyl)benzamide or a pharmaceutically acceptable salt thereof.

17. The method of claim 1, wherein the compound is (+)2-chloro-3-fluoro-N-[3-[1-(trifluoromethyl)cyclopropyl]-2-[2-(trifluoromethyl)pyrimidin-5-yl]propyl]benzamide or a pharmaceutically acceptable salt thereof.

18. The method of claim 1, wherein the compound is (−)2,6-dichloro-N-[3-cyclopropyl-2-(2-methylpyrimidin-5-yl)propyl]benzamide or a pharmaceutically acceptable salt thereof.

* * * * *